(12) United States Patent
Narva et al.

(10) Patent No.: US 9,534,232 B2
(45) Date of Patent: *Jan. 3, 2017

(54) NUCLEIC ACID MOLECULES THAT TARGET RPS6 AND CONFER RESISTANCE TO COLEOPTERAN PESTS

(71) Applicant: Dow AgroSciences LLC, Indianapolis, IN (US)

(72) Inventors: Kenneth E. Narva, Zionsville, IN (US); Huarong Li, Zionsville, IN (US); Chaoxian Geng, Zionsville, IN (US); Ignacio Larrinua, Indianapolis, IN (US); Monica Britt Olson, Lebanon, IN (US); Navin Elango, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 601 days.

This patent is subject to a terminal disclaimer.

(21) Appl. No.: 13/646,524

(22) Filed: Oct. 5, 2012

(65) Prior Publication Data

US 2013/0097730 A1 Apr. 18, 2013

Related U.S. Application Data

(60) Provisional application No. 61/544,219, filed on Oct. 6, 2011.

(51) Int. Cl.
| | | |
|---|---|---|
| *C12N 15/82* | (2006.01) | |
| *C12N 5/14* | (2006.01) | |
| *C12N 15/113* | (2010.01) | |
| *C07K 14/435* | (2006.01) | |

(52) U.S. Cl.
CPC ..... *C12N 15/8286* (2013.01); *C07K 14/43563* (2013.01); *C12N 15/113* (2013.01); *C12N 15/8218* (2013.01); *C12N 2310/11* (2013.01); *C12N 2310/111* (2013.01); *C12N 2310/14* (2013.01)

(58) Field of Classification Search
None
See application file for complete search history.

(56) References Cited

U.S. PATENT DOCUMENTS

| 9,238,822 B2 * | 1/2016 | Baum | |
| 2006/0021087 A1 | 1/2006 | Baum et al. | |
| 2007/0124836 A1 * | 5/2007 | Baum | C07H 21/04 800/279 |
| 2012/0164205 A1 * | 6/2012 | Baum | A01N 63/02 424/409 |
| 2012/0174258 A1 | 7/2012 | Narva et al. | |

OTHER PUBLICATIONS

GenBank Accession No. EW772867.1, published 2007.*
The Promega Technical Bulletin: pGEM-11ZF+ vector (2006) pp. 1-8.*
The Invitrogen manual: ElectroMAX DH12S Cells (2006) pp. 1-4.*
Smith et al (2000) Nature 407:319-320.*
Stewart et al, Molecular and Cellular Biology (1993) 13: 2524-2535.*
Thomas et al, Plant J (2001) 25: 417-425.*
Klahre et al, PNAS (2002) 99: 11981-11986.*
International Search Report and written Opinion for International Application No. PCT/US2012/059115, dated Mar. 29, 2013.
Price Daniel R.G., "RNAi-mediated crop protection against insects," Trends in biotechnology, Jul. 2008, vol. 26, No. 7, pp. 393-400.
Zhao, Y. Y. et al., PsOr1, a potential target for RNA interference-based pest management, Insect Molecular Biology, Feb. 2011, vol. 20, No. 1, pp. 97-104.

* cited by examiner

*Primary Examiner* — Eileen B O Hara
*Assistant Examiner* — Steven Bernacki
(74) *Attorney, Agent, or Firm* — James Daly IV; Magleby Cataxinos & Greenwood

(57) ABSTRACT

This disclosure concerns nucleic acid molecules and methods of use thereof for control of coleopteran pests through RNA interference-mediated inhibition of target coding and transcribed non-coding sequences in coleopteran pests. The disclosure also concerns methods for making transgenic plants that express nucleic acid molecules useful for the control of coleopteran pests, and the plant cells and plants obtained thereby.

25 Claims, 7 Drawing Sheets

NUCLEIC ACID MOLECULES THAT TARGET RPS6 AND CONFER RESISTANCE TO COLEOPTERAN PESTS

RELATED APPLICATIONS

This application claims priority to U.S. Provisional Patent Application No. 61/544,219, filed on Oct. 6, 2011.

FIELD OF THE DISCLOSURE

The present invention relates generally to genetic control of plant damage caused by coleopteran pests. In particular embodiments, the present invention relates to identification of target coding and non-coding sequences, and the use of recombinant DNA technologies for post-transcriptionally repressing or inhibiting expression of target coding and non-coding sequences in the cells of a coleopteran pest to provide a plant protective effect.

BACKGROUND

The western corn rootworm (WCR), *Diabrotica virgifera virgifera* LeConte, is one of the most devastating corn rootworm species in North America and is a particular concern in corn-growing areas of the Midwestern United States. The northern corn rootworm (NCR), *Diabrotica barberi* Smith and Lawrence, is a closely-related species that co-inhabits much of the same range as WCR. There are several other related subspecies of *Diabrotica* that are significant pests in North America: the Mexican corn rootworm (MCR), *D. virgifera zeae* Krysan and Smith; the southern corn rootworm (SCR), *D. undecimpunctata howardi* Barber; *D. balteata* LeConte; *D. undecimpunctata tenella*; and *D. u. undecimpunctata* Mannerheim. The United States Department of Agriculture currently estimates that corn rootworms cause $1 billion in lost revenue each year, including $800 million in yield loss and $200 million in treatment costs.

Both WCR and NCR are deposited in the soil as eggs during the summer. The insects remain in the egg stage throughout the winter. The eggs are oblong, white, and less than 0.004 inch (0.010 cm) in length. The larvae hatch in late May or early June, with the precise timing of egg hatching varying from year to year due to temperature differences and location. The newly hatched larvae are white worms that are less than 0.125 inch (0.318 cm) in length. Once hatched, the larvae begin to feed on corn roots. Corn rootworms go through three larval instars. After feeding for several weeks, the larvae molt into the pupal stage. They pupate in the soil, and then they emerge from the soil as adults in July and August. Adult rootworms are about 0.25 inch (0.635 cm) in length.

Corn rootworm larvae complete development on corn and several other species of grasses. Larvae reared on yellow foxtail emerge later and have a smaller head capsule size as adults than larvae reared on corn. Ellsbury et al. (2005) Environ. Entomol. 34:627-34. WCR adults feed on corn silk, pollen, and kernels on exposed ear tips. If WCR adults emerge before corn reproductive tissues are present, they may feed on leaf tissue, thereby slowing plant growth and occasionally killing the host plant. However, the adults will quickly shift to preferred silks and pollen when they become available. NCR adults also feed on reproductive tissues of the corn plant, but in contrast rarely feed on corn leaves.

Most of the rootworm damage in corn is caused by larval feeding. Newly hatched rootworms initially feed on fine corn root hairs and burrow into root tips. As the larvae grow larger, they feed on and burrow into primary roots. When corn rootworms are abundant, larval feeding often results in the pruning of roots all the way to the base of the corn stalk. Severe root injury interferes with the roots' ability to transport water and nutrients into the plant, reduces plant growth, and results in reduced grain production, thereby often drastically reducing overall yield. Severe root injury also often results in lodging of corn plants, which makes harvest more difficult and further decreases yield. Furthermore, feeding by adults on the corn reproductive tissues can result in pruning of silks at the ear tip. If this "silk clipping" is severe enough during pollen shed, pollination may be disrupted.

Control of corn rootworms may be attempted by crop rotation, chemical insecticides, biopesticides (e.g., the spore-forming gram-positive bacterium, *Bacillus thuringiensis*), or a combination thereof. Crop rotation suffers from the significant disadvantage of placing unwanted restrictions upon the use of farmland. Moreover, oviposition of some rootworm species may occur in soybean fields, thereby mitigating the effectiveness of crop rotation practiced with corn and soybean.

Chemical insecticides are the most heavily relied upon strategy for achieving corn rootworm control. Chemical insecticide use, though, is an imperfect corn rootworm control strategy; over $1 billion may be lost in the United States each year due to corn rootworm when the costs of the chemical insecticides are added to the costs of the rootworm damage that may occur despite the use of the insecticides. High populations of larvae, heavy rains, and improper application of the insecticide(s) may all result in inadequate corn rootworm control. Furthermore, the continual use of insecticides may select for insecticide-resistant rootworm strains, as well as raise significant environmental concerns due to the toxicity of many of them to non-target species.

RNA interference (RNAi) is a process utilizing endogenous cellular pathways, whereby an interfering RNA (iRNA) molecule (e.g., a dsRNA molecule) that is specific for all, or any portion of adequate size, of a target gene sequence results in the degradation of the mRNA encoded thereby. In recent years, RNAi has been used to perform gene "knockdown" in a number of species and experimental systems; for example, *Caenorhabitis elegans*, plants, insect embryos, and cells in tissue culture. See, e.g., Fire et al. (1998) Nature 391:806-11; Martinez et al. (2002) Cell 110:563-74; McManus and Sharp (2002) Nature Rev. Genetics 3:737-47.

RNAi accomplishes degradation of mRNA through an endogenous pathway including the DICER protein complex. DICER cleaves long dsRNA molecules into short fragments of approximately 20 nucleotides, termed small interfering RNA (siRNA). The siRNA is unwound into two single-stranded RNAs: the passenger strand and the guide strand. The passenger strand is degraded, and the guide strand is incorporated into the RNA-induced silencing complex (RISC). Micro inhibitory ribonucleic acid (miRNA) molecules may be similarly incorporated into RISC. Post-transcriptional gene silencing occurs when the guide strand binds specifically to a complementary sequence of an mRNA molecule and induces cleavage by Argonaute, the catalytic component of the RISC complex. This process is known to spread systemically throughout the organism despite initially limited concentrations of siRNA and/or miRNA in some eukaryotes such as plants, nematodes, and some insects.

Only transcripts complementary to the siRNA and/or miRNA are cleaved and degraded, and thus the knock-down of mRNA expression is sequence-specific. In plants, several functional groups of DICER genes exist. The gene silencing effect of RNAi persists for days and, under experimental conditions, can lead to a decline in abundance of the targeted transcript of 90% or more, with consequent reduction in levels of the corresponding protein.

U.S. Pat. No. 7,612,194, and U.S. Patent Publication Nos. 2007/0050860 and 2010/0192265, disclose a library of 9112 expressed sequence tag (EST) sequences isolated from *D. v. virgifera* LeConte pupae. It is suggested in U.S. Pat. No. 7,612,194 and U.S. Patent Publication No. 2007/0050860 to operably link to a promoter a nucleic acid molecule that is complementary to one of several particular partial sequences of *D. v. virgifera* vacuolar-type H+-ATPase (V-ATPase) disclosed therein for the expression of anti-sense RNA in plant cells. U.S. Patent Publication No. 2010/0192265 suggests operably linking a promoter to a nucleic acid molecule that is complementary to a particular partial sequence of a *D. v. virgifera* gene of unknown and undisclosed function (the partial sequence is stated to be 58% identical to C56C10.3 gene product in *C. elegans*) for the expression of anti-sense RNA in plant cells.

No further suggestion is provided in these publications to use any particular sequence of the more than nine thousand sequences listed therein for RNA interference, other than the several particular partial sequences of V-ATPase and the particular partial sequence of a gene of unknown function. Furthermore, none of U.S. Pat. No. 7,612,194, and U.S. Patent Publication Nos. 2007/0050860 and 2010/0192265 provides any guidance as to which other of the over nine thousand sequences provided would be lethal, or even otherwise useful, in species of corn rootworm when used as dsRNA or siRNA. The overwhelming majority of these sequences are not lethal in species of corn rootworm when used as dsRNA or siRNA. For example, Baum et al. (2007) Nat. Biotech. 25(11):1322-6, describe the effects of inhibiting several WCR gene targets by RNAi. These authors reported that 8 of 26 target genes they tested were not able to provide experimentally significant coleopteran pest mortality at a very high iRNA (e.g., dsRNA) concentration of more than 520 ng/cm$^2$.

SUMMARY OF THE DISCLOSURE

Disclosed herein are nucleic acid molecules (e.g., target genes, DNAs, dsRNAs, siRNAs, miRNAs, and hpRNAs), and methods of use thereof, for the control of coleopteran pests, including, for example, *D. v. virgifera* LeConte (western corn rootworm, "WCR"); *D. barberi* Smith and Lawrence (northern corn rootworm, "NCR"); *D. u. howardi* Barber (southern corn rootworm, "SCR"); *D. v. zeae* Krysan and Smith (Mexican corn rootworm, "MCR"); *D. balteata* LeConte; *D. u. tenella*; and *D. u. undecimpunctata* Mannerheim. In particular examples, exemplary nucleic acid molecules are disclosed that may be homologous to at least a portion of one or more native nucleic acid sequences in a coleopteran pest.

In these and further examples, the native nucleic acid sequence may be a target gene, the product of which may be, for example and without limitation: involved in a metabolic process; involved in a reproductive process; or involved in larval development. In some examples, post-translation inhibition of the expression of a target gene by a nucleic acid molecule comprising a sequence homologous thereto may be lethal in coleopteran pests, or result in reduced growth and/or reproduction. In specific examples, at least one gene selected from the list consisting of PP1-87B full length (sometimes referred to herein as "PP1-87B"); contig0011_87B protein phosphatase; RPA70 full length (sometimes referred to herein as "RPA70"); D_vir_c43870_RPA70 (sometimes referred to herein as "RPA70 region 1" or "RPA70 Reg1"); D_vir_c18764 RPA70 (sometimes referred to herein as "RPA70 region 2" or "RPA70 Reg2"); D_vir_c7971_RPA70 (sometimes referred to herein as "RPA70 region 3" or "RPA70 Reg3"); and RPS6 may be selected as a target gene for post-transcriptional silencing. In particular examples, a target gene useful for post-transcriptional inhibition is RPS6.

Also disclosed are nucleic acid molecules comprising a nucleotide sequence that encodes a polypeptide that is at least 85% identical to an amino acid sequence within a target gene product (for example, a product of a gene selected from the group consisting of PP1-87B; contig0011_87B protein phosphatase; RPA70; RPA70 Reg1; RPA70 Reg2; RPA70 Reg3; and RPS6). For example, a nucleic acid molecule may comprise a nucleotide sequence encoding a polypeptide that is at least 85% identical to an amino acid sequence selected from the group consisting of SEQ ID NO:67 (PP1-87B); SEQ ID NO:95 (contig0011_87B protein phosphatase); SEQ ID NO:68 (RPA70); SEQ ID NO:96 (RPA70 Reg1); SEQ ID NO:97 (RPA70 Reg2); SEQ ID NO:98 (RPA70 Reg3); and SEQ ID NO:69 (RPS6). In particular examples, a nucleic acid molecule comprises a nucleotide sequence encoding a polypeptide that is at least 85% identical to an amino acid sequence within a product of RPS6. Further disclosed are nucleic acid molecules comprising a nucleotide sequence that is the reverse complement of a nucleotide sequence that encodes a polypeptide at least 85% identical to an amino acid sequence within a target gene product.

Also disclosed are cDNA sequences that may be used for the production of iRNA (e.g., dsRNA, siRNA, miRNA, and hpRNA) molecules that are complementary to all or part of a coleopteran pest target gene, for example: PP1-87B; RPA70; RPA70 Reg1; RPA70 Reg2; RPA70 Reg3; and/or RPS6. In particular embodiments, dsRNAs, siRNAs, miRNAs, and/or hpRNAs may be produced in vitro, or in vivo by a genetically-modified organism, such as a plant or bacterium. In particular examples, cDNA molecules are employed that may be used to produce iRNA molecules that are complementary to all or part of RPS6 (SEQ ID NO:7).

Further disclosed are means for inhibiting expression of an essential gene in a coleopteran pest, and means for providing coleopteran pest resistance to a plant. A means for inhibiting expression of an essential gene in a coleopteran pest is a single- or double-stranded RNA molecule consisting of any of SEQ ID NOs:25-28, or the complement thereof. Functional equivalents of means for inhibiting expression of an essential gene in a coleopteran pest include single- or double-stranded RNA molecules that are substantially homologous to all or part of a WCR gene comprising any of SEQ ID NOs:3, 5, 6, and 7. A means for providing coleopteran pest resistance to a plant is a DNA molecule comprising a nucleic acid sequence encoding a means for inhibiting expression of an essential gene in a coleopteran pest operably linked to a promoter, wherein the DNA molecule is capable of being integrated into the genome of a maize plant.

Disclosed are methods for controlling a population of a coleopteran pest, comprising providing to a coleopteran pest an iRNA (e.g., dsRNA, siRNA, miRNA, and hpRNA) molecule that functions upon being taken up by the coleopteran pest to inhibit a biological function within the coleopteran pest, wherein the iRNA molecule comprises all or part of a nucleotide sequence selected from the group consisting of: SEQ ID NO:1; the complement of SEQ ID NO:1; SEQ ID NO:2; the complement of SEQ ID NO:2; SEQ ID NO:3; the complement of SEQ ID NO:3; SEQ ID NO:4; the complement of SEQ ID NO:4; SEQ ID NO:5; the complement of SEQ ID NO:5; SEQ ID NO:6; the complement of SEQ ID NO:6; SEQ ID NO:7; the complement of SEQ ID NO:7; a native coding sequence of a *Diabrotica* organism (e.g., WCR) comprising all or part of any of SEQ ID NOs:1-7; the complement of a native coding sequence of a *Diabrotica* organism comprising all or part of any of SEQ ID NOs:1-7; a native non-coding sequence of a *Diabrotica* organism that is transcribed into a native RNA molecule comprising all or part of any of SEQ ID NOs:1-7; and the complement of a native non-coding sequence of a *Diabrotica* organism that is transcribed into a native RNA molecule comprising all or part of any of SEQ ID NOs:1-7.

In particular examples, methods are disclosed for controlling a population of a coleopteran pest, comprising providing to a coleopteran pest an iRNA (e.g., dsRNA, siRNA, miRNA, and hpRNA) molecule that functions upon being taken up by the coleopteran pest to inhibit a biological function within the coleopteran pest, wherein the iRNA molecule comprises a nucleotide sequence selected from the group consisting of: all or part of SEQ ID NO:1; the complement of all or part of SEQ ID NO:1; all or part of SEQ ID NO:2; the complement of all or part of SEQ ID NO:2; all or part of SEQ ID NO:7; the complement of all or part of SEQ ID NO:7; all or part of a native coding sequence of a *Diabrotica* organism (e.g., WCR) comprising SEQ ID NO:1; all or part of the complement of a native coding sequence of a *Diabrotica* organism comprising SEQ ID NO:1; all or part of a native non-coding sequence of a *Diabrotica* organism that is transcribed into a native RNA molecule comprising SEQ ID NO:1; all or part of the complement of a native non-coding sequence of a *Diabrotica* organism that is transcribed into a native RNA molecule comprising SEQ ID NO:1; all or part of a native coding sequence of a *Diabrotica* organism (e.g., WCR) comprising SEQ ID NO:2; all or part of the complement of a native coding sequence of a *Diabrotica* organism comprising SEQ ID NO:2; all or part of a native non-coding sequence of a *Diabrotica* organism that is transcribed into a native RNA molecule comprising SEQ ID NO:2; all or part of the complement of a native non-coding sequence of a *Diabrotica* organism that is transcribed into a native RNA molecule comprising SEQ ID NO:2; all or part of a native coding sequence of a *Diabrotica* organism (e.g., WCR) comprising SEQ ID NO:7; all or part of the complement of a native coding sequence of a *Diabrotica* organism comprising SEQ ID NO:7; all or part of a native non-coding sequence of a *Diabrotica* organism that is transcribed into a native RNA molecule comprising SEQ ID NO:7; and all or part of the complement of a native non-coding sequence of a *Diabrotica* organism that is transcribed into a native RNA molecule comprising SEQ ID NO:7.

Also disclosed herein are methods wherein dsRNAs, siRNAs, miRNAs, and/or hpRNAs may be provided to a coleopteran pest in a diet-based assay, or in genetically-modified plant cells expressing the dsRNAs, siRNAs, miRNAs, and/or hpRNAs. In these and further examples, the dsRNAs, siRNAs, miRNAs, and/or hpRNAs may be ingested by coleopteran pest larvae. Ingestion of dsRNAs, siRNA, miRNAs, and/or hpRNAs of the invention may then result in RNAi in the larvae, which in turn may result in silencing of a gene essential for viability of the coleopteran pest and leading ultimately to larval mortality. Thus, methods are disclosed wherein nucleic acid molecules comprising exemplary nucleic acid sequence(s) useful for control of coleopteran pests are provided to a coleopteran pest. In particular examples, the coleopteran pest controlled by use of nucleic acid molecules of the invention may be WCR or NCR.

The foregoing and other features will become more apparent from the following Detailed Description of several embodiments, which proceeds with reference to the accompanying FIGURES.

SEQUENCE LISTING

Figure 1:
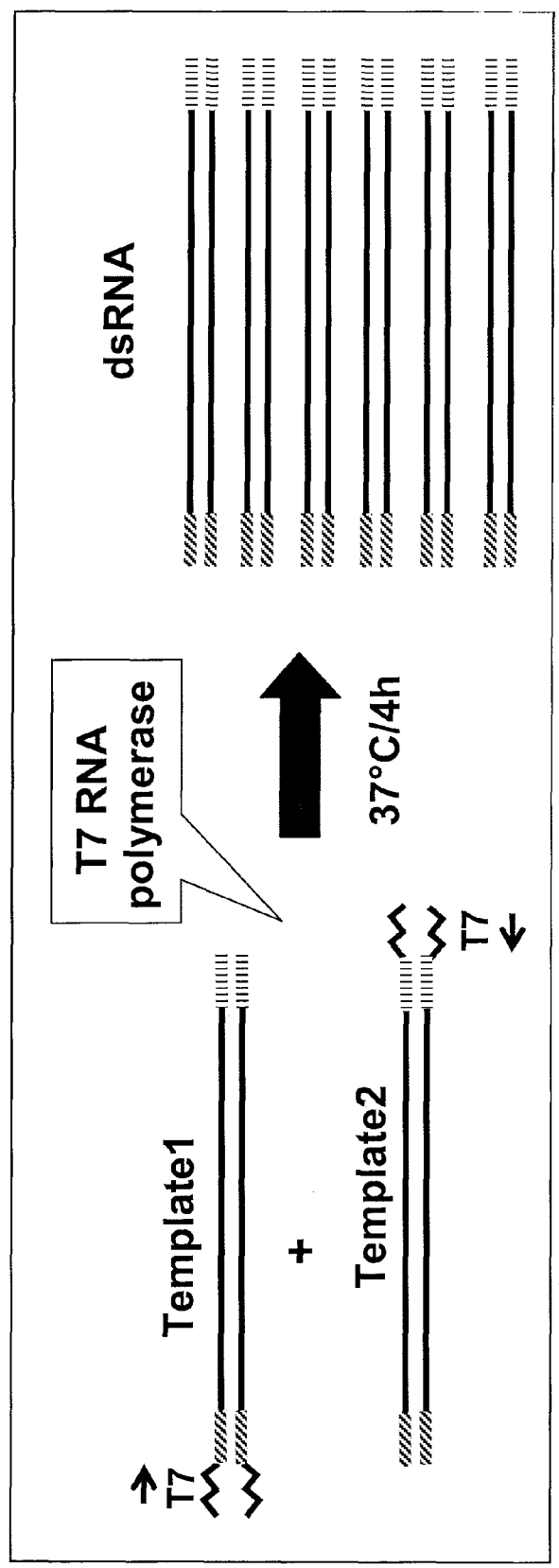
FIG. 1 includes a depiction of the strategy used to provide specific templates for dsRNA production.

The nucleic acid sequences listed in the accompanying sequence listing are shown using standard letter abbreviations for nucleotide bases, as defined in 37 C.F.R. §1.822. Only one strand of each nucleic acid sequence is shown, but the complementary strand is understood as included by any reference to the displayed strand. As the complement and reverse complement of a primary nucleic acid sequence are necessarily disclosed by the primary sequence, the complementary sequence and reverse complementary sequence of a nucleic acid sequence are included by any reference to the nucleic acid sequence, unless it is explicitly stated to be otherwise (or it is clear to be otherwise from the context in which the sequence appears). In the accompanying sequence listing:

SEQ ID NO:1 shows an exemplary *Diabrotica* cDNA sequence, referred to as protein phosphatase PP1-87B (full-length):

CGCAAAAAAGTGTTGTTTGGTTTGTAGTTAAAAGGCTCTGTAAAAATCATTAAAAATCCGAGCCAT

CTTTTAGTTTTAAGTTTCTTAAATATTGTCAAAGAGTATCACAAGGATTTCTCAAATGGCAGAAGC

AGATAAATTGAATATCGACAGTATAATAGCCCGTTTATTAGAAGTGCGTGGAGCAAGACCAGGCAA

AAATGTACAACTCACAGAAAATGAAATTAGGGGGCTCTGTTTAAAATCTAGAGAGATCTTCCTTAG

CCAGCCGATTTTGTTGGAACTTGAAGCTCCTCTGAAGATTTGCGGTGATATACATGGTCAGTACTA

TGACTTGCTTCGTCTCTTTGAATATGGAGGTTTCCCTCCCGAATCAAACTACTTATTTTTGGGAGA

TTATGTAGATCGTGGTAAACAATCATTGGAAACCATCTGCTTACTTCTCGCTTACAAAATTAAATA

CCCAGAAAACTTTTTCCTACTCAGAGGCAACCACGAATGCGCATCAATTAATCGTATATATGGATT

CTATGATGAATGCAAAAGAAGGTATAACATCAAGTTGTGGAAAACTTTTACGGACTGTTTCAATTG

CCTACCTGTAGCAGCCATCGTCGATGAAAAAATTTTCTGTTGCCATGGTGGTTTAAGTCCGGACCT

ACAATCAATGGAACAAATTAGAAGAATTATGAGACCGACTGATGTACCTGACCAAGGGCTTCTTTG

TGACCTTTTATGGTCTGATCCAGACAAAGACCAGATGGGATGGGGAGAAAACGATAGAGGAGTTAG

TTTTACTTTTGGTGCTGAAGTTGTAGGAAAGTTCTTGCACAAACACGATTTTGATTTGATATGTCG

AGCGCATCAAGTCGTAGAAGATGGATATGAATTCTTCGCCAAAAGACAGTTAGTCACACTGTTTAG

TGCGCCAAATTATTGTGGAGAGTTTGATAACGCAGGTGCGATGATGTCGGTGGATGAGACACTAAT

GTGTAGTTTTCAAATTTTAAAGCCAGCAGACAAGAGGAAATTCCAGTACAACATGAACGCAGGCAG

ACCTGTGACGCCGCCAAGAGGCGCAACGAATAAAAACAAGAAGAAGTGAATGAATAATATATTTAT

AAGGTTAGGTTTAGTCGCAACATAAACATGTTCAAAACATTTTAAATACTAAAATTTTCTAAAGGT

TACAAAGATTCAAGATAAATTAAGATTTTCTTCATGTTTTTGTTGGTTGTTTTATAGGTTAGGATA

GTAAACTATATAATAATAAAGTTCTCAATATTGTTAAAAAGAAGTGAATGTTAGTATTTAAAATGT

TCGATTATTTCGGCCGTTTTACTTTATTTTATATCTGATATTACTAGAAAAGGGTGATATCTATGA

ACCCAGACAACTAAACGTTCGATTTGAACAAATGAAAATTTATTGAAAACATTAATCCTCACAACC

TTGCTTATTTAATTAAAGAACAAGATCAGTAATACATTAAAGTCTATCATTAATAA

SEQ ID NO:2 shows an exemplary *Diabrotica* cDNA sequence, referred to as RPA70 (full-length):

CAAAGGTTTCGTTTCAAACTTCACACCGATAAAGACTTGTTTGTTCTTGTCAGTGTCAGTTCTGGC

GGTAAAATATTTGCGGTATACACATTTTTTACGTCGTACGTAATTTGCAGGGGTTGATTACTGATC

TTTATTTGATAATTTGTTTATTTATTTTGCAACATAAGCAAAATGCGTTCGCCTCAAACCTATAAC

ATGTCAGAAGGATCACTCCAGACAATCATGTCTGGAGGTGAATTTCCAAATCCCATTATGCAAGTT

TTGGGTAGCAAAAAGATAAACGCCGGATTGGGTGATAAAGAAAGAATTCGTATTTTACTGTCAGAT

GGAAAATACACTATTTCTTTTGCCATGCTAACAGCCCAAATTAATGATCGACTTGGTCCAAATGGT

GTGGAAACTTTTAGCATTATACAAATAGATAGATATGTTACGAGTATCATCAACAATTCTGGGAAA

GGAGAAGCACGAGTACTTTTAATCCTCGATATGCATGTTGTTGTCCCTGGAACTGAAGTTACAGAA

AAAGTAGGCTCTCCCATTCCCCTACCAACTGATGCTGACGCAGCTAAAGGCTCTACTGCCGCTCCA

GCTACAAACAATTCCATTAAGAATGTAACTGTTGCTAAACCAAACATCAGTAATGGCAATGGCACA

ACTGCAATGAATGCCAGTACTAATGATGATATAGCCACACATATGATCCATCCTATTTCAAGTCTC

ACACCTTACCAAAACAGATGGACTATCAAAGCGAGAATTACTAATAAACCTCCAATAAGAACGTGG

TCAAATTCTAGAGGGGAAGGAAAATTATTTAGTTTTGATCTGGTGGATGAAAGTGGCGAAATCCGT

TGCACAGCTTTTAAAGAAATGGTTGATAAATTCTATGATTACCTGCAGGTGGATAAAGTATATTAC

ATCAACAAATGTCAACTTAAACAAGCCAACAAACAGTACAGCACTCTAAAACATGAGTATGAAATG

-continued

```
ACTGTTACGCATGATACTGTCATTAAAGAATGCCTTGATGCAGATTCTACAATACCCACCACACAG

TATAACTTTGTTCCTATAGATAAAATTGCTGATAAAGAAGTAAATTCTGTTGTAGATGTAATAGGT

ATTGCCAAAAGTGTCAGTGAATTACAAACATTCCAAGCAAGATCAACAGGAAGAGAATTGAAAAAG

AAAGAAGTTGTCTTGGTTGATCAGTCACAAACAGCTATATCGTTAACACTTTGGGGCCAAGAAGCC

GAAAATTTTGATGGTACCAATAATCCTGTCGTAGTTATAAAAAGTGCCAAAATTGGCGAGTTTGGA

GGTGGCAAGAATTTAACTACTCTTGTTAGCAGCACTGTAAAAATAAATCCCGAATTAAAAGAATGT

TACAGGATCAGAGGATGGTACGACAGTGAGGGTGAAAATCTGAATGCAAAGAATATTAGTGCCAGA

GTTGGATCCTCGAATATGTCTGCCACTTGGATGACCTTTAAGGAAGTTAAAGATCAAAAATTAGGA

TCATCTGAAAAAGGTGATTATTATAAAGCTATTGCTACTGTTCTTCTTGTCAAAGCCGATAATATT

GTGTATAGAGCTTGTCCCACCGCTGAATGTAATAAGAAAGTTGTTGATATGGAAAATAGTATGTAC

AGATGTGAAAAATGTAATAGAGAATTTCCAAATTTCAAATACAGACTGTTAGCCAGCATGAATGTT

GGAGACCACACAGGAAACCAATGGGTTAGCATGTTCAGTTCAGAAGCCGAAAAAATTCTGGGGATG

ACTGCTGAGGAAGTAGGACAGACCTTGGAACACAATAAAGAAGAAATAGCCAACATCGTAGATAGA

GCTCATTTTAAAGTATTTAGTCTTACTTGCAGGGCAAAAATTGAGACTTACAATGATGAAGCTCGT

TTAAAAACTGTTTGTATAAGAGTCGATCCAATTAATTATGAGGAGTATAGTGCATTGCTCACAGAA

AAAATTCAGCAGTTAACAGGCGAATCTCATGATTAGATATACACCAACACTACAGCTATGCTATTA

TTTCTAGTTCTTTTTTTTTAGAAAATATCGTTAAGAAATCTGTGTTTTGTATTTATTTTTATA

AACAGTGAATCAGTGAATAAGATTTTATTAGAAAGGTACTGTATAAATAAAAATCTGTATGTTCAC

AATATTTTTATTTATTTAAATATACATTGGTACAAAATAAAATATATATTCGTAACAACTATATTA

TTGTTTATTATTGTTTATTCTTAAGCCCCATCATCTAAAGAGGTTCTAAATGTGCTTGTTTTCTTG

CATACGCACCTAAACAAGCTAAAATTAGTATTACACTCATAAATAATCCTATTAATAAGGCTAAAG

TATCTCCAAAATCAAACATTTTGCTGTATTATTGAGTGTTTAAATAATTACATCAAAATAAAATAT

TTTTTATTTTTTGCTTGTCTTGTATGTTTATTTACGTTTTACTTGTCAATCAGCTGTCTATTTCTT

CTTTTTAATTA
```

SEQ ID NO:3: shows an exemplary *Diabrotica* cDNA sequence, referred to in some places as contig0011_PP1-87B:

SEQ ID NO:4: shows an exemplary *Diabrotica* cDNA sequence, referred to in some places as D_vir_c43870_RPA70, RPA70 region 1, or RPA70 Reg1:

```
AATTCAAGCTGCCGCAAAAAAGTGTTGTTTGGTTTGTAGTTAAAAGGCTCTGTAAAAATCATTAAA

AATCCGAGCCATCTTTTAGTTTTAAGTTTCTTAAATATTGTCAAAGAGTATCACAAGGATTTCTCA

AATGGCAGAAGCAGATAAATTGAATATCGACAGTATAATAGCCCGTTTATTAGAAGTGCGTGGAGC

AAGACCAGGCAAAAATGTACAACTCACAGAAAATGAAATTAGGGGGCTCTGTTTAAAATCTAGAGA

GATCTTCCTTAGCCAGCCGATTTTGTTGGAACTTGAAGCTCCTCTGAAGATTTGCGGTGATATACA

TGGTCAGTACTATGACTTGCTTCGTCTCTTTGAATATGGAGGTTTCCCTCCCGAATCAAACTACTT

ATTTTTGGGAGATTATGTAGATCGTGGTAAACAATCATTGGAAACCATCTGCTTACTTCTCGCTTA

CAAAATTAAATACCCAGAAAACTTTTTCCTACTCAGAGGCAACCACGAATGCGCATCAATTAATCG

TATATATGGATTCTATGATGAATGCAAAAGAAGGTATAACATCAAGTTGTGGAAAACTTTTACGGA

CTGTTTCAATTGCCTACCTGTAGCAGCCATCGTCGATGAAAAAATTTTCTGTTGCCATGGTGGTTT

AAGTCCGGACCTACAATCAATGGAACAAATTAGAAGRATTAATAGAGACCGACTGATGTACCTGAC

CAAGGSTTTCTTTGTGACCTTTTANGGTCTGATCCAGACAAAGACC
```

ATAATTTGCAGGGGTTGATTACTGATCTTTATTTGATTAATTTGTTTATTTATTTTTGCAACATAA

GCAAAATGCGTTCGCCTCAAACCTATAACATGTCAGAAGGATCACTCCAGACAATCATGTCTGGAG

GTGAATTTCCAAATCCCATTATGCAAGTTTTGGGTAGCAAAAAGATAAACGCCGGATTGGGTGATA

AAGAAAGAATTCGTATTTTACTGTCAGATGGAAAATACACTATTTCTTTTGCCATGCTAACAGCCC

AAATTAATGATCGACTTGGTCCAAATGGTGTGGAAACTTTTTAGCATTATACAAATAGATAGATAT

GTTACGAGTATCATCAACAATTCTGGGAAAGGAGAAGCACGAGTACTTTTAATCCTCGATATGCAT

GTTGTTGTCCCTGGAACTGAAGTTACAGAAAAAGTAGGCTCTCCCATTCCCCTACCAACTGATGCT

GACKCAGCTAAAGGCTCTACTGCCGCTCCAGCTACAAACAATTCCATTAAGAATGTAACTGTTGCT

AAACCAAACATCAGTAATGGCAATGGCACAACTGCAATGAATGCCAGTACTAATGATGATATAGCC

ACACATATGATCCATCCTATTTCAAGTCTCACACCTTA

SEQ ID NO:5 shows an exemplary *Diabrotica* cDNA sequence, referred to in some places as D_vir_c18764_RPA70, RPA70 region 2, or RPA70 Reg2:

ATGGTCAAATTCTAGAGGGGAAGGAAAATTATTTAGTTTTGATCTGGTGGATGAAAGTGGCGAAAT

CCGTTGCACAGCTTTTAAAGAAATGGTTGATAAWTTCTATGATTACCTGCAGGTGGATAAAGTATA

TTACATCAACAAATGTCAACTTAAACAAGCCAACAAACAGTACAGCACTCTAAAACATGAGTATGA

AATGACTGTTACGCATGATACTGTCATTAAAGAATGCCTTGATGCAGATTCTACAATACCCACCAC

ACAGTATAACTTTGTTCCTATAGATAAAATTGCTGATAAAGAAGTAAATTCTGTTGTAGATGTAAT

AGGTATTGCCAAAAGTGTCAGTGAATTACAAACATTCCAAGCAAGATCAACAGGAAGAGAATTGAA

AAAGAAAGAAGTTGTCTTGGTTGATCAGTCACAAACAGCTATATCGTTAACACTTTGGGGCCAAGA

AGCCGAAAATTTTGATGGTACCAATAATCCTGTCGTAGTTATAAAAA

SEQ ID NO:6 shows an exemplary *Diabrotica* cDNA sequence, referred to in some places as D_vir_c7971_RPA70, RPA70 region 3, or RPA70 Reg3:

AACTCTTGTTAGCAGCAMTRTAAAAATAAATCCCGAATTAAAAGAATGTTACAGGATCAGAGGATG

GTACGACAGTGAGGGTGAAAATCTGAATGCAAAGAATATTAGTGCCAGAGTTGGATCCTCGAATAT

GTCTGCCACTTGGATGACCTTTAAGGAAGTTAAAGATCAAAAATTAGGATCATCTGAAAAAGGTGA

TTATTATAAAGCTATTGCTACTGTTCTTCTTGTCAAAGCCGATAATATTGTGTATAGAGCTTGTCC

CACCGCTGAATGTAATAAGAAAGTTGTTGATATGGAAATAGTATGTACAGATGTGAAAAATGTAA

TAGAGAATTTCCAAATTTCAAATACAGACTGTTAGCCAGCATGAATGTTGGAGACCACACAGGAAA

CCAATGGGTTAGCATGTTCAGTTCAGAAGCCGAAAAAATTCTGGGGATGACTGCTGAGGAAGTAGG

ACAGACCTTGGAACACAATAAAGAAGAAATAGCCAACATCGTAGATAGAGCTCATTTTAAAGTATT

TAGTCTTACTTGCAGGGCAAAAATTGAGACTTACAATGATGAAGCTCGTTTAAAAACTGTTTGTAT

AAGAGTCGATCCAATTAATTATGAGGAGTATAGTGCATTGCTCACAGAAAAAATTCAGCAGTTAAC

AGGCGAATCTCATGATTAGATATACACCAACACTACAGCTATGCTATTATTTCTAG

SEQ ID NO:7 shows an exemplary *Diabrotica* cDNA sequence, referred to herein as RPS6:

ATTAATTTTCTGAAATATCCTTTTTGAAACATGGCAGTTCCATGTGCACACTAACGAGAAGTTTTT

CCCGTATTTAGTGTAATTTGCCAAAAATAAAGTGTGAAATAGTAGTTTTCGAGTGCAAAATAAGTC

-continued

```
AATATGAAGTTGAACGTATCGTACCCGGCCACGGGTTGCCAAAAACTTTTCGAAGTTGTTGACGAA

CACAAAATTCGTATCTTTTACGAAAAACGCATGGGTCAAGAAGTTGAGGCTGATGCTCTTGGTGAC

GAATGGAAGGGCTACATCTTGAAAATATCTGGAGGTAACGACAAACAAGGATTCCCCATGAAACAA

GGTGTTCTTACAAACGGTAGAGTAAGACTTTTACTTTCAAAAGGTCACTCCTGCTACAGACCCAGA

CGTACCGGTGAACGTAAAAGGAAATCAGTTCGTGGGTGCATTGTTGATGGGAACCTCAGCGTGTTG

GCCCTAGTCATTGTAAGAAAAGGAGAACAAGAAATTCCCGGACTTACTGACACCACCATCCCACGT

CGCCTGGGACCCAAGAGAGCATCCAGAATCCGTAAGCTCTTCAACCTTAGCAAAGAAGACGATGTA

CGTCAATATGTAGTAAAGAGACCTTTGGCCCAAAAAGAAGGTAAGAAGTTAAGAACCAAGGCCCCC

AAAATCCAACGTCTTATTACACCCGTTGTTTTGCAAAGAAAACGTCATCGTCTTGCTTTGAAGAAG

AAGAGGTGCCTTAAACGTAAAGAACAAGAAGATGCATATGCTAAACTATTGGCTCAACGTAAGAAG

GAATCCAAGGCTCGTCGTGAGATGTTGAAGAGGCGTAGGTCTGCCAGTATGCGTGATAGTAAATCC

AGCACGCAGAGTGGTCAGAAGTAAATTGTAATTTTTTATATTTTAAGACAATGTATGAAATAAACG

TTGTTGCTT
```

SEQ ID NO:8 shows a T7 phage promoter sequence.

SEQ ID NOs:9-24 show sequences of primers used to amplify portions of coding regions of exemplary target genes by PCR.

SEQ ID NO:25 shows an exemplary amplified fragment of PP1-87B used as a template for dsRNA synthesis:

```
CAAATGGCAGAAGCAGATAAATTGAATATCGACAGTATAATAGCCCGTTTATTAGAAGTGCGTGGA

GCAAGACCAGGCAAAAATGTACAACTCACAGAAAATGAAATTAGGGGGCTCTGTTTAAAATCTAGA

GAGATCTTCCTTAGCCAGCCGATTTTGTTGGAACTTGAAGCTCCTCTGAAGATTTGCGGTGATATA

CATGGTCAGTACTATGACTTGCTTCGTCTCTTTGAATATGGAGGTTTCCCTCCCGAATCAAACTAC

TTATTTTTGGGAGATTATGTAGATCGTGGTAAACAATCATTGGAAACCATCTGCTTACTTCTCGCT

TACAAAATTAAATACCCAGAAAACTTTTTCCTACTCAGAGGCAACCACGAATGCGCATCAATTAAT

CGTATATATGGATTCTATGATGAATGCAAAAGAAGGTATAACATCAAGTTGTGGAAAACTTTTACG

GACTGTTTCAATTGCCTACCTGTAGCAGCCATCGTCGATGAAAAAATTTTCTGTTGCCATGGTGGT

TTAAGTCCGGACCTACAATCAATGGAACAAATTAG
```

SEQ ID NO:26 shows an exemplary amplified fragment of RPA70 Reg2 used as a template for dsRNA synthesis:

```
ATGGTCAAATTCTAGAGGGGAAGGAAAATTATTTAGTTTTGATCTGGTGGATGAAAGTGGCGAAAT

CCGTTGCACAGCTTTTAAAGAAATGGTTGATAAWTTCTATGATTACCTGCAGGTGGATAAAGTATA

TTACATCAACAAATGTCAACTTAAACAAGCCAACAAACAGTACAGCACTCTAAAACATGAGTATGA

AATGACTGTTACGCATGATACTGTCATTAAAGAATGCCTTGATGCAGATTCTACAATACCCACCAC

ACAGTATAACTTTGTTCCTATAGATAAAATTGCTGATAAAGAAGTAAATTCTGTTGTAGATGTAAT

AGGTATTGCCAAAAGTGTCAGTGAATTACAAACATTCCAAGCAAGATCAACAGGAAGAGAATTGAA

AAAGAAAGAAGTTGTCTTGGTTGATCAGTCACAAACAGCTATATCGTTAACACTTTGGGGCCAAGA

AGCCGAAAATTTTGATGGTACCAATAATCCTGTCGTAG
```

SEQ ID NO:27 shows an exemplary amplified fragment of RPA70 Reg3 used as a template for dsRNA synthesis:

TCCCGAATTAAAAGAATGTTACAGGATCAGAGGATGGTACGACAGTGAGGGTGAAAATCTGAATGC

AAAGAATATTAGTGCCAGAGTTGGATCCTCGAATATGTCTGCCACTTGGATGACCTTTAAGGAAGT

TAAAGATCAAAAATTAGGATCATCTGAAAAAGGTGATTATTATAAAGCTATTGCTACTGTTCTTCT

TGTCAAAGCCGATAATATTGTGTATAGAGCTTGTCCCACCGCTGAATGTAATAAGAAAGTTGTTGA

TATGGAAAATAGTATGTACAGATGTGAAAAATGTAATAGAGAATTTCCAAATTTCAAATACAGACT

GTTAGCCAGCATGAATGTTGGAGACCACACAGGAAACCAATGGGTTAGCATGTTCAGTTCAGAAGC

CGAAAAAATTCTGGGGATGACTGCTGAGGAAGTAGGACAGACCTTGGAACACAATAAAGAAGAAAT

AGCCAACATCGTAGATAGAGCTCATTTTAAAGTATTTAGTCTTACTTGCAGGGCAAAAATTGAGAC

TTACAATGATGAAGCTCG

SEQ ID NO:28 shows an exemplary amplified fragment of RPS6 used as a template for dsRNA synthesis:

TCAATATGAAGTTGAACGTATCGTACCCGGCCACGGGTTGCCAAAAACTTTTCGAAGTTGTTGACG

AACACAAAATTCGTATCTTTTACGAAAAACGCATGGGTCAAGAAGTTGAGGCTGATGCTCTTGGTG

ACGAATGGAAGGGCTACATCTTGAAAATATCTGGAGGTAACGACAAACAAGGATTCCCCATGAAAC

AAGGTGTTCTTACAAACGGTAGAGTAAGACTTTTACTTTCAAAAGGTCACTCCTGCTACAGACCCA

GACGTACCGGTGAACGTAAAAGGAAATCAGTTCGTGGGTGCATTGTTGATGGGAACCTCAGCGTGT

TGGCCCTAGTCATTGTAAGAAAAGGAGAACAAGAAATTCCCGGACTTACTGACACCACCATCCCAC

GTCGCCTGGGACCCAAGAGAGCAT

SEQ ID NO:29 shows a PP1-87B hairpin RNA-forming sequence containing an ST-LS1 intron (underlined):

CCTCTGAAGATTTGCGGTGATATACATGGTCAGTACTATGACTTGCTTCGTCTCTTTGAATATG

GAGGTTTCCCTCCCGAATCAAACTACTTATTTTTGGGAGATTATGTAGATCGTGGTAAACAATC

ATTGGAAACCATCTGCTTACTTCTCGCTTACAAAATTAAATACCCAGAAAACTTTTTCCTACTC

AGAGGCAACCACGAATGCGCATCAATTAATCGTATATATGGATTCTATGATGAATGCAAAAGAA

GGTATAACATCAAGTTGTGGAAAACTTTTACGGACTGTTTGACTAGTACCGGTTGGGAAA<u>GTA</u>

<u>TGTTTCTGCTTCTACCTTTGATATATATATAATAATTATCACTAATTAGTAGTAATATAGTATT</u>

<u>TCAAGTATTTTTTCAAAATAAAAGAATGTAGTATATAGCTATTGCTTTTCTGTAGTTTATAAG</u>

<u>TGTGTATATTTAATTTATAACTTTTCTAATATATGACCAAAACATGGTGATGTGCAGG</u>TTGAT

CCGCGGTTAAAACAGTCCGTAAAAGTTTTCCACAACTTGATGTTATACCTTCTTTTGCATTCAT

CATAGAATCCATATATACGATTAATTGATGCGCATTCGTGGTTGCCTCTGAGTAGGAAAAAGTT

TTCTGGGTATTTAATTTTGTAAGCGAGAAGTAAGCAGATGGTTTCCAATGATTGTTTACCACGA

TCTACATAATCTCCCAAAAATAAGTAGTTTGATTCGGGAGGGAAACCTCCATATTCAAAGAGAC

GAAGCAAGTCATAGTACTGACCATGTATATCACCGCAAATCTTCAGAGG

SEQ ID NO:30 shows an RPA70 Reg2 hairpin RNA-forming sequence containing an ST-LS1 intron (underlined):

TACCTGCAGGTGGATAAAGTATATTACATCAACAAATGTCAACTTAAACAAGCCAACAAACAGT

ACAGCACTCTAAAACATGAGTATGAAATGACTGTTACGCATGATACTGTCATTAAAGAATGCCT

-continued

```
TGATGCAGATTCTACAATACCCACCACACAGTATAACTTTGTTCCTATAGATAAAATTGCTGAT

AAAGAAGTAAATTCTGTTGTAGATGTAATAGGTATTGCCAAAAGTGTCAGTGAATTACAAACAT

TCCAAGCAAGATCAACAGGAAGAGAATTGAAAAAGGACTAGTACCGGTTGGGAAAGGTATGTTT

CTGCTTCTACCTTTGATATATATATAATAATTATCACTAATTAGTAGTAATATAGTATTTCAAG

TATTTTTTTCAAAATAAAAGAATGTAGTATATAGCTATTGCTTTTCTGTAGTTTATAAGTGTGT

ATATTTTAATTTATAACTTTTCTAATATATGACCAAAACATGGTGATGTGCAGGTTGATCCGCG

GTTACTTTTTCAATTCTCTTCCTGTTGATCTTGCTTGGAATGTTTGTAATTCACTGACACTTTT

GGCAATACCTATTACATCTACAACAGAATTTACTTCTTTATCAGCAATTTTATCTATAGGAACA

AAGTTATACTGTGTGGTGGGTATTGTAGAATCTGCATCAAGGCATTCTTTAATGACAGTATCAT

GCGTAACAGTCATTTCATACTCATGTTTTAGAGTGCTGTACTGTTTGTTGGCTTGTTTAAGTTG

ACATTTGTTGATGTAATATACTTTATCCACCTGCAGGTA
```

SEQ ID NO:31 shows an RPS6 hairpin RNA-forming sequence containing an ST-LS1 intron (underlined):

```
AACGACAAACAAGGATTCCCCATGAAACAAGGTGTTCTTACAAACGGTAGAGTAAGACTTTTAC

TTTCAAAAGGTCACTCCTGCTACAGACCCAGACGTACCGGTGAACGTAAAAGGAAATCAGTTCG

TGGGTGCATTGTTGATGGGAACCTCAGCGTGTTGGCCCTAGTCATTGTAAGAAAAGGAGAACAA

GAAATTCCCGGACTTACTGACACCACCATCCCACGTCGCCTGGGACCCAAGAGAGCATCCAGAA

TCCGTAAGCTCTTCAACCTTAGCAAAGAAGACGATGTACGTCAAGACTAGTACCGGTTGGGAAA

GGTATGTTTCTGCTTCTACCTTTGATATATATATAATAATTATCACTAATTAGTAGTAATATAG

TATTTCAAGTATTTTTTTCAAAATAAAGAATGTAGTATATAGCTATTGCTTTTCTGTAGTTTA

TAAGTGTGTATATTTTAATTTATAACTTTTCTAATATATGACCAAAACATGGTGATGTGCAGGT

TGATCCGCGGTTATTGACGTACATCGTCTTCTTTGCTAAGGTTGAAGAGCTTACGGATTCTGGA

TGCTCTCTTGGGTCCCAGGCGACGTGGGATGGTGGTGTCAGTAAGTCCGGGAATTTCTTGTTCT

CCTTTTCTTACAATGACTAGGGCCAACACGCTGAGGTTCCCATCAACAATGCACCCACGAACTG

ATTTCCTTTTACGTTCACCGGTACGTCTGGGTCTGTAGCAGGAGTGACCTTTTGAAAGTAAAAG

TCTTACTCTACCGTTTGTAAGAACACCTTGTTTCATGGGGAATCCTTGTTTGTCGTT
```

SEQ ID NO:32 shows a DNA sequence of annexin region 1.
SEQ ID NO:33 shows a DNA sequence of annexin region 2.
SEQ ID NO:34 shows a DNA sequence of beta spectrin 2 region 1.
SEQ ID NO:35 shows a DNA sequence of beta spectrin 2 region 2.
SEQ ID NO:36 shows a DNA sequence of mtRP-L4 region 1.
SEQ ID NO:37 shows a DNA sequence of mtRP-L4 region 2.
SEQ ID NO:38 shows a YFP sequence.
SEQ ID NOs:39-66 show sequences of primers used to amplify gene regions of annexin, beta spectrin 2, mtRP-L4, and YFP for dsRNA synthesis.
SEQ ID NO:67 shows a protein sequence encoded by an exemplary *Diabrotica* cDNA sequence, referred to in some places as 87B protein phosphatase:

```
MAEADKLNIDSIIARLLEVRGARPGKNVQLTENEIRGLCLKSREIFLSQPILLELEAPLKICGDIH

GQYYDLLRLFEYGGFPPESNYLFLGDYVDRGKQSLETICLLLAYKIKYPENFFLLRGNHECASINR

IYGFYDECKRRYNIKLWKTFTDCFNCLPVAAIVDEKIFCCHGGLSPDLQSMEQIRRIMRPTDVPDQ

GLLCDLLWSDPDKDQMGWGENDRGVSFTFGAEVVGKFLHKHDFDLICRAHQVVEDGYEFFAKRQLV

TLFSAPNYCGEFDNAGAMMSVDETLMCSFQILKPADKRKFQYNMNAGRPVTPPRGATNKNKKK
```

SEQ ID NO:68 shows a protein sequence encoded by an exemplary *Diabrotica* cDNA sequence, referred to in some places as RPA70:

MRSPQTYNMSEGSLQTIMSGGEFPNPIMQVLGSKKINAGLGDKERIRILLSDGKYTISFAMLTAQI

NDRLGPNGVETFSIIQIDRYVTSIINNSGKGEARVLLILDMHVVVPGTEVTEKVGSPIPLPTDADA

AKGSTAAPATNNSIKNVTVAKPNISNGNGTTAMNASTNDDIATHMIHPISSLTPYQNRWTIKARIT

NKPPIRTWSNSRGEGKLFSFDLVDESGEIRCTAFKEMVDKFYDYLQVDKVYYINKCQLKQANKQYS

TLKHEYEMTVTHDTVIKECLDADSTIPTTQYNFVPIDKIADKEVNSVVDVIGIAKSVSELQTFQAR

STGRELKKKEVVLVDQSQTAISLTLWGQEAENFDGTNNPVVVIKSAKIGEFGGGKNLTTLVSSTVK

INPELKECYRIRGWYDSEGENLNAKNISARVGSSNMSATWMTFKEVKDQKLGSSEKGDYYKAIATV

LLVKADNIVYRACPTAECNKKVVDMENSMYRCEKCNREFPNFKYRLLASMNVGDHTGNQWVSMFSS

EAEKILGMTAEEVGQTLEHNKEEIANIVDRAHFKVFSLTCRAKIETYNDEARLKTVCIRVDPINYE

EYSALLTEKIQQLTGESHD

SEQ ID NO:69 shows a protein sequence encoded by an exemplary *Diabrotica* cDNA sequence, referred to in some places as RPS6:

MKLNVSYPATGCQKLFEVVDEHKIRIFYEKRMGQEVEADALGDEWKGYILKISGGNDKQGFPMKQG

VLTNGRVRLLLSKGHSCYRPRRTGERKRKSVRGCIVDGNLSVLALVIVRKGEQEIPGLTDTTIPRR

LGPKRASRIRKLFNLSKEDDVRQYVVKRPLAQKEGKKLRTKAPKIQRLITPVVLQRKRHRLALKKK

RCLKRKEQEDAYAKLLAQRKKESKARREMLKRRRSASMRDSKSSTQSGQK

SEQ ID NO:70 shows a maize DNA sequence encoding a TIP41-like protein.

SEQ ID NOs:71-74 show sequences of primers used for molecular analyses of transcript levels in transgenic maize.

SEQ ID NO:75 shows a maize DNA sequence encoding an invertase protein.

SEQ ID NO:76 shows an *Escherichia coli* DNA sequence encoding an SpnR protein.

SEQ ID NO:77 shows an exemplary ST-L1 intron DNA sequence.

SEQ ID NOs:78-89 show sequences of oligonucleotides used for hydrolysis probe molecular analyses of transcript levels in transgenic maize.

SEQ ID NOs:90-94 show sequences of oligonucleotides used for hairpin hydrolysis probe molecular analyses of transcript levels in transgenic maize.

SEQ ID NO:95 shows an amino acid sequence encoded by an exemplary *Diabrotica* cDNA sequence, referred to in some places as Contig0011_87B protein phosphatase:

MAEADKLNIDSIIARLLEVRGARPGKNVQLTENEIRGLCLKSREIFLSQPILLELEAPLKICGDIH

GQYYDLLRLFEYGGFPPESNYLFLGDYVDRGKQSLETICLLLAYKIKYPENFFLLRGNHECASINR

IYGFYDECKRRYNIKLWKTFTDCFNCLPVAAIVDEKIFCCHGGLSPDLQSMEQIRRINRDRLMYLT

KXFFVTFXGLIQTKT

SEQ ID NO:96 shows an amino acid sequence encoded by an exemplary *Diabrotica* cDNA sequence, referred to in some places as RPA70 Reg1:

MIDLVQMVWKLFSIIQIDRYVTSIINNSGKGEARVLLILDMHVVVPGT

EVTEKVGSPIPLPTDADXAKGSTAAPATNNSIKNVTVAKPNISNGNGT

TAMNASTNDDIATHMIHPISSLTP

SEQ ID NO:97 shows an amino acid sequence encoded by an exemplary *Diabrotica* cDNA sequence, referred to in some places as RPA70 Reg2:

WSNSRGEGKLFSFDLVDESGEIRCTAFKEMVDXFYDYLQVDKVYYINK

CQLKQANKQYSTLKHEYEMTVTHDTVIKECLDADSTIPTTQYNFVPID

KIADKEVNSVVDVIGIAKSVSELQTFQARSTGRELKKKEVVLVDQSQT

AISLTLWGQEAENFDGTNNPVVVIK

SEQ ID NO:98 shows an amino acid sequence encoded by an exemplary *Diabrotica* cDNA sequence, referred to in some places as RPA70 Reg3:

TLVSSXXKINPELKECYRIRGWYDSEGENLNAKNISARVGSSNMSATW

MTFKEVKDQKLGSSEKGDYYKAIATVLLVKADNIVYRACPTAECNKKV

VDMENSMYRCEKCNREFPNFKYRLLASMNVGDHTGNQWVSMFSSEAEK

ILGMTAEEVGQTLEHNKEEIANIVDRAHFKVFSLTCRAKIETYNDEAR

LKTVCIRVDPINYEEYSALLTEKIQQLTGESHD

SEQ ID NOs:99 and 100 show exemplary segments of a *Diabrotica* PP1-87B cDNA sequence:
AATTCAAGCTGCCGCAA (SEQ ID NO:99); and

```
                                            (SEQ ID NO: 100)
TTTTCTGTTGCCATGGTGGTTTAAGTCCGGACCTACAATCAATGGAAC

AAATTAGAAGRATTAATAGAGACCGACTGATGTACCTGACCAAGGSTT

TCTTTGTGACCTTTTANGGTCTGATCCAGACAAAGACC
```

SEQ ID NO:101 shows an exemplary segment of a *Diabrotica* RPA70 Reg1 cDNA sequence:

```
TGGAACTGAAGTTACAGAAAAAGTAGGCTCTCCCATTCCCCTACCAAC

TGATGCTGACKCAGCTAAAGGCTCTACTGCCGCTCCAGCTACAAACAA

TTCCATTAAGAATGTAACTGTTGCTAAACCAAACATCAGTAATGGCAA

TGGCACAACTGCAATGAATGCCAGTACTAATGATGATATAGCCACACA

TATGATCCATCCTATTTCAAGTCTCACACCTTA
```

SEQ ID NO:102 shows an exemplary segment of a *Diabrotica* RPA70 Reg3 cDNA sequence:

```
AACTCTTGTTAGCAGCAMTRTAAAAATAAATCCCGAATTAAAAGAATG

TTACAGGATCAGAGGATGGTACGACAGTGAGGGTGAAAATCTGAATGC

AAAGAATATTAGTGCCAGAGTTGGATCCTCGAATATGTCTGCCACTTG

GATGACCTTTAAGGAAGTTAAAGATCAAAAATTAGGATCATCTGAAAA

AGGTGATTATTATAAAGCTATTGCTACTGTTCTTCTTGTCAAAGCCGA

TAAT
```

SEQ ID NO:103 shows an exemplary *Diabrotica* cDNA sequence encoding a Brahma protein:

```
ACAGTTAAATATTGAAAATGGCCTGGTGTTTTGATAAAACGGAAGAGGCGAATTTCTAGTAGCATT

TTAAGGTTTCATTTGCATTTAAAACAAATTCATGTATTATAAAATGTAGGATACGTTTCCTCGTAT

CCATCTACTTAATTTAGGATAACAATAAAGGGTGTGAGACAGTTAAATATTGAAAATGGCCAGTGC

TTCATTATTACCCAAAACTTTCACTTCTATTGGTGGCAAAGCCCTACCTACCAACTCACAACAAA

CATTCAGTCAAAATTTAAAGAGATTACAGTTCCACCAGGAAATACTCCTCAAGATGTTAAAGAAGG

CCCCAGTCACCAATCAAATCCAAACCATTTGGCTTCTCTTCAAAAGGCCATTGAAACTATGGAAGA

GAAGGGCTTACAAGCTGATCCTAGATATTCACAGTTACTTGCATTGCGAGCTAGCATTCCTGGGGC

AGAAGAAAATGGTTCTCCCTTCTCAAACAACCAAATCAAGCAATTAAGAAACCAATAATGGCTTA

CAGGTGTTTGGCAAGAAATCAACCTGTTCCAAACAATTTAGTATTAGGTTTGCATGGAAAAACTCC

TGAAAAAGTTCCACATATTGTACCTCCACCGCAACCTCAAGAAGTACCTAATGGGGCGATCCAGG

ACCTTCAACAAGTTCTGCTGCTGCTGTAGCTCCTAGAACACCACAAAAGCTGCCAGCAAAACCAAT

TGAGGCTCAGCTTGTCAACAGAGAACCAAGAGTCACTACTTTATCTAAACCATCTTCCATAGACCC

TGTTGTTCTATTACAAGAACGAGAAAACAGGGTAGCAGCTCGTATAGCAGCGAGGATTGAACAAGT

CAGTAATCTGCCGACTGATATGTCTGAGGCATTACGTATTCGGGCACAAATAGAACTCAGAGCTTT

GAGATGTCTAAACCTCCAGAGACAACTTCGTAGTGAGGTTTTGAGCTGTATTCGACGGGACACAAC

ATTAGAAACAGCAGTAAATGTAAAAGCGTTTAAACGGACCAAACGTCAAGGTCTTCGAGAAGCTAG

AGCAACAGAAAACTTGAGAAACAACAAAAGCTGGAAGCAGAGAGAAAGAAACGCCAGAAGAACCA

AGAGTTCTTAAACAATGTGATGGCACACGCTAAAGATTTCAAAGAATTCCACAGGCAGAACCAAGC

AAAACTTTCTAAACTTAATAAAGCTATTCTTACTTATCACGCTAATGCGGAGAGAGAACAAAAGAA

GGAACAAGAGAGAAGAGAAAAGGAACGTATGAAGAAATTGATGGCAGAAGATGAAGAAGGTTATAG

ACAGTTGATCGATCAAAAGAAAGACAAACGTCTAGCGTTCTTGCTTTCGCAAACAGATGAGTATAT

AACTAACCTCACGGAGATGGTAAAGCAACACAAGTTGGAACAAACCAATAAAAAGAAAGAGGAGGA

AAAACGCAAGAAGAAGCAGCAGAAAATGCAACAACCAGATAGGAAAGTTACAGTTCTGGAAACTGC

AACAGGTAAAAAAGTAACAGGAGAGGCTGCTCCTACACTGCGACAAGTTCAGGAATGGTTAATCCA

ACATCCTGGATGGGAGATGGTCGATACAGATGATGAGGATGATGAAAACGGGGAGAAGAGGGATGA
```

-continued

```
TGACTATGATGAAAATCAAGAAGTGGATGATGCAAAAGAAGTTATTAAAAAAGCTAAAGTTGAAGA

TGACGAATATCACAAAAACACAAAAGAAGAACAGACTTACTACAGTATTGCTCACACTGTTCATGA

AGTGGTAACAGAACAAGCATCCATTCTGGTTAATGGAAAGCTTAAGGAATATCAAATTAGAGGGTT

AGAATGGATGGTGTCTTTGTACAATAACAATCTGAATGGTATTCTAGCAGATGAGATGGGTCTAGG

TAAAACCATTCAAACGATTGGCTTGTTGACCTATTTGATGGAAAAAAAGAAGATAAATGGACCGTT

TTTGATCATAGTGCCACTTTCAACCATTTCTAATTGGATGTTGGAATTTCAAAAGTGGGCCCCTAC

TGTAGTTGTCATTTCATACAAAGGCTCTCCTGTGGTTAGAAAAGTGATCCAGAGCCAGTTAAAAGC

TGCTAAATTCAATGTGCTTCTCACTACCTACGAGTACATTATTAAGGACAAGGGTGTATTAGCAAA

AATCCCATTTAAATATATGATCATAGATGAGGGTCATCGTATGAAAAACCACCACTGCAAATTGAC

TCAAGTCCTGAATACGCACTATTTGGCGCCCTACAGACTCCTGCTTACTGGTACTCCCCTACAAAA

TAAATTACCAGAATTATGGGCCTTGTTGAATTTCTTGTTGCCTTCGATTTTCAAGAGTTGCTCCAC

TTTTGAACAATGGTTCAATGCGCCATTCGCAACAACAGGAGAAAAGGTTGAGTTAAACGAAGAAGA

AACTATCCTTATCATCCGTCGTCTTCACAAAGTACTCAGGCCGTTTCTCCTGAGACGTCTCAAGAA

AGAAGTCGAATCTCAGCTTCCAGACAAAGTGGAATATATCATAAAGTGTGACATGTCGGGCCTACA

AAAGGTTCTCTATGCACACATGCAGAGCAAGGGTGTGTTACTTACCGATGGTTCCGAGAAGGGCAG

TAAAGGAAGGGGATCTAAGGCACTGATGAACACCATTATGCAGCTGAGGAAACTGTGCAATCATCC

GTTTATGTTCCAAAATATCGAAGAGAAATATTGTGATCATGTTGGTATTGCTGGTGGAGTGGTTTC

TGGACCCGACACTTATAGGGTATCTGGTAAGTTTGAGCTCTTGGACAGAATATTGCCCAAAATGAA

AGCAACTAACCATAGGATTCTTCTTTTCTGTCAAATGACTCAATTAATGACCATCATGGAAGATTA

TCTAAATTGGAGAGGATTCAAATATCTTCGTCTTGATGGTACAATCAAATCAGAAGATCGCGGGGA

CCTATTATCGAAATTTAATGATAAAAATAGTGAATATTTTTTGTTTTGCTATCTACACGGGCTGG

AGGTCTGGGACTTAATTTGCAGACAGCTGATACTGTGATTATCTTCGATTCCGATTGGAATCCTCA

TCAGGATTTACAAGCTCAGGATCGAGCTCATCGTATTGGACAGCAAAATGAGGTCCGAGTTTTGCG

TTTGATGACTGTTAACTCTGTTGAGGAACGAATTTTAGCTGCAGCTAAATACAAGCTTACTATGGA

CGAAAAGGTCATTCAAGCTGGTATGTTCGATCAGAAGTCTACAGGCTCAGAGAGACATCAGTTTTT

GCAGAGTATTTTACACCATGACGGAAGCGACGAAGAAGAGGAAAACGAAGTTCCTGATGACGAAAC

AGTGAACCAGATGTTGGCCCGAAGGGAAAACGAATTTCAGCTTTTCCAGAAGATGGATCAGGAAAG

AAAGGAAGAAGATGAAAAGACCGGAAAGTCGCGACTTATTCAAGAAAGCGAATTGCCCGAATGGCT

GTTGAAGCAAGACGATGAAATCTACTCGTGGGCCTTGATGATCCAGATGCTGTTTTAGGAAGGGG

TAGTAGGCAAAGAAAAGAAGTTGATTATGTTGACAGCCTGACGGAGAAAGAGTGGCTTAAGGCTAT

TGACGAAGAGGGAGAATTTGAGGAAGAACAAGAAGGTGATAAAGAAGGTCTCAGAAAGAAAAGAGG

GAGGAAGAGGAAGAAGCGCGATGATGACGAAGAGGCAAGCCAAATTAAGAGAAGAAAGGTGCATCT

AGCCGAGATCAAGATGAAGAAAAAGATGAAGAGGCTTATGGAAGTTGTTGTGAACTACAGGGACAG

GGATGGTAGAGTATTGAGCGAACCGTTTATGAAACTTCCATCAAAGAAGGAGTTACCTGAGTATTA

CGATACGATTAAGAAACCTATTGATATTGAAAAAGTCGTTGCCAACGTAGAAGAAGGAAAATATTT

CACGATGCACGATTTGGAAAGAGATTTCGACTTGCTGTGCCAAAACGCCCAACAATACAACGAAGA

AGACTCCATGATCTACGAGGACAGCCTCGTTCTTCGACAGGTGTTTAGAAGCGCGAGGGAAAAGAT

CGACGGTACCTCAGACCACGACGACAACGCCGATGGACCGGCGGTGGCTCAGATCAAACGACCTCG

TGGTAGACCTCGAAAACACAAGAGACCCGAAGAGATCGAGGCCGAAGCGGCGGCTCAGAAAGCTAT

GGAGGAGGCATCGAAGCTGAGAGCTCAAGCTGAGGCGGAAGAGCTTAGATCTAAGGTGGAGGAGGC

ATCTCAGAGAGCCAAAGAGGAAGCGAAAGCAAGGGAGGAAGCCAAAGCTAGGGAAGAAGCCGAAAT
```

```
CGAGAACATGGAGGAGATTCCCACAAGCACATGATCTATAGAGCAACCGGAAACAAAAAGGCAAAA

AAGAAATATTATATAGAAAAGATGTACATGTTCAATGGAGATACATTTTCGCCGAGTTACAACGGG

TAATGCTTTTACAACGGATATTTTGACGTATGAATGTTGACGTTCAGATGAAGTATATTTATAAAA

TAATCCAGACCTTTACGTTTTGGTTGATTTGTTTTCTGTATTGTTCAGTTTATTGAACAACCATTA

ATAGCAGCTTACCTAAATGATTTAGAAAAGCATCTGAGTTATTTAGATAAGTTTTGAGATTATATT

TATTAACTTTAATATTACTATCTTTATTATAGCATATTGTAATTATTTTTTCCTGTCCTTCTTTCG

TTGTGTGGTAGATAATCCGAGAGTCAACAGTTATAAGCAAATGAAATTCAGTTAAACCTCAAATGT

ACAAAATGATCAAATTAATGTTTACAATTTATTTTTTTACCACGCACATTCACTATTACTATTGTC

AGTCATTGAGATATCATTTTATATAGCTCCATGTCTGTCTTCCTCAATTTACAGAGAAGCAATTAG

ACAAGTAATGACATAATATGGTGCTGAAATAATGTGCTTGATAGTGATGTTCACAAAGTAACTATT

CGTTACAAAGTACTCGTTACTTACAAATACCGAAACTAACGATTACTATACAGAGAGGCAAATCGT

TACTTTGATTACACTGATTACTTCGTATCAATCGTATCAGAGCGAGTAACGA
```

SEQ ID NO:104 shows an exemplary *Diabrotica* cDNA sequence, referred to in some places as F5XY5 KV01DBWKAbrahma_587-707 or Brahma Reg1:

```
ATTCTGGTTAATAGGAAAGCTTAAGGAATATTCAAATTAGAGGGTTAGAATGGATGGTGTCTTTGT

ACAATAACAATCTGAATGGTATTCTAGCAGATGAGATGGGTCTAGGTAAACCNTTCAAACGNTTGG

CTTGTTGACCTATTTGATGGAAAAAAAGAAGATAAATGGACCGTTTTTGATCATAGTGCCACTTTC

AACCATTCTAATTGGATAGTTGGAATTTCAAAGTAGGGCCCTACTAGTAGTTGTCATTTCATACAA

AGGCTCTCCTGTGGTTAGAAAAGTNATCCAGAGCCAGTTAAAAGCTGCTAAATTCAATGTGCTTCT

CACTACCTACGAGTACATTATTAAGGCAAGGTGATTAGCAAAAAATCCCAGTTTAAATATATGATC

ATAGATNAGGTCATCATNAAACACACTGCAATTGAACTCAAGGCCTGAATACGCA
```

SEQ ID NO:105 shows an exemplary *Diabrotica* cDNA sequence, referred to in some places as Contig[0001]_brahma_949-1126 or Brahma Reg2:

```
AGTGTATTAGCAAAAATCCCATTTAAATATATGATCATAGATGAGGGTCATCGTATGAAAAACCAC

CACTGCAAATTGACTCAAGTCCTGAATACGCACTATTTGGCGCCCTACAGACTCCTGCTTACTGGT

ACTCCCCTACAAATAAATTACCAGAATTATGGGCCTTGTTGAATTTCTTGTTGCCTTCGATTTTC

AAGAGTTGCTCCACTTTTGAACAATGGTTCAATGCGCCATTCGCAACAACAGGAGAAAAGGTTGAG

TTAAACGAAGAAGAAACTATCCTTATCATCCGTCGTCTTCACAAAGTACTCAGGCCGTTTCTCCTG

AGACGTCTCAAGAAAGAAGTCGAATCTCAGCTTCCAGACAAAGTGGAATATATCATAAAGTGTGAC

ATGTCGGGCCTACAAAAGGTTCTCTATGCACACATGCAGAGCAAGGGTGTGTTACTTACCGATGGT

TCCGAGAAGGGCAGTAAAGGAAGGGGATCTAAGGACAACTAGATGAACACCATTATGCAGCTGAGG

AAACTGTGCT
```

SEQ ID NO:106 shows an exemplary *Diabrotica* cDNA sequence, referred to in some places as F5XY5 KV01D0IM6_brahma_1237-1333 or Brahma Reg3:

```
AGGGCTGGAGGTCTGGGACTTAATTTGCAGACAGCTGATACTGTGATT

ATCTTCGATTCCGATTGGAATCCTCATCAGGATTTACAAGCTCAGGAT

CGAGCTCATCGTATTGGACAGCAAAATGAGGTCCGAGTTTTGCGTTTG

ATGACTGTTAACTCTGTTGAGGAACGAATTTTAGCTGCAGCTAAATAC

AAGCTTACTATGGACGAAAAGGTCATTCAAGCTGGTATGTTCGATCAG
```

-continued

AAGTCTACGGGATCTGAAAGGCAGCAGTTTCTTCAGAGTATTTTACAC

AATGATGGTAGTGAT

SEQ ID NO:107 shows an exemplary segment of a *Diabrotica* Brahma Reg3 cDNA sequence:

AGGGCTGGAGGTCT

SEQ ID NO:108 shows an exemplary amplified fragment of Brahma Reg2 used as a template for dsRNA synthesis:

ATGAGGGTCATCGTATGAAAAACCACCACTGCAAATTGACTCAAGTCC

TGAATACGCACTATTTGGCGCCCTACAGACTCCTGCTTACTGGTACTC

CCCTACAAAATAAATTACCAGAATTATGGGCCTTGTTGAATTTCTTGT

TGCCTTCGATTTTCAAGAGTTGCTCCACTTTTGAACAATGGTTCAATG

CGCCATTCGCAACAACAGGAGAAAAGGTTGAGTTAAACGAAGAAGAAA

CTATCCTTATCATCCGTCGTCTTCACAAAGTACTCAGGCCGTTTCTCC

TGAGACGTCTCAAGAAAGAAGTCGAATCTCAGCTTCCAGACAAAGTGG

AATATATCATAAAGTGTGACATGTCGGGCCTACAAAAGGTTCTCTATG

CACACATGCAGAGCAAGGGTGTGTTACTTACCGATGGTTCCGAGAAGG

GCAGTAAAGGAAGGGGATCTAAGGACA

SEQ ID NO:109 shows a Brahma Reg2 hairpin RNA-forming sequence containing an ST-LS1 intron (underlined):

GCGCCCTACAGACTCCTGCTTACTGGTACTCCCCTACAAAATAAATTACCAGAATTATGGGCCTTG

TTGAATTTCTTGTTGCCTTCGATTTTCAAGAGTTGCTCCACTTTTGAACAATGGTTCAATGCGCCA

TTCGCAACAACAGGAGAAAAGGTTGAGTTAAACGAAGAAGAAACTATCCTTATCATCCGTCGTCTT

CACAAAGTACTCAGGCCGTTTCTCCTGAGACGTCTCAAGAAAGAAGTCGAATCTCAGCTTCCAGAC

AAAGTGGAATATATCATAAAGTGTGACATGTGACTAGTACCGGTTGGGAAAG<u>GTATGTTTCTGCTT</u>

<u>CTACCTTTGATATATATAATAATTATCACTAATTAGTAGTAATATAGTATTTCAAGTATTTTTT</u>

<u>TCAAAATAAAGAATGTAGTATATAGCTATTGCTTTTCTGTAGTTTATAAGTGTGTATATTTTAAT</u>

<u>TTATAACTTTTCTAATATATGACCAAAACATGGTGATGTGCAG</u>GTTGATCCGCGGACATGTCACAC

TTTATGATATATTCCACTTTGTCTGGAAGCTGAGATTCGACTTCTTTCTTGAGACGTCTCAGGAGA

AACGGCCTGAGTACTTTGTGAAGACGACGGATGATAAGGATAGTTTCTTCTTCGTTTAACTCAACC

TTTTCTCCTGTTGTTGCGAATGGCGCATTGAACCATTGTTCAAAAGTGGAGCAACTCTTGAAAATC

GAAGGCAACAAGAAATTCAACAAGGCCCATAATTCTGGTAATTTATTTTGTAGGGGAGTACCAGTA

AGCAGGAGTCTGTAGGGCGC

SEQ ID NO:110 shows a protein sequence encoded by the exemplary *Diabrotica* cDNA sequence, referred to in some places as Contig[0001]_brahma_949-1126 (Brahma Reg2):

SVLAKIPFKYMIIDEGHRMKNHHCKLTQVLNTHYLAPYRLLLTGTPLQ

NKLPELWALLNFLLPSIFKSCSTFEQWFNAPFATTGEKVELNEEETIL

IIRRLHKVLRPFLLRRLKKEVESQLPDKVEYIIKCDMSGLQKVLYAHM

QSKGVLLTDGSEKGSKGRGSKDN

DETAILED DESCRIPTION

I. Overview of Several Embodiments

Disclosed herein are methods and compositions for genetic control of coleopteran pest infestations. Methods for identifying one or more gene(s) essential to the lifecycle of a coleopteran pest for use as a target gene for RNAi-mediated control of a coleopteran pest population are also provided. DNA plasmid vectors encoding an RNA molecule may be designed to suppress one or more target gene(s) essential for growth, survival, development, and/or reproduction. In some embodiments, the RNA molecule may be capable of forming dsRNA molecules. In some embodiments, methods are provided for post-transcriptional repression of expression or inhibition of a target gene via nucleic acid molecules that are complementary to a coding or non-coding sequence of the target gene in a coleopteran pest. In these and further embodiments, a coleopteran pest may ingest one or more dsRNA, siRNA, miRNA, and/or hpRNA molecules transcribed from all or a portion of a nucleic acid molecule that is complementary to a coding or non-coding sequence of a target gene, thereby providing a plant-protective effect.

Thus, some embodiments involve sequence-specific inhibition of expression of target gene products, using dsRNA, siRNA, miRNA and/or hpRNA that is complementary to coding and/or non-coding sequences of the target gene(s) to achieve at least partial control of a coleopteran pest. Disclosed is a set of isolated and purified nucleic acid molecules comprising a nucleotide sequence, for example, as set forth in one of SEQ ID NOs:1-7 and 103-106, and fragments thereof. In some embodiments, a stabilized dsRNA molecule may be expressed from these sequences, fragments thereof, or a gene comprising one of these sequences, for the post-transcriptional silencing or inhibition of a target gene. In certain embodiments, isolated and purified nucleic acid molecules comprise all or part of SEQ ID NO:7.

Some embodiments involve a recombinant host cell (e.g., a plant cell) having in its genome at least one recombinant DNA sequence encoding at least one iRNA (e.g., dsRNA) molecule(s). In particular embodiments, the dsRNA molecule(s) may be produced when ingested by a coleopteran pest to post-transcriptionally silence or inhibit the expression of a target gene in the coleopteran pest. The recombinant DNA sequence may comprise, for example, any of SEQ ID NOs:1-7 and 103-106, fragments of any of SEQ ID NOs:1-7 and 103-106, or a partial sequence of a gene comprising one of SEQ ID NOs:1-7 and 103-106, or complements thereof.

Particular embodiments involve a recombinant host cell having in its genome a recombinant DNA sequence encoding at least one iRNA (e.g., dsRNA) molecule(s) comprising all or part of SEQ ID NO:7. When ingested by a coleopteran pest, the iRNA molecule(s) may silence or inhibit the expression of a target gene comprising SEQ ID NO:7 in the coleopteran pest, and thereby result in cessation of growth, development, reproduction, and/or feeding in the coleopteran pest.

In some embodiments, a recombinant host cell having in its genome at least one recombinant DNA sequence encoding at least one RNA molecule capable of forming a dsRNA molecule may be a transformed plant cell. Some embodiments involve transgenic plants comprising such a transformed plant cell. In addition to such transgenic plants, progeny plants of any transgenic plant generation, transgenic seeds, and transgenic plant products, are all provided, each of which comprises recombinant DNA sequence(s). In particular embodiments, an RNA molecule capable of forming a dsRNA molecule of the invention may be expressed in a transgenic plant cell. Therefore, in these and other embodiments, a dsRNA molecule of the invention may be isolated from a transgenic plant cell. In particular embodiments, the transgenic plant is a plant selected from the group consisting of corn (*Zea mays*), soybean (*Glycine max*), and plants of the family Poaceae.

Some embodiments involve a method for modulating the expression of a target gene in a coleopteran pest cell. In these and other embodiments, a nucleic acid molecule may be provided, wherein the nucleic acid molecule comprises a nucleotide sequence encoding an RNA molecule capable of forming a dsRNA molecule. In particular embodiments, a nucleotide sequence encoding an RNA molecule capable of forming a dsRNA molecule may be operatively linked to a promoter, and may also be operatively linked to a transcription termination sequence. In particular embodiments, a method for modulating the expression of a target gene in a coleopteran pest cell may comprise: (a) transforming a plant cell with a vector comprising a nucleotide sequence encoding an RNA molecule capable of forming a dsRNA molecule; (b) culturing the transformed plant cell under conditions sufficient to allow for development of a plant cell culture comprising a plurality of transformed plant cells; (c) selecting for a transformed plant cell that has integrated the vector into its genome; and (d) determining that the selected transformed plant cell comprises the RNA molecule capable of forming a dsRNA molecule encoded by the nucleotide sequence of the vector. A plant may be regenerated from a plant cell that has the vector integrated in its genome and comprises the dsRNA molecule encoded by the nucleotide sequence of the vector.

Thus, also disclosed is a transgenic plant comprising a vector having a nucleotide sequence encoding an RNA molecule capable of forming a dsRNA molecule integrated in its genome, wherein the transgenic plant comprises the dsRNA molecule encoded by the nucleotide sequence of the vector. In particular embodiments, expression of an RNA molecule capable of forming a dsRNA molecule in the plant is sufficient to modulate the expression of a target gene in a cell of a coleopteran pest that contacts the transformed plant or plant cell, for example, by feeding on the transformed plant, a part of the plant (e.g., root) or plant cell. Transgenic plants disclosed herein may display resistance and/or enhanced tolerance to coleopteran pest infestations. Particular transgenic plants may display resistance and/or enhanced tolerance to one or more coleopteran pests selected from the group consisting of: WCR; NCR; SCR; MCR; *D. balteata* LeConte; *D. u. tenella*; and *D. u. undecimpunctata* Mannerheim.

Also disclosed herein are methods for delivery of control agents, such as an iRNA molecule, to a coleopteran pest. Such control agents may cause, directly or indirectly, an impairment in the ability of the coleopteran pest to feed, grow or otherwise cause damage in a host. In some embodiments, a method is provided comprising delivery of a stabilized dsRNA molecule to a coleopteran pest to suppress at least one target gene in the coleopteran pest, thereby reducing or eliminating plant damage in a coleopteran pest host. In some embodiments, a method of inhibiting expression of a target gene in a coleopteran pest may result in the cessation of growth, development, reproduction, and/or feeding in the coleopteran pest. In some embodiments, the method may eventually result in death of the coleopteran pest.

In some embodiments, compositions (e.g., a topical composition) are provided that comprise an iRNA (e.g., dsRNA) molecule of the invention for use in plants, animals, and/or the environment of a plant or animal to achieve the elimination or reduction of a coleopteran pest infestation. In particular embodiments, the composition may be a nutritional composition or food source to be fed to the coleopteran pest. Some embodiments comprise making the nutritional composition or food source available to the coleopteran pest. Ingestion of a composition comprising iRNA molecules may result in the uptake of the molecules by one or more cells of the coleopteran pest, which may in turn result in the inhibition of expression of at least one target gene in cell(s) of the coleopteran pest. Ingestion of or damage to a plant or plant cell by a coleopteran pest may be limited or eliminated in or on any host tissue or environment in which the coleopteran pest is present by providing one or more compositions comprising an iRNA molecule of the invention in the host of the coleopteran pest.

The compositions and methods disclosed herein may be used together in combinations with other methods and compositions for controlling damage by coleopteran pests. For example, an iRNA molecule as described herein for protecting plants from coleopteran pests may be used in a method comprising the additional use of one or more chemical agents effective against a coleopteran pest, biopesticides effective against a coleopteran pest, crop rotation, or recombinant genetic techniques that exhibit features different from the features of the RNAi-mediated methods and RNAi compositions of the invention (e.g., recombinant production of proteins in plants that are harmful to a coleopteran pest (e.g., Bt toxins)).

II. Abbreviations dsRNA double-stranded ribonucleic acid
GI growth inhibition
NCBI National Center for Biotechnology Information
gDNA genomic DNA
iRNA inhibitory ribonucleic acid
ORF open reading frame
RNAi ribonucleic acid interference
miRNA micro inhibitory ribonucleic acid
siRNA small inhibitory ribonucleic acid hpRNA hairpin ribonucleic acid
UTR untranslated region
WCR western corn rootworm (*Diabrotica virgifera virgifera* LeConte)
NCR northern corn rootworm (*Diabrotica barberi* Smith and Lawrence)
MCR Mexican corn rootworm (*Diabrotica virgifera zeae* Krysan and Smith)
PCR Polymerase chain reaction
RISC RNA-induced Silencing Complex
SCR southern corn rootworm (*Diabrotica undecimpunctata howardi* Barber)

III. Terms

In the description and tables which follow, a number of terms are used. In order to provide a clear and consistent understanding of the specification and claims, including the scope to be given such terms, the following definitions are provided:

Coleopteran pest: As used herein, the term "coleopteran pest" refers to pest insects of the order Coleoptera, including pest insects in the genus *Diabrotica*, which feed upon agricultural crops and crop products, including corn and other true grasses. In particular examples, a coleopteran pest is selected from the list comprising *D. v. virgifera* LeConte (WCR); *D. barberi* Smith and Lawrence (NCR); *D. u. howardi* (SCR); *D. v. zeae* (MCR); *D. balteata* LeConte; *D. u. tenella*; and *D. u. undecimpunctata* Mannerheim.

Contact (with an organism): As used herein, the term "contact with" or "uptake by" an organism (e.g., a coleopteran pest), with regard to a nucleic acid molecule, includes internalization of the nucleic acid molecule into the organism, for example and without limitation: ingestion of the molecule by the organism (e.g., by feeding); contacting the organism with a composition comprising the nucleic acid molecule; and soaking of organisms with a solution comprising the nucleic acid molecule.

Contig: As used herein the term "contig" refers to a DNA sequence that is reconstructed from a set of overlapping DNA segments derived from a single genetic source.

Corn plant: As used herein, the term "corn plant" refers to a plant of the species, *Zea mays* (maize).

Encoding a dsRNA: As used herein, the descriptor "encoding a dsRNA" refers to a DNA polynucleotide whose RNA transcription product is capable of forming an intramolecular dsRNA structure (e.g., a hairpin) or intermolecular dsRNA structure (e.g., by hybridizing to a target RNA molecule).

Expression: As used herein, "expression" of a coding sequence (for example, a gene or a transgene) refers to the process by which the coded information of a nucleic acid transcriptional unit (including, e.g., genomic DNA or cDNA) is converted into an operational, non-operational, or structural part of a cell, often including the synthesis of a protein. Gene expression can be influenced by external signals; for example, exposure of a cell, tissue, or organism to an agent that increases or decreases gene expression. Expression of a gene can also be regulated anywhere in the pathway from DNA to RNA to protein. Regulation of gene expression occurs, for example, through controls acting on transcription, translation, RNA transport and processing, degradation of intermediary molecules such as mRNA, or through activation, inactivation, compartmentalization, or degradation of specific protein molecules after they have been made, or by combinations thereof. Gene expression can be measured at the RNA level or the protein level by any method known in the art, including, without limitation, northern blot, RT-PCR, western blot, or in vitro, in situ, or in vivo protein activity assay(s).

Genetic material: As used herein, the term "genetic material" includes all genes, and nucleic acid molecules, such as DNA and RNA.

Inhibition: As used herein, the term "inhibition," when used to describe an effect on a coding sequence (for example, a gene), refers to a measurable decrease in the cellular level of mRNA transcribed from the coding sequence and/or peptide, polypeptide, or protein product of the coding sequence. In some examples, expression of a coding sequence may be inhibited such that expression is approximately eliminated. "Specific inhibition" refers to the inhibition of a target coding sequence without consequently affecting expression of other coding sequences (e.g., genes) in the cell wherein the specific inhibition is being accomplished.

Isolated: An "isolated" biological component (such as a nucleic acid or protein) has been substantially separated, produced apart from, or purified away from other biological components in the cell of the organism in which the component naturally occurs (i.e., other chromosomal and extra-chromosomal DNA and RNA, and proteins), while effecting a chemical or functional change in the component (e.g., a nucleic acid may be isolated from a chromosome by breaking chemical bonds connecting the nucleic acid to the remaining DNA in the chromosome). Nucleic acid molecules and proteins that have been "isolated" include nucleic acid molecules and proteins purified by standard purification methods. The term also embraces nucleic acids and proteins prepared by recombinant expression in a host cell, as well as chemically-synthesized nucleic acid molecules, proteins, and peptides.

Nucleic acid molecule: As used herein, the term "nucleic acid molecule" may refer to a polymeric form of nucleotides, which may include both sense and anti-sense strands of RNA, cDNA, genomic DNA, and synthetic forms and mixed polymers of the above. A nucleotide or nucleobase may refer to a ribonucleotide, deoxyribonucleotide, or a modified form of either type of nucleotide. A "nucleic acid molecule" as used herein is synonymous with "nucleic acid" and "polynucleotide." A nucleic acid molecule is usually at least 10 bases in length, unless otherwise specified. By convention, the nucleotide sequence of a nucleic acid molecule is read from the 5' to the 3' end of the molecule. The "complement" of a nucleotide sequence refers to the sequence of nucleobases that may form base pairs with the nucleobases of the nucleotide sequence (i.e., A-T/U, and G-C).

Some embodiments include nucleic acids comprising a template DNA that is transcribed into an RNA molecule that is the complement of an mRNA molecule. In these embodiments, the complement of the nucleotide sequence transcribed into the mRNA molecule is present in the 5' to 3' orientation, such that RNA polymerase (which transcribes DNA in the 5' to 3' direction) will transcribe a nucleic acid from the complement that can hybridize to the mRNA molecule. Unless explicitly stated otherwise, or it is clear to be otherwise from the context, the term "complement" therefore refers to the sequence, from 5' to 3', of nucleobases that may form base pairs with the nucleobases of a particular nucleotide sequence. Similarly, unless it is explicitly stated to be otherwise (or it is clear to be otherwise from the context), the "reverse complement" of a nucleic acid sequence refers to the sequence of the complement in reverse orientation. The foregoing is demonstrated in the following illustration:

```
ATGATGATG
nucleotide sequence

TACTACTAC
"complement" of the nucleotide sequence

CATCATCAT
"reverse complement" of the nucleotide sequence
```

Some embodiments of the invention may include hairpin RNA-forming RNAi molecules. In these RNAi molecules, both the complement of a nucleotide sequence to be targeted by RNA interference and the reverse complement of the sequence may be found in the same molecule, such that the single-stranded RNA molecule may "fold over" and hybridize to itself over region comprising the complementary and reverse complementary sequences.

"Nucleic acid molecules" include single- and double-stranded forms of DNA; single-stranded forms of RNA; and double-stranded forms of RNA (dsRNA). The term "nucleotide sequence" or "nucleic acid sequence" refers to both the sense and antisense strands of a nucleic acid as either individual single strands or in the duplex. The term "ribonucleic acid" (RNA) is inclusive of iRNA (inhibitory RNA), dsRNA (double stranded RNA), siRNA (small interfering RNA), mRNA (messenger RNA), miRNA (micro-RNA), hpRNA (hairpin RNA), tRNA (transfer RNAs, whether charged or discharged with a corresponding acylated amino acid), and cRNA (complementary RNA). The term "deoxyribonucleic acid" (DNA) is inclusive of cDNA, genomic DNA, and DNA-RNA hybrids. The terms "nucleic acid segment" and "nucleotide sequence segment," or more generally "segment," will be understood by those in the art as a functional term that includes both genomic sequences, ribosomal RNA sequences, transfer RNA sequences, messenger RNA sequences, operon sequences, and smaller engineered nucleotide sequences that encode or may be adapted to encode, peptides, polypeptides, or proteins.

Oligonucleotide: An oligonucleotide is a short nucleic acid polymer. Oligonucleotides may be formed by cleavage of longer nucleic acid segments, or by polymerizing individual nucleotide precursors. Automated synthesizers allow the synthesis of oligonucleotides up to several hundred bases in length. Because oligonucleotides may bind to a complementary nucleotide sequence, they may be used as probes for detecting DNA or RNA. Oligonucleotides composed of DNA (oligodeoxyribonucleotides) may be used in PCR, a technique for the amplification of DNA sequences. In PCR, the oligonucleotide is typically referred to as a "primer," which allows a DNA polymerase to extend the oligonucleotide and replicate the complementary strand.

A nucleic acid molecule may include either or both naturally occurring and modified nucleotides linked together by naturally occurring and/or non-naturally occurring nucleotide linkages. Nucleic acid molecules may be modified chemically or biochemically, or may contain non-natural or derivatized nucleotide bases, as will be readily appreciated by those of skill in the art. Such modifications include, for example, labels, methylation, substitution of one or more of the naturally occurring nucleotides with an analog, internucleotide modifications (e.g., uncharged linkages: for example, methyl phosphonates, phosphotriesters, phosphoramidates, carbamates, etc.; charged linkages: for example, phosphorothioates, phosphorodithioates, etc.; pendent moieties: for example, peptides; intercalators: for example, acridine, psoralen, etc.; chelators; alkylators; and modified linkages: for example, alpha anomeric nucleic acids, etc.). The term "nucleic acid molecule" also includes any topological conformation, including single-stranded, double-stranded, partially duplexed, triplexed, hairpinned, circular, and padlocked conformations.

As used herein with respect to DNA, the term "coding sequence," "structural nucleotide sequence," or "structural nucleic acid molecule" refers to a nucleotide sequence that is ultimately translated into a polypeptide, via transcription and mRNA, when placed under the control of appropriate regulatory sequences. With respect to RNA, the term "coding sequence" refers to a nucleotide sequence that is translated into a peptide, polypeptide, or protein. The boundaries of a coding sequence are determined by a translation start codon at the 5'-terminus and a translation stop codon at the 3'-terminus. Coding sequences include, but are not limited to: genomic DNA; cDNA; EST; and recombinant nucleotide sequences.

As used herein, "transcribed non-coding sequence" refers to segments of mRNA molecules such as 5'UTR, 3'UTR and intron segments that are not translated into a peptide, polypeptide, or protein. Further, "transcribed non-coding sequence" refers to a nucleotide sequence that is transcribed into an RNA that functions in the cell, for example, structural RNAs (e.g., ribosomal RNA (rRNA) as exemplified by 5S rRNA, 5.8S rRNA, 16S rRNA, 18S rRNA, 23S rRNA, and 28S rRNA, and the like); transfer RNA (tRNA); and snRNAs such as U4, U5, U6, and the like. Transcribed non-coding sequences also include, for example and without limitation, small RNAs (sRNA), which term is often used to describe small bacterial non-coding RNAs; small nucleolar RNAs (snoRNA); microRNAs; small interfering RNAs (siRNA); Piwi-interacting RNAs (piRNA); and long non-coding RNAs. Further still, "transcribed non-coding sequence" refers to a nucleotide sequence that may natively exist as an intragenic "spacer" sequence in an organism and which is transcribed into an RNA molecule.

Genome: As used herein, the term "genome" refers to chromosomal DNA found within the nucleus of a cell, and also refers to organelle DNA found within subcellular components of the cell. In some embodiments of the invention, a DNA molecule may be introduced into a plant cell such that the DNA molecule is integrated into the genome of the plant cell. In these and further embodiments, the DNA molecule may be either integrated into the nuclear DNA of the plant cell, or integrated into the DNA of the chloroplast or mitochondrion of the plant cell. The term "genome" as it applies to bacteria refers to both the chromosome and plasmids within the bacterial cell. In some embodiments of the invention, a DNA molecule may be introduced into a bacterium such that the DNA molecule is integrated into the genome of the bacterium. In these and further embodiments, the DNA molecule may be either chromosomally-integrated or located as or in a stable plasmid.

Sequence identity: The term "sequence identity" or "identity," as used herein in the context of two nucleic acid or polypeptide sequences, refers to the residues in the two sequences that are the same when aligned for maximum correspondence over a specified comparison window.

As used herein, the term "percentage of sequence identity" may refer to the value determined by comparing two optimally aligned sequences (e.g., nucleic acid sequences or polypeptide sequences) over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleotide or amino acid residue occurs in both sequences to yield the number of matched positions, dividing the number of matched positions by the total number of positions in the comparison window, and multiplying the result by 100 to yield the percentage of sequence identity. A sequence that is identical at every position in comparison to a reference sequence is said to be 100% identical to the reference sequence, and vice-versa.

Methods for aligning sequences for comparison are well-known in the art. Various programs and alignment algorithms are described in, for example: Smith and Waterman (1981) Adv. Appl. Math. 2:482; Needleman and Wunsch (1970) J. Mol. Biol. 48:443; Pearson and Lipman (1988) Proc. Natl. Acad. Sci. U.S.A. 85:2444; Higgins and Sharp (1988) Gene 73:237-44; Higgins and Sharp (1989) CABIOS 5:151-3; Corpet et al. (1988) Nucleic Acids Res. 16:10881-90; Huang et al. (1992) Comp. Appl. Biosci. 8:155-65; Pearson et al. (1994) Methods Mol. Biol. 24:307-31; Tatiana et al. (1999) FEMS Microbiol. Lett. 174:247-50. A detailed consideration of sequence alignment methods and homology calculations can be found in, e.g., Altschul et al. (1990) J. Mol. Biol. 215:403-10.

The National Center for Biotechnology Information (NCBI) Basic Local Alignment Search Tool (BLAST™; Altschul et al. (1990)) is available from several sources, including the National Center for Biotechnology Information (Bethesda, Md.), and on the internet, for use in connection with several sequence analysis programs. A description of how to determine sequence identity using this program is available on the internet under the "help" section for BLAST™. For comparisons of nucleic acid sequences, the "Blast 2 sequences" function of the BLAST™ (Blastn) program may be employed using the default BLOSUM62 matrix set to default parameters. Nucleic acid sequences with even greater similarity to the reference sequences will show increasing percentage identity when assessed by this method.

Specifically hybridizable/Specifically complementary: As used herein, the terms "Specifically hybridizable" and "Specifically complementary" are terms that indicate a sufficient degree of complementarity such that stable and specific binding occurs between the nucleic acid molecule and a target nucleic acid molecule. Hybridization between two nucleic acid molecules involves the formation of an anti-parallel alignment between the nucleic acid sequences of the two nucleic acid molecules. The two molecules are then able to form hydrogen bonds with corresponding bases on the opposite strand to form a duplex molecule that, if it is sufficiently stable, is detectable using methods well known in the art. A nucleic acid molecule need not be 100% complementary to its target sequence to be specifically hybridizable. However, the amount of sequence complementarity that must exist for hybridization to be specific is a function of the hybridization conditions used.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ and/or $Mg^{++}$ concentration) of the hybridization buffer will determine the stringency of hybridization, though wash times also influence stringency. Calculations regarding hybridization conditions required for attaining particular degrees of stringency are known to those of ordinary skill in the art, and are discussed, for example, in Sambrook et al. (ed.) *Molecular Cloning: A Laboratory Manual*, $2^{nd}$ ed., vol. 1-3, Cold Spring Harbor Laboratory Press, Cold Spring Harbor, N.Y., 1989, chapters 9 and 11; and Hames and Higgins (eds.) *Nucleic Acid Hybridization*, IRL Press, Oxford, 1985. Further detailed instruction and guidance with regard to the hybridization of nucleic acids may be found, for example, in Tijssen, "Overview of principles of hybridization and the strategy of nucleic acid probe assays," in *Laboratory Techniques in Biochemistry and Molecular Biology—Hybridization with Nucleic Acid Probes*, Part I, Chapter 2, Elsevier, N.Y., 1993; and Ausubel et al., Eds., *Current Protocols in Molecular Biology*, Chapter 2, Greene Publishing and Wiley-Interscience, NY, 1995.

As used herein, "stringent conditions" encompass conditions under which hybridization will only occur if there is less than 20% mismatch between the hybridization molecule and a homologous sequence within the target nucleic acid molecule. "Stringent conditions" include further particular levels of stringency. Thus, as used herein, "moderate stringency" conditions are those under which molecules with more than 20% sequence mismatch will not hybridize; conditions of "high stringency" are those under which sequences with more than 10% mismatch will not hybridize; and conditions of "very high stringency" are those under which sequences with more than 5% mismatch will not hybridize.

The following are representative, non-limiting hybridization conditions.

High Stringency condition (detects sequences that share at least 90% sequence identity): Hybridization in 5×SSC buffer at 65° C. for 16 hours; wash twice in 2×SSC buffer at room temperature for 15 minutes each; and wash twice in 0.5×SSC buffer at 65° C. for 20 minutes each.

Moderate Stringency condition (detects sequences that share at least 80% sequence identity): Hybridization in 5×-6×SSC buffer at 65-70° C. for 16-20 hours; wash twice in 2×SSC buffer at room temperature for 5-20 minutes each; and wash twice in 1×SSC buffer at 55-70° C. for 30 minutes each.

Non-stringent control condition (sequences that share at least 50% sequence identity will hybridize): Hybridization in 6×SSC buffer at room temperature to 55° C. for 16-20 hours; wash at least twice in 2×-3×SSC buffer at room temperature to 55° C. for 20-30 minutes each.

As used herein, the term "substantially homologous" or "substantial homology," with regard to a contiguous nucleic acid sequence, refers to contiguous nucleotide sequences comprised within nucleic acid molecules that hybridize under stringent conditions to a nucleic acid molecule having the reference nucleic acid sequence. For example, nucleic acid molecules comprising sequences that are substantially homologous to a reference nucleic acid sequence of any of SEQ ID NOs:1-7 and 103-106 are those nucleic acid molecules that hybridize under stringent conditions (e.g., the Moderate Stringency conditions set forth, supra) to a nucleic acid molecule comprising the reference nucleic acid sequence of any of SEQ ID NOs:1-7 and 103-106. Substantially homologous sequences may have at least 80% sequence identity. For example, substantially homologous sequences may have from about 80% to 100% sequence identity, such as about 81%; about 82%; about 83%; about 84%; about 85%; about 86%; about 87%; about 88%; about 89%; about 90%; about 91%; about 92%; about 93%; about 94% about 95%; about 96%; about 97%; about 98%; about 98.5%; about 99%; about 99.5%; and about 100%. The property of substantial homology is closely related to specific hybridization. For example, a nucleic acid molecule is specifically hybridizable when there is a sufficient degree of complementarity to avoid non-specific binding of the nucleic acid to non-target sequences under conditions where specific binding is desired, for example, under stringent hybridization conditions.

As used herein, the term "ortholog" refers to a gene in two or more species that has evolved from a common ancestral nucleotide sequence, and may retain the same function in the two or more species.

As used herein, two nucleic acid sequence molecules are said to exhibit "complete complementarity" when every nucleotide of a sequence read in the 5' to 3' direction is complementary to every nucleotide of the other sequence when read in the 3' to 5' direction. A nucleotide sequence that is complementary to a reference nucleotide sequence will exhibit a sequence identical to the reverse complement sequence of the reference nucleotide sequence. These terms and descriptions are well defined in the art and are easily understood by those of ordinary skill in the art.

Operably linked: A first nucleotide sequence is operably linked with a second nucleic acid sequence when the first nucleic acid sequence is in a functional relationship with the second nucleic acid sequence. When recombinantly produced, operably linked nucleic acid sequences are generally contiguous, and, where necessary to join two protein-coding regions, in the same reading frame (e.g., in a translationally fused ORF). However, nucleic acids need not be contiguous to be operably linked.

The term, "operably linked," when used in reference to a regulatory sequence and a coding sequence, means that the regulatory sequence affects the expression of the linked coding sequence. "Regulatory sequences," or "control elements," refer to nucleotide sequences that influence the timing and level/amount of transcription, RNA processing or stability, or translation of the associated coding sequence. Regulatory sequences may include promoters; translation leader sequences; introns; enhancers; stem-loop structures; repressor binding sequences; termination sequences; polyadenylation recognition sequences; etc. Particular regulatory sequences may be located upstream and/or downstream of a coding sequence operably linked thereto. Also, particular regulatory sequences operably linked to a coding sequence may be located on the associated complementary strand of a double-stranded nucleic acid molecule.

Promoter: As used herein, the term "promoter" refers to a region of DNA that may be upstream from the start of transcription, and that may be involved in recognition and binding of RNA polymerase and other proteins to initiate transcription. A promoter may be operably linked to a coding sequence for expression in a cell, or a promoter may be operably linked to a nucleotide sequence encoding a signal sequence which may be operably linked to a coding sequence for expression in a cell. A "plant promoter" may be a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters which initiate transcription only in certain tissues are referred to as "tissue-specific." A "cell type-specific" promoter primarily drives expression in certain cell types in one or more organs, for example, vascular cells in roots or leaves. An "inducible" promoter may be a promoter which may be under environmental control. Examples of environmental conditions that may initiate transcription by inducible promoters include anaerobic conditions and the presence of light. Tissue-specific, tissue-preferred, cell type specific, and inducible promoters constitute the class of "non-constitutive" promoters. A "constitutive" promoter is a promoter which may be active under most environmental conditions or in most tissue or cell types.

Any inducible promoter can be used in some embodiments of the invention. See Ward et al. (1993) Plant Mol. Biol. 22:361-366. With an inducible promoter, the rate of transcription increases in response to an inducing agent. Exemplary inducible promoters include, but are not limited to: Promoters from the ACEI system that respond to copper; In2 gene from maize that responds to benzenesulfonamide herbicide safeners; Tet repressor from Tn10; and the inducible promoter from a steroid hormone gene, the transcriptional activity of which may be induced by a glucocorticosteroid hormone (Schena et al. (1991) Proc. Natl. Acad. Sci. USA 88:0421).

Exemplary constitutive promoters include, but are not limited to: Promoters from plant viruses, such as the 35S promoter from Cauliflower Mosaic Virus (CaMV); promoters from rice actin genes; ubiquitin promoters; pEMU; MAS; maize H3 histone promoter; and the ALS promoter, Xba1/NcoI fragment 5' to the *Brassica napus* ALS3 structural gene (or a nucleotide sequence similar to said Xba1/NcoI fragment) (International PCT Publication No. WO96/30530).

Additionally, any tissue-specific or tissue-preferred promoter may be utilized in some embodiments of the invention. Plants transformed with a nucleic acid molecule comprising a coding sequence operably linked to a tissue-specific promoter may produce the product of the coding sequence exclusively, or preferentially, in a specific tissue. Exemplary tissue-specific or tissue-preferred promoters include, but are not limited to: A seed-preferred promoter, such as that from the phaseolin gene; a leaf-specific and light-induced promoter such as that from cab or rubisco; an anther-specific promoter such as that from LAT52; a pollen-specific promoter such as that from Zm13; and a microspore-preferred promoter such as that from apg.

Transformation: As used herein, the term "transformation" or "transduction" refers to the transfer of one or more nucleic acid molecule(s) into a cell. A cell is "transformed" by a nucleic acid molecule transduced into the cell when the nucleic acid molecule becomes stably replicated by the cell, either by incorporation of the nucleic acid molecule into the cellular genome, or by episomal replication. As used herein, the term "transformation" encompasses all techniques by which a nucleic acid molecule can be introduced into such a cell. Examples include, but are not limited to: transfection with viral vectors; transformation with plasmid vectors; electroporation (Fromm et al. (1986) Nature 319:791-3); lipofection (Feigner et al. (1987) Proc. Natl. Acad. Sci. USA 84:7413-7); microinjection (Mueller et al. (1978) Cell 15:579-85); *Agrobacterium*-mediated transfer (Fraley et al. (1983) Proc. Natl. Acad. Sci. USA 80:4803-7); direct DNA uptake; and microprojectile bombardment (Klein et al. (1987) Nature 327:70).

Transgene: An exogenous nucleic acid sequence. In some examples, a transgene may be a sequence that encodes one or both strand(s) of an RNA capable of forming a dsRNA molecule that comprises a nucleotide sequence that is complementary to a nucleic acid molecule found in a coleopteran pest. In further examples, a transgene may be an antisense nucleic acid sequence, wherein expression of the antisense nucleic acid sequence inhibits expression of a target nucleic acid sequence. In still further examples, a transgene may be a gene sequence (e.g., a herbicide-resistance gene), a gene encoding an industrially or pharmaceutically useful compound, or a gene encoding a desirable agricultural trait. In these and other examples, a transgene may contain regulatory sequences operably linked to a coding sequence of the transgene (e.g., a promoter).

Vector: A nucleic acid molecule as introduced into a cell, for example, to produce a transformed cell. A vector may include nucleic acid sequences that permit it to replicate in the host cell, such as an origin of replication. Examples of vectors include, but are not limited to: a plasmid; cosmid; bacteriophage; or virus that carries exogenous DNA into a cell. A vector may also include one or more genes, including ones that produce antisense molecules, and/or selectable marker genes and other genetic elements known in the art. A vector may transduce, transform, or infect a cell, thereby causing the cell to express the nucleic acid molecules and/or proteins encoded by the vector. A vector optionally includes materials to aid in achieving entry of the nucleic acid molecule into the cell (e.g., a liposome, protein coating, etc.).

Yield: A stabilized yield of about 100% or greater relative to the yield of check varieties in the same growing location growing at the same time and under the same conditions. In particular embodiments, "improved yield" or "improving yield" means a cultivar having a stabilized yield of 105% or greater relative to the yield of check varieties in the same growing location containing significant densities of coleopteran pests that are injurious to that crop growing at the same time and under the same conditions.

Unless specifically indicated or implied, the terms "a," "an," and "the" signify "at least one" as used herein.

Unless otherwise specifically explained, all technical and scientific terms used herein have the same meaning as commonly understood by those of ordinary skill in the art to which this disclosure belongs. Definitions of common terms in molecular biology can be found in, for example, Lewin's *Genes X*, Jones & Bartlett Publishers, 2009 (ISBN 10 0763766321); Krebs et al. (eds.), *The Encyclopedia of Molecular Biology*, Blackwell Science Ltd., 1994 (ISBN 0-632-02182-9); and Meyers R. A. (ed.), *Molecular Biology and Biotechnology: A Comprehensive Desk Reference*, VCH Publishers, Inc., 1995 (ISBN 1-56081-569-8). All percentages are by weight and all solvent mixture proportions are by volume unless otherwise noted. All temperatures are in degrees Celsius.

IV. Nucleic Acid Molecules Comprising a Coleopteran Pest Sequence

A. Overview

Described herein are nucleic acid molecules useful for the control of coleopteran pests. Described nucleic acid molecules include target sequences (e.g., native genes, and non-coding sequences), dsRNAs, siRNAs, hpRNAs, and miRNAs. For example, dsRNA, siRNA, miRNA and/or hpRNA molecules are described in some embodiments that may be specifically complementary to all or part of one or more native nucleic acid sequences in a coleopteran pest. In these and further embodiments, the native nucleic acid sequence(s) may be one or more target gene(s), the product of which may be, for example and without limitation: involved in a metabolic process; involved in a reproductive process; or involved in larval development. Nucleic acid molecules described herein, when introduced into a cell comprising at least one native nucleic acid sequence(s) to which the nucleic acid molecules are specifically complementary, may initiate RNAi in the cell, and consequently reduce or eliminate expression of the native nucleic acid sequence(s). In some examples, reduction or elimination of the expression of a target gene by a nucleic acid molecule comprising a sequence specifically complementary thereto may be lethal in coleopteran pests, or result in reduced growth and/or reproduction.

In some embodiments, at least one target gene in a coleopteran pest may be selected, wherein the target gene comprises a nucleotide sequence selected from the list comprising protein phosphatase PP1-87B (SEQ ID NO:1), D_vir_Contig0011_87B (SEQ ID NO:3), RPA70 (SEQ ID NO:2), D_vir_c43870_RPA70 or RPA70 region 1 (SEQ ID NO:4), D_vir_c18764 RPA70 or RPA70 region 2 (SEQ ID NO:5), D_vir_c7971_RPA70 or RPA70 region (SEQ ID NO:6), RPS6 (SEQ ID NO:7), Brahma (SEQ ID NO:103); F5XY5 KV01DBWKA_brahma_587-707 or Brahma Reg1 (SEQ ID NO:104), D_vir_Contig[0001]_brahma_949-1126 or Brahma Reg2 (SEQ ID NO:105), and F5XY5 KV01D0IM6_brahma_1237-1333 or Brahma Reg3 (SEQ ID NO:106). In particular examples, a target gene in a coleopteran pest is selected, wherein the target gene comprises the novel nucleotide sequence of SEQ ID NO:7.

In some embodiments, a target gene may be a nucleic acid molecule comprising a nucleotide sequence that encodes a polypeptide comprising a contiguous amino acid sequence that is at least 85% identical (e.g., about 90%, about 95%, about 96%, about 97%, about 98%, about 99%, about 100%, or 100% identical) to the amino acid sequence of the protein product of one of PP1-87B (SEQ ID NO:1), RPA70 (SEQ ID NO:2), D_vir_Contig0011_87B (SEQ ID NO:3), D_vir_c43870_RPA70 or RPA70 region 1 (SEQ ID NO:4), D_vir_c18764_RPA70 or RPA70 region 2 (SEQ ID NO:5), D_vir_c7971_RPA70 or RPA70 region 3 (SEQ ID NO:6), RPS6 (SEQ ID NO:7), Brahma (SEQ ID NO:103); F5XY5 KV01DBWKA_brahma_587-707 or Brahma Reg1 (SEQ ID NO:104), D_vir_Contig[0001]_brahma_949-1126 or Brahma Reg2 (SEQ ID NO:105), and F5XY5 KV01D0IM6_brahma_1237-1333 or Brahma Reg3 (SEQ ID NO:106).

A target gene may be any nucleic acid sequence in a coleopteran pest, the post-transcriptional inhibition of which has a deleterious effect on the coleopteran pest, or provides a protective benefit against the coleopteran pest to a plant. In particular examples, a target gene is a nucleic acid molecule comprising a nucleotide sequence that encodes a polypeptide comprising a contiguous amino acid sequence that is at least 85% identical, about 90% identical, about 95% identical, about 96% identical, about 97% identical, about 98% identical, about 99% identical, about 100% identical, or 100% identical to the amino acid sequence of the protein product of SEQ ID NO:7.

Provided according to the invention are nucleotide sequences, the expression of which results in an RNA molecule comprising a nucleotide sequence that is specifically complementary to all or part of a native RNA molecule that is encoded by a coding sequence in a coleopteran pest. In some embodiments, after ingestion of the expressed RNA molecule by a coleopteran pest, down-regulation of the coding sequence in cells of the coleopteran pest may be obtained. In particular embodiments, down-regulation of the coding sequence in cells of the coleopteran pest may result in a deleterious effect on the growth, viability, proliferation, and/or reproduction of the coleopteran pest.

In some embodiments, target sequences include transcribed non-coding RNA sequences, such as 5'UTRs; 3'UTRs; spliced leader sequences; intron sequences; outron sequences (e.g., 5'UTR RNA subsequently modified in trans splicing); donatron sequences (e.g., non-coding RNA required to provide donor sequences for trans splicing); and other non-coding transcribed RNA of target coleopteran pest genes. Such sequences may be derived from both monocistronic and poly-cistronic genes.

Thus, also described herein in connection with some embodiments are iRNA molecules (e.g., dsRNAs, siRNAs, miRNAs and hpRNAs) that comprise at least one nucleotide sequence that is specifically complementary to all or part of a target sequence in a coleopteran pest. In some embodiments an iRNA molecule may comprise nucleotide sequence(s) that are complementary to all or part of a plurality of target sequences; for example, 2, 3, 4, 5, 6, 7, 8, 9, 10, or more target sequences. In particular embodiments, an iRNA molecule may be produced in vitro, or in vivo by a genetically-modified organism, such as a plant or bacterium. Also disclosed are cDNA sequences that may be used for the production of dsRNA molecules, siRNA molecules, miRNA and/or hpRNA molecules that are specifically complementary to all or part of a target sequence in a coleopteran pest. Further described are recombinant DNA constructs for use in achieving stable transformation of particular host targets. Transformed host targets may express effective levels of dsRNA, siRNA, miRNA and/or hpRNA molecules from the recombinant DNA constructs. Therefore, also described is a plant transformation vector comprising at least one nucleotide sequence operably linked to a heterologous promoter functional in a plant cell, wherein expression of the nucleotide sequence(s) results in an RNA molecule comprising a nucleotide sequence that is specifically complementary to all or part of a target sequence in a coleopteran pest.

In some embodiments, nucleic acid molecules useful for the control of coleopteran pests may include: all or part of the native nucleic acid sequence isolated from Diabrotica of RPS6 (SEQ ID NO:7); a nucleotide sequence that when expressed results in an RNA molecule comprising a nucleotide sequence that is specifically complementary to all or part of a native RNA molecule that is encoded by RPS6 (SEQ ID NO:7); iRNA molecules (e.g., dsRNAs, siRNAs, miRNAs and hpRNAs) that comprise at least one nucleotide sequence that is specifically complementary to all or part of RPS6 (SEQ ID NO:7); and recombinant DNA constructs for use in achieving stable transformation of particular host targets, wherein a transformed host target comprises one or more of the foregoing nucleic acid molecules.

In these and further embodiments, additional nucleic acid molecules useful for the control of coleopteran pests may include: PP1-87B (SEQ ID NO:1), RPA70 (SEQ ID NO:2), D_vir_Contig0011_87B protein phosphatase or PP1-87B (SEQ ID NO:3), D_vir_c43870_RPA70 or RPA70 region 1 (SEQ ID NO:4), D_vir_c18764_RPA70 or RPA70 region 2 (SEQ ID NO:5), D_vir_c7971_RPA70 or RPA70 region 3 (SEQ ID NO:6), Brahma (SEQ ID NO:103); F5XY5 KV01DBWKA_brahma_587-707 or Brahma Reg1 (SEQ ID NO:104), D_vir_Contig[0001]_brahma_949-1126 or Brahma Reg2 (SEQ ID NO:105), and F5XY5 KV01D0IM6_brahma_1237-1333 or Brahma Reg3 (SEQ ID NO:106); iRNA molecules (e.g., dsRNAs, siRNAs, miRNAs and hpRNAs) that comprise at least one nucleotide sequence that is specifically complementary to all or part of PP1-87B (SEQ ID NO:1), RPA70 (SEQ ID NO:2), D_vir_Contig0011_87B protein phosphatase or PP1-87B (SEQ ID NO:3), D_vir_c43870 RPA70 or RPA70 region 1 (SEQ ID NO:4), D_vir_c18764_RPA70 or RPA70 region 2 (SEQ ID NO:5), D_vir_c7971_RPA70 or RPA70 region 3 (SEQ ID NO:6), Brahma (SEQ ID NO:103); F5XY5 KV01DBWKAbrahma_587-707 or Brahma Reg1 (SEQ ID NO:104), D_vir_Contig[0001]_brahma_949-1126 or Brahma Reg2 (SEQ ID NO:105), and F5XY5 KV01D0IM6_brahma_1237-1333 or Brahma Reg3 (SEQ ID NO:106); nucleotide sequences that when expressed result in an RNA molecule comprising a nucleotide sequence that is specifically complementary to a native RNA molecule that is encoded by PP1-87B (SEQ ID NO:1), RPA70 (SEQ ID NO:2), D_vir_Contig0011_87B protein phosphatase or PP1-87B (SEQ ID NO:3), D_vir_c43870_RPA70 or RPA70 region 1 (SEQ ID NO:4), D_vir_c18764_RPA70 or RPA70 region 2 (SEQ ID NO:5), D_vir_c7971 RPA70 or RPA70 region 3 (SEQ ID NO:6), Brahma (SEQ ID NO:103); F5XY5 KV01 DBWKA_brahma_587-707 or Brahma Reg1 (SEQ ID NO:104), D_vir_Contig[0001]_brahma_949-1126 or Brahma Reg2 (SEQ ID NO:105), and F5XY5 KV01D0IM6_brahma_1237-1333 or Brahma Reg3 (SEQ ID NO:106); iRNA molecules (e.g., dsRNAs, siRNAs, miRNAs and hpRNAs) that comprise at least one nucleotide sequence that is specifically complementary to all or part of PP1-87B (SEQ ID NO:1), RPA70 (SEQ ID NO:2), D_vir_Contig0011_87B protein phosphatase or PP1-87B (SEQ ID NO:3), D_vir_c43870_RPA70 or RPA70 region 1 (SEQ ID NO:4), D_vir_c18764_RPA70 or RPA70 region 2 (SEQ ID NO:5), D_vir_c7971_RPA70 or RPA70 region 3 (SEQ ID NO:6), Brahma (SEQ ID NO:103); F5XY5 KV01DBWKA_brahma_587-707 or Brahma Reg1 (SEQ ID NO:104), D_vir_Contig[0001]_brahma_949-1126 or Brahma Reg2 (SEQ ID NO:105), and F5XY5 KV01D0IM6_brahma_1237-1333 or Brahma Reg3 (SEQ ID NO:106); iRNA molecules (e.g., dsRNAs, siRNAs, miRNAs and hpRNAs) that comprise at least one nucleotide sequence that is specifically complementary to PP1-87B (SEQ ID NO:1), RPA70 (SEQ ID NO:2), D_vir_Contig0011_87B protein phosphatase or PP1-87B (SEQ ID NO:3), D_vir_c43870_RPA70 or RPA70 region 1 (SEQ ID NO:4), D_vir_c18764 RPA70 or RPA70 region 2 (SEQ ID NO:5), D_vir_c7971_RPA70 or RPA70 region 3 (SEQ ID NO:6), Brahma (SEQ ID NO:103); F5XY5 KV01DBWKA_brahma_587-707 or Brahma Reg1 (SEQ ID NO:104), D_vir_Contig[0001]_brahma_949-1126 or Brahma Reg2 (SEQ ID NO:105), and F5XY5 KV01D0IM6_brahma_1237-1333 or Brahma Reg3 (SEQ ID NO:106); iRNA molecules (e.g., dsRNAs, siRNAs, miRNAs and hpRNAs) that comprise at least one nucleotide sequence that is specifically complementary to all or part of PP1-87B (SEQ ID NO:1), RPA70 (SEQ ID NO:2), D_vir_Contig0011_87B protein phosphatase or PP1-87B (SEQ ID NO:3), D_vir_c43870_RPA70 or RPA70 region 1 (SEQ ID NO:4), D_vir_c18764_RPA70 or RPA70 region 2 (SEQ ID NO:5), D_vir_c7971_RPA70 or RPA70 region 3 (SEQ ID NO:6), Brahma (SEQ ID NO:103); F5XY5 KV01DBWKA_brahma_587-707 or Brahma Reg1 (SEQ ID NO:104), D_vir_Contig[0001]_brahma_949-1126 or Brahma Reg2 (SEQ ID NO:105), and F5XY5 KV01D0IM6_brahma_1237-1333 or Brahma Reg3 (SEQ ID NO:106); cDNA sequences that may be used for the production of dsRNA molecules, siRNA molecules, miRNA and/or hpRNA molecules that are specifically complementary to PP1-87B (SEQ ID NO:1), RPA70 (SEQ ID NO:2), D_vir_Contig0011_87B protein phosphatase or PP1-87B (SEQ ID NO:3), D_vir_c43870 RPA70 or RPA70 region 1 (SEQ ID NO:4), D_vir_c18764_RPA70 or RPA70 region 2

(SEQ ID NO:5), D_vir_c7971 RPA70 or RPA70 region 3 (SEQ ID NO:6), Brahma (SEQ ID NO:103); F5XY5 KV01DBWKAbrahma_587-707 or Brahma Reg1 (SEQ ID NO:104), D_vir_Contig[0001]_brahma_949-1126 or Brahma Reg2 (SEQ ID NO:105), and F5XY5 KV01D0IM6_brahma_1237-1333 or Brahma Reg3 (SEQ ID NO:106); iRNA molecules (e.g., dsRNAs, siRNAs, miR-NAs and hpRNAs) that comprise at least one nucleotide sequence that is specifically complementary to all or part of PP1-87B (SEQ ID NO:1), RPA70 (SEQ ID NO:2), D_vir_Contig0011_87B protein phosphatase or PP1-87B (SEQ ID NO:3), D_vir_c43870 RPA70 or RPA70 region 1 (SEQ ID NO:4), D_vir_c18764_RPA70 or RPA70 region 2 (SEQ ID NO:5), D_vir_c7971_RPA70 or RPA70 region 3 (SEQ ID NO:6), Brahma (SEQ ID NO:103); F5XY5 KV01DBWKA_brahma_587-707 or Brahma Reg1 (SEQ ID NO:104), D_vir_Contig[0001]_brahma_949-1126 or Brahma Reg2 (SEQ ID NO:105), and F5XY5 KV01D0IM6_brahma_1237-1333 or Brahma Reg3 (SEQ ID NO:106); and recombinant DNA constructs for use in achieving stable transformation of particular host targets, wherein a transformed host target comprises one or more of the foregoing nucleic acid molecules.

B. Nucleic Acid Molecules

The present invention provides, inter alia, iRNA (e.g., dsRNA, siRNA, miRNA and hpRNA) molecules that inhibit target gene expression in a cell, tissue, or organ of a coleopteran pest; and DNA molecules capable of being expressed as an iRNA molecule in a cell or microorganism to inhibit target gene expression in a cell, tissue, or organ of a coleopteran pest.

Some embodiments of the invention provide an isolated nucleic acid molecule comprising the nucleotide sequence of: SEQ ID NO:7; the complement of SEQ ID NO:7; a fragment of at least 19 contiguous nucleotides of SEQ ID NO:7; the complement of a fragment of at least 19 contiguous nucleotides of SEQ ID NO:7; a native coding sequence of a *Diabrotica* organism (e.g., WCR) comprising SEQ ID NO:7; the complement of a native coding sequence of a *Diabrotica* organism comprising SEQ ID NO:7; a native non-coding sequence of a *Diabrotica* organism that is transcribed into a native RNA molecule comprising SEQ ID NO:7; the complement of a native non-coding sequence of a *Diabrotica* organism that is transcribed into a native RNA molecule comprising SEQ ID NO:7; a fragment of at least 19 contiguous nucleotides of a native coding sequence of a *Diabrotica* organism comprising SEQ ID NO:7; the complement of a fragment of at least 19 contiguous nucleotides of a native coding sequence of a *Diabrotica* organism comprising SEQ ID NO:7; a fragment of at least 19 contiguous nucleotides of a native non-coding sequence of a *Diabrotica* organism that is transcribed into a native RNA molecule comprising SEQ ID NO:7; and the complement of a fragment of at least 19 contiguous nucleotides of a native non-coding sequence of a *Diabrotica* organism that is transcribed into a native RNA molecule comprising SEQ ID NO:7. In particular embodiments, contact with or uptake by a coleopteran pest of the isolated nucleic acid sequence inhibits the growth, development, reproduction and/or feeding of the coleopteran pest.

In some embodiments, an isolated nucleic acid molecule of the invention may comprise at least one (e.g., one, two, three, or more) nucleotide sequence(s) selected from the group consisting of: SEQ ID NO:1; the complement of SEQ ID NO:1; SEQ ID NO:2; the complement of SEQ ID NO:2; SEQ ID NO:3; the complement of SEQ ID NO:3; SEQ ID NO:4; the complement of SEQ ID NO:4; SEQ ID NO:5; the complement of SEQ ID NO:5; SEQ ID NO:6; the complement of SEQ ID NO:6; SEQ ID NO:103; the complement of SEQ ID NO:103; SEQ ID NO:104; the complement of SEQ ID NO:104; SEQ ID NO:105; the complement of SEQ ID NO:105; SEQ ID NO:106; the complement of SEQ ID NO:106; a fragment of at least 19 contiguous nucleotides of any of SEQ ID NOs:1-6 and 103-106; the complement of a fragment of at least 19 contiguous nucleotides of any of SEQ ID NOs:1-6 and 103-106; a native coding sequence of a *Diabrotica* organism comprising any of SEQ ID NOs:1-6 and 103-106; the complement of a native coding sequence of a *Diabrotica* organism comprising any of SEQ ID NOs:1-6 and 103-106; a native non-coding sequence of a *Diabrotica* organism that is transcribed into a native RNA molecule comprising any of SEQ ID NOs:1-6 and 103-106; the complement of a native non-coding sequence of a *Diabrotica* organism that is transcribed into a native RNA molecule comprising any of SEQ ID NOs:1-6 and 103-106; a fragment of at least 19 contiguous nucleotides of a native coding sequence of a *Diabrotica* organism comprising any of SEQ ID NOs:1-6 and 103-106; the complement of a fragment of at least 19 contiguous nucleotides of a native coding sequence of a *Diabrotica* organism comprising any of SEQ ID NOs:1-6 and 103-106; a fragment of at least 19 contiguous nucleotides of a native non-coding sequence of a *Diabrotica* organism that is transcribed into a native RNA molecule comprising any of SEQ ID NOs:1-6 and 103-106; and the complement of a fragment of at least 19 contiguous nucleotides of a native non-coding sequence of a *Diabrotica* organism that is transcribed into a native RNA molecule comprising any of SEQ ID NOs:1-6 and 103-106. In particular embodiments, contact with or uptake by a coleopteran pest of the isolated nucleic acid sequence inhibits the growth, development, reproduction and/or feeding of the coleopteran pest.

In particular examples, an isolated nucleic acid molecule of the invention may comprise at least one (e.g., one, two, three, or more) segments of SEQ ID NO:1-7, 103, and/or 106 (e.g., a nucleotide sequence selected from the group consisting of SEQ ID NOs:99-102 and 107, which can be found as fragments in SEQ ID NOs:3-6 and 106).

In some embodiments, a nucleic acid molecule of the invention may comprise at least one (e.g., one, two, three, or more) DNA sequence(s) capable of being expressed as an iRNA molecule in a cell or microorganism to inhibit target gene expression in a cell, tissue, or organ of a coleopteran pest. Such DNA sequence(s) may be operably linked to a promoter sequence that functions in a cell comprising the DNA molecule to initiate or enhance the transcription of the encoded RNA capable of forming a dsRNA molecule(s). In one embodiment, the at least one (e.g., one, two, three, or more) DNA sequence(s) may be derived from the nucleotide sequence of SEQ ID NO:7. Derivatives of SEQ ID NO:7 includes fragments of SEQ ID NO:7. In some embodiments, such a fragment may comprise, for example, at least about 19 contiguous nucleotides of SEQ ID NO:7, or a complement thereof. Thus, such a fragment may comprise, for example, 19, 20, 21, 22, 23, 24, 25, 26, 27, 28, 29, or 30 contiguous nucleotides of SEQ ID NO:7, or a complement thereof. In these and further embodiments, such a fragment may comprise, for example, more than about 19 contiguous nucleotides of SEQ ID NO:7, or a complement thereof. Thus, a fragment of SEQ ID NO:7 may comprise, for example, 19, 20, 21, 25, 30, 40, 50, 60, 70, 80, 90, 100, or more contiguous nucleotides of SEQ ID NO:7, or a complement thereof.

In particular embodiments, at least one DNA sequence(s) capable of being expressed as an iRNA molecule in a cell or microorganism to inhibit target gene expression in a cell, tissue, or organ of a coleopteran pest may comprise DNA sequence(s) that are derived from a nucleotide sequence selected from the group consisting of SEQ ID NOs:1-6 and 103-106. Derivatives of a nucleotide sequence selected from the group consisting of SEQ ID NOs:1-6 and 103-106 include fragments of SEQ ID NOs:1-6 and/or 103-106. In some embodiments, such a fragment may comprise, for example, at least about 19 contiguous nucleotides of SEQ ID NOs:1-6 and/or 103-106, or a complement thereof. Thus, such a fragment may comprise, for example, 19, 20, 21, 22, 23, 24, 25, 26, 27, 28, 29, or 30 contiguous nucleotides of SEQ ID NOs:1-6 and/or 103-106, or a complement thereof. In these and further embodiments, such a fragment may comprise, for example, more than about 19 contiguous nucleotides of SEQ ID NOs:1-6 and/or 103-106, or a complement thereof. Thus, a fragment of a nucleotide sequence selected from the group consisting of SEQ ID NOs:1-6 and 103-106 may comprise, for example, 19, 20, 21, 25, 30, 40, 50, 60, 70, 80, 90, 100, or more contiguous nucleotides of the SEQ ID NOs:1-6 and/or 103-106, or a complement thereof. In some particular embodiments, the fragments may comprise, for example, more than about 19 contiguous nucleotides of a nucleotide sequence selected from the group consisting of SEQ ID NOs:99-102, or a complement thereof. In certain embodiments, the fragments may comprise, for example, the 14 contiguous nucleotides of SEQ ID NO:107, or a complement thereof.

Some embodiments comprise introducing partial- or fully-stabilized dsRNA molecules into a coleopteran pest to inhibit expression of a target gene in a cell, tissue, or organ of the coleopteran pest. When expressed as an iRNA molecule (e.g., dsRNA, siRNA, miRNA, and hpRNA) and taken up by a coleopteran pest, nucleic acid sequences comprising one or more fragments of any of SEQ ID NOs:1-7 may cause one or more of death, growth inhibition, change in sex ratio, reduction in brood size, cessation of infection, and/or cessation of feeding by a coleopteran pest. For example, in some embodiments, a dsRNA molecule comprising a nucleotide sequence including about 19 to about 300 nucleotides that are substantially homologous to a coleopteran pest target gene sequence and comprising one or more fragments of the nucleotide sequence of SEQ ID NO:7 is provided. These and further dsRNA molecules may further comprise one or more fragments of a nucleotide sequence selected from the group consisting of SEQ ID NOs:1-6. Expression of such a dsRNA molecule may, for example, lead to mortality and/or growth inhibition in a coleopteran pest that takes up the dsRNA molecule.

In certain embodiments, dsRNA molecules provided by the invention comprise nucleotide sequences complementary to a target gene comprising SEQ ID NO:7 and/or nucleotide sequences complementary to a fragment of SEQ ID NO:7, the inhibition of which target gene in a coleopteran pest results in the reduction or removal of a protein or nucleotide sequence agent that is essential for the coleopteran pest's growth, development, or other biological function. A selected nucleotide sequence may exhibit from about 80% to about 100% sequence identity to SEQ ID NO:7, a contiguous fragment of the nucleotide sequence set forth in SEQ ID NO:7, or the complement of either of the foregoing. For example, a selected nucleotide sequence may exhibit about 81%; about 82%; about 83%; about 84%; about 85%; about 86%; about 87%; about 88%; about 89%; about 90%; about 91%; about 92%; about 93%; about 94% about 95%; about 96%; about 97%; about 98%; about 98.5%; about 99%; about 99.5%; or about 100% sequence identity to SEQ ID NO:7, a contiguous fragment of the nucleotide sequence set forth in SEQ ID NO:7, or the complement of either of the foregoing. In particular embodiments, a dsRNA molecule provided by the invention may further comprise one or more nucleotide sequences complementary to a target gene comprising one of SEQ ID NOs:1-6, the inhibition of which target gene in a coleopteran pest results in the reduction or removal of a protein or nucleotide sequence agent that is essential for the coleopteran pest's growth, development, or other biological function.

In some embodiments, a DNA molecule capable of being expressed as an iRNA molecule in a cell or microorganism to inhibit target gene expression may comprise a single nucleotide sequence that is specifically complementary to all or part of a native nucleic acid sequence found in one or more target coleopteran pest species, or the DNA molecule can be constructed as a chimera from a plurality of such specifically complementary sequences.

In some embodiments, a nucleic acid molecule may comprise a first and a second nucleotide sequence separated by a "spacer sequence." A spacer sequence may be a region comprising any sequence of nucleotides that facilitates secondary structure formation between the first and second nucleotide sequences, where this is desired. In one embodiment, the spacer sequence is part of a sense or antisense coding sequence for mRNA. The spacer sequence may alternatively comprise any combination of nucleotides or homologues thereof that are capable of being linked covalently to a nucleic acid molecule.

For example, in some embodiments, the DNA molecule may comprise a nucleotide sequence coding for one or more different RNA molecules, wherein each of the different RNA molecules comprises a first nucleotide sequence and a second nucleotide sequence, wherein the first and second nucleotide sequences are complementary to each other. The first and second nucleotide sequences may be connected within an RNA molecule by a spacer sequence. The spacer sequence may constitute part of the first nucleotide sequence or the second nucleotide sequence. Expression of an RNA molecule comprising the first and second nucleotide sequences may lead to the formation of a dsRNA molecule of the present invention, by specific intramolecular base-pairing of the first and second nucleotide sequences. The first nucleotide sequence or the second nucleotide sequence may be substantially identical to a nucleic acid sequence native to a coleopteran pest (e.g., a target gene, or transcribed non-coding sequence), a derivative thereof, or a complementary sequence thereto.

dsRNA nucleic acid molecules comprise double strands of polymerized ribonucleotide sequences, and may include modifications to either the phosphate-sugar backbone or the nucleoside. Modifications in RNA structure may be tailored to allow specific inhibition. In one embodiment, dsRNA molecules may be modified through a ubiquitous enzymatic process so that siRNA molecules may be generated. This enzymatic process may utilize an RNAse III enzyme, such as DICER in eukaryotes, either in vitro or in vivo. See Elbashir et al. (2001) Nature 411:494-8; and Hamilton and Baulcombe (1999) Science 286(5441):950-2. DICER or functionally-equivalent RNAse III enzymes cleave larger dsRNA strands and/or hpRNA molecules into smaller oligonucleotides (e.g., siRNAs), each of which is about 19-25 nucleotides in length. The siRNA molecules produced by these enzymes have 2 to 3 nucleotide 3' overhangs, and 5' phosphate and 3' hydroxyl termini. The siRNA molecules generated by RNAse III enzymes are unwound and separated into single-stranded RNA in the cell. The siRNA molecules then specifically hybridize with RNA sequences transcribed from a target gene, and both RNA molecules are subsequently degraded by an inherent cellular RNA-degrading mechanism. This process may result in the effective degradation or removal of the RNA sequence encoded by the target gene in the target organism. The outcome is the post-transcriptional silencing of the targeted gene. In some embodiments, siRNA molecules produced by endogenous RNAse III enzymes from heterologous nucleic acid molecules may efficiently mediate the down-regulation of target genes in coleopteran pests.

In some embodiments, a nucleic acid molecule of the invention may include at least one non-naturally occurring nucleotide sequence that can be transcribed into a single-stranded RNA molecule capable of forming a dsRNA molecule in vivo through intermolecular hybridization. Such dsRNA sequences typically self-assemble, and can be provided in the nutrition source of a coleopteran pest to achieve the post-transcriptional inhibition of a target gene. In these and further embodiments, a nucleic acid molecule of the invention may comprise two different non-naturally occurring nucleotide sequences, each of which is specifically complementary to a different target gene in a coleopteran pest. When such a nucleic acid molecule is provided as a dsRNA molecule to a coleopteran pest, the dsRNA molecule inhibits the expression of at least two different target genes in the coleopteran pest.

C. Obtaining Nucleic Acid Molecules

A variety of native sequences in coleopteran pests may be used as target sequences for the design of nucleic acid molecules of the invention, such as iRNAs and DNA molecules encoding iRNAs. Selection of native sequences is not, however, a straight-forward process. Only a small number of native sequences in the coleopteran pest will be effective targets. For example, it cannot be predicted with certainty whether a particular native sequence can be effectively down-regulated by nucleic acid molecules of the invention, or whether down-regulation of a particular native sequence will have a detrimental effect on the growth, viability, proliferation, and/or reproduction of the coleopteran pest. The vast majority of native coleopteran pest sequences, such as ESTs isolated therefrom (for example, as listed in U.S. Pat. No. 7,612,194), do not have a detrimental effect on the growth, viability, proliferation, and/or reproduction of the coleopteran pest, such as WCR or NCR. Neither is it predictable which of the native sequences which may have a detrimental effect on a coleopteran pest are able to be used in recombinant techniques for expressing nucleic acid molecules complementary to such native sequences in a host plant and providing the detrimental effect on the coleopteran pest upon feeding without causing harm to the host plant.

In some embodiments, nucleic acid molecules of the invention (e.g., dsRNA molecules to be provided in the host plant of a coleopteran pest) are selected to target cDNA sequences that encode proteins or parts of proteins essential for coleopteran pest survival, such as amino acid sequences involved in metabolic or catabolic biochemical pathways, cell division, reproduction, energy metabolism, digestion, host plant recognition, and the like. As described herein, ingestion of compositions by a target organism containing one or more dsRNAs, at least one segment of which is specifically complementary to at least a substantially identical segment of RNA produced in the cells of the target pest organism, can result in the death or other inhibition of the target. A nucleotide sequence, either DNA or RNA, derived from a coleopteran pest can be used to construct plant cells resistant to infestation by the coleopteran pests. The host plant of the coleopteran pest (e.g., Z. mays or G. max), for example, can be transformed to contain one or more of the nucleotide sequences derived from the coleopteran pest as provided herein. The nucleotide sequence transformed into the host may encode one or more RNAs that form into a dsRNA sequence in the cells or biological fluids within the transformed host, thus making the dsRNA available if/when the coleopteran pest forms a nutritional relationship with the transgenic host. This may result in the suppression of expression of one or more genes in the cells of the coleopteran pest, and ultimately death or inhibition of its growth or development.

Thus, in some embodiments, a gene is targeted that is essentially involved in the growth, development and reproduction of a coleopteran pest. Other target genes for use in the present invention may include, for example, those that play important roles in coleopteran pest viability, movement, migration, growth, development, infectivity, establishment of feeding sites and reproduction. A target gene may therefore be a housekeeping gene or a transcription factor. Additionally, a native coleopteran pest nucleotide sequence for use in the present invention may also be derived from a homolog (e.g., an ortholog), of a plant, viral, bacterial or insect gene, the function of which is known to those of skill in the art, and the nucleotide sequence of which is specifically hybridizable with a target gene in the genome of the target coleopteran pest. Methods of identifying a homolog of a gene with a known nucleotide sequence by hybridization are known to those of skill in the art.

In some embodiments, the invention provides methods for obtaining a nucleic acid molecule comprising a nucleotide sequence for producing an iRNA (e.g., dsRNA, siRNA, miRNA, and hpRNA) molecule. One such embodiment comprises: (a) analyzing one or more target gene(s) for their expression, function, and phenotype upon dsRNA-mediated gene suppression in a coleopteran pest; (b) probing a cDNA or gDNA library with a probe comprising all or a portion of a nucleotide sequence or a homolog thereof from a targeted coleopteran pest that displays an altered (e.g., reduced) growth or development phenotype in a dsRNA-mediated suppression analysis; (c) identifying a DNA clone that specifically hybridizes with the probe; (d) isolating the DNA clone identified in step (b); (e) sequencing the cDNA or gDNA fragment that comprises the clone isolated in step (d), wherein the sequenced nucleic acid molecule comprises all or a substantial portion of the RNA sequence or a homolog thereof; and (f) chemically synthesizing all or a substantial portion of a gene sequence, or a siRNA or miRNA or hpRNA or mRNA or dsRNA.

In further embodiments, a method for obtaining a nucleic acid fragment comprising a nucleotide sequence for producing a substantial portion of an iRNA (e.g., dsRNA, siRNA, miRNA, and hpRNA) molecule includes: (a) synthesizing first and second oligonucleotide primers specifically complementary to a portion of a native nucleotide sequence from a targeted coleopteran pest; and (b) amplifying a cDNA or gDNA insert present in a cloning vector using the first and second oligonucleotide primers of step (a), wherein the amplified nucleic acid molecule comprises a substantial portion of a siRNA or miRNA or hpRNA or mRNA or dsRNA molecule.

Nucleic acids of the invention can be isolated, amplified, or produced by a number of approaches. For example, an iRNA (e.g., dsRNA, siRNA, miRNA, and hpRNA) molecule may be obtained by PCR amplification of a target nucleic acid sequence (e.g., a target gene or a target transcribed non-coding sequence) derived from a gDNA or cDNA library, or portions thereof. DNA or RNA may be extracted from a target organism, and nucleic acid libraries may be prepared therefrom using methods known to those ordinarily skilled in the art. gDNA or cDNA libraries generated from a target organism may be used for PCR amplification and sequencing of target genes. A confirmed PCR product may be used as a template for in vitro transcription to generate sense and antisense RNA with minimal promoters. Alternatively, nucleic acid molecules may be synthesized by any of a number of techniques (See, e.g., Ozaki et al. (1992) Nucleic Acids Research, 20: 5205-5214; and Agrawal et al. (1990) Nucleic Acids Research, 18: 5419-5423), including use of an automated DNA synthesizer (for example, a P.E. Biosystems, Inc. (Foster City, Calif.) model 392 or 394 DNA/RNA Synthesizer), using standard chemistries, such as phosphoramidite chemistry. See, e.g., Beaucage et al. (1992) Tetrahedron, 48: 2223-2311; U.S. Pat. Nos. 4,980,460, 4,725,677, 4,415,732, 4,458,066, and 4,973,679. Alternative chemistries resulting in non-natural backbone groups, such as phosphorothioate, phosphoramidate, and the like, can also be employed.

An RNA, dsRNA, siRNA, miRNA, or hpRNA molecule of the present invention may be produced chemically or enzymatically by one skilled in the art through manual or automated reactions, or in vivo in a cell comprising a nucleic acid molecule comprising a sequence encoding the RNA, dsRNA, siRNA, miRNA, or hpRNA molecule. RNA may also be produced by partial or total organic synthesis—any modified ribonucleotide can be introduced by in vitro enzymatic or organic synthesis. An RNA molecule may be synthesized by a cellular RNA polymerase or a bacteriophage RNA polymerase (e.g., T3 RNA polymerase, T7 RNA polymerase, and SP6 RNA polymerase). Expression constructs useful for the cloning and expression of nucleotide sequences are known in the art. See, e.g., International PCT Publication No. WO97/32016; and U.S. Pat. Nos. 5,593,874, 5,698,425, 5,712,135, 5,789,214, and 5,804,693. RNA molecules that are synthesized chemically or by in vitro enzymatic synthesis may be purified prior to introduction into a cell. For example, RNA molecules can be purified from a mixture by extraction with a solvent or resin, precipitation, electrophoresis, chromatography, or a combination thereof. Alternatively, RNA molecules that are synthesized chemically or by in vitro enzymatic synthesis may be used with no or a minimum of purification, for example, to avoid losses due to sample processing. The RNA molecules may be dried for storage or dissolved in an aqueous solution. The solution may contain buffers or salts to promote annealing, and/or stabilization of dsRNA molecule duplex strands.

In embodiments, a dsRNA molecule may be formed by a single self-complementary RNA strand or from two complementary RNA strands. dsRNA molecules may be synthesized either in vivo or in vitro. An endogenous RNA polymerase of the cell may mediate transcription of the one or two RNA strands in vivo, or cloned RNA polymerase may be used to mediate transcription in vivo or in vitro. Post-transcriptional inhibition of a target gene in a coleopteran pest may be host-targeted by specific transcription in an organ, tissue, or cell type of the host (e.g., by using a tissue-specific promoter); stimulation of an environmental condition in the host (e.g., by using an inducible promoter that is responsive to infection, stress, temperature, and/or chemical inducers); and/or engineering transcription at a developmental stage or age of the host (e.g., by using a developmental stage-specific promoter). RNA strands that form a dsRNA molecule, whether transcribed in vitro or in vivo, may or may not be polyadenylated, and may or may not be capable of being translated into a polypeptide by a cell's translational apparatus.

D. Recombinant Vectors and Host Cell Transformation

In some embodiments, the invention also provides a DNA molecule for introduction into a cell (e.g., a bacterial cell, a yeast cell, or a plant cell), wherein the DNA molecule comprises a nucleotide sequence that, upon expression to RNA and ingestion by a coleopteran pest, achieves suppression of a target gene in a cell, tissue, or organ of the coleopteran pest. Thus, some embodiments provide a recombinant nucleic acid molecule comprising a nucleic acid sequence capable of being expressed as an iRNA (e.g., dsRNA, siRNA, miRNA, and hpRNA) molecule in a plant cell to inhibit target gene expression in a coleopteran pest. In order to initiate or enhance expression, such recombinant nucleic acid molecules may comprise one or more regulatory sequences, which regulatory sequences may be operably linked to the nucleic acid sequence capable of being expressed as an iRNA. Methods to express a gene suppression molecule in plants are known, and may be used to express a nucleotide sequence of the present invention. See, e.g., International PCT Publication No. WO06/073727; and U.S. Patent Publication No. 2006/0200878 A1)

In specific embodiments, a recombinant DNA molecule of the invention may comprise a nucleic acid sequence encoding an RNA that may form a dsRNA molecule. Such recombinant DNA molecules may encode RNAs that may form dsRNA molecules capable of inhibiting the expression of endogenous target gene(s) in a coleopteran pest cell upon ingestion. In many embodiments, a transcribed RNA may form a dsRNA molecule that may be provided in a stabilized form; e.g., as a hairpin and stem and loop structure.

In these and further embodiments, one strand of a dsRNA molecule may be formed by transcription from a nucleotide sequence which is substantially homologous to the nucleotide sequence of SEQ ID NO:7; the complement of SEQ ID NO:7; a fragment of at least 19 contiguous nucleotides of SEQ ID NO:7; the complement of a fragment of at least 19 contiguous nucleotides of SEQ ID NO:7; a native coding sequence of a *Diabrotica* organism (e.g., WCR) comprising SEQ ID NO:7; the complement of a native coding sequence of a *Diabrotica* organism comprising SEQ ID NO:7; a native non-coding sequence of a *Diabrotica* organism that is transcribed into a native RNA molecule comprising SEQ ID NO:7; the complement of a native non-coding sequence of a *Diabrotica* organism that is transcribed into a native RNA molecule comprising SEQ ID NO:7; a fragment of at least 19 contiguous nucleotides of a native coding sequence of a *Diabrotica* organism (e.g., WCR) comprising SEQ ID NO:7; the complement of a fragment of at least 19 contiguous nucleotides of a native coding sequence of a *Diabrotica* organism comprising SEQ ID NO:7; a fragment of at least 19 contiguous nucleotides of a native non-coding sequence of a *Diabrotica* organism that is transcribed into a native RNA molecule comprising SEQ ID NO:7; and the complement of a fragment of at least 19 contiguous nucleotides of a native non-coding sequence of a *Diabrotica* organism that is transcribed into a native RNA molecule comprising SEQ ID NO:7.

One strand of a dsRNA molecule may also be formed by transcription from a nucleotide sequence which is substantially homologous to a nucleotide sequence selected from the group consisting of: SEQ ID NO:1; the complement of SEQ ID NO:1; SEQ ID NO:2; the complement of SEQ ID NO:2; SEQ ID NO:3; the complement of SEQ ID NO:3; SEQ ID NO:4; the complement of SEQ ID NO:4; SEQ ID NO:5; the complement of SEQ ID NO:5; SEQ ID NO:6; the complement of SEQ ID NO:6; SEQ ID NO:103; the complement of SEQ ID NO:103; SEQ ID NO:104; the complement of SEQ ID NO:104; SEQ ID NO:105; the complement of SEQ ID NO:105; SEQ ID NO:106; the complement of SEQ ID NO:106; a fragment of at least 19 contiguous nucleotides of any of SEQ ID NOs:1-6 and 103-106; the complement of a fragment of at least 19 contiguous nucleotides of any of SEQ ID NOs:1-6 and 103-106; a native coding sequence of a *Diabrotica* organism (e.g., WCR) comprising any of SEQ ID NOs:1-6 and 103-106; the complement of a native coding sequence of a *Diabrotica* organism (e.g., WCR) comprising any of SEQ ID NOs:1-6 and 103-106; a native non-coding sequence of a *Diabrotica* organism that is transcribed into a native RNA molecule comprising any of SEQ ID NOs:1-6 and 103-106; the complement of a native non-coding sequence of a *Diabrotica* organism that is transcribed into a native RNA molecule comprising any of SEQ ID NOs:1-6 and 103-106; a fragment of at least 19 contiguous nucleotides of a native coding sequence of a *Diabrotica* organism (e.g., WCR) comprising any of SEQ ID NOs:1-6 and 103-106; the complement of a fragment of at least 19 contiguous nucleotides of a native coding sequence of a *Diabrotica* organism comprising any of SEQ ID NOs:1-6 and 103-106; a fragment of at least 19 contiguous nucleotides of a native non-coding sequence of a *Diabrotica* organism that is transcribed into a native RNA molecule comprising any of SEQ ID NOs:1-6 and 103-106; and the complement of a fragment of at least 19 contiguous nucleotides of a native non-coding sequence of a *Diabrotica* organism that is transcribed into a native RNA molecule comprising any of SEQ ID NOs:1-6 and 103-106.

In particular embodiments, a recombinant DNA molecule encoding a dsRNA molecule may comprise at least two nucleotide sequences within a transcribed sequence, wherein the sequences are arranged such that the transcribed sequence comprises one of the nucleotide sequences in a sense orientation, and another of the nucleotide sequences (comprising the complement of the first nucleotide sequence) is in an antisense orientation, relative to at least one promoter, wherein the sense nucleotide sequence and the antisense nucleotide sequence are linked or connected by a spacer sequence of from about five (~5) to about one thousand (~1000) nucleotides. The spacer sequence may form a loop between the sense and antisense sequences in the dsRNA molecule. The sense nucleotide sequence or the antisense nucleotide sequence may be substantially homologous to the nucleotide sequence of a target gene (e.g., a gene comprising one of SEQ ID NOs:1-7 and 103-106) or fragment thereof. In some embodiments, however, a recombinant DNA molecule may encode an RNA that may form a dsRNA molecule without a spacer sequence. In embodiments, a sense coding sequence and an antisense coding sequence may be different lengths.

Sequences identified as having a deleterious effect on coleopteran pests or a plant-protective effect with regard to coleopteran pests may be readily incorporated into expressed dsRNA molecules through the creation of appropriate expression cassettes in a recombinant nucleic acid molecule of the invention. For example, such sequences may be expressed as a hairpin with stem and loop structure by taking a first segment corresponding to a target gene sequence (e.g., any of SEQ ID NOs:1-7 and 103-106, and fragments thereof); linking this sequence to a second segment spacer region that is not homologous or complementary to the first segment; and linking this to a third segment, wherein at least a portion of the third segment is substantially complementary to the first segment. Such a construct forms a stem and loop structure by intramolecular base-pairing of the first segment with the third segment, wherein the loop structure forms and comprises the second segment. See, e.g., U.S. Patent Publication Nos. 2002/0048814 and 2003/0018993; and International PCT Publication Nos. WO94/01550 and WO98/05770. A dsRNA molecule may be generated, for example, in the form of a double-stranded structure such as a stem-loop structure (e.g., hairpin), whereby production of siRNA targeted for a native coleopteran pest sequence is enhanced by co-expression of a fragment of the targeted gene, for instance on an additional plant expressible cassette, that leads to enhanced siRNA production, or reduces methylation to prevent transcriptional gene silencing of the dsRNA hairpin promoter.

Embodiments of the invention include introduction of a recombinant nucleic acid molecule of the present invention into a plant (i.e., transformation) to achieve coleopteran pest-inhibitory levels of expression of one or more iRNA molecules. A recombinant DNA molecule may, for example, be a vector, such as a linear or a closed circular plasmid. The vector system may be a single vector or plasmid, or two or more vectors or plasmids that together contain the total DNA to be introduced into the genome of a host. In addition, a vector may be an expression vector. Nucleic acid sequences of the invention can, for example, be suitably inserted into a vector under the control of a suitable promoter that functions in one or more hosts to drive expression of a linked coding sequence or other DNA sequence. Many vectors are available for this purpose, and selection of the appropriate vector will depend mainly on the size of the nucleic acid to be inserted into the vector and the particular host cell to be transformed with the vector. Each vector contains various components depending on its function (e.g., amplification of DNA or expression of DNA) and the particular host cell with which it is compatible.

To impart coleopteran pest resistance to a transgenic plant, a recombinant DNA may, for example, be transcribed into an iRNA molecule (e.g., an RNA molecule that forms a dsRNA molecule) within the tissues or fluids of the recombinant plant. An iRNA molecule may comprise a nucleotide sequence that is substantially homologous and specifically hybridizable to a corresponding transcribed nucleotide sequence within a coleopteran pest that may cause damage to the host plant species. The coleopteran pest may contact the iRNA molecule that is transcribed in cells of the transgenic host plant, for example, by ingesting cells or fluids of the transgenic host plant that comprise the iRNA molecule. Thus, expression of a target gene is suppressed by the iRNA molecule within coleopteran pests that infest the transgenic host plant. In some embodiments, suppression of expression of the target gene in the target coleopteran pest may result in the plant being resistant to attack by the pest.

In order to enable delivery of iRNA molecules to a coleopteran pest in a nutritional relationship with a plant cell that has been transformed with a recombinant nucleic acid molecule of the invention, expression (i.e., transcription) of iRNA molecules in the plant cell is required. Thus, a recombinant nucleic acid molecule may comprise a nucleotide sequence of the invention operably linked to one or more regulatory sequences, such as a heterologous promoter sequence that functions in a host cell, such as a bacterial cell wherein the nucleic acid molecule is to be amplified, and a plant cell wherein the nucleic acid molecule is to be expressed.

Promoters suitable for use in nucleic acid molecules of the invention include those that are inducible, viral, synthetic, or constitutive, all of which are well known in the art. Non-limiting examples describing such promoters include U.S. Pat. No. 6,437,217 (maize RS81 promoter); U.S. Pat. No. 5,641,876 (rice actin promoter); U.S. Pat. No. 6,426,446 (maize RS324 promoter); U.S. Pat. No. 6,429,362 (maize PR-1 promoter); U.S. Pat. No. 6,232,526 (maize A3 promoter); U.S. Pat. No. 6,177,611 (constitutive maize promoters); U.S. Pat. Nos. 5,322,938, 5,352,605, 5,359,142, and 5,530,196 (CaMV 35S promoter); U.S. Pat. No. 6,433,252 (maize L3 oleosin promoter); U.S. Pat. No. 6,429,357 (rice actin 2 promoter, and rice actin 2 intron); U.S. Pat. No. 6,294,714 (light-inducible promoters); U.S. Pat. No. 6,140,078 (salt-inducible promoters); U.S. Pat. No. 6,252,138 (pathogen-inducible promoters); U.S. Pat. No. 6,175,060 (phosphorous deficiency-inducible promoters); U.S. Pat. No. 6,388,170 (bidirectional promoters); U.S. Pat. No. 6,635,806 (gamma-coixin promoter); and U.S. Patent Publication No. 2009/757,089 (maize chloroplast aldolase promoter). Additional promoters include the nopaline synthase (NOS) promoter (Ebert et al. (1987) Proc. Natl. Acad. Sci. USA 84(16):5745-9) and the octopine synthase (OCS) promoters (which are carried on tumor-inducing plasmids of *Agrobacterium tumefaciens*); the caulimovirus promoters such as the cauliflower mosaic virus (CaMV) 19S promoter (Lawton et al. (1987) Plant Mol. Biol. 9:315-24); the CaMV 35S promoter (Odell et al. (1985) Nature 313:810-2; the figwort mosaic virus 35S-promoter (Walker et al. (1987) Proc. Natl. Acad. Sci. USA 84(19):6624-8); the sucrose synthase promoter (Yang and Russell (1990) Proc. Natl. Acad. Sci. USA 87:4144-8); the R gene complex promoter (Chandler et al. (1989) Plant Cell 1:1175-83); the chlorophyll a/b binding protein gene promoter; CaMV 35S (U.S. Pat. Nos. 5,322,938, 5,352,605, 5,359,142, and 5,530,196); FMV 35S (U.S. Pat. Nos. 6,051,753, and 5,378,619); a PC1SV promoter (U.S. Pat. No. 5,850,019); the SCP1 promoter (U.S. Pat. No. 6,677,503); and AGRtu.nos promoters (GenBank™ Accession No. V00087; Depicker et al. (1982) J. Mol. Appl. Genet. 1:561-73; Bevan et al. (1983) Nature 304:184-7).

In particular embodiments, nucleic acid molecules of the invention comprise a tissue-specific promoter, such as a root-specific promoter. Root-specific promoters drive expression of operably-linked coding sequences exclusively or preferentially in root tissue. Examples of root-specific promoters are known in the art. See, e.g., U.S. Pat. Nos. 5,110,732; 5,459,252 and 5,837,848; and Opperman et al. (1994) Science 263:221-3; and Hirel et al. (1992) Plant Mol. Biol. 20:207-18. In some embodiments, a nucleotide sequence or fragment for coleopteran pest control according to the invention may be cloned between two root-specific promoters oriented in opposite transcriptional directions relative to the nucleotide sequence or fragment, and which are operable in a transgenic plant cell and expressed therein to produce RNA molecules in the transgenic plant cell that subsequently may form dsRNA molecules, as described, supra. The iRNA molecules expressed in plant tissues may be ingested by a coleopteran pest so that suppression of target gene expression is achieved.

Additional regulatory sequences that may optionally be operably linked to a nucleic acid molecule of interest include 5'UTRs located between a promoter sequence and a coding sequence that function as a translation leader sequence. The translation leader sequence is present in the fully-processed mRNA, and it may affect processing of the primary transcript, and/or RNA stability. Examples of translation leader sequences include maize and petunia heat shock protein leaders (U.S. Pat. No. 5,362,865), plant virus coat protein leaders, plant rubisco leaders, and others. See, e.g., Turner and Foster (1995) Molecular Biotech. 3(3):225-36. Non-limiting examples of 5'UTRs include GmHsp (U.S. Pat. No. 5,659,122); PhDnaK (U.S. Pat. No. 5,362,865); AtAnt1; TEV (Carrington and Freed (1990) J. Virol. 64:1590-7); and AGRtunos (GenBank™ Accession No. V00087; and Bevan et al. (1983) Nature 304:184-7).

Additional regulatory sequences that may optionally be operably linked to a nucleic acid molecule of interest also include 3' non-translated sequences, 3' transcription termination regions, or poly-adenylation regions. These are genetic elements located downstream of a nucleotide sequence, and include polynucleotides that provide polyadenylation signal, and/or other regulatory signals capable of affecting transcription or mRNA processing. The polyadenylation signal functions in plants to cause the addition of polyadenylate nucleotides to the 3' end of the mRNA precursor. The polyadenylation sequence can be derived from a variety of plant genes, or from T-DNA genes. A non-limiting example of a 3' transcription termination region is the nopaline synthase 3' region (nos 3'; Fraley et al. (1983) Proc. Natl. Acad. Sci. USA 80:4803-7). An example of the use of different 3' nontranslated regions is provided in Ingelbrecht et al., (1989) Plant Cell 1:671-80. Non-limiting examples of polyadenylation signals include one from a *Pisum sativum* RbcS2 gene (Ps.RbcS2-E9; Coruzzi et al. (1984) EMBO J. 3:1671-9) and AGRtu.nos (GenBank™ Accession No. E01312).

Some embodiments may include a plant transformation vector that comprises an isolated and purified DNA molecule comprising at least one of the above-described regulatory sequences operatively linked to one or more nucleotide sequences of the present invention. When expressed, the one or more nucleotide sequences result in one or more RNA molecule(s) comprising a nucleotide sequence that is specifically complementary to all or part of a native RNA molecule in a coleopteran pest. Thus, the nucleotide sequence(s) may comprise a segment encoding all or part of a ribonucleotide sequence present within a targeted coleopteran pest RNA transcript, and may comprise inverted repeats of all or a part of a targeted coleopteran pest transcript. A plant transformation vector may contain sequences specifically complementary to more than one target sequence, thus allowing production of more than one dsRNA for inhibiting expression of two or more genes in cells of one or more populations or species of target coleopteran pests. Segments of nucleotide sequence specifically complementary to nucleotide sequences present in different genes can be combined into a single composite nucleic acid molecule for expression in a transgenic plant. Such segments may be contiguous or separated by a space sequence.

In some embodiments, a plasmid of the present invention already containing at least one nucleotide sequence(s) of the invention can be modified by the sequential insertion of additional nucleotide sequence(s) in the same plasmid, wherein the additional nucleotide sequence(s) are operably linked to the same regulatory elements as the original at least one nucleotide sequence(s). In some embodiments, a nucleic acid molecule may be designed for the inhibition of multiple target genes. In some embodiments, the multiple genes to be inhibited can be obtained from the same coleopteran pest species, which may enhance the effectiveness of the nucleic acid molecule. In other embodiments, the genes can be derived from different coleopteran pests, which may broaden the range of coleopteran pests against which the agent(s) is/are effective. When multiple genes are targeted for suppression or a combination of expression and suppression, a polycistronic DNA element can be fabricated.

A recombinant nucleic acid molecule or vector of the present invention may comprise a selectable marker that confers a selectable phenotype on a transformed cell, such as a plant cell. Selectable markers may also be used to select for plants or plant cells that comprise a recombinant nucleic acid molecule of the invention. The marker may encode biocide resistance, antibiotic resistance (e.g., kanamycin, Geneticin (G418), bleomycin, hygromycin, etc.), or herbicide resistance (e.g., glyphosate, etc.). Examples of selectable markers include, but are not limited to: a neo gene which codes for kanamycin resistance and can be selected for using kanamycin, G418, etc.; a bar gene which codes for bialaphos resistance; a mutant EPSP synthase gene which encodes glyphosate resistance; a nitrilase gene which confers resistance to bromoxynil; a mutant acetolactate synthase (ALS) gene which confers imidazolinone or sulfonylurea resistance; and a methotrexate resistant DHFR gene. Multiple selectable markers are available that confer resistance to ampicillin, bleomycin, chloramphenicol, gentamycin, hygromycin, kanamycin, lincomycin, methotrexate, phosphinothricin, puromycin, spectinomycin, rifampicin, streptomycin and tetracycline, and the like. Examples of such selectable markers are illustrated in, e.g., U.S. Pat. Nos. 5,550,318; 5,633,435; 5,780,708 and 6,118,047.

A recombinant nucleic acid molecule or vector of the present invention may also include a screenable marker. Screenable markers may be used to monitor expression. Exemplary screenable markers include a β-glucuronidase or uidA gene (GUS) which encodes an enzyme for which various chromogenic substrates are known (Jefferson et al. (1987) Plant Mol. Biol. Rep. 5:387-405); an R-locus gene, which encodes a product that regulates the production of anthocyanin pigments (red color) in plant tissues (Dellaporta et al. (1988) "Molecular cloning of the maize R-nj allele by transposon tagging with Ac." In 18$^{th}$ Stadler Genetics Symposium, P. Gustafson and R. Appels, eds. (New York: Plenum), pp. 263-82); a β-lactamase gene (Sutcliffe et al. (1978) Proc. Natl. Acad. Sci. USA 75:3737-41); a gene which encodes an enzyme for which various chromogenic substrates are known (e.g., PADAC, a chromogenic cephalosporin); a luciferase gene (Ow et al. (1986) Science 234:856-9); an xylE gene that encodes a catechol dioxygenase that can convert chromogenic catechols (Zukowski et al. (1983) Gene 46(2-3):247-55); an amylase gene (Ikatu et al. (1990) Bio/Technol. 8:241-2); a tyrosinase gene which encodes an enzyme capable of oxidizing tyrosine to DOPA and dopaquinone which in turn condenses to melanin (Katz et al. (1983) J. Gen. Microbiol. 129:2703-14); and an α-galactosidase.

In some embodiments, recombinant nucleic acid molecules, as described, supra, may be used in methods for the creation of transgenic plants and expression of heterologous nucleic acids in plants to prepare transgenic plants that exhibit reduced susceptibility to coleopteran pests. Plant transformation vectors can be prepared, for example, by inserting nucleic acid molecules encoding iRNA molecules into plant transformation vectors and introducing these into plants.

Suitable methods for transformation of host cells include any method by which DNA can be introduced into a cell, such as by transformation of protoplasts (See, e.g., U.S. Pat. No. 5,508,184), by desiccation/inhibition-mediated DNA uptake (See, e.g., Potrykus et al. (1985) Mol. Gen. Genet. 199:183-8), by electroporation (See, e.g., U.S. Pat. No. 5,384,253), by agitation with silicon carbide fibers (See, e.g., U.S. Pat. Nos. 5,302,523 and 5,464,765), by *Agrobacterium*-mediated transformation (See, e.g., U.S. Pat. Nos. 5,563,055; 5,591,616; 5,693,512; 5,824,877; 5,981,840; and 6,384,301) and by acceleration of DNA-coated particles (See, e.g., U.S. Pat. Nos. 5,015,580; 5,550,318; 5,538,880; 6,160,208; 6,399,861; and 6,403,865), etc. Techniques that are particularly useful for transforming corn are described, for example, in U.S. Pat. Nos. 7,060,876 and 5,591,616; and International PCT Publication WO95/06722. Through the application of techniques such as these, the cells of virtually any species may be stably transformed. In some embodiments, transforming DNA is integrated into the genome of the host cell. In the case of multicellular species, transgenic cells may be regenerated into a transgenic organism. Any of these techniques may be used to produce a transgenic plant, for example, comprising one or more nucleic acid sequences encoding one or more iRNA molecules in the genome of the transgenic plant.

The most widely utilized method for introducing an expression vector into plants is based on the natural transformation system of *Agrobacterium*. *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. The Ti (tumor-inducing)-plasmids contain a large segment, known as T-DNA, which is transferred to transformed plants. Another segment of the Ti plasmid, the Vir region, is responsible for T-DNA transfer. The T-DNA region is bordered by terminal repeats. In modified binary vectors, the tumor-inducing genes have been deleted, and the functions of the Vir region are utilized to transfer foreign DNA bordered by the T-DNA border sequences. The T-region may also contain a selectable marker for efficient recovery of transgenic cells and plants, and a multiple cloning site for inserting sequences for transfer such as a dsRNA encoding nucleic acid.

Thus, in some embodiments, a plant transformation vector is derived from a Ti plasmid of *A. tumefaciens* (See, e.g., U.S. Pat. Nos. 4,536,475, 4,693,977, 4,886,937, and 5,501,967; and European Patent No. EP 0 122 791) or a Ri plasmid of *A. rhizogenes*. Additional plant transformation vectors include, for example and without limitation, those described by Herrera-Estrella et al. (1983) Nature 303:209-13; Bevan et al. (1983) Nature 304:184-7; Klee et al. (1985) Bio/Technol. 3:637-42; and in European Patent No. EP 0 120 516, and those derived from any of the foregoing. Other bacteria such as *Sinorhizobium, Rhizobium*, and *Mesorhizobium* that interact with plants naturally can be modified to mediate gene transfer to a number of diverse plants. These plant-associated symbiotic bacteria can be made competent for gene transfer by acquisition of both a disarmed Ti plasmid and a suitable binary vector.

After providing exogenous DNA to recipient cells, transformed cells are generally identified for further culturing and plant regeneration. In order to improve the ability to identify transformed cells, one may desire to employ a selectable or screenable marker gene, as previously set forth, with the transformation vector used to generate the transformant. In the case where a selectable marker is used, transformed cells are identified within the potentially transformed cell population by exposing the cells to a selective agent or agents. In the case where a screenable marker is used, cells may be screened for the desired marker gene trait.

Cells that survive the exposure to the selective agent, or cells that have been scored positive in a screening assay, may be cultured in media that supports regeneration of plants. In some embodiments, any suitable plant tissue culture media (e.g., MS and N6 media) may be modified by including further substances, such as growth regulators. Tissue may be maintained on a basic medium with growth regulators until sufficient tissue is available to begin plant regeneration efforts, or following repeated rounds of manual selection, until the morphology of the tissue is suitable for regeneration (e.g., at least 2 weeks), then transferred to media conducive to shoot formation. Cultures are transferred periodically until sufficient shoot formation has occurred. Once shoots are formed, they are transferred to media conducive to root formation. Once sufficient roots are formed, plants can be transferred to soil for further growth and maturation.

To confirm the presence of a nucleic acid molecule of interest (for example, a DNA sequence encoding one or more iRNA molecules that inhibit target gene expression in a coleopteran pest) in the regenerating plants, a variety of assays may be performed. Such assays include, for example: molecular biological assays, such as Southern and northern blotting, PCR, and nucleic acid sequencing; biochemical assays, such as detecting the presence of a protein product, e.g., by immunological means (ELISA and/or western blots) or by enzymatic function; plant part assays, such as leaf or root assays; and analysis of the phenotype of the whole regenerated plant.

Integration events may be analyzed, for example, by PCR amplification using, e.g., oligonucleotide primers specific for a nucleic acid molecule of interest. PCR genotyping is understood to include, but not be limited to, polymerase-chain reaction (PCR) amplification of genomic DNA derived from isolated host plant callus tissue predicted to contain a nucleic acid molecule of interest integrated into the genome, followed by standard cloning and sequence analysis of PCR amplification products. Methods of PCR genotyping have been well described (for example, Rios, G. et al. (2002) Plant J. 32:243-53) and may be applied to genomic DNA derived from any plant species (e.g., *Z. mays* or *G. max*) or tissue type, including cell cultures.

A transgenic plant formed using *Agrobacterium*-dependent transformation methods typically contains a single recombinant DNA sequence inserted into one chromosome. The single recombinant DNA sequence is referred to as a "transgenic event" or "integration event." Such transgenic plants are heterozygous for the inserted exogenous sequence. In some embodiments, a transgenic plant homozygous with respect to a transgene may be obtained by sexually mating (selling) an independent segregant transgenic plant that contains a single exogenous gene sequence to itself, for example a $T_0$ plant, to produce $T_1$ seed. One fourth of the $T_1$ seed produced will be homozygous with respect to the transgene. Germinating $T_1$ seed results in plants that can be tested for heterozygosity, typically using an SNP assay or a thermal amplification assay that allows the distinction between heterozygotes and homozygotes (i.e., a zygosity assay).

In particular embodiments, at least 2, 3, 4, 5, 6, 7, 8, 9 or 10 or more different iRNA molecules are produced in a plant cell that have a coleopteran pest-inhibitory effect. The iRNA molecules (e.g., dsRNA molecules) may be expressed from multiple nucleic acid sequences introduced in different transformation events, or from a single nucleic acid sequence introduced in a single transformation event. In some embodiments, a plurality of iRNA molecules are expressed under the control of a single promoter. In other embodiments, a plurality of iRNA molecules are expressed under the control of multiple promoters. Single iRNA molecules may be expressed that comprise multiple nucleic acid sequences that are each homologous to different loci within one or more coleopteran pests (for example, the loci defined by SEQ ID NO:7, and one or more of SEQ ID NOs:1-6 and 103-106), both in different populations of the same species of coleopteran pest, or in different species of coleopteran pests.

In addition to direct transformation of a plant with a recombinant nucleic acid molecule, transgenic plants can be prepared by crossing a first plant having at least one transgenic event with a second plant lacking such an event. For example, a recombinant nucleic acid molecule comprising a nucleotide sequence that encodes an iRNA molecule may be introduced into a first plant line that is amenable to transformation to produce a transgenic plant, which transgenic plant may be crossed with a second plant line to introgress the nucleotide sequence that encodes the iRNA molecule into the second plant line.

The invention also includes commodity products containing one or more of the sequences of the present invention. Particular embodiments include commodity products produced from a recombinant plant or seed containing one or more of the nucleotide sequences of the present invention. A commodity product containing one or more of the sequences of the present invention is intended to include, but not be limited to, meals, oils, crushed or whole grains or seeds of a plant, or any food product comprising any meal, oil, or crushed or whole grain of a recombinant plant or seed containing one or more of the sequences of the present invention. The detection of one or more of the sequences of the present invention in one or more commodity or commodity products contemplated herein is de facto evidence that the commodity or commodity product is produced from a transgenic plant designed to express one or more of the nucleotides sequences of the present invention for the purpose of controlling plant disease using dsRNA-mediated gene suppression methods.

In some aspects, seeds and commodity products produced by transgenic plants derived from transformed plant cells are included, wherein the seeds or commodity products comprise a detectable amount of a nucleic acid sequence of the invention. In some embodiments, such commodity products may be produced, for example, by obtaining transgenic plants and preparing food or feed from them. Commodity products comprising one or more of the nucleic acid sequences of the invention includes, for example and without limitation: meals, oils, crushed or whole grains or seeds of a plant, and any food product comprising any meal, oil, or crushed or whole grain of a recombinant plant or seed comprising one or more of the nucleic acid sequences of the invention. The detection of one or more of the sequences of the invention in one or more commodity or commodity products is de facto evidence that the commodity or commodity product is produced from a transgenic plant designed to express one or more of the iRNA molecules of the invention for the purpose of controlling coleopteran pests.

In some embodiments, a transgenic plant or seed comprising a nucleic acid molecule of the invention also may comprise at least one other transgenic event in its genome, including without limitation: a transgenic event from which is transcribed an iRNA molecule targeting a locus in a coleopteran pest other than the ones defined by SEQ ID NOs:1-7 and 103-106 (for example and without limitation, Caf1-180 (PCT International Application No. PCT/US2011/068062 (filed Dec. 30, 2011)), VatpaseC (PCT International Application No. PCT/US2011/068144 (filed Dec. 30, 2011)), VatpaseH (PCT International Application No. PCT/US2011/068162 (filed Dec. 30, 2011)) and Rho1 (PCT International Application No. PCT/US2011/068188 (filed Dec. 30, 2011)); a transgenic event from which is transcribed an iRNA molecule targeting a gene in an organism other than a coleopteran pest (e.g., a plant-parasitic nematode); a gene encoding an insecticidal protein (e.g., a *Bacillus thuringiensis* insecticidal protein, such as for example, Cry34Ab1 (U.S. Pat. Nos. 6,127,180, 6,624,145 and 6,340,593), Cry35Ab1 (U.S. Pat. Nos. 6,083,499, 6,548,291 and 6,340,593), a "Cry34/35Ab1" combination in a single event (e.g., maize event DAS-59122-7; U.S. Pat. No. 7,323,556), Cry3A (e.g., U.S. Pat. No. 7,230,167), Cry3B (e.g., PCT International Application No. PCT/US1999/018883), Cry6A (e.g., U.S. Pat. No. 6,831,062), and combinations thereof (e.g., PCT International Application Nos. PCT/US11/033618 (filed Apr. 15, 2011), PCT/US11/033618 (filed Apr. 22, 2011) and PCT/US11/033617 (filed Apr. 22, 2011)); an herbicide tolerance gene (e.g., a gene providing tolerance to glyphosate, glufosinate, dicamba or 2,4-D (e.g., U.S. Pat. No. 7,838,733)); and a gene contributing to a desirable phenotype in the transgenic plant, such as increased yield, altered fatty acid metabolism, or restoration of cytoplasmic male sterility). In particular embodiments, sequences encoding iRNA molecules of the invention may be combined with other insect control and disease traits in a plant to achieve desired traits for enhanced control of plant disease and insect damage. Combining insect control traits that employ distinct modes-of-action may provide protected transgenic plants with superior durability over plants harboring a single control trait, for example, because of the reduced probability that resistance to the trait(s) will develop in the field.

V. Target Gene Suppression in a Coleopteran Pest

A. Overview

In some embodiments of the invention, at least one nucleic acid molecule useful for the control of coleopteran pests may be provided to a coleopteran pest, wherein the nucleic acid molecule leads to RNAi-mediated gene silencing in the coleopteran pest. In particular embodiments, an iRNA molecule (e.g., dsRNA, siRNA, miRNA, and hpRNA) may be provided to the coleopteran host. In some embodiments, a nucleic acid molecule useful for the control of coleopteran pests may be provided to a coleopteran pest by contacting the nucleic acid molecule with the coleopteran pest. In these and further embodiments, a nucleic acid molecule useful for the control of coleopteran pests may be provided in a feeding substrate of the coleopteran pest, for example, a nutritional composition. In these and further embodiments, a nucleic acid molecule useful for the control of coleopteran pests may be provided through ingestion of plant material comprising the nucleic acid molecule that is ingested by the coleopteran pest. In certain embodiments, the nucleic acid molecule is present in plant material through expression of a recombinant nucleic acid sequence introduced into the plant material, for example, by transformation of a plant cell with a vector comprising the recombinant nucleic acid sequence and regeneration of a plant material or whole plant from the transformed plant cell.

B. RNAi-mediated Target Gene Suppression

In embodiments, the invention provides iRNA molecules (e.g., dsRNA, siRNA, miRNA, and hpRNA) that may be designed to target essential native nucleotide sequences (e.g., essential genes) in the transcriptome of a coleopteran pest (e.g., WCR or NCR), for example by designing an iRNA molecule that comprises at least one strand comprising a nucleotide sequence that is specifically complementary to the target sequence. The sequence of an iRNA molecule so designed may be identical to the target sequence, or may incorporate mismatches that do not prevent specific hybridization between the iRNA molecule and its target sequence.

iRNA molecules of the invention may be used in methods for gene suppression in a coleopteran pest, thereby reducing the level or incidence of damage caused by the pest on a plant (for example, a protected transformed plant comprising an iRNA molecule). As used herein the term "gene suppression" refers to any of the well-known methods for reducing the levels of protein produced as a result of gene transcription to mRNA and subsequent translation of the mRNA, including the reduction of protein expression from a gene or a coding sequence including post-transcriptional inhibition of expression and transcriptional suppression. Post-transcriptional inhibition is mediated by specific homology between all or a part of an mRNA transcribed from a gene targeted for suppression and the corresponding iRNA molecule used for suppression. Additionally, post-transcriptional inhibition refers to the substantial and measurable reduction of the amount of mRNA available in the cell for binding by ribosomes.

In embodiments wherein an iRNA molecule is a dsRNA molecule, the dsRNA molecule may be cleaved by the enzyme, DICER, into short siRNA molecules (approximately 20 nucleotides in length). The double-stranded siRNA molecule generated by DICER activity upon the dsRNA molecule may be separated into two single-stranded siRNAs; the "passenger strand" and the "guide strand." The passenger strand may be degraded, and the guide strand may be incorporated into RISC. Post-transcriptional inhibition occurs by specific hybridization of the guide strand with a specifically complementary sequence of an mRNA molecule, and subsequent cleavage by the enzyme, Argonaute (catalytic component of the RISC complex).

In embodiments of the invention, any form of iRNA molecule may be used. Those of skill in the art will understand that dsRNA molecules typically are more stable during preparation and during the step of providing the iRNA molecule to a cell than are single-stranded RNA molecules, and are typically also more stable in a cell. Thus, while siRNA and miRNA molecules, for example, may be equally effective in some embodiments, a dsRNA molecule may be chosen due to its stability.

In particular embodiments, a nucleic acid molecule is provided that comprises a nucleotide sequence, which nucleotide sequence may be expressed in vitro to produce an iRNA molecule that is substantially homologous to a nucleic acid molecule encoded by a nucleotide sequence within the genome of a coleopteran pest. In certain embodiments, the in vitro transcribed iRNA molecule may be a stabilized dsRNA molecule that comprises a stem-loop structure. After a coleopteran pest contacts the in vitro transcribed iRNA molecule, post-transcriptional inhibition of a target gene in the coleopteran pest (for example, an essential gene) may occur.

In some embodiments of the invention, expression of a nucleic acid molecule comprising at least 19 contiguous nucleotides of a nucleotide sequence is used in a method for post-transcriptional inhibition of a target gene in a coleopteran pest, wherein the nucleotide sequence is selected from the group consisting of: SEQ ID NO:7; the complement of SEQ ID NO:7; a fragment of at least 19 contiguous nucleotides of SEQ ID NO:7; the complement of a fragment of at least 19 contiguous nucleotides of SEQ ID NO:7; a native coding sequence of a *Diabrotica* organism (e.g., WCR) comprising SEQ ID NO:7; the complement of a native coding sequence of a *Diabrotica* organism comprising SEQ ID NO:7; a native non-coding sequence of a *Diabrotica* organism that is transcribed into a native RNA molecule comprising SEQ ID NO:7; the complement of a native non-coding sequence of a *Diabrotica* organism that is transcribed into a native RNA molecule comprising SEQ ID NO:7; a fragment of at least 19 contiguous nucleotides of a native coding sequence of a *Diabrotica* organism (e.g., WCR) comprising SEQ ID NO:7; the complement of a fragment of at least 19 contiguous nucleotides of a native coding sequence of a *Diabrotica* organism comprising SEQ ID NO:7; a fragment of at least 19 contiguous nucleotides of a native non-coding sequence of a *Diabrotica* organism that is transcribed into a native RNA molecule comprising SEQ ID NO:7; and the complement of a fragment of at least 19 contiguous nucleotides of a native non-coding sequence of a *Diabrotica* organism that is transcribed into a native RNA molecule comprising SEQ ID NO:7. In certain embodiments, expression of a nucleic acid molecule that is at least 80% identical (e.g., 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100%, and 100%) with any of the foregoing may be used. In these and further embodiments, a nucleic acid molecule may be expressed that specifically hybridizes to an RNA molecule present in at least one cell of a coleopteran pest.

In some embodiments, expression of at least one nucleic acid molecule comprising at least 19 contiguous nucleotides of a nucleotide sequence may be used in a method for post-transcriptional inhibition of a target gene in a coleopteran pest, wherein the nucleotide sequence is selected from the group consisting of: SEQ ID NO:1; the complement of SEQ ID NO:1; SEQ ID NO:2; the complement of SEQ ID NO:2; SEQ ID NO:3; the complement of SEQ ID NO:3; SEQ ID NO:4; the complement of SEQ ID NO:4; SEQ ID NO:5; the complement of SEQ ID NO:5; SEQ ID NO:6; the complement of SEQ ID NO:6; SEQ ID NO:103; the complement of SEQ ID NO:103; SEQ ID NO:104; the complement of SEQ ID NO:104; SEQ ID NO:105; the complement of SEQ ID NO:105; SEQ ID NO:106; the complement of SEQ ID NO:106; a fragment of at least 19 contiguous nucleotides of any of SEQ ID NOs:1-6 and 103-106; the complement of a fragment of at least 19 contiguous nucleotides of any of SEQ ID NOs:1-6 and 103-106; a native coding sequence of a *Diabrotica* organism (e.g., WCR) comprising any of SEQ ID NOs:1-6 and 103-106; the complement of a native coding sequence of a *Diabrotica* organism (e.g., WCR) comprising any of SEQ ID NOs:1-6 and 103-106; a native non-coding sequence of a *Diabrotica* organism that is transcribed into a native RNA molecule comprising any of SEQ ID NOs:1-6 and 103-106; the complement of a native non-coding sequence of a *Diabrotica* organism that is transcribed into a native RNA molecule comprising any of SEQ ID NOs:1-6 and 103-106; a fragment of at least 19 contiguous nucleotides of a native coding sequence of a *Diabrotica* organism (e.g., WCR) comprising any of SEQ ID NOs:1-6 and 103-106; the complement of a fragment of at least 19 contiguous nucleotides of a native coding sequence of a *Diabrotica* organism comprising any of SEQ ID NOs:1-6 and 103-106; a fragment of at least 19 contiguous nucleotides of a native non-coding sequence of a *Diabrotica* organism that is transcribed into a native RNA molecule comprising any of SEQ ID NOs:1-6 and 103-106; and the complement of a fragment of at least 19 contiguous nucleotides of a native non-coding sequence of a *Diabrotica* organism that is transcribed into a native RNA molecule comprising any of SEQ ID NOs:1-6 and 103-106. In certain embodiments, expression of a nucleic acid molecule that is at least 80% identical (e.g., 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100%, and 100%) with any of the foregoing may be used. In these and further embodiments, a nucleic acid molecule may be expressed that specifically hybridizes to an RNA molecule present in at least one cell of a coleopteran pest. In particular examples, such a nucleic acid molecule may comprise a nucleotide sequence selected from the group consisting of SEQ ID NOs:99-102 and 107.

It is an important feature of some embodiments of the invention that the RNAi post-transcriptional inhibition system is able to tolerate sequence variations among target genes that might be expected due to genetic mutation, strain polymorphism, or evolutionary divergence. The introduced nucleic acid molecule may not need to be absolutely homologous to either a primary transcription product or a fully-processed mRNA of a target gene, so long as the introduced nucleic acid molecule is specifically hybridizable to either a primary transcription product or a fully-processed mRNA of the target gene. Moreover, the introduced nucleic acid molecule may not need to be full-length, relative to either a primary transcription product or a fully processed mRNA of the target gene.

Inhibition of a target gene using the iRNA technology of the present invention is sequence-specific; i.e., nucleotide sequences substantially homologous to the mRNA molecule(s) are targeted for genetic inhibition. In some embodiments, an RNA molecule comprising a nucleotide sequence identical to a portion of a target gene sequence may be used for inhibition. In these and further embodiments, an RNA molecule comprising a nucleotide sequence with one or more insertion, deletion, and/or point mutations relative to a target gene sequence may be used. In particular embodiments, an iRNA molecule and a portion of a target gene may share, for example, at least from about 80%, at least from about 81%, at least from about 82%, at least from about 83%, at least from about 84%, at least from about 85%, at least from about 86%, at least from about 87%, at least from about 88%, at least from about 89%, at least from about 90%, at least from about 91%, at least from about 92%, at least from about 93%, at least from about 94%, at least from about 95%, at least from about 96%, at least from about 97%, at least from about 98%, at least from about 99%, at least from about 100%, and 100% sequence identity. Alternatively, the duplex region of a dsRNA molecule may be specifically hybridizable with a portion of a target gene transcript. In specifically hybridizable molecules, a less than full length sequence exhibiting a greater homology compensates for a longer, less homologous sequence. The length of the nucleotide sequence of a duplex region of a dsRNA molecule that is identical to a portion of a target gene transcript may be at least about 25, 50, 100, 200, 300, 400, 500, or at least about 1000 bases. In some embodiments, a sequence of greater than 20-100 nucleotides may be used. In particular embodiments, a sequence of greater than about 200-300 nucleotides may be used. In particular embodiments, a sequence of greater than about 500-1000 nucleotides may be used, depending on the size of the target gene.

In certain embodiments, expression of a target gene in a coleopteran pest may be inhibited by at least 10%; at least 33%; at least 50%; or at least 80% within a cell of the coleopteran pest, such that a significant inhibition takes place. Significant inhibition refers to inhibition over a threshold that results in a detectable phenotype (e.g., cessation of growth, feeding, development, mortality, etc.), or a detectable decrease in RNA and/or gene product corresponding to the target gene being inhibited. Although in certain embodiments of the invention inhibition occurs in substantially all cells of the coleopteran pest, in other embodiments inhibition occurs only in a subset of cells expressing the target gene.

In some embodiments, transcriptional suppression is mediated by the presence in a cell of a dsRNA molecule exhibiting substantial sequence identity to a promoter DNA sequence or the complement thereof to effect what is referred to as "promoter trans suppression." Gene suppression may be effective against target genes in a coleopteran pest that may ingest or contact such dsRNA molecules, for example, by ingesting or contacting plant material containing the dsRNA molecules. dsRNA molecules for use in promoter trans suppression may be specifically designed to inhibit or suppress the expression of one or more homologous or complementary sequences in the cells of the coleopteran pest. Post-transcriptional gene suppression by antisense or sense oriented RNA to regulate gene expression in plant cells is disclosed in U.S. Pat. Nos. 5,107,065; 5,759,829; 5,283,184; and 5,231,020.

C. Expression of iRNA Molecules Provided to a Coleopteran Pest

Expression of iRNA molecules for RNAi-mediated gene inhibition in a coleopteran pest may be carried out in any one of many in vitro or in vivo formats. The iRNA molecules may then be provided to a coleopteran pest, for example, by contacting the iRNA molecules with the pest, or by causing the pest to ingest or otherwise internalize the iRNA molecules. Some embodiments of the invention include transformed host plants of a coleopteran pest, transformed plant cells, and progeny of transformed plants. The transformed plant cells and transformed plants may be engineered to express one or more of the iRNA molecules, for example, under the control of a heterologous promoter, to provide a pest-protective effect. Thus, when a transgenic plant or plant cell is consumed by a coleopteran pest during feeding, the pest may ingest iRNA molecules expressed in the transgenic plants or cells. The nucleotide sequences of the present invention may also be introduced into a wide variety of prokaryotic and eukaryotic microorganism hosts to produce iRNA molecules. The term "microorganism" includes prokaryotic and eukaryotic species, such as bacteria and fungi.

Modulation of gene expression may include partial or complete suppression of such expression. In another embodiment, a method for suppression of gene expression in a coleopteran pest comprises providing in the tissue of the host of the pest a gene-suppressive amount of at least one dsRNA molecule formed following transcription of a nucleotide sequence as described herein, at least one segment of which is complementary to an mRNA sequence within the cells of the coleopteran pest. A dsRNA molecule, including its modified form such as an siRNA, miRNA, or hpRNA molecule, ingested by a coleopteran pest in accordance with the invention may be at least from about 80%, 81%, 82%, 83%, 84%, 85%, 86%, 87%, 88%, 89%, 90%, 91%, 92%, 93%, 94%, 95%, 96%, 97%, 98%, 99%, or about 100% identical to an RNA molecule transcribed from a nucleic acid molecule comprising a nucleotide sequence selected from the group consisting of SEQ ID NOs:1-7 and 103-106. Isolated and substantially purified nucleic acid molecules including, but not limited to, non-naturally occurring nucleotide sequences and recombinant DNA constructs for providing dsRNA molecules of the present invention are therefore provided, which suppress or inhibit the expression of an endogenous coding sequence or a target coding sequence in the coleopteran pest when introduced thereto.

Particular embodiments provide a delivery system for the delivery of iRNA molecules for the post-transcriptional inhibition of one or more target gene(s) in a coleopteran plant pest and control of a population of the coleopteran plant pest. In some embodiments, the delivery system comprises ingestion of a host transgenic plant cell or contents of the host cell comprising RNA molecules transcribed in the host cell. In these and further embodiments, a transgenic plant cell or a transgenic plant is created that contains a recombinant DNA construct providing a stabilized dsRNA molecule of the invention. Transgenic plant cells and transgenic plants comprising nucleic acid sequences encoding a particular iRNA molecule may be produced by employing recombinant DNA technologies (which basic technologies are well-known in the art) to construct a plant transformation vector comprising a nucleotide sequence encoding an iRNA molecule of the invention (e.g., a stabilized dsRNA molecule); to transform a plant cell or plant; and to generate the transgenic plant cell or the transgenic plant that contains the transcribed iRNA molecule.

To impart coleopteran pest resistance to a transgenic plant, a recombinant DNA molecule may, for example, be transcribed into an iRNA molecule, such as a dsRNA molecule, an siRNA molecule, an miRNA molecule, or an hpRNA molecule. In some embodiments, an RNA molecule transcribed from a recombinant DNA molecule may form a dsRNA molecule within the tissues or fluids of the recombinant plant. Such a dsRNA molecule may be comprised in part of a nucleotide sequence that is identical to a corresponding nucleotide sequence transcribed from a DNA sequence within a coleopteran pest of a type that may infest the host plant. Expression of a target gene within the coleopteran pest is suppressed by the ingested or otherwise contacted dsRNA molecule, and the suppression of expression of the target gene in the coleopteran pest results in, for example, cessation of feeding by the coleopteran pest, with an ultimate result being, for example, that the transgenic plant is protected from further damage by the coleopteran pest. The modulatory effects of dsRNA molecules have been shown to be applicable to a variety of genes expressed in pests, including, for example, endogenous genes responsible for cellular metabolism or cellular transformation, including house-keeping genes; transcription factors; molting-related genes; and other genes which encode polypeptides involved in cellular metabolism or normal growth and development.

For transcription from a transgene in vivo or an expression construct, a regulatory region (e.g., promoter, enhancer, silencer, and polyadenylation signal) may be used in some embodiments to transcribe the RNA strand (or strands). Therefore, in some embodiments, as set forth, supra, a nucleotide sequence for use in producing iRNA molecules may be operably linked to one or more promoter sequences functional in a plant host cell. The promoter may be an endogenous promoter, normally resident in the host genome. The nucleotide sequence of the present invention, under the control of an operably linked promoter sequence, may further be flanked by additional sequences that advantageously affect its transcription and/or the stability of a resulting transcript. Such sequences may be located upstream of the operably linked promoter, downstream of the 3' end of the expression construct, and may occur both upstream of the promoter and downstream of the 3' end of the expression construct.

Some embodiments provide methods for reducing the damage to a host plant (e.g., a corn plant) caused by a coleopteran pest that feeds on the plant, wherein the method comprises providing in the host plant a transformed plant cell expressing at least one nucleic acid molecule of the invention, wherein the nucleic acid molecule(s) functions upon being taken up by the coleopteran pest to inhibit the expression of a target sequence within the coleopteran pest, which inhibition of expression results in mortality, reduced growth, and/or reduced reproduction of the coleopteran pest, thereby reducing the damage to the host plant caused by the coleopteran pest. In some embodiments, the nucleic acid molecule(s) comprise dsRNA molecules. In these and further embodiments, the nucleic acid molecule(s) comprise dsRNA molecules that each comprise more than one nucleotide sequence that is specifically hybridizable to a nucleic acid molecule expressed in a coleopteran pest cell. In some embodiments, the nucleic acid molecule(s) consist of one nucleotide sequence that is specifically hybridizable to a nucleic acid molecule expressed in a coleopteran pest cell.

In some embodiments, a method for increasing the yield of a corn crop is provided, wherein the method comprises introducing into a corn plant at least one nucleic acid molecule of the invention; cultivating the corn plant to allow the expression of an iRNA molecule comprising the nucleic acid sequence, wherein expression of an iRNA molecule comprising the nucleic acid sequence inhibits coleopteran pest damage and/or growth, thereby reducing or eliminating a loss of yield due to coleopteran pest infestation. In some embodiments, the iRNA molecule is a dsRNA molecule. In these and further embodiments, the nucleic acid molecule(s) comprise dsRNA molecules that each comprise more than one nucleotide sequence that is specifically hybridizable to a nucleic acid molecule expressed in a coleopteran pest cell. In some embodiments, the nucleic acid molecule(s) consists of one nucleotide sequence that is specifically hybridizable to a nucleic acid molecule expressed in a coleopteran pest cell.

In some embodiments, a method for modulating the expression of a target gene in a coleopteran pest is provided, the method comprising: transforming a plant cell with a vector comprising a nucleic acid sequence encoding at least one nucleic acid molecule of the invention, wherein the nucleotide sequence is operatively-linked to a promoter and a transcription termination sequence; culturing the transformed plant cell under conditions sufficient to allow for development of a plant cell culture including a plurality of transformed plant cells; selecting for transformed plant cells that have integrated the nucleic acid molecule into their genomes; screening the transformed plant cells for expression of an iRNA molecule encoded by the integrated nucleic acid molecule; selecting a transgenic plant cell that expresses the iRNA molecule; and feeding the selected transgenic plant cell to the coleopteran pest. Plants may also be regenerated from transformed plant cells that express an iRNA molecule encoded by the integrated nucleic acid molecule. In some embodiments, the iRNA molecule is a dsRNA molecule. In these and further embodiments, the nucleic acid molecule(s) comprise dsRNA molecules that each comprise more than one nucleotide sequence that is specifically hybridizable to a nucleic acid molecule expressed in a coleopteran pest cell. In some embodiments, the nucleic acid molecule(s) consists of one nucleotide sequence that is specifically hybridizable to a nucleic acid molecule expressed in a coleopteran pest cell.

iRNA molecules of the invention can be incorporated within the seeds of a plant species (e.g., corn), either as a product of expression from a recombinant gene incorporated into a genome of the plant cells, or as incorporated into a coating or seed treatment that is applied to the seed before planting. A plant cell comprising a recombinant gene is considered to be a transgenic event. Also included in embodiments of the invention are delivery systems for the delivery of iRNA molecules to coleopteran pests. For example, the iRNA molecules of the invention may be directly introduced into the cells of a coleopteran pest. Methods for introduction may include direct mixing of iRNA with plant tissue from a host for the coleopteran pest, as well as application of compositions comprising iRNA molecules of the invention to host plant tissue. For example, iRNA molecules may be sprayed onto a plant surface. Alternatively, an iRNA molecule may be expressed by a microorganism, and the microorganism may be applied onto the plant surface, or introduced into a root or stem by a physical means such as an injection. As discussed, supra, a transgenic plant may also be genetically engineered to express at least one iRNA molecule in an amount sufficient to kill the coleopteran pests known to infest the plant. iRNA molecules produced by chemical or enzymatic synthesis may also be formulated in a manner consistent with common agricultural practices, and used as spray-on products for controlling plant damage by a coleopteran pest. The formulations may include the appropriate stickers and wetters required for efficient foliar coverage, as well as UV protectants to protect iRNA molecules (e.g., dsRNA molecules) from UV damage. Such additives are commonly used in the bioinsecticide industry, and are well known to those skilled in the art. Such applications may be combined with other spray-on insecticide applications (biologically based or otherwise) to enhance plant protection from coleopteran pests.

All references, including publications, patents, and patent applications, cited herein are hereby incorporated by reference to the extent they are not inconsistent with the explicit details of this disclosure, and are so incorporated to the same extent as if each reference were individually and specifically indicated to be incorporated by reference and were set forth in its entirety herein. The references discussed herein are provided solely for their disclosure prior to the filing date of the present application. Nothing herein is to be construed as an admission that the inventors are not entitled to antedate such disclosure by virtue of prior invention.

The following EXAMPLES are provided to illustrate certain particular features and/or aspects. These EXAMPLES should not be construed to limit the disclosure to the particular features or aspects described.

EXAMPLES

Example 1

Materials and Methods

Sample Preparation and Bioassays.

A number of dsRNA molecules (including those corresponding to PP1-87B, RPA70 Reg1, RPA70 Reg2, RPA70 Reg3, and RPS6) were synthesized and purified using a MEGAscript® RNAi kit. The purified dsRNA molecules were prepared in TE buffer, and all bioassays contained a control treatment consisting of this buffer, which served as a background check for mortality or growth inhibition of WCR. The concentrations of dsRNA molecules in the bioassay buffer were measured using a NanoDrop™ 8000 spectrophotometer (Thermo Scientific, Wilmington, Del.).

Samples were tested for insect activity in bioassays conducted with neonate insect larvae on artificial insect diet. WCR eggs were obtained from Crop Characteristics, Inc. (Farmington, Minn.).

The bioassays were conducted in 128-well plastic trays specifically designed for insect bioassays (C-D International, Pitman, N.J.). Each well contained approximately 1.0 mL of a diet designed for growth of coleopteran insects. A 60 µL aliquot of dsRNA sample was delivered by pipette onto the 1.5 cm$^2$ diet surface of each well (40 µL/cm$^2$). dsRNA sample concentrations were calculated as the amount of dsRNA per square centimeter (ng/cm$^2$) of surface area in the well. The treated trays were held in a fume hood until the liquid on the diet surface evaporated or was absorbed into the diet.

Within a few hours of eclosion, individual larvae were picked up with a moistened camel hair brush and deposited on the treated diet (one or two larvae per well). The infested wells of the 128-well plastic trays were then sealed with adhesive sheets of clear plastic, and vented to allow gas exchange. Bioassay trays were held under controlled environmental conditions (28° C., ~40% Relative Humidity, 16:8 (Light:Dark)) for 9 days, after which the total number of insects exposed to each sample, the number of dead insects, and the weight of surviving insects were recorded. Percent mortality, average live weights, and growth inhibition were calculated for each treatment. Stunting was defined as a decrease in average live weights. Growth inhibition (GI) was calculated as follows:

$$GI=[1-(TWIT/TNIT)/(TWIBC/TNIBC)]$$

where TWIT is the Total Weight of live Insects in the Treatment;

TNIT is the Total Number of Insects in the Treatment;

TWIBC is the Total Weight of live Insects in the Background Check (Buffer control); and TNIBC is the Total Number of Insects in the Background Check (Buffer control).

The $GI_{50}$ is determined to be the concentration of sample in the diet at which the GI value is 50%. The $LC_{50}$ (50% Lethal Concentration) is recorded as the concentration of sample in the diet at which 50% of test insects are killed. Statistical analysis was done using JMP™ software (SAS, Cary, N.C.).

Replicated bioassays demonstrated that ingestion of particular samples resulted in a surprising and unexpected mortality and growth inhibition of corn rootworm larvae.

Example 2

Identification of Candidate Target Genes

Multiple stages of WCR (*Diabrotica virgifera virgifera* LeConte) development were selected for pooled transcriptome analysis to provide candidate target gene sequences for control by RNAi transgenic plant insect resistance technology.

Total RNA was isolated from about 0.9 g whole first-instar WCR larvae (*Diabrotica virgifera virgifera* LeConte; 4 to 5 days post-hatch, held at 16° C.) and purified using the following phenol/TRI REAGENT®-based method (Molecular Research Center, Cincinnati, Ohio; Cat. No. TR 118):

Larvae were homogenized at room temperature in a 15 mL homogenizer with 10 mL of TRI REAGENT® until a homogenous suspension was obtained. Following 5 min. incubation at room temperature, the homogenate was dispensed into 1.5 mL microfuge tubes (1 mL per tube), 200 µL of chloroform was added, and the mixture was vigorously shaken for 15 seconds. After allowing the extraction to sit at room temperature for 10 min, the phases were separated by centrifugation at 12,000×g at 4° C. The upper phase (comprising about 0.6 mL) was carefully transferred into another sterile 1.5 mL tube, and an equal volume (0.6 mL) of room temperature isopropanol was added. After incubation at room temperature for 5 to 10 min, the mixture was centrifuged 8 min at 12,000×g (4° C. or 25° C.).

The supernatant was carefully removed and discarded, and the RNA pellet was washed twice by vortexing with 75% ethanol, with recovery by centrifugation for 5 min at 7,500×g (4° C. or 25° C.) after each wash. The ethanol was carefully removed, the pellet was allowed to air-dry for 3 to 5 min, and then was dissolved in nuclease-free sterile water. RNA concentration was determined by measuring the absorbance (A) at 260 nm and 280 nm. A typical extraction from about 0.9 g of larvae yielded over 1 mg of total RNA, with an A260/A280 ratio of 1.9. The RNA thus extracted was stored at −80° C. until further processed.

RNA quality was determined by running an aliquot through a 1% agarose gel. The agarose gel solution was made using autoclaved 10×TAE buffer (Tris-acetate EDTA, 1× concentration is 0.04 M Tris-acetate, 1 mM EDTA (ethylenediamine tetra-acetic acid sodium salt), pH 8.0) diluted with DEPC (diethyl pyrocarbonate)-treated water in an autoclaved container. 1×TAE was used as the running buffer. Before use, the electrophoresis tank and the well-forming comb were cleaned with RNAseAway™ (Invitrogen Inc., Carlsbad, Calif.). Two µL of RNA sample were mixed with 8 µL of TE buffer (10 mM Tris HCl pH 7.0; 1 mM EDTA) and 10 µL of RNA sample buffer (Novagen® Catalog No 70606; EMD4 Bioscience, Gibbstown, N.J.). The sample was heated at 70° C. for 3 min, cooled to room temperature, and 5 µL (containing 1 µg to 2 µg RNA) were loaded per well. Commercially available RNA molecular weight markers were simultaneously run in separate wells for molecular size comparison. The gel was run at 60 v for 2 hr.

A normalized cDNA library was prepared from the larval total RNA by a commercial service provider (Eurofins MWG Operon, Huntsville, Ala.), using random priming.

The normalized larval cDNA library was sequenced at ½ plate scale by GS FLX 454 Titanium™ series chemistry at Eurofins MWG Operon, which resulted in over 600,000 reads with an average read length of 348 bp. 350,000 reads were assembled into over 50,000 contigs. Both the unassembled reads and the contigs were converted into BLASTable databases using the publicly available program, FORMATDB (available from NCBI).

Total RNA and normalized cDNA libraries were similarly prepared from materials harvested at other WCR developmental stages. A pooled transcriptome library for target gene screening was constructed by combining cDNA library members representing the various developmental stages Candidate genes for RNAi targeting were selected using information regarding lethal RNAi effects of particular genes in other insects such as *Drosophila* and *Tribolium*. These genes were hypothesized to be essential for survival and growth in coleopteran insects. Selected target gene homologs were identified in the transcriptome sequence database as described below. Full-length or partial sequences of the target genes were amplified by PCR to prepare templates for double-stranded RNA (dsRNA) production.

TBLASTN searches using candidate protein coding sequences were run against BLASTable databases containing the unassembled *Diabrotica* sequence reads or the assembled contigs. Significant hits to a *Diabrotica* sequence (defined as better than $e^{-20}$ for contigs homologies and better than $e^{-10}$ for unassembled sequence reads homologies) were confirmed using BLASTX against the NCBI non-redundant database. The results of this BLASTX search confirmed that the *Diabrotica* homolog candidate gene sequences identified in the TBLASTN search indeed comprised *Diabrotica* genes, or were the best hit available in the *Diabrotica* sequences to the non-*Diabrotica* candidate gene sequence. In most cases, *Tribolium* candidate genes which were annotated as encoding a protein gave an unambiguous sequence homology to a sequence or sequences in the *Diabrotica* transcriptome sequences. In a few cases, it was clear that some of the *Diabrotica* contigs or unassembled sequence reads selected by homology to a non-*Diabrotica* candidate gene overlapped, and that the assembly of the contigs had failed to join these overlaps. In those cases, Sequencher™ v4.9 (Gene Codes Corporation, Ann Arbor, Mich.) was used to assemble the sequences into longer contigs.

A plurality of candidate target genes were identified as genes that may lead to coleopteran pest mortality or growth, development, or reproduction inhibition in WCR, including SEQ ID NOs:1-7. Full-length or partial clones of sequences of *Diabrotica* candidate gene homologs were used to generate PCR amplicons for dsRNA synthesis.

SEQ ID NO:1 comprises a sequence encoding a protein phosphatase protein (herein referred to as PP1-87B), which corresponds to a metallo-dependent, serine/threonine-specific protein phosphatase catalytic subunit.

SEQ ID NO:2 comprises a sequence encoding an RPA70 protein (herein referred to as RPA70), which corresponds to Replication protein A-70, a subunit of a single-stranded DNA binding protein.

SEQ ID NO:3 represents contig0011_87B, a fragment of a coding region for a PP1-87B protein phosphatase.

SEQ ID NO:4 represents D_vir_c43870 RPA70, a fragment of a coding region for an RPA70 protein, and referred to herein as RPA70 region 1, or RPA70 Reg1.

SEQ ID NO:5 represents D_vir_c18764 RPA70, a fragment of a coding region for an RPA70 protein, and referred to herein as RPA70 Reg2.

SEQ ID NO:6 represents D_vir_c7971_RPA70, a fragment of a coding region for an RPA70 protein, and referred to herein as RPA70 Reg3.

SEQ ID NO:7 comprises a sequence encoding an RPS6 protein, which is Ribosomal Protein S-6.

Example 3

Amplification of Target Genes

Primers were designed to amplify portions of coding regions of each target gene by PCR. See Table 1. Where appropriate, a T7 phage promoter sequence (TTAATACGACTCACTATAGGGAGA (SEQ ID NO:8)) was incorporated into the 5' ends of the amplified sense or antisense strands. See Table 1. Total RNA was extracted from WCR, and first-strand cDNA was used as template for PCR reactions using opposing primers positioned to amplify all or part of the native target gene sequence.

TABLE 1

Primers and Primer Pairs used to amplify portions of coding regions of exemplary target genes.

| | Gene (Region) | Primer Name | SEQ ID NO: | Sequence |
|---|---|---|---|---|
| Pair 1 | PP1-87B | PP1-87B-F_T7 | SEQ ID NO: 9 | TTAATACGACTCACTATAGGGAGACAAATGGCAGAAGCAGATAAATTG |
| | PP1-87B | PP1-87B-R | SEQ ID NO: 10 | CTAATTTGTTCCATTGATTGTAGGTCC |
| Pair 2 | PP1-87B | PP1-87B-F | SEQ ID NO: 11 | CAAATGGCAGAAGCAGATAAATTG |
| | PP1-87B | PP1-87B-R_T7 | SEQ ID NO: 12 | TTAATACGACTCACTATAGGGAGACTAATTTGTTCCATTGATTGTAGGTCC |
| Pair 3 | RPA70 (region 2) | RPA70-F1_T7 | SEQ ID NO: 13 | TTAATACGACTCACTATAGGGAGAATGGTCAAATTCTAGAGGGGAA |
| | RPA70 (region 2) | RPA70-R1 | SEQ ID NO: 14 | CTACGACAGGATTATTGGTACCATC |
| Pair 4 | RPA70 (region 2) | RPA70-F1 | SEQ ID NO: 15 | ATGGTCAAATTCTAGAGGGGAA |
| | RPA70 (region 2) | RPA70-R1-T7 | SEQ ID NO: 16 | TTAATACGACTCACTATAGGGAGACTACGACAGGATTATTGGTACCATC |

TABLE 1-continued

Primers and Primer Pairs used to amplify portions of coding regions of exemplary target genes.

| | Gene (Region) | Primer Name | SEQ ID NO: | Sequence |
|---|---|---|---|---|
| Pair 5 | RPA70 (region 3) | RPA70-F2_T7 | SEQ ID NO: 17 | TTAATACGACTCACTATAGGGAGATCC CGAATTAAAAGAATGTTACAGGA |
| | RPA70 (region 3) | RPA70-R2 | SEQ ID NO: 18 | CGAGCTTCATCATTGTAAGTCTCAAT |
| Pair 6 | RPA70 (region 3) | RPA70-F2 | SEQ ID NO: 19 | TCCCGAATTAAAAGAATGTTACAGGA |
| | RPA70 (region 3) | RPA70-R2_T7 | SEQ ID NO: 20 | TTAATACGACTCACTATAGGGAGACGA GCTTCATCATTGTAAGTCTCAAT |
| Pair 7 | RPS6 | RPS-F_T7 | SEQ ID NO: 21 | TTAATACGACTCACTATAGGGAGATCA ATATGAAGTTGAACGTATCG |
| | RPS6 | RPS-R | SEQ ID NO: 22 | ATGCTCTCTTGGGTCCCAGG |
| Pair 8 | RPS6 | RPS-F | SEQ ID NO: 23 | TCAATATGAAGTTGAACGTATCG TTAATACGACTCACTATAGGGAGAATG |
| | RPS6 | RPS-R_T7 | SEQ ID NO: 24 | CTCTCTTGGGTCCCAGG |

Example 4

RNAi Constructs

Template Preparation by PCR and dsRNA Synthesis

The strategy used to provide specific templates for dsRNA production is shown in FIG. 1. Template DNAs intended for use in dsRNA synthesis were prepared by PCR using the primer pairs in Table 1 and (as PCR template) first-strand cDNA prepared from total RNA isolated from WCR first-instar larvae. For each selected target gene region, two separate PCR amplifications were performed. The first PCR amplification introduced a T7 promoter sequence at the 5' end of the amplified sense strands. The second reaction incorporated the T7 promoter sequence at the 5' ends of the antisense strands. The two PCR amplified fragments for each region of the target genes were then mixed in approximately equal amounts, and the mixture was used as transcription template for dsRNA production. FIG. 1. The sequences of the dsRNA templates amplified with the particular primers were: SEQ ID NO:25 (PP1-87B); SEQ ID NO:26 (RPA70 Reg2); SEQ ID NO:27 (RPA70 Reg3), and SEQ ID NO:28 (RPS6). Double-stranded RNA was synthesized and purified using an Ambion® MEGAscript® RNAi kit following the manufacturer's instructions (Invitrogen). The concentrations of dsRNAs were measured using a NanoDrop™ 8000 spectrophotometer (Thermo Scientific, Wilmington, Del.).

Construction of Plant Transformation Vectors

Two types of hairpin RNA expression vectors, one set for WHISKERS™-mediated maize cell transformation and a second set for conventional Agrobacterium-mediated transformation, were assembled using standard Gateway® (Invitrogen) cloning methods. Target gene constructs for hairpin formation comprising segments of PP1-87B (SEQ ID NO:1; segment SEQ ID NO:3), RPA70 (SEQ ID NO:2; segment SEQ ID NO:5), and RPS6 (SEQ ID NO:7) were assembled using a combination of chemically synthesized fragments (DNA2.0, Menlo Park, Calif.) and standard molecular cloning methods. Intramolecular hairpin formation by RNA primary transcripts was facilitated by arranging (within a single transcription unit) two copies of the target gene fragments in opposite orientation to one another, the two fragments being separated by an ST-LS1 intron sequence (Vancanneyt et al. (1990) Mol. Gen. Genet. 220(2):245-50). Entry vectors containing expression cassettes of the hairpin constructs of PP1-87B, RPA70 region 2, and RPS6 were assembled using Gateway® cloning methods and standard cloning methods. Production of the primary mRNA transcript is driven by a copy of the maize ubiquitin 1 promoter (U.S. Pat. No. 5,510,474). Thus, the primary mRNA transcript contains the two gene fragment sequences as large inverted repeats of one another, separated by the intron sequence. A fragment comprising a 3' untranslated region from a maize peroxidase 5 gene (ZmPer5 3'UTR v2; U.S. Pat. No. 6,699,984) was used to terminate transcription of the target genes.

The same set of entry vectors was used for Gateway® cloning into two starting destination vectors to construct two types of hairpin RNA expression transformation vectors; one set for WHISKERS™-mediated maize cell transformation, and a second set for Agrobacterium-mediated transformation. All hairpin RNA expression vectors for WHISKERS™-mediated transformation were constructed using a starting destination vector (pDAB108916), and one of the constructed entry vectors by means of a standard Gateway® recombination reaction. The destination vector comprised two marker genes: a yellow fluorescent protein gene (YFP; Shagin et al. (2004) Mol. Biol. Evol. 21(5):841-50) and an herbicide tolerance gene (phosphinothricin acetyl transferase (PAT); Wehrmann et al. (1996) Nat. Biotechnol. 14(10):1274-8). The expressions of both the YFP and PAT were driven by a copy of a strong sugarcane bacilliform badnavirus (ScBV) promoter respectively (Schenk et al. (1999) Plant Molec. Biol. 39:1221-30). A fragment comprising a 3' untranslated region from a maize lipase gene (ZmLip 3'UTR; U.S. Pat. No. 7,179,902) was used to terminate transcription of the YFP gene, while transcription termination of PAT gene was controlled by a fragment containing a potato pinII gene 3'UTR (StPinII 3'UTR; essentially GenBank™ Accession No. X04118.1).

All hairpin RNA expression transformation vectors for Agrobacterium-mediated maize embryo transformation were constructed using a typical binary destination vector (pDAB101847) and one of the entry vectors described above through use of a standard Gateway® recombination reaction. The binary destination vector comprised another herbicide resistance gene (aryloxyalknoate dioxygenase; AAD-1 v3) (Wright et al. (2010) Proc. Natl. Acad. Sci. U.S.A. 107:20240-5) under the regulation of the ScBV promoter and ZmLip 3'UTR terminator. The binary vector plasmids were pDAB109818 (comprising the RPA70 hairpin construct), pDAB109822 (comprising the PP1-87B hairpin construct), and pDAB109823 (comprising the RPS6 hairpin construct).

TABLE 2

Results of diet feeding assays obtained with western corn rootworm larvae.

| Sample Name | $LC_{50}$ | $LC_{50}$ Range | $GI_{50}$ | $GI_{50}$ Range |
|---|---|---|---|---|
| PP1-87B | 50 | 23-117 | ND | ND |
| RPA70 Reg2 | 42 | 17-100 | ND | ND |
| RPA70 Reg3 | 61 | 15-331 | ND | ND |
| RPS6 | 282 | 113-1000+ | 5 | 2.5-8.7 |

*Dose units are ng/cm².
**ND = Not Done

TABLE 3

Results of diet feeding assays obtained with western corn rootworm larvae.

| Sample Name | Dose (ng/cm²) | Number of Rows (Replications) | Mean % Mortality | Mean GI | Mean Weight per Insect (mg) (All Replicate Data) |
|---|---|---|---|---|---|
| RPS6 | 1000 | 4 | 53 (A)* | 0.7075 | 0.2175 |
| TE buffer | 0 | 4 | 16.5 (B) | 0 | 0.43 |
| Water | 0 | 4 | 10 (B) | 0 | 1.07 |
| YFP | 1000 | 4 | 4 (B) | −0.7955 | 0.625 |

*Letters in parentheses designate statistical levels. Levels not connected by same letter are significantly different (Contingency Analysis, P < 0.05)

SEQ ID NO:29 presents a PP1-87B hairpin forming sequence, SEQ ID NO:30 presents an RPA70 Reg2 hairpin-forming sequence, and SEQ ID NO:31 presents an RPS6 hairpin-forming sequence.

Fragment purification for WHISKERS™-mediated transformation is accomplished on a preparative scale by high pressure liquid chromatography (HPLC) after the YFP/hpRNA/PAT expression vector DNAs had been digested with appropriate restriction enzymes to remove a bacterial spectinomycin resistance gene present in the vector backbone.

Example 5

Screening of Candidate Target Genes

Synthetic dsRNA designed to inhibit some, but not all, target gene sequences identified in EXAMPLE 2 caused mortality and growth inhibition when administered to WCR in diet-based assays. PP1-87B, RPA70 Reg2, RPA70 Reg3, and RPS6 were observed to exhibit greatly increased efficacy in this assay over other dsRNAs screened.

Figure 2:
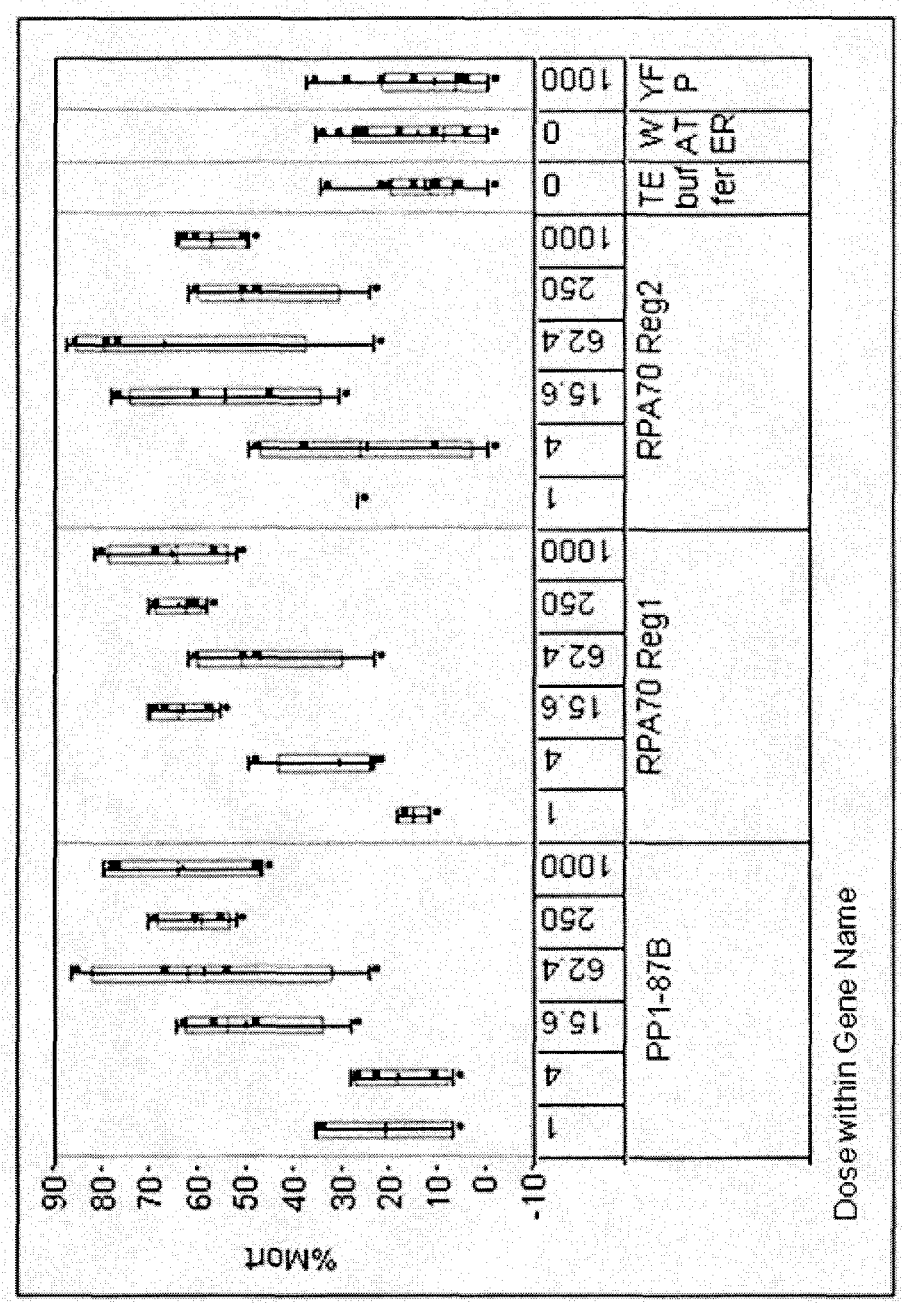
FIG. 2 includes a variability chart for the percent mortality of exemplary coleopteran pests (i.e., western corn rootworm larvae) treated with exemplary nucleic acid molecules targeting PP1-87B, RPA70 Reg1, and RPA70 Reg2.
Figure 3:
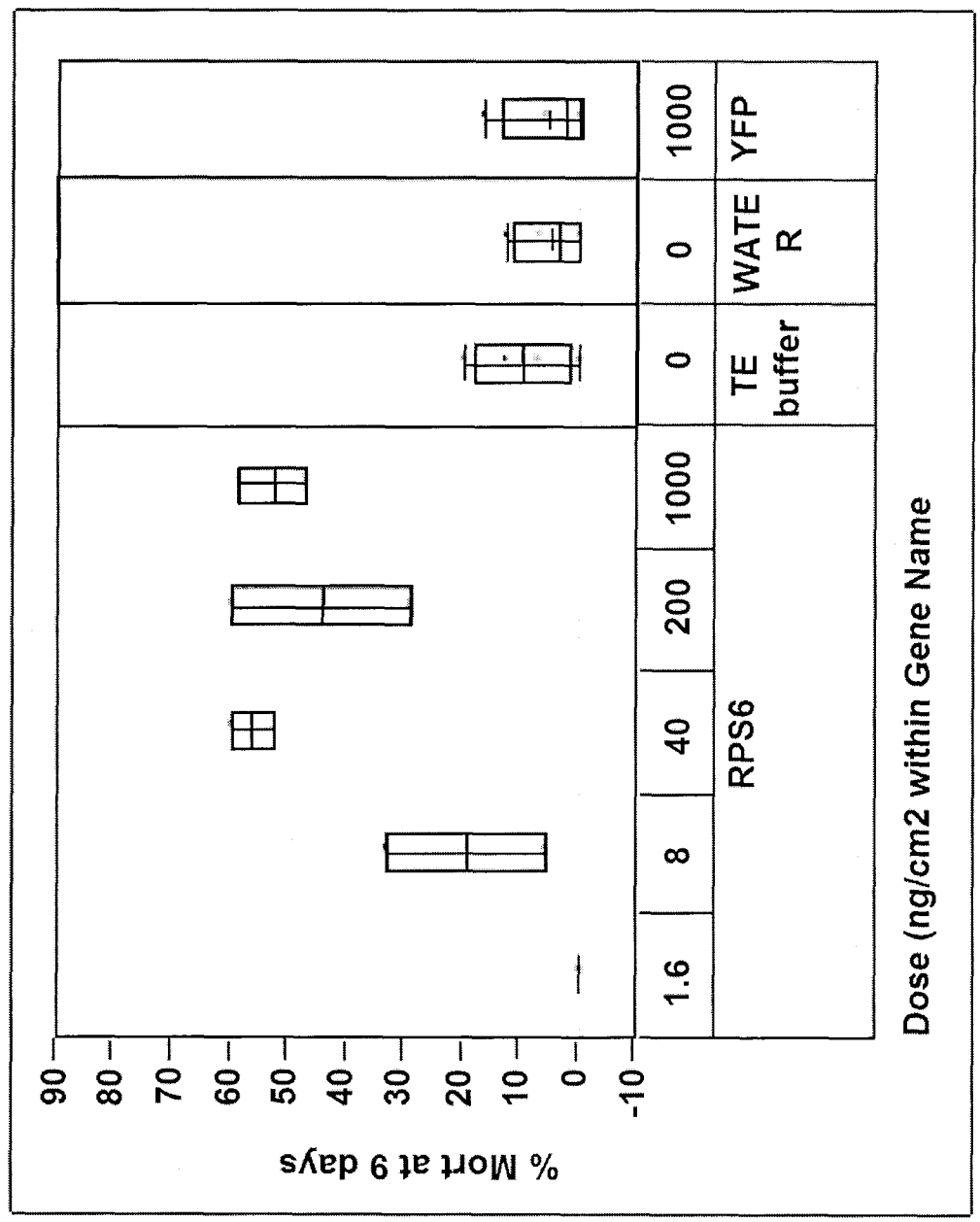
FIG. 3 includes a variability chart for the percent mortality of exemplary coleopteran pests (i.e., western corn rootworm larvae) treated with exemplary nucleic acid molecules targeting RPS6.
Figure 4:
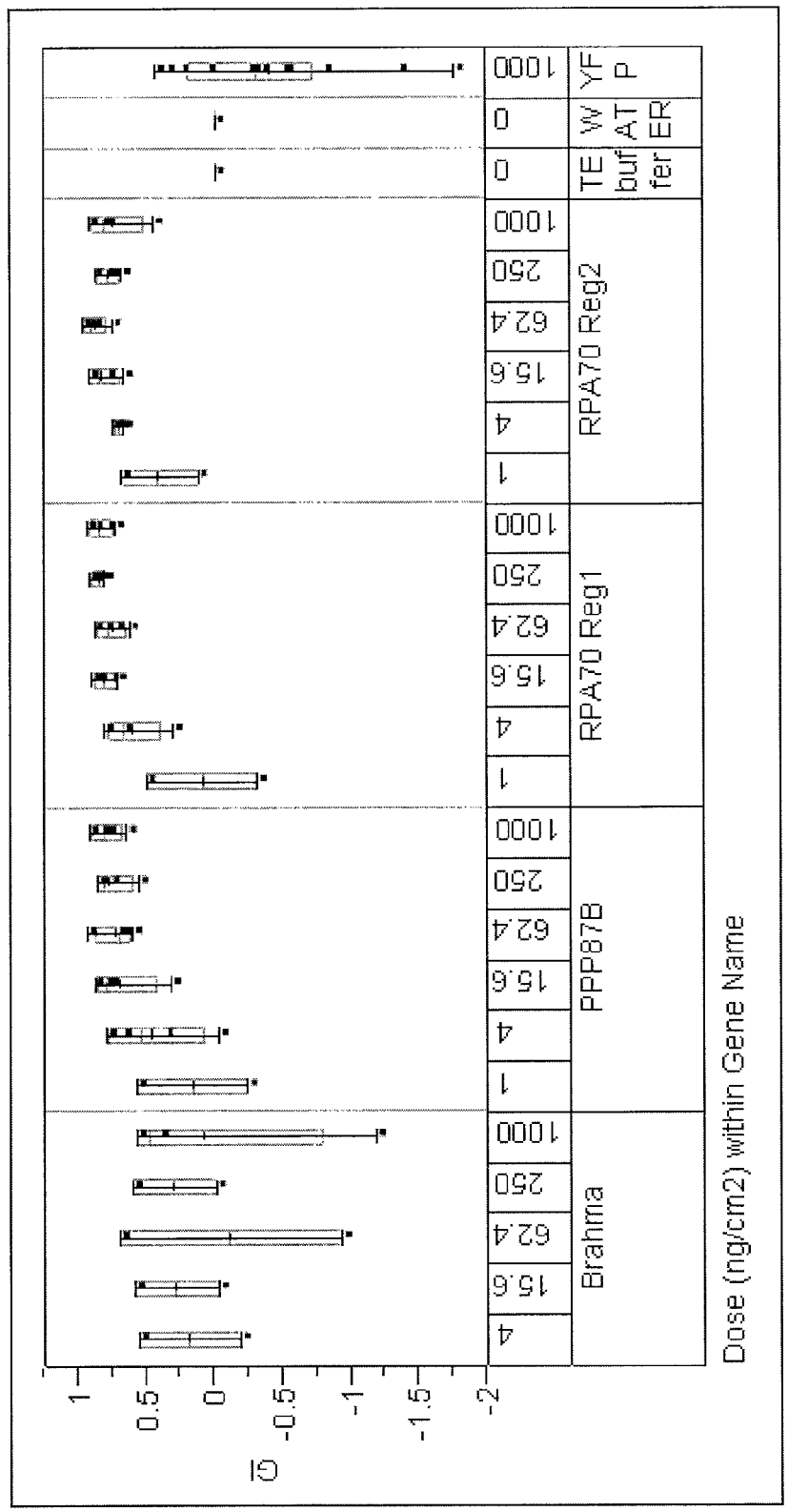
FIG. 4 includes a variability chart for the growth inhibition (GI) of exemplary coleopteran pests (i.e., western corn rootworm larvae) treated with exemplary nucleic acid molecules targeting PP1-87B, RPA70 Reg1, and RPA70 Reg2.
Figure 5:
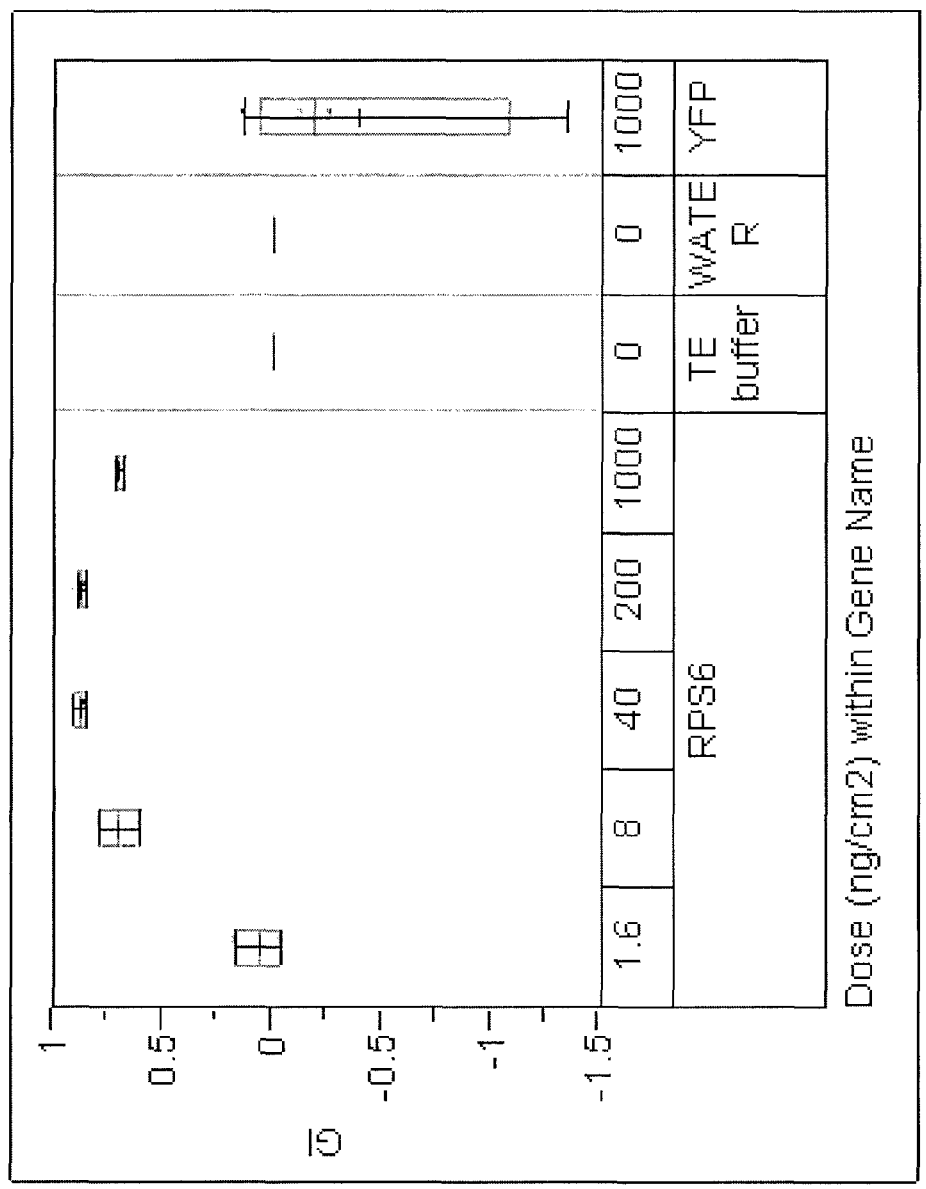
FIG. 5 includes a variability chart for the growth inhibition (GI) of exemplary coleopteran pests (i.e., western corn rootworm larvae) treated with exemplary nucleic acid molecules targeting RPS6.

Replicated bioassays demonstrated that ingestion of dsRNA preparations derived from PP1-87B, RPA70 Reg2, RPA70 Reg3, and RPS6 each resulted in mortality and/or growth inhibition of western corn rootworm larvae. Table 2 and Table 3 show the results of diet-based feeding bioassays of WCR larvae following 9-day exposure to these dsRNAs. FIG. 2 and FIG. 3 show variability charts for the mortality data, and FIG. 4 and FIG. 5 show variability charts for the growth inhibition data of coleopteran pests treated with exemplary nucleic acid molecules.

It has previously been suggested that certain genes of Diabrotica spp. may be exploited for RNAi-mediated insect control. See U.S. Patent Publication No. 2007/0124836, which discloses 906 sequences, and U.S. Pat. No. 7,614,924, which discloses 9,112 sequences. However, it was determined that many genes suggested to have utility for RNAi-mediated insect control are not efficacious in controlling Diabrotica. It was also determined that PP1-87B, RPA70 Reg2, RPA70 Reg3, and RPS6 each provide surprising and unexpected superior control of Diabrotica, compared to other genes suggested to have utility for RNAi-mediated insect control.

For example, annexin, beta spectrin 2, and mtRP-L4 were each suggested in U.S. Pat. No. 7,614,924 to be efficacious in RNAi-mediated insect control. SEQ ID NO:32 is the DNA sequence of annexin region 1, and SEQ ID NO:33 is the DNA sequence of annexin region 2. SEQ ID NO:34 is the DNA sequence of beta spectrin 2 region 1, and SEQ ID NO:35 is the DNA sequence of beta spectrin 2 region 2. SEQ ID NO:36 is the DNA sequence of mtRP-L4 region 1, and SEQ ID NO:37 is the DNA sequence of mtRP-L4 region 2. A YFP sequence (SEQ ID NO:38) was also used to produce dsRNA as a negative control.

Each of the aforementioned sequences was used to produce dsRNA by the methods of EXAMPLE 4, and the dsRNAs were each tested by the same diet-based bioassay methods described above. Table 4 lists the sequences of the primers used to produce the annexin, beta spectrin 2, and mtRP-L4 dsRNA molecules. Table 5 presents the results of diet-based feeding bioassays of WCR larvae following 9-day exposure to these dsRNA molecules. Replicated bioassays demonstrated that ingestion of these dsRNAs resulted in no mortality or growth inhibition of western corn rootworm larvae above that seen with control samples of TE buffer, YFP, or water.

TABLE 4

Primers and Primer Pairs used to amplify portions of coding regions of genes.

| | Gene (Region) | Primer Name | SEQ ID NO: | Sequence |
|---|---|---|---|---|
| Pair 9 | annexin (1) | Ann-F1_T7 | SEQ ID NO: 39 | TTAATACGACTCACTATAGGGAGAGCTCCAACAGTGGTTCCTTATC |
| | annexin (1) | Ann-R1 | SEQ ID NO: 40 | CTAATAATTCTTTTTTAATGTTCCTGAGG |
| Pair 10 | annexin (1) | Ann-F1 | SEQ ID NO: 41 | GCTCCAACAGTGGTTCCTTATC |
| | annexin (1) | Ann-R1T7 | SEQ ID NO: 42 | TTAATACGACTCACTATAGGGAGACTAATAATTCTTTTTTAATGTTCCTGAGG |
| Pair 11 | annexin (2) | Ann-F2_T7 | SEQ ID NO: 43 | TTAATACGACTCACTATAGGGAGATTGTTACAAGCTGGAGAACTTCTC |
| | annexin (2) | Ann-R2 | SEQ ID NO: 44 | CTTAACCAACAACGGCTAATAAGG |
| Pair 12 | annexin (2) | Ann-F2 | SEQ ID NO: 45 | TTGTTACAAGCTGGAGAACTTCTC |
| | annexin (2) | Ann-R2T7 | SEQ ID NO: 46 | TTAATACGACTCACTATAGGGAGACTTAACCAACAACGGCTAATAAGG |
| Pair 13 | beta-spect2 (1) | Betasp2-F1_T7 | SEQ ID NO: 47 | TTAATACGACTCACTATAGGGAGAAGATGTTGGCTGCATCTAGAGAA |
| | beta-spect2 (1) | Betasp2-R1 | SEQ ID NO: 48 | GTCCATTCGTCCATCCACTGCA |
| Pair 14 | beta-spect2 (1) | Betasp2-F1 | SEQ ID NO: 49 | AGATGTTGGCTGCATCTAGAGAA |
| | beta-spect2 (1) | Betasp2-R1_T7 | SEQ ID NO: 50 | TTAATACGACTCACTATAGGGAGAGTCCATTCGTCCATCCACTGCA |
| Pair 15 | beta-spect2 (2) | Betasp2-F2_T7 | SEQ ID NO: 51 | TTAATACGACTCACTATAGGGAGAGCAGATGAACACCAGCGAGAAA |
| | beta-spect2 (2) | Betasp2-R2 | SEQ ID NO: 52 | CTGGGCAGCTTCTTGTTTCCTC |
| Pair 16 | beta-spect2 (2) | Betasp2-F2 | SEQ ID NO: 53 | GCAGATGAACACCAGCGAGAAA |
| | beta-spect2 (2) | Betasp2-R2_T7 | SEQ ID NO: 54 | TTAATACGACTCACTATAGGGAGACTGGGCAGCTTCTTGTTTCCTC |
| Pair 17 | mtRP-L4 (1) | L4-F1_T7 | SEQ ID NO: 55 | TTAATACGACTCACTATAGGGAGAAGTGAAATGTTAGCAAATATAACATCC |
| | mtRP-L4 (1) | L4-R1 | SEQ ID NO: 56 | ACCTCTCACTTCAAATCTTGACTTTG |
| Pair 18 | mtRP-L4 (1) | L4-F1 | SEQ ID NO: 57 | AGTGAAATGTTAGCAAATATAACATCC |
| | mtRP-L4 (1) | L4-R1_T7 | SEQ ID NO: 58 | TTAATACGACTCACTATAGGGAGAGTCTCACTTCAAATCTTGACTTTG |
| Pair 19 | mtRP-L4 (2) | L4-F2_T7 | SEQ ID NO: 59 | TTAATACGACTCACTATAGGGAGACAAAGTCAAGATTTGAAGTGAGAGGT |
| | mtRP-L4 (2) | L4-R2 | SEQ ID NO: 60 | CTACAAATAAAACAAGAAGGACCCC |
| Pair 20 | mtRP-L4 (2) | L4-F2 | SEQ ID NO: 61 | CAAAGTCAAGATTTGAAGTGAGAGGT |
| | mtRP-L4 (2) | L4-R2_T7 | SEQ ID NO: 62 | TTAATACGACTCACTATAGGGAGACTACAAATAAAACAAGAAGGACCCC |
| Pair 21 | YFP | YFP-F_T7 | SEQ ID NO: 63 | TTAATACGACTCACTATAGGGAGACACCATGGGCTCCAGCGGCGCCC |
| | YFP | YFP-R | SEQ ID NO: 64 | AGATCTTGAAGGCGCTCTTCAGG |
| Pair 22 | YFP | YFP-F | SEQ ID NO: 65 | CACCATGGGCTCCAGCGGCGCCC |
| | YFP | YFP-R_T7 | SEQ ID NO: 66 | TTAATACGACTCACTATAGGGAGAAGATCTTGAAGGCGCTCTTCAGG |

TABLE 5

Results of diet feeding assays obtained with western corn rootworm larvae.

| Gene Name | Dose (ng/cm$^2$) | Mean weight per insect (mg) | Mean % Mortality | Mean Growth Inhibition |
|---|---|---|---|---|
| annexin-region 1 | 1000 | 0.545 | 0 | −0.262 |
| annexin-region 2 | 1000 | 0.565 | 0 | −0.301 |
| beta spectrin2 region 1 | 1000 | 0.340 | 12 | −0.014 |
| beta spectrin2 region 2 | 1000 | 0.465 | 18 | −0.367 |
| mtRP-L4 region 1 | 1000 | 0.305 | 4 | −0.168 |
| mtRP-L4 region 2 | 1000 | 0.305 | 7 | −0.180 |
| TE buffer | 0 | 0.430 | 13 | 0.000 |
| Water | 0 | 0.535 | 12 | 0.000 |
| YFP | 1000 | 0.480 | 9 | −0.386 |

Example 6

Production of Transgenic Maize Tissues Comprising Insecticidal Hairpin dsRNAs Plants that produce one or more insecticidal dsRNA molecules (for example, at least one dsRNA molecule including a dsRNA molecule targeting a gene comprising one of SEQ ID NOs:1-7) through expression of a chimeric gene stably-integrated into the plant genome are produced. Preparations of plant transformation DNA molecules prepared essentially as described in EXAMPLE 4 are delivered into maize Hi-II suspension cell cultures via WHISKERS™-mediated transformation (essentially as described in U.S. Pat. Nos. 5,302,523 and 5,464,765; U.S. Patent Publication No. 2008/0182332; and Petolino and Arnold (2009) Methods Mol. Biol. 526:59-67, which are herein incorporated by this reference in their entirety). Transformed tissues are selected by their ability to grow on BASTA™- or haloxyfop-containing medium and are screened for YFP production, as appropriate. Portions of such transformed tissue cultures may be presented to neonate corn rootworm larvae for bioassay, essentially as described in EXAMPLE 7.

*Agrobacterium*-Mediated Transformation

Alternatively, transgenic maize cells, tissues, and plants that produce one or more insecticidal dsRNA molecules (for example, at least one dsRNA molecule including a dsRNA molecule targeting a gene comprising one of SEQ ID NOs:1-7) through expression of a chimeric gene stably integrated into the plant genome were produced following *Agrobacterium*-mediated transformation. Maize transformation methods employing superbinary or binary transformation vectors are known in the art, as described, for example, in International PCT Publication No. WO2010/120452. Transformed tissues were selected by their ability to grow on haloxyfop-containing medium and were screened for dsRNA production, as appropriate. Portions of such transformed tissue cultures may be presented to neonate corn rootworm larvae for bioassay, essentially as described in EXAMPLE 7.

Ear Sterilization and Embryo Isolation.

Maize immature embryos were obtained from plants of *Zea mays* inbred line B104 grown in the greenhouse and self- or sib-pollinated to produce ears. The ears were harvested approximately 9 to 12 days post-pollination. On the experimental day, de-husked ears were surface-sterilized by immersion in a 20% solution of sodium hypochlorite (6.15%), and shaken for 20 to 30 minutes, followed by three rinses in sterile water. After sterilization, immature zygotic embryos (1.5 to 2.4 mm) were aseptically dissected from each ear, and randomly distributed into microcentrifuge tubes containing liquid Inoculation Medium. Inoculation Medium contained: 2.2 gm/L MS salts and 1×ISU Modified MS Vitamins (Frame et al. (2011) "Genetic Transformation Using Maize Immature Zygotic Embryos." In *Plant Embryo Culture Methods and Protocols: Methods in Molecular Biology*. T. A. Thorpe and E. C. Yeung, (Eds.), SPRINGER SCIENCE AND BUSINESS MEDIA, LLC., pp 327-341); 68.4 gm/L sucrose; 36 gm/L glucose; 115 mg/L L-proline; 100 mg/L myo-inositol; and 200 µM acetosyringone (prepared in DMSO); at pH 5.4. For a given set of experiments, embryos from pooled ears were used for each transformation.

*Agrobacterium* Culture Initiation.

Glycerol stocks of *Agrobacterium* strain DAt13192 containing a binary transformation vector, such as pDAB109818, pDAB109822 or pDAB109823, were streaked on AB minimal medium plates (Watson et al. (1975) J. Bacteriol. 123:255-64) containing appropriate antibiotics, and were grown at 20° C. for 3 to 4 days. A single colony was picked and streaked onto YEP plates (10 gm/L yeast extract; 10 gm/L Peptone; 5 gm/L NaCl) containing the same antibiotics and the plates were incubated at 20° C. for 1-2 days.

*Agrobacterium* Culture and Co-Cultivation.

*Agrobacterium* colonies were taken from a YEP plate, suspended in 10 mL of Inoculation Medium in a 50 mL disposable tube, and the cell density was adjusted to an $OD_{550}$ of 0.2 to 0.4 (Optical Density measured at 550 nm, an indirect measure of cell concentration) using a spectrophotometer. The *Agrobacterium* cultures were incubated on a rotary shaker at 125 rpm (room temperature) while embryo dissection was performed. Immature zygotic embryos (previously isolated from the sterilized maize kernels and placed in 1 mL of Inoculation Medium) were washed once in the same medium.

Two mL of the *Agrobacterium* suspension were added to each tube of embryos, and the tubes were placed on a shaker platform for 10 to 15 minutes. The embryos were transferred onto Co-cultivation Medium, oriented with the scutellum facing up, and incubated at 25° C., under 24-hour light at 50 $\mu m^{-2} sec^{-1}$ light intensity for 3 days. Co-cultivation Medium contained 4.33 gm/L MS salts; 1×ISU Modified MS Vitamins; 30 gm/L sucrose; 700 mg/L L-proline; 3.3 mg/L Dicamba (3,6-dichloro-o-anisic acid or 3,6-dichloro-2-methoxybenzoic acid) in KOH; 100 mg/L myo-inositol; 100 mg/L Casein Enzymatic Hydrolysate; 15 mg/L $AgNO_3$; 100 µM acetosyringone in DMSO; and 3 gm/L GELZAN™ (SIGMA-ALDRICH); at pH 5.8.

Callus Selection and Regeneration of Putative Events.

Following the co-cultivation period, embryos were transferred to Resting Medium and incubated at 25° C. under 24-hour light at 50 $\mu m^{-2} sec^{-1}$ light intensity, for 3 days. Resting Medium contained 4.33 gm/L MS salts; 1×ISU Modified MS Vitamins; 30 gm/L sucrose; 700 mg/L L-proline; 3.3 mg/L Dicamba in KOH; 100 mg/L myo-inositol; 100 mg/L Casein Enzymatic Hydrolysate; 15 mg/L $AgNO_3$; 0.5 gm/L MES (2-(N-morpholino)ethanesulfonic acid monohydrate; PHYTOTECHNOLOGIES LABR.; Lenexa, Kans.); 250 mg/L Carbenicillin; and 2.3 gm/L GELZAN™; at pH 5.8. Embryos were transferred onto Selection Medium 1 (which consisted of the Resting Medium (above) with 100 nM R-Haloxyfop acid (0.0362 mg/L)), and incubated in either dark and/or under 24-hour light at 50 $\mu m^{-2} sec^{-1}$ light intensity for 7 to 14 days at 28° C.

Proliferating embryogenic calli were transferred onto Selection Medium 2 (which consisted of Resting Medium (above), with 500 nM R-Haloxyfop acid (0.1810 mg/L)), and were incubated in 24-hour light at 50 $\mu Em^{-2} sec^{-1}$ light intensity for 14 to 21 days at 28° C. This selection step allowed transgenic callus to further proliferate and differentiate.

Proliferating, embryogenic calli were transferred onto PreRegeneration Medium, and cultured under 24-hour light at 50 $\mu m^{-2} sec^{-1}$ light intensity for 7 days at 28° C. PreRegeneration Medium contained 4.33 gm/L MS salts; 1×ISU Modified MS Vitamins; 45 gm/L sucrose; 350 mg/L L-proline; 100 mg/L myo-inositol; 50 mg/L Casein Enzymatic Hydrolysate; 1.0 mg/L $AgNO_3$; 0.25 gm/L MES; 0.5 mg/L naphthaleneacetic acid in NaOH; 2.5 mg/L abscisic acid in ethanol; 1 mg/L 6-benzylaminopurine; 250 mg/L Carbenicillin; 2.5 gm/L GELZAN™; and 500 nM R-Haloxyfop acid; at pH 5.8.

Embryogenic calli with shoot-like buds were transferred onto Regeneration Medium and cultured under 24-hour light at 50 µEm$^{-2}$ sec$^{-1}$ light intensity for 7 days. Regeneration Medium I contained 4.33 gm/L MS salts; 1×ISU Modified MS Vitamins; 60 gm/L sucrose; 100 mg/L myo-inositol; 125 mg/L Carbenicillin; 3.0 gm/L GELZAN™; and 500 nM R-Haloxyfop acid; at pH 5.8.

Small shoots with primary roots were transferred to Shoot/Root medium in PHYTATRAYS™ (PHYTOTECHNOLOGIES LABR.; Lenexa, Kans.) and were incubated under 16:8 hr. light:dark at 140 to 190 µEm$^{-2}$ sec$^{-1}$ light intensity for 7 days at 27° C. Shoot/Root Medium contained 4.33 gm/L MS salts; 1×ISU Modified MS Vitamins; 30 gm/L sucrose; 100 mg/L myo-inositol; 3.5 gm/L GELZAN™; at pH 5.8.

Putative transgenic plantlets were analyzed for transgene copy number by quantitative real-time PCR assays using primers designed to detect relative copy numbers of the ZmPer5 3' UTR (used to terminate transcription of the reptin hairpin-RNA expression gene), and were transferred to soil.

Transfer and Establishment of $T_0$ Plants in the Greenhouse for Bioassay and Seed Production.

Transformed plant tissues selected by their ability to grow on medium containing 500 nM R-Haloxyfop acid were assigned unique identifiers, transplanted into METROMIX™ 360 soilless growing medium (SUN GRO HORTICULTURE) and hardened-off in a growth room (~28° C. day temp./~24° C. night temp/16:8 supplemental lighting). Plants were then transplanted into SUNSHINE CUSTOM BLEND™ 160 soil mixture and grown to flowering in the greenhouse.

Plants to be used for insect bioassays were transplanted from small pots to TINUS™ 350-4 ROOTRAINERS® (Spencer-Lemaire Industries, Acheson, Alberta, Canada) (one plant per event per ROOTRAINER®). Approximately four days after transplanting to ROOTRAINERS®, $T_0$ plants were infested for bioassay.

Plants of the $T_1$ generation were obtained by pollinating the silks of $T_0$ transgenic plants with pollen collected from plants of non-transgenic elite inbred line B104, and planting the resultant seeds.

Example 7

Insect Bioassays

Plants that produce an insecticidal dsRNA were bioassayed in the greenhouse for root feeding damage. Western corn rootworm (WCR, *Diabrotica virgifera virgifera* LeConte) eggs were received in soil from Crop Characteristics (Farmington, Minn.), and the eggs were incubated at 28° C. for 10-11 days. Eggs were washed from the soil, placed into a 0.15% agar solution, and the concentration was adjusted to approximately 75 to 100 eggs per 0.25 mL aliquot. A hatch plate was set up in a Petri dish with an aliquot of egg suspension to monitor hatch rates.

The soil around the maize plants was infested with 150 to 200 WCR eggs. The insects were allowed to feed for 2 weeks, after which time a "Root Rating" was given to each plant. A Node-Injury Scale was utilized for grading, essentially according to Oleson et al. (2005) *J. Econ. Entomol.* 98(1):1-8. Plants which passed this bioassay were transplanted immediately to 5-gallon (18.92-liter) pots for hand-pollination and seed production. Seeds produced by these plants were saved for evaluation at the $T_1$ and subsequent generations of plants.

Negative control plants for the bioassays consisted of non-transformed B104 plants produced from seed or plants transformed with a binary vector harboring a YFP coding region under expression control of a maize-derived ubiquitin) promoter and Per5 3' UTR, and an AAD1 coding region under the expression control of a maize-derived ubiquitin) promoter and Lip 3' UTR. The negative control binary vector did not comprise a construct encoding a dsRNA.

$T_0$ generation plants regenerated from transformations utilizing binary vectors comprising: a construct encoding an RPA70 hairpin dsRNA (Table 14); a construct encoding a PP1-87B hairpin dsRNA (Table 12); and a construct encoding an RPS6 hairpin dsRNA (Table 13) were bioassayed in the greenhouse as described. A few of the PP1-87B and RPS6 $T_0$ events tested demonstrated evidence of protection from damage by western corn rootworm feeding. Tables 12 and 13.

Figure 6:
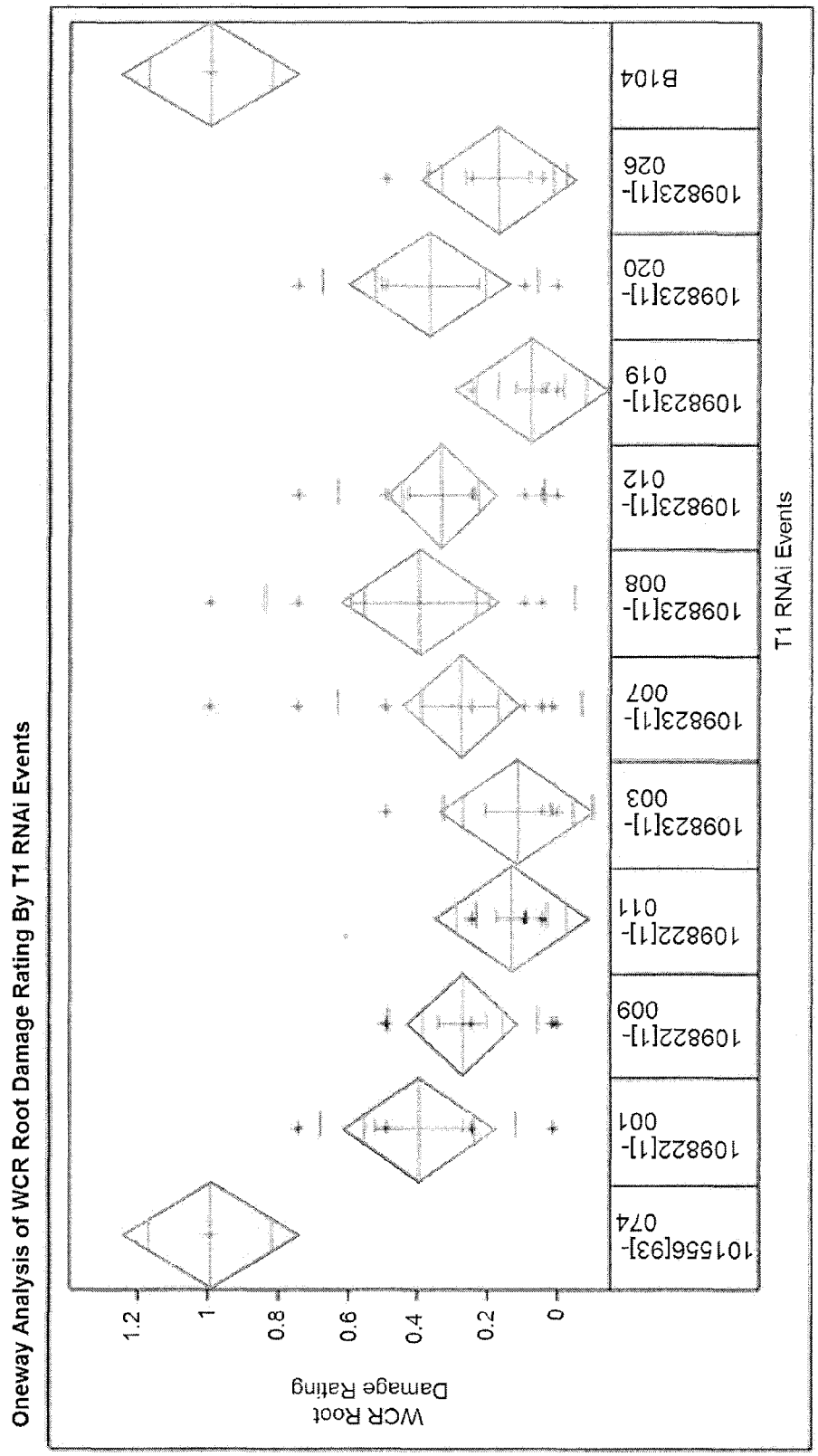
FIG. 6 provides a variability chart of root feeding damage caused by feeding by exemplary coleopteran pests (i.e., western corn rootworm larvae) on roots of $T_1$ greenhouse plants from events comprising a PP1-87B hairpin dsRNA construct and other events comprising an RPS6 hairpin dsRNA construct.
Figure 7:
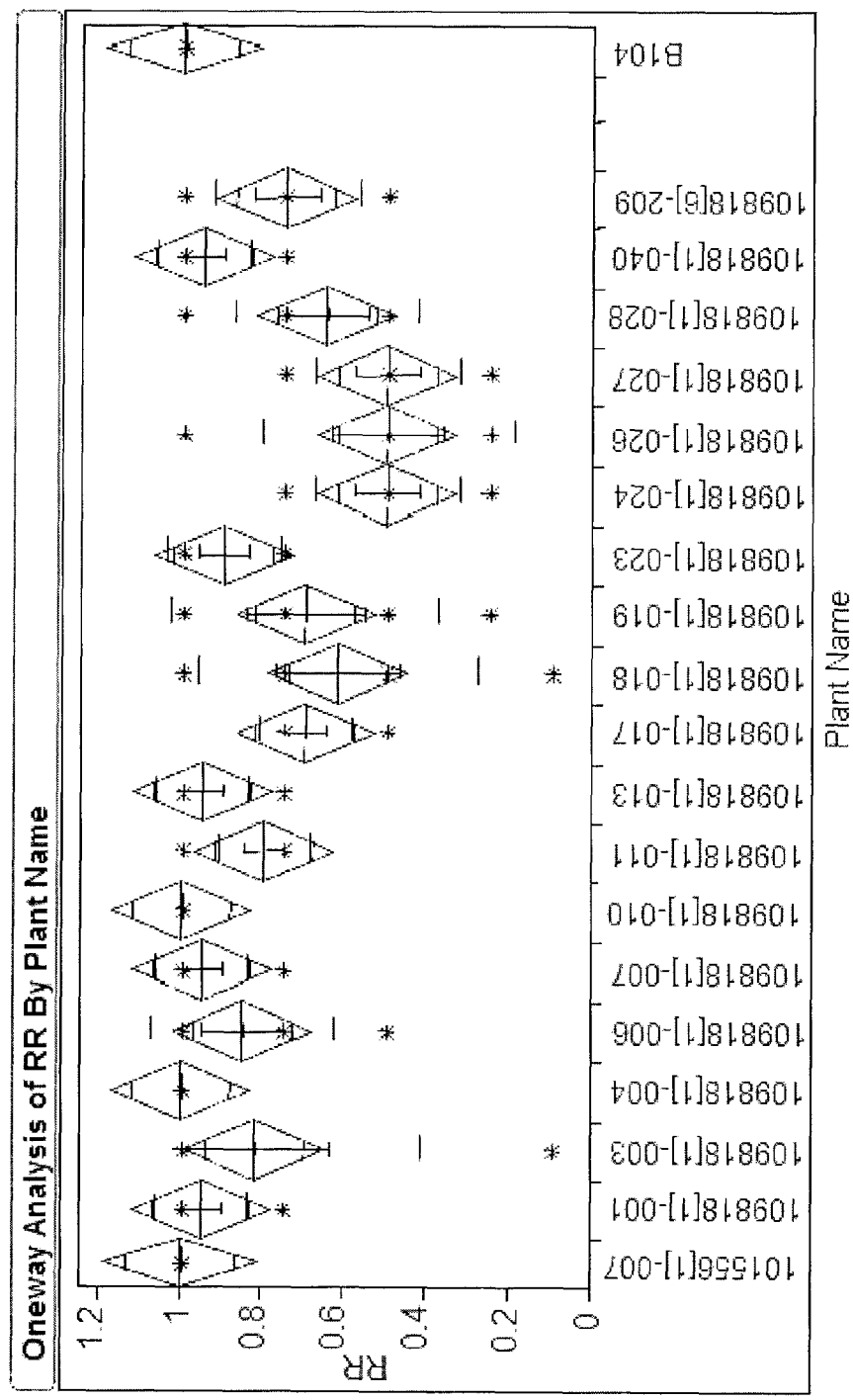
FIG. 7 includes an Analysis of Variance (ANOVA) summary of root feeding damage caused by feeding by exemplary coleopteran pests (i.e., western corn rootworm larvae) on roots of $T_1$ greenhouse plants from events comprising an RPA70 hairpin dsRNA construct.

$T_1$ generation seeds were produced by pollinating silks of $T_0$ plants with pollen collected from plants of non-transgenic elite inbred line B104. Plants of selected events were challenged in bioassays with western corn rootworm larvae as described. FIGS. 6 and 7 show variability data of mean root rating damage scores of $T_1$ plants comprising constructs encoding hairpin dsRNAs of PP1-87B, RPS6, or RPA70. The data shown in the FIGURES are further provided in Tables 6 and 7.

TABLE 6

Western corn rootworm Mean Root Damage Ratings of $T_1$ greenhouse plants from events comprising a construct encoding a PP1-87B hairpin dsRNA (pDAB109822; described as Event 109822), and plants from other events comprising constructs encoding an RPS6 hairpin dsRNA (pDAB109823; described as Event 109823).

|  | Level* | No. Plants | Mean Root Damage Rating | Std Error of Mean |
|---|---|---|---|---|
| PP1-87B Event |  |  |  |  |
| 109822[1]-001 | B | 5 | 0.404 | 0.12 |
| 109822[1]-009 | B | 10 | 0.279 | 0.07 |
| 109822[1]-011 | B | 5 | 0.140 | 0.05 |
| RPS6 Event |  |  |  |  |
| 109823[1]-008 | B | 5 | 0.400 | 0.20 |
| 109823[1]-020 | B | 5 | 0.372 | 0.14 |
| 109823[1]-012 | B | 10 | 0.342 | 0.09 |
| 109823[1]-007 | B | 10 | 0.287 | 0.11 |
| 109823[1]-026 | B | 5 | 0.180 | 0.09 |
| 109823[1]-003 | B | 5 | 0.120 | 0.10 |
| 109823[1]-019 | B | 5 | 0.082 | 0.04 |
| Negative Controls |  |  |  |  |
| 101556[93]-074 | A | 4.00 | 1.000 | 0 |
| B104 | A | 4.00 | 1.000 | 0 |

*Letters designate statistical levels as separated by the Tukey-Kramer test on the means. Event/plant names not connected by the same letter are significantly different (P < 0.05).

TABLE 7

Western corn rootworm Mean Root Damage Ratings of $T_1$ greenhouse plants from events comprising a construct encoding an RPA70 hairpin dsRNA.

| Event | Level* | No. Plants | Mean Root Damage Rating | Std Error of Mean |
|---|---|---|---|---|
| 109818[1]-004 | A | 5 | 1.00 | 0.00 |
| 109818[1]-010 | A | 5 | 1.00 | 0.00 |
| 109818[1]-001 | A | 5 | 0.95 | 0.05 |
| 109818[1]-007 | A | 5 | 0.95 | 0.05 |
| 109818[1]-013 | A | 5 | 0.95 | 0.05 |
| 109818[1]-040 | A | 5 | 0.95 | 0.05 |
| 109818[1]-023 | AB | 5 | 0.90 | 0.06 |
| 109818[1]-006 | AB | 5 | 0.85 | 0.10 |
| 109818[1]-003 | AB | 5 | 0.82 | 0.18 |
| 109818[1]-011 | AB | 5 | 0.80 | 0.05 |
| 109818[6]-209 | AB | 5 | 0.75 | 0.08 |
| 109818[1]-017 | AB | 5 | 0.70 | 0.05 |
| 109818[1]-019 | AB | 5 | 0.70 | 0.15 |
| 109818[1]-028 | AB | 5 | 0.65 | 0.10 |
| 109818[1]-018 | AB | 5 | 0.62 | 0.15 |
| 109818[1]-024 | BC | 5 | 0.50 | 0.08 |
| 109818[1]-026 | BC | 5 | 0.50 | 0.14 |
| 109818[1]-027 | BC | 5 | 0.50 | 0.08 |
| Negative Controls | | | | |
| 101556[1]-007 | A | 4 | 1.00 | 0.00 |
| B104 | A | 4 | 1.00 | 0.00 |

*Letters designate statistical levels as separated by the Tukey-Kramer test on the means. Event/plant names not connected by the same letter are significantly different ($P < 0.05$).

Example 9

In Vitro Insect Bioassays

Bioactivity of the dsRNA of the subject invention produced in plant cells is demonstrated by bioassay methods. See, e.g., Baum et al. (2007) Nat. Biotechnol. 25(11):1322-6. One is able to demonstrate efficacy, for example, by feeding various plant tissues or tissue pieces derived from a plant producing an insecticidal dsRNA to target insects in a controlled feeding environment. Alternatively, extracts are prepared from various plant tissues derived from a plant producing the insecticidal dsRNA and the extracted nucleic acids are dispensed on top of artificial diets for bioassays as previously described herein. The results of such feeding assays are compared to similarly conducted bioassays that employ appropriate control tissues from host plants that do not produce an insecticidal dsRNA, or to other control samples.

Example 10

Molecular Analyses of Transgenic Maize Tissues

Hairpin RNA Transcript Expression Level: Per 5 3'UTR qPCR.

Callus cell events or transgenic plants were analyzed by real-time quantitative PCR (qPCR) of the Per 5 3'UTR sequence to determine the relative expression level of the full length hairpin transcript, as compared to the transcript level of an internal maize gene (SEQ ID NO:70; GENBANK Accession No. BT069734) that encodes a TIP41-like protein (i.e., a maize homolog of GENBANK Accession No. AT4G34270; tBLASTX score of 74% identity).

RNA was isolated using the RNAEASY™ 96 kit (QIAGEN, Valencia, Calif.). After the first wash (RW1), the columns were treated with QIAGEN RNase-free DNase in buffer RDD™ (according to the kit's suggested alternate protocol). First strand cDNA was prepared using a HIGH CAPACITY cDNA SYNTHESIS KIT (INVITROGEN) in a 10 μL reaction volume with 5 μL denatured RNA, substantially according to the manufacturer's recommended protocol. The protocol was modified slightly to include the addition of 10 μl, 100 μM T20VN oligonucleotide (IDT) into the 1 mL tube of random primer stock mix, in order to prepare a working stock of combined random primers and oligo dT.

Following cDNA synthesis, samples were diluted 1:3 with nuclease-free water, and stored at −20° C. until assayed. Real-time PCR was performed on a LIGHTCYCLER™ 480 (ROCHE DIAGNOSTICS, Indianapolis, Ind.) in 10 μL reaction volume. All assays included negative controls of no-template (mix only). For the standard curves, a blank (water in source well) was also included in the source plate to check for sample cross-contamination. Reactions were run with the ROCHE UNIVERSAL PROBE™ at 0.5 μM and the primers for the target and reference genes at 10 μM. The primer sequences are set forth in Table 8. PCR reactions conditions were as follows: (1) Target activation at 95° C. for 10 min; (2) 43 cycles of (denature at 95° C. for 10 sec and extension at 60° C.); (3) acquire at 72° C. for 1 sec; and (4) cool at 40° C. for 10 sec.

TABLE 8

Primer sequences used for molecular analyses of transcript levels in transgenic maize.

| Target | Primer | SEQ ID NO. | Primer Sequence |
|---|---|---|---|
| TIP41* | MZTIPU67F | 71 | AGCCAAGCCAGTGGTACTTC |
| TIP41 | MZTIPU67R | 72 | TCGCAGACAAAGTAGCAAATGT |
| Per5 3'UTR | P5U76S (F) | 73 | TTGTGATGTTGGTGGCGTAT |
| Per5 3'UTR | P5U76A (R) | 74 | TGTTAAATAAAACCCCAAAGATCG |

*TIP41-like protein.

Data were analyzed using LIGHTCYCLER™ Software v1.5 by relative quantification using a second derivative max algorithm for calculation of Cq values, according to the supplier's recommendations. For expression analyses, expression values were calculated using the ΔCq method (i.e., 2−(Cq TARGET−Cq REF)), which relies on the comparison of differences of Cq values between two targets, with the base value of 2 being selected under the assumption that, for optimized PCR reactions, the product doubles every cycle.

Hairpin Transcript Size and Integrity: Northern Blot Assay.

Additional molecular characterization of some of the transgenic plants was performed by the use of northern blot (RNA blot) analysis to determine the molecular size of the reptin hairpin RNA in transgenic plants expressing a reptin hairpin dsRNA. A full-length nascent transcript is expected to have a molecular size of about 900 bp, depending on the amount of polyadenylation of the RNA.

All materials and equipment were treated with RNAZAP™ (AMBION/INVITROGEN) before use. Tissue samples (100 mg to 500 mg) were collected in 2 mL SAFELOCK™ EPPENDORF tubes, disrupted with a KLECKO™ tissue pulverizer (Garcia Manufacturing, Visalia, Calif.) with three tungsten beads in 1 mL of TRIZOL™ (INVITROGEN) for 5 minutes, then incubated at room temperature (RT) for 10 minutes. Optionally, the samples were centrifuged for 10 minutes at 4° C. at 11,000 rpm and the supernatant was transferred into a fresh 2 mL SAFE-LOCK™ EPPENDORF tube.

After 200 µL of chloroform were added to the homogenate, the tube was mixed by inversion for 2 to 5 minutes, incubated at RT for 10 minutes, and centrifuged at 12,000×g for 15 minutes at 4° C. The top phase was transferred into a sterile 1.5 mL EPPENDORF tube, and 600 µL of 100% isopropanol were added, followed by incubation at RT for between 10 minutes and 2 hours, then centrifugation at 12,000×g for 10 minutes at from 4° C. to 25° C. The supernatant was discarded, and the RNA pellet was washed twice with 1 mL of 70% ethanol, with centrifugation at 7,500×g for 10 minutes at from 4° C. to 25° C. between washes. The ethanol was discarded, and the pellet was briefly air-dried for 3 to 5 minutes before resuspending in 50 µL of nuclease-free water.

Total RNA was quantified using the NANODROP® 8000 (Thermo-Fisher), and samples were normalized to 5 µg/10 µL. 10 µL of glyoxal (AMBION/INVITROGEN) was then added to each sample. 5 to 14 ng of DIG RNA standard marker mix (Roche Applied Science, Indianapolis, Ind.) was dispensed, and added to an equal volume of glyoxal. Samples and marker RNAs were denatured at 50° C. for 45 minutes, and stored on ice until loading on a 1.25% SEAKEM® GOLD agarose (Lonza, Allendale, N.J.) gel in NORTHERNMAX™ 10× glyoxal running buffer (AMBION/INVITROGEN). RNAs were separated by electrophoresis at 65 volts/30 mA for 2 hours 15 minutes.

Following electrophoresis, the gel was rinsed in 2×SSC for 5 minutes and imaged on a GEL DOC™ station (BioRad, Hercules, Calif.). Then, the RNA was passively transferred to a nylon membrane (MILLIPORE) overnight at room temperature, using 10×SSC as the transfer buffer (20×SSC consists of 3 M NaCl and 300 mM trisodium citrate, at pH 7.0). Following the transfer, the membrane was rinsed in 2×SSC for 5 minutes, the RNA was UV-cross-linked to the membrane (Agilent/Stratagene), and the membrane was allowed to dry at room temperature for up to 2 days.

The membrane was pre-hybridized in ULTRAHYB™ buffer (AMBION/INVITROGEN) for 1 to 2 hours. The probe consisted of a PCR amplified product containing the sequence of interest, (for example, the antisense sequence portions of one of SEQ ID NOs:29-31) labeled with digoxygenin by means of a Roche Applied Science DIG procedure. Hybridization in recommended buffer was performed overnight at a temperature of 60° C. in hybridization tubes. Following hybridization, the blot was subjected to DIG washes, wrapped, exposed to film for 1 to 30 minutes, and then the film was developed, all by methods recommended by the supplier of the DIG kit.

Hairpin Transcript Size and Integrity: ST-LS1 Intron Hydrolysis Probe Assay.

A hydrolysis probe assay (as described below; "Hydrolysis Probe Assays") targeting the ST-LS1 intron spacer sequence (SEQ ID NO:77) in the hairpin RNAs (SEQ ID NOs:29-31) was developed to measure integrity of the dsRNA transcript. The oligonucleotides used are listed in Table 7.

Hydrolysis Probe Transgene Copy Number Assays.

Tissues of transgenic maize plants were screened via a hydrolysis probe assay to confirm the aad-1 coding region (*Agrobacterium*-transformed B104 events). The data were used to estimate the transgene copy number, compared to results obtained in similar assays to detect a two-copy native chromosomal invertase gene (SEQ ID NO:75). The oligonucleotides used are listed in Table 9.

Tissue samples were macerated with a KLECO™ tissue pulverizer and stainless steel beads (Hoover Precision Products, Cumming, Ga.), in QIAGEN RLT™ buffer. Genomic DNA was isolated in high-throughput format using a BIOSPRINT™ 96 Plant kit (QIAGEN), according to the manufacturer's suggested protocol, and quantified by QUANT-IT™ PICO GREEN DNA ASSAY KIT (MOLECULAR PROBES/INVITROGEN). DNA concentration was adjusted to around 2 ng/µL for the hydrolysis probe assay using a BIOROBOT™ 3000 automated liquid handler (QIAGEN). Transgene copy number determination was performed by real-time PCR using the LIGHTCYCLER® 480 system (Roche Applied Science, Indianapolis, Ind.).

Assays were designed for aad-1, and an internal reference invertase gene (SEQ ID NO:75; GENBANK Accession No: U16123.1) using the LIGHTCYCLER® PROBE DESIGN SOFTWARE v2.0. For amplification, LIGHTCYCLER® 480 Probes Master mix was prepared at 1× final concentration in a 10 µL volume multiplex reaction, containing 0.4 µM of each primer for aad-1 and 0.2 µM of each probe (Table 9). A two-step amplification reaction was performed with an extension at 60° C. for 40 seconds with fluorescence acquisition. All samples were run, and the averaged Cycle threshold (Ct) values were used for analysis of each sample. Analysis of real-time PCR data was performed using LIGHTCYCLER® SOFTWARE release 1.5, using the relative quant module, and was based on the ΔΔCt method. Controls included a sample of genomic DNA from a single copy calibrator line, and known two copy checks that were included in each run.

Vector Backbone Hydrolysis Probe Assays.

Transgenic tissues were analyzed by means of a hydrolysis probe assay designed to detect the SpnR (bacterial spectinomycin resistance) gene (SEQ ID NO:76) harbored on the transforming plasmid, to determine if any vector backbone DNA had been integrated into the maize genome. The oligonucleotides used are listed in Table 9.

TABLE 9

Primer and probe sequences used for hydrolysis probe assays.

| Target | Oligonucleotide Name | SEQ ID NO: | Sequence |
|---|---|---|---|
| aad-1 | GAAD1F (forward primer) | 78 | TGTTCGGTTCCCTCTACCAA |
| aad-1 | GAAD1R (reverse primer) | 79 | CAACATCCATCACCTTGACTGA |
| aad-1 | GAAD1P (probe) | 80 | CACAGAACCGTCGCTTCAGCAACA |
| Invertase | IVF-Taq (forward primer) | 81 | TGGCGGACGACGACTTGT |
| Invertase | IVR-Taq (reverse primer) | 82 | AAAGTTTGGAGGCTGCCGT |
| Invertase | IV-P (probe) | 83 | CGAGCAGACCGCCGTGTACTTCTACC |
| ST-LS1 Intron | RNAi DNA F (forward primer) | 84 | GTATGTTTCTGCTTCTACCTTTGAT |
| ST-LS1 Intron | RNAi DNA R (reverse primer) | 85 | CCATGTTTTGGTCATATATTAGAAAAGTT |
| ST-LS1 Intron | RNAi DNA FAM (probe) | 86 | AGTAATATAGTATTTCAAGTATTTTTTCAAAAT |
| SpnR | SPC1A (reverse primer) | 87 | CTTAGCTGGATAACGCCAC |
| SpnR | SPC1S (forward primer) | 88 | GACCGTAAGGCTTGATGAA |
| SpnR | TQSPEC (probe) | 89 | CGAGATTCTCCGCGCTGTAGA |

Hairpin Loop Hydrolysis Probe Assays.

Transgenic tissues were analyzed for the presence of a hairpin loop as provided in constructs comprising hairpin sequences set forth in SEQ ID NOs:29-31. The hairpin constructs were designed such that the loop of the hairpin comprises a sequence of an ST-L1 intron (SEQ ID NO:77). Components and reaction conditions of the hairpin loop hydrolysis probe assay are given in Table 10, and the sequences of the oligonucleotides are presented in Table 11. The component and reaction parameters given in Table 10 were standard for other hydrolysis probe assays.

TABLE 10

Hairpin loop qPCR Components and reaction parameters.

| Components | Stock | Amt (μL) | Final (μM) |
|---|---|---|---|
| 2 X Roche Buffer | 2× | 5 | 1× |
| OrfB-rxn1 F | 10 μM | 0.025 | 0.025 |
| OrfB-rxn1 R | 10 μM | 0.025 | 0.025 |
| OrfB-rxn 2 F | 10 μM | 0.175 | 0.175 |
| OrfB-rxn2 R | 10 μM | 0.175 | 0.175 |
| RNAi MGB 12 BP Probe | 10 μM | 0.1 | 0.1 |
| cDNA | NA | 2 | NA |
| H₂O | | 2.5 | |
| | | 10 (Total) | |

| Thermocycler Step | Temp. | Time | No. cycles |
|---|---|---|---|
| Activate | 95° C. | 10 min | 1 |
| Denature | 95° C. | 10 sec | 5 |
| Extend | 50° C. | 40 sec | |
| Denature | 95° C. | 10 sec | 40 (Acquire FAM) |
| Extend | 50° C. | 40 sec | |
| Cool | 40° C. | Hold | 1 |

TABLE 11

Sequences of oligonucleotides used in hairpin hydrolysis probe assays

| Name | SEQ ID NO: | Sequence |
|---|---|---|
| OrfB-rxn 2 F | 90 | GAATCCTTGCGTCATTTGGT |
| OrfB-rxn 2 R | 91 | CAATGGACTCACGCACAACT |

TABLE 11-continued

Sequences of oligonucleotides used in hairpin hydrolysis probe assays

| Name | SEQ ID NO: | Sequence |
|---|---|---|
| OrfB-rxn1 F | 92 | GAATCCTTGCGTCATTTGGTGACTAGTACCGGTTGGGA |
| OrfB-rxn1 R | 93 | CAATGGACTCACGCACAACTTAACCGCGGATCAA |
| MGB 12 BP Probe | 94 | TGGGAAAGGTTG |

$T_0$ plants comprising hairpin constructs were analyzed as described above, and the results are given in Tables 12; 13; and 14.

TABLE 12

Molecular analysis results of $T_0$ transgenic B104 plants comprising a construct encoding an PP1-87B hairpin dsRNA.

| Event | Copy No. AAD1 | Copy No. Intron | qPCR SpecR | Transcript RTL Per5* | Root Rating | Full length Northern |
|---|---|---|---|---|---|---|
| 109822[1]-001.001 | 3.3 | 0.7 | 0.0 | 10.3 (25.6) | 0.50 | Positive |
| 109822[1]-002.001 | 1.2 | 0.5 | 0.0 | 2.9 | 1.00 | |
| 109822[1]-003.001 | 1.3 | 0.5 | 0.0 | 3.2 (20.3) | 1.00 | |
| 109822[1]-004.001 | 1.3 | 0.0 | 1.7 | 0.0 | 1.00 | |
| 109822[1]-005.001 | 0.9 | 0.5 | 0.0 | 2.3 (3.5) | 0.02 | Positive |
| 109822[1]-006.001 | 1.4 | 0.4 | 0.0 | 3.0 (7.6) | 1.00 | |
| 109822[1]-007.001 | 1.6 | 0.6 | 0.0 | 2.8 (14.0) | 1.00 | |
| 109822[1]-009.001 | 1.9 | 0.9 | 0.0 | 5.9 | 0.25 | Positive |
| 109822[1]-010.001 | 1.4 | 0.0 | 0.0 | 0.0 | NT** | |
| 109822[1]-011.001 | 1.6 | 0.5 | 0.0 | 1.8 (5.3) | 0.75 | Positive |
| 109822[1]-012.001 | 1.5 | 0.4 | 0.0 | 3.9 (5.4) | 1.0 | |
| 109822[1]-013.001 | 1.3 | 0.6 | 0.0 | 3.2 (6.4) | 1.0 | |
| 109822[1]-014.001 | 1.6 | 0.0 | 0.0 | 0.0 | NT | |
| 109822[1]-015.001 | 1.7 | 0.6 | 0.0 | 3.3 (9.6) | 1.0 | |
| 109822[1]-016.001 | 1.3 | 0.5 | 0.0 | 3.2 (5.7) | 1.0 | |
| 109822[1]-017.001 | 1.7 | 0.0 | 0.0 | 0.0 | NT | |
| 109822[1]-018.001 | 1.6 | 0.4 | 0.0 | 2.3 (8.5) | 1.0 | |
| 109822[1]-019.001 | 2.9 | 1.0 | 2.1 | 4.2 (12.1) | 1.0 | |
| 109822[1]-020.001 | 1.5 | 0.5 | 0.0 | 2.5 (5.3) | 1.0 | |
| 109822[1]-021.001 | 0.0 | 0.0 | 0.0 | 0.0 | NT | |
| 109822[1]-022.001 | 1.5 | 0.6 | 0.0 | 2.3 (5.7) | 1.0 | |
| 109822[1]-024.001 | 1.3 | 0.0 | 0.0 | 0.0 | NT | |
| 109822[1]-028.001 | 1.5 | 0.0 | 0.0 | 0.0 | NT | |
| 109822[1]-029.001 | 1.4 | 0.0 | 0.0 | 0.0 | NT | |
| 109822[1]-033.001 | 1.5 | 0.6 | 0.0 | 3.0 (8.0) | 1.0 | |
| 109822[1]-034.001 | 1.5 | 0.5 | 0.0 | 2.2 (7.8) | 1.0 | |
| 109822[1]-035.001 | 1.6 | 0.4 | 2.1 | 1.8 (1.0) | 1.0 | |
| 109822[1]-036.001 | 1.1 | 0.3 | 1.3 | 2.3 | 1.0 | |
| 109822[1]-037.001 | 1.6 | 0.5 | 0.0 | 1.9 (11.1) | 1.0 | |
| 109822[1]-038.001 | 1.8 | 0.5 | 0.0 | 2.2 (6.0) | 1.0 | |

*Transcript Level relative to Per5 transcript level. Numbers in parentheses are were obtained in repeats of the assay.
**NT = Not Tested

TABLE 13

Molecular analysis results of $T_0$ transgenic B104 plants comprising a construct encoding an RPS6 hairpin dsRNA.

| Event | Copy No. AAD1 | Copy No. Intron | qPCR SpecR | Transcript RTL Per5* | Root Rating | Full length Northern |
|---|---|---|---|---|---|---|
| 109823[1]-001.001 | 0.8 | 0.6 | 2.2 | 2.8 (13.9) | 1.0 | |
| 109823[1]-002.001 | 0.8 | 0.5 | 2.1 | 2.8 (6.2) | 1.0 | |
| 109823[1]-003.001 | 1.7 | 0.4 | 0.0 | 2.7 (9.4) | 0.8 | Positive |
| 109823[1]-004.001 | 1.7 | 0.5 | 0.0 | 3.3 (11.8) | 1.0 | |
| 109823[1]-005.001 | 4.2 | 0.9 | 0.0 | 4.7 (0.0) | 1.0 | |
| 109823[1]-006.001 | 1.3 | 0.4 | 0.0 | 2.3 (3.1) | 1.0 | |
| 109823[1]-007.001 | 2.2 | 0.6 | 0.0 | 4.0 (15.6) | 0.5 | Positive |
| 109823[1]-008.001 | 1.0 | 0.5 | 0.0 | 3.1 (30.3) | 0.8 | Positive |
| 109823[1]-009.001 | 0.0 | 0.0 | 0.0 | 0.0 (NT*) | NT | |

TABLE 13-continued

Molecular analysis results of T₀ transgenic B104 plants comprising a construct encoding an RPS6 hairpin dsRNA.

| Event | Copy No. AAD1 | Copy No. Intron | qPCR SpecR | Transcript RTL Per5* | Root Rating | Full length Northern |
|---|---|---|---|---|---|---|
| 109823[1]-010.001 | 4.1 | 1.3 | 1.8 | 3.8 (26.5) | 1.0 | |
| 109823[1]-011.001 | 1.6 | 0.5 | 0.0 | 2.1 (7.8) | 1.0 | |
| 109823[1]-012.001 | 1.7 | 0.5 | 0.0 | 3.8 (11.9) | 0.3 | Positive |
| 109823[1]-013.001 | 2.7 | 0.9 | 2.8 | 3.3 (11.0) | 1.0 | |
| 109823[1]-014.001 | 0.9 | 0.5 | 0.0 | 1.7 (5.6) | 1.0 | |
| 109823[1]-015.001 | 0.9 | 1.0 | 1.9 | 3.9 (8.8) | 1.0 | |
| 109823[1]-016.001 | 0.7 | 0.5 | 0.0 | 3.6 (11.1) | 1.0 | |
| 109823[1]-017.001 | 3.4 | 0.6 | 0.0 | 3.0 (9.3) | 1.0 | |
| 109823[1]-018.001 | 1.7 | 0.4 | 0.0 | 2.9 (6.5) | 1.0 | |
| 109823[1]-019.001 | 1.6 | 0.9 | 2.0 | 3.2 (8.1) | 0.3 | Positive |
| 109823[1]-020.001 | 4.7 | 1.4 | 0.0 | 11.7 (17.8) | 0.8 | Positive |
| 109823[1]-021.001 | 1.1 | 0.6 | 0.0 | 1.2 (9.2) | 1.0 | |
| 109823[1]-022.001 | 1.8 | 0.0 | 0.0 | 0.0 (NT) | NT | |
| 109823[1]-023.001 | 1.5 | 0.5 | 0.0 | 3.7 (7.8) | 1.0 | |
| 109823[1]-024.001 | 1.0 | 0.6 | 0.0 | 3.0 (13.5) | 1.0 | |
| 109823[1]-025.001 | 1.3 | 0.0 | 0.0 | 0.0 (NT) | NT | |
| 109823[1]-026.001 | 1.2 | 0.5 | 1.9 | 1.9 (8.8) | 0.8 | Positive |
| 109823[1]-027.001 | 1.3 | 0.0 | 0.0 | 0.0 (NT) | NT | |
| 109823[1]-028.001 | 1.6 | 0.0 | 2.2 | 1.9 (NT) | NT | |
| 109823[1]-029.001 | 3.3 | 0.6 | 0.0 | 1.8 (6.2) | 1.0 | |
| 109823[1]-030.001 | 2.7 | 0.9 | 3.2 | 2.7 (11.6) | 0.8 | Positive |
| 109823[1]-031.001 | 0.8 | 0.5 | 0.0 | 1.3 (11.2) | 1.0 | |

*Transcript Level relative to Per5 transcript level. Numbers in parentheses are were obtained in repeats of the assay.
**NT = Not Tested

TABLE 14

Molecular analysis results of T₀ transgenic B104 plants comprising a construct encoding an RPA70 hairpin dsRNA.

| Event | qPCR SpecR | Copy No. AAD1 | Intron (RNAi hairpin) 1 = Positive 0 = Negative | Transcript RTL Per5* | Northern Analyses Full length 1 = Pos 0 = Neg | siRNA** 1 = Pos 0 = Neg |
|---|---|---|---|---|---|---|
| 109818[1]-031.001 | − | 0.8 | 1 | 1.75 | | |
| 109818[1]-036.001 | − | 0.7 | 1 | 1.79 | | |
| 109818[1]-002.001 | − | 1.1 | | 1.87 | | |
| 109818[1]-009.001 | − | 0.6 | 1 | 1.94 | | |
| 109818[1]-016.001 | − | 0.9 | 1 | 1.95 | | |
| 109818[1]-005.001 | − | 1.0 | 1 | 1.96 | | |
| 109818[1]-012.001 | − | 0.6 | 1 | 2.05 | | |
| 109818[1]-029.001 | − | 0.7 | 1 | 2.14 | | |
| 109818[1]-001.001 | − | 0.9 | 1 | 2.15 | 1 | 1 |
| 109818[1]-006.001 | − | 1.1 | 1 | 2.42 | 1 | 1 |
| 109818[1]-027.001 | − | 1.0 | 1 | 2.44 | 1 | 1 |
| 109818[1]-014.001 | − | 1.2 | 1 | 2.48 | 1 | 1 |
| 109818[1]-010.001 | − | 1.2 | 1 | 2.49 | 1 | 1 |
| 109818[1]-017.001 | − | 0.9 | 1 | 2.51 | 1 | 1 |
| 109818[1]-011.001 | − | 0.9 | 1 | 2.59 | 1 | 1 |
| 109818[1]-007.001 | − | 0.8 | 1 | 2.67 | 1 | 1 |
| 109818[1]-004.001 | − | 1.2 | 1 | 2.85 | 1 | 1 |
| 109818[1]-024.001 | − | 0.5 | 1 | 3.07 | 1 | 1 |
| 109818[1]-019.001 | − | 1.0 | 1 | 3.66 | 1 | 1 |
| 109818[1]-018.001 | − | 0.5 | 1 | 4.22 | 1 | 1 |
| 109818[1]-026.001 | − | 1.1 | 1 | 4.25 | 1 | 1 |
| 109818[1]-023.001 | − | 0.7 | 1 | 4.41 | 1 | 1 |
| 109818[1]-028.001 | − | 1.4 | 1 | 5.35 | 1 | 1 |
| 109818[1]-003.001 | − | 1.9 | 1 | 5.15 | 1 | 1 |
| 109818[6]-209.001 | + | 1.7 | 1 | 9.3 | 1 | NT |
| 109818[1]-040.001 | − | 1.1 | 1 | NT*** | NT | NT |
| 109818[1]-013.001 | − | 1.8 | 1 | 0.97 | | |
| 109818[1]-008.001 | + | 1.0 | 1 | 6.88 | | |
| 109818[1]-015.001 | + | 1.1 | 1 | 5.89 | | |
| 109818[1]-020.001 | + | 0.9 | 0 | | | |
| 109818[1]-021.001 | + | 1.1 | 1 | 3.89 | | |
| 109818[1]-025.001 | + | 0.6 | 0 | | | |
| 109818[1]-032.001 | + | 1.1 | 1 | 3.22 | | |
| 109818[1]-039.001 | + | 1.2 | 1 | 3.38 | | |

TABLE 14-continued

Molecular analysis results of $T_0$ transgenic B104 plants comprising a construct encoding an RPA70 hairpin dsRNA.

| Event | qPCR SpecR | Copy No. AAD1 | Intron (RNAi hairpin) 1 = Positive 0 = Negative | Transcript RTL Per5* | Northern Analyses Full length 1 = Pos 0 = Neg | siRNA** 1 = Pos 0 = Neg |
|---|---|---|---|---|---|---|
| 109818[1]-044.001 | + | 1.3 | 1 | | | |
| 109818[1]-046.001 | + | 1.2 | 1 | | | |
| 109818[1]-022.001 | − | 0.0 | 0 | | | |
| 109818[1]-030.001 | − | 1.0 | 0 | | | |
| 109818[1]-033.001 | − | 0.0 | 0 | | | |
| 109818[1]-034.001 | − | 1.4 | 0 | | | |
| 109818[1]-035.001 | − | 0.6 | 0 | | | |
| 109818[1]-037.001 | − | 0.6 | 0 | | | |
| 109818[1]-038.001 | − | 0.8 | 0 | | | |
| 109818[1]-040.001 | − | 1.1 | 1 | | | |
| 109818[1]-041.001 | − | 0.7 | 0 | | | |
| 109818[1]-042.001 | − | 0.9 | 1 | | | |
| 109818[1]-043.001 | − | 1.2 | 1 | | | |
| 109818[1]-045.001 | − | 0.9 | 1 | | | |
| 109818[1]-047.001 | − | 0.9 | 1 | | | |
| 109818[1]-048.001 | − | 2.5 | 1 | | | |
| 109818[1]-049.001 | − | 1.3 | 1 | | | |
| 109818[1]-050.001 | − | 1.2 | 1 | | | |
| 109818[1]-051.001 | − | 1.0 | 1 | | | |
| 109818[1]-052.001 | − | 1.3 | 1 | | | |
| 109818[1]-053.001 | − | 1.1 | 1 | | | |
| 109818[1]-054.001 | − | 1.5 | 1 | | | |
| 109818[1]-055.001 | − | 1.3 | 1 | | | |
| 109818[1]-056.001 | − | 1.1 | 0 | | | |
| 109818[1]-187.001 | − | 0.7 | 1 | | | |
| 109818[1]-188.001 | − | 1.2 | 1 | | | |
| 109818[1]-189.001 | − | 0.8 | 1 | | | |
| 109818[1]-190.001 | − | 1.0 | 1 | | | |

*Transcript Level relative to Per5 transcript level. Numbers in parentheses are were obtained in repeats of the assay.
**siRNA = Northern blot analysis for short interfering RNA
***NT = Not Tested $T_1$ plants comprising hairpin constructs were analyzed as described above, and the results are given in Tables 15; 16; and 17.

TABLE 15

Molecular analysis results of $T_1$ transgenic B104 plants comprising a construct encoding an PP1-87B hairpin dsRNA.

| Event | Tissue | Transcript RTL Per5* | Transcript RTL hairpin loop** | Northern Blot Results Full length transcript (Band intensity) |
|---|---|---|---|---|
| 109822[1]-001.AJ001.031 | Leaf | 43.7 | 0.11 | Positive (Weak signal) |
| 109822[1]-009.001AJ032 | Leaf | 24.3 | 0.10 | Positive (Weak signal) |
| 109822[1]-009.AJ001.046 | Leaf | 22.9 | 0.06 | Positive (Weak signal) |
| 109822[1]-011.AJ001.040 | Leaf | 10.7 | 0.02 | Positive (Weak signal) |
| 109822[1]-001.AJ001.031 | Root | 19.0 | 0.03 | Positive (very weak signal) |
| 109822[1]-009.001AJ032 | Root | 20.3 | 0.02 | Positive (very weak signal) |
| 109822[1]-009.AJ001.046 | Root | 108.4 | 0.02 | Positive (very weak signal) |
| 109822[1]-011.AJ001.040 | Root | 34.8 | 0.00 | Negative (very weak signal) |
| Negative Controls | | | | |
| B104 = 55265 | Leaf | 0.0 | 0.00 | Negative (No signal) |
| 101556[93]-074.001 AJ.113*** | Leaf | 0.0 | 0.00 | Negative (No signal) |

TABLE 15-continued

Molecular analysis results of $T_1$ transgenic B104 plants comprising a construct encoding an PP1-87B hairpin dsRNA.

| Event | Tissue | Transcript RTL Per5* | Transcript RTL hairpin loop** | Northern Blot Results Full length transcript (Band intensity) |
|---|---|---|---|---|
| B104 = 55265 | Root | 0.4 | 0.00 | Negative (No signal) |
| 101556[93]-074.001 AJ.113 | Root | 0.4 | 0.00 | Negative (No signal) |

*Transcript Level relative to Per5 transcript level.
**Transcript Level relative to hairpin loop level.
***101556[93] plants are B104 transgenic events that were obtained following *Agrobacterium*-mediated transformation with a pDAB101556 binary vector by the methods disclosed herein.

TABLE 16

Molecular analysis results of $T_1$ transgenic B104 plants comprising a construct encoding an RPS6 hairpin dsRNA.

| Event | Tissue | Transcript RTL Per5* | Transcript RTL hairpin loop** | Northern Blot Results Full length transcript (Band intensity) |
|---|---|---|---|---|
| 109823[1]-003.AJ001.031 | Leaf | 8.9 | 0.33 | Positive (Medium signal) |
| 109823[1]-007.001AJ.032 | Leaf | 8.7 | 0.30 | Positive (Medium signal) |
| 109823[1]-007.AJ001.036 | Leaf | 10.9 | 0.43 | Positive (Medium signal) |
| 109823[1]-008.AJ001.041 | Leaf | 34.1 | 0.86 | Positive (Medium signal) |
| 109823[1]-012.001AJ.034 | Leaf | 12.7 | 0.28 | Positive (Medium signal) |
| 109823[1]-012.AJ001.032 | Leaf | 14.8 | 0.33 | Positive (Medium signal) |
| 109823[1]-019.AJ001.034 | Leaf | 10.3 | 0.33 | Positive (Medium signal) |
| 109823[1]-020.AJ001.036 | Leaf | 9.8 | 0.24 | Positive (Medium signal) |
| 109823[1]-026.AJ001.036 | Leaf | 9.7 | 0.26 | Positive (Medium signal) |
| 109823[1]-003.AJ001.031 | Root | 38.1 | 0.05 | Positive (Medium signal) |
| 109823[1]-007.001AJ.032 | Root | 39.1 | 0.03 | Positive (Medium signal) |
| 109823[1]-007.AJ001.036 | Root | 11.1 | 0.07 | Positive (Medium signal) |
| 109823[1]-008.AJ001.041 | Root | 86.8 | 0.09 | Positive (Medium signal) |
| 109823[1]-012.001AJ.034 | Root | 109.1 | 0.06 | Positive (Medium signal) |
| 109823[1]-012.AJ001.032 | Root | 55.3 | 0.04 | Positive (Medium signal) |
| 109823[1]-019.AJ001.034 | Root | 43.1 | 0.06 | Positive (Medium signal) |
| 109823[1]-020.AJ001.036 | Root | 11.1 | 0.10 | Positive (Medium signal) |
| 109823[1]-026.AJ001.036 | Root | 32.9 | 0.03 | Positive (Medium signal) |
| Negative Controls | | | | |
| B104 = 55265 | Leaf | 0.0 | 0.00 | Negative (No signal) |
| 101556[93]-074.001 AJ.113*** | Leaf | 0.0 | 0.00 | Negative (No signal) |
| B104 = 55265 | Root | 0.4 | 0.00 | Negative (No signal) |
| 101556[93]-074.001AJ.113 | Root | 0.4 | 0.00 | Negative (No signal) |

*Transcript Level relative to Per5 transcript level.
**Transcript Level relative to hairpin loop level.
***101556[93] *Agrobacterium*-mediated transformation with a pDAB101556 binary vector by the methods disclosed herein.

TABLE 17

Molecular analysis results of T₁ transgenic B104 plants comprising a construct encoding an RPA70 hairpin dsRNA.

| Event | Root Rating | Tissue | Transcript RTL Per5* | Northern Blot Results Full length Transcript |
|---|---|---|---|---|
| 109818[1]-001.001AJ.#1 | 0.75 | Leaf | 11.2 | Positive |
| 109818[1]-003.AJ001.#19 | 1 | Leaf | 13.9 | Positive |
| 109818[1]-004.001AJ.#1 | 1 | Leaf | 15.5 | Positive |
| 109818[1]-006.AJ001.#2 | 0.5 | Leaf | 16.6 | Positive |
| 109818[1]-007.AJ001.#19 | 0.75 | Leaf | 5.1 | Negative |
| 109818[1]-010.001AJ.#4 | 1 | Leaf | 11.2 | Positive |
| 109818[1]-011.AJ001.#13 | 0.75 | Leaf | 10.1 | Positive |
| 109818[1]-013.AJ001.#7 | 1 | Leaf | 0.2 | Negative |
| 109818[1]-017.AJ001.#14 | 0.75 | Leaf | 7.6 | Positive |
| 109818[1]-018.AJ001.#5 | 0.1 | Leaf | 6.8 | Positive |
| 109818[1]-019.AJ001.#7 | 0.25 | Leaf | 7.1 | Positive |
| 109818[1]-023.AJ001.#27 | 1 | Leaf | 13.5 | Positive |
| 109818[1]-024.AJ001.#5 | 0.25 | Leaf | 8.6 | Positive |
| 109818[1]-026.AJ001.#13 | 0.5 | Leaf | 7.6 | Positive |
| 109818[1]-027.AJ001.#8 | 0.5 | Leaf | 6.7 | Positive |
| 109818[1]-028.AJ001.#1 | 0.5 | Leaf | 41.9 | Positive |
| 109818[1]-040.AJ001.#7 | 0.75 | Leaf | 5.8 | Positive |
| 109818[6]-209.AJ001.#22 | 0.25 | Leaf | 15.8 | Positive |
| 109818[1]-001.001AJ.#1 | 0.75 | Root | 16.7 | Positive |
| 109818[1]-003.AJ001.#19 | 1 | Root | 29.4 | Positive |
| 109818[1]-004.001AJ.#1 | 1 | Root | 16.1 | NT** |
| 109818[1]-006.AJ001.#2 | 0.5 | Root | 11.1 | NT |
| 109818[1]-007.AJ001.#19 | 0.75 | Root | 7.3 | NT |
| 109818[1]-010.001AJ.#4 | 1 | Root | 12.4 | Positive |
| 109818[1]-011.AJ001.#13 | 0.75 | Root | 17.8 | Positive |
| 109818[1]-013.AJ001.#7 | 1 | Root | 3.0 | Negative |
| 109818[1]-017.AJ001.#14 | 0.75 | Root | 26.9 | Positive |
| 109818[1]-018.AJ001.#5 | 0.1 | Root | 31.1 | Positive |
| 109818[1]-019.AJ001.#7 | 0.25 | Root | 28.1 | Positive |
| 109818[1]-023.AJ001.#27 | 1 | Root | 26.4 | Positive |
| 109818[1]-024.AJ001.#5 | 0.25 | Root | 29.7 | Positive |
| 109818[1]-026.AJ001.#13 | 0.5 | Root | 61.0 | Positive |
| 109818[1]-027.AJ001.#8 | 0.5 | Root | 54.9 | Positive |
| 109818[1]-028.AJ001.#1 | 0.5 | Root | 39.4 | Positive |
| 109818[1]-040.AJ001.#7 | 0.75 | Root | 24.4 | Positive |
| 109818[6]-209.AJ001.#22 | 0.25 | Root | 26.0 | Positive |
| Negative Controls | | | | |
| B104 | 1 | Leaf | 0.0 | Negative |
| 101556*** | 1 | Leaf | 0.0 | Negative |
| B104 | 1 | Root | 0.2 | Negative |
| 101556 | 1 | Root | 5.8 | Negative |

*Transcript Level relative to Per5 transcript level.
**NT = Not Tested
***101556 plants are B104 transgenic events that were obtained following Agrobacterium-mediated transformation with a pDAB101556 binary vector by the methods disclosed herein The foregoing data show that certain coleopteran pests, especially *Diabrotica* pests of plants, may be controlled by targeting certain transcripts produced in the pests, through contacting the pests with effective amounts of dsRNA that hybridize (i.e., are homologous) to the target transcripts.

Example 9

Transgenic *Zea mays* Comprising Coleopteran Pest Sequences 10 to 20 transgenic T₀ *Zea mays* plants are generated as described in EXAMPLE 6. A further 10-20 T₁ *Zea mays* independent lines expressing hairpin dsRNA for an RNAi construct as set forth in SEQ ID NOs:1-7 are obtained for corn rootworm challenge. These are confirmed through RT-PCR. Total RNA from selected independent T₁ lines are optionally used for RT-PCR with primers designed to bind in the ST-LS1 intron of the hairpin cassette in each of the RNAi constructs. In addition, specific primers for each target gene in an RNAi construct are optionally used to amplify and confirm the production of the pre-processed mRNA required for siRNA production in planta. The amplification of the desired bands for each target gene confirms the expression of the hairpin RNA in each transgenic *Zea mays*. Processing of the dsRNA hairpin of the target genes into siRNA is subsequently optionally confirmed in independent transgenic lines using RNA blot hybridizations.

Phenotypic Comparison of Transgenic RNAi Lines and Wild-Type *Zea mays*

Target coleopteran pest genes or sequences selected for creating hairpin dsRNA have no similarity to any known plant gene or sequence. Hence it is not expected that the production or the activation of (systemic) RNAi by constructs targeting these genes or sequences will have any deleterious effect on transgenic plants. However, development and morphological characteristics of transgenic lines are compared with wild-type plants, as well as those of transgenic lines transformed with an empty hairpin vector. Plant root, shoot, foliage and reproduction characteristics are compared. There is no observable difference in root length and growth patterns of transgenic and wild-type plants. Plant shoot characteristics such as height, leaf numbers and sizes, time of flowering, floral size and appearance are similar. In general, there are no observable morphological differences between transgenic lines and those without expression of target iRNA molecules when cultured in vitro and in soil in the glasshouse.

Example 10

Transgenic Zea mays Comprising a Coleopteran Pest Sequence and Additional RNAi Constructs A transgenic *Zea mays* plant comprising a heterologous coding sequence in its genome that is transcribed into an iRNA molecule that targets an organism other than a coleopteran pest is transformed via WHISKERS™ to produce one or more insecticidal dsRNA molecules (for example, at least one dsRNA molecule including a dsRNA molecule targeting a gene comprising one of SEQ ID NOs:1-7). WHISKERS™-mediated transformation is employed to produce Preparations of plant transformation DNA molecules prepared essentially as described in EXAMPLE 4 are delivered into maize Hi-II suspension cell cultures obtained from a transgenic *Zea mays* plant comprising a heterologous coding sequence in its genome that is transcribed into an iRNA molecule that targets an organism other than a coleopteran pest.

Example 11

Transgenic Coleopteran Pest-resistant Plants

In planta delivery of dsRNA, siRNA or miRNA corresponding to target genes and the subsequent uptake by coleopteran pests through feeding results in down-regulation of the target genes through RNA-mediated gene silencing. When the function of a target gene is important, growth, development, and reproduction of the coleopteran pest is affected, and in the case of at least one of WCR, NCR, SCR, MCR, *D. balteata* LeConte, *D. u. tenella*, and *D. u. undecimpunctata* Mannerheim leads to failure to successfully infest, feed, develop, and/or reproduce, or leads to death of the coleopteran pest at one or more stage(s) of development. The choice of target genes and the successful application of RNAi is then used to control coleopteran pests. Five to ten replicates of 10-20 independent $T_1$ *Z. mays* transgenic lines for each RNAi construct are challenged with a corn rootworm species. The challenge is duplicated for each corn rootworm species. $T_1$ seeds of RNAi lines are germinated, and resistant plants transferred to modified Knop's medium 10-15 days after germination. Wild-type control *Z. mays* seeds are germinated at the same time, and used for corn rootworm infection.

There are significantly more (>50%) surviving corn rootworms on controls than on transgenic *Z. mays* lines harboring one or more RNAi constructs. iRNA abundance is measured in corn rootworms feeding on roots of wild-type and transgenic plants using quantitative real-time RT-PCR. There are significantly more iRNA molecules found in transgenic *Z. mays* lines harboring one or more RNAi constructs than in control plants. These results indicate that the transgenic lines process siRNAs corresponding to target genes and that these siRNAs are available for uptake by feeding corn rootworms. More importantly, the results indicate that RNAi-mediated inhibition of all the target genes affects growth, development, and viability of the target corn rootworm. Moreover, RNAi molecules with mismatch sequences with more than 80% sequence identity to target genes affect corn rootworms in a similar way to wild-type sequences. The pairing of mismatch sequence with native sequences to form a hairpin dsRNA in the same RNAi construct delivers plant-processed siRNAs capable of affecting the growth, development and viability of feeding coleopteran pests.

What is claimed is:

1. A transgenic plant cell comprising a polynucleotide comprising at least one nucleotide sequence(s) selected from the group consisting of:
   SEQ ID NO:7;
   the complement of SEQ ID NO:7
   a native coding sequence comprising SEQ ID NO:7 of a *Diabrotica* organism;
   the complement of a native coding sequence comprising SEQ ID NO:7 of a *Diabrotica* organism;
   SEQ ID NO:28; and
   the complement of SEQ ID NO:28,
   wherein the polynucleotide is expressed in the transgenic plant cell as a ribonucleic acid molecule, and wherein contacting the ribonucleic acid molecule with a coleopteran pest inhibits the expression of an endogenous nucleic acid comprising a nucleotide sequence specifically complementary to the nucleotide sequence comprised in the polynucleotide.

2. The transgenic plant cell of claim 1, wherein the at least one nucleotide sequence(s) is operably linked to a heterologous promoter.

3. The transgenic plant cell of claim 1, wherein the *Diabrotica* organism is selected from the group consisting of *Diabrotica virgifera virgifera* LeConte; *Diabrotica barberi* Smith and Lawrence; *Diabrotica undecimpunctata howardi*; *Diabrotica virgifera zeae*; *Diabrotica balteata* LeConte; *Diabrotica undecimpunctata tenella*; and *Diabrotica undecimpunctata undecimpunctata* Mannerheim.

4. The transgenic plant cell of claim 1, wherein the polynucleotide further comprises at least one nucleotide sequence encoding a polypeptide from *Bacillus thuringiensis*.

5. The transgenic plant cell of claim 4, wherein the polypeptide from *B. thuringiensis* is selected from the group consisting of Cry3, Cry34, and Cry35.

6. The transgenic plant cell of claim 1, wherein the polynucleotide is transcribed to produce a double-stranded ribonucleic acid molecule in the cell.

7. The transgenic plant cell of claim 6, wherein contacting the double-stranded ribonucleic acid molecule with the coleopteran pest kills or inhibits the growth, reproduction, and/or feeding of the coleopteran pest.

8. The transgenic plant cell of claim 6, wherein the double-stranded ribonucleic acid molecule comprises a first, a second, and a third polyribonucleotide,
   wherein the first polyribonucleotide comprises the polyribonucleotide encoded by the at least one nucleotide sequence(s),
   wherein the third polyribonucleotide is linked to the first polyribonucleotide by the second polyribonucleotide, and
   wherein the third polyribonucleotide is substantially the reverse complement of the first polyribonucleotide, such that the portions of the ribonucleic acid molecule comprising each of the first and the third polyribonucleotides hybridize to each other in the double-stranded ribonucleotide molecule.

9. The transgenic plant cell of claim 1, wherein the polynucleotide is operably linked to a heterologous promoter functional in a plant cell.

10. A plant comprising the transgenic plant cell of claim 9.

11. A seed of the plant of claim 10, wherein the seed comprises the polynucleotide.

12. The plant of claim 10, wherein the polynucleotide is expressed in the plant as a double-stranded ribonucleic acid molecule.

13. The plant of claim 10, wherein the plant is *Zea mays*.

14. The plant of claim 10, wherein the polynucleotide is expressed in the plant as a ribonucleic acid molecule, and the ribonucleic acid molecule inhibits the expression of an endogenous coleopteran pest nucleotide sequence specifically complementary to the at least one nucleotide sequence(s) when the coleopteran pest ingests a part of the plant.

15. A commodity product produced from a plant according to claim 10, wherein the commodity product comprises a detectable amount of the polynucleotide.

16. The transgenic plant cell of claim 9, wherein the cell is a *Zea mays* cell.

17. A method for improving the yield of a corn crop, the method comprising cultivating a transgenic corn plant comprising the transgenic corn cell of claim 16 to allow the expression of a nucleic acid molecule comprising the polyribonucleotide encoded by the at least one nucleotide sequence(s), wherein expression of the nucleic acid molecule inhibits coleopteran pest infection or growth and loss of yield due to coleopteran pest infection.

18. The method according to claim 17, wherein the nucleic acid molecule suppresses at least a first target gene in a coleopteran pest that has contacted a portion of the corn plant.

19. A method for controlling a coleopteran pest population, the method comprising cultivating a host plant of a coleopteran pest,
   wherein the host plant comprises the transgenic plant cell of claim 9, and
   wherein the polynucleotide is expressed to produce a ribonucleic acid molecule that functions upon contact with a coleopteran pest belonging to the population to inhibit the expression of a target sequence within the coleopteran pest and results in decreased growth of the coleopteran pest or coleopteran pest population, relative to growth on a host plant of the same species lacking the transformed plant cell.

20. The method according to claim 19, wherein the ribonucleic acid molecule is a double-stranded ribonucleic acid molecule.

21. The method according to claim 19, wherein the coleopteran pest population is reduced relative to a coleopteran pest population infesting a host plant of the same species lacking the transformed plant cell.

22. A method of controlling plant coleopteran pest infestation in a plant, the method comprising providing in the diet of a coleopteran pest the transgenic plant cell of claim 9.

23. A method for selecting a transgenic plant cell, the method comprising:
   culturing the transgenic plant cell of claim 9 under conditions sufficient to allow for development of a plant cell culture comprising a plurality of transgenic plant cells;
   selecting for transgenic plant cells that have integrated the polynucleotide into their genomes;
   screening the transgenic plant cells for expression of a ribonucleic acid molecule comprising the polyribonucleotide encoded by the at least one nucleotide sequence(s); and
   selecting a transgenic plant cell that expresses the ribonucleic acid molecule.

24. A method for producing a coleopteran pest-resistant transgenic plant, the method comprising regenerating a transgenic plant from the transgenic plant cell of claim 1, wherein expression of the ribonucleic acid molecule encoded by the polynucleotide is sufficient to inhibit the expression of the endogenous nucleic acid when the coleopteran pest feeds on the transgenic plant.

25. The transgenic plant cell of claim 1, wherein the polynucleotide is SEQ ID NO:31.

* * * * *

SEQUENCE LISTING

```
<160> NUMBER OF SEQ ID NOS: 110

<210> SEQ ID NO 1
<211> LENGTH: 1508
<212> TYPE: DNA
<213> ORGANISM: Diabrotica virgifera

<400> SEQUENCE: 1
cgcaaaaaag tgttgtttgg tttgtagtta aaaggctctg taaaaatcat taaaaatccg      60
agccatcttt tagtttttaag tttcttaaat attgtcaaag agtatcacaa ggatttctca    120
aatggcagaa gcagataaat tgaatatcga cagtataata gcccgtttat tagaagtgcg    180
tggagcaaga ccaggcaaaa atgtacaact cacagaaaat gaaattaggg ggctctgttt    240
aaaatctaga gagatcttcc ttagccagcc gattttgttg gaacttgaag ctcctctgaa    300
gatttgcggt gatatacatg gtcagtacta tgacttgctt cgtctctttg aatatggagg    360
tttccctccc gaatcaaact acttatttt gggagattat gtagatcgtg gtaaacaatc     420
attggaaacc atctgcttac ttctcgctta caaaattaaa tacccagaaa acttttcct      480 actcagaggc aaccacgaat gcgcatcaat taatcgtata tatggattct atgatgaatg    540
caaaagaagg tataacatca agttgtggaa aacttttacg gactgtttca attgcctacc     600
tgtagcagcc atcgtcgatg aaaaaatttt ctgttgccat ggtggtttaa gtccggacct    660
```

```
acaatcaatg gaacaaatta gaagaattat gagaccgact gatgtacctg accaagggct        720
tctttgtgac cttttatggt ctgatccaga caaagaccag atgggatggg agaaaacga         780 tagaggagtt agttttactt ttggtgctga agttgtagga aagttcttgc acaaacacga        840
ttttgatttg atatgtcgag cgcatcaagt cgtagaagat ggatatgaat tcttcgccaa        900
aagacagtta gtcacactgt ttagtgcgcc aaattattgt ggagagtttg ataacgcagg        960
tgcgatgatg tcggtggatg agacactaat gtgtagtttt caaattttaa agccagcaga       1020
caagaggaaa ttccagtaca acatgaacgc aggcagacct gtgacgccgc caagaggcgc       1080
aacgaataaa aacaagaaga agtgaatgaa taatatattt ataaggttag gtttagtcgc       1140
aacataaaca tgttcaaaac attttaaata ctaaattttt ctaaaggtta caaagattca       1200
agataaatta agattttctt catgtttttg ttggttgttt tataggttag gatagtaaac       1260
tatataataa taaagttctc aatattgtta aaaagaagtg aatgttagta tttaaaatgt       1320
tcgattattt cggccgtttt actttatttt atatctgata ttactagaaa agggtgatat       1380
ctatgaaccc agacaactaa acgttcgatt tgaacaaatg aaaatttatt gaaaacatta       1440
atcctcacaa ccttgcttat ttaattaaag aacaagatca gtaatacatt aaagtctatc       1500
attaataa                                                                1508

<210> SEQ ID NO 2
<211> LENGTH: 2519
<212> TYPE: DNA
<213> ORGANISM: Diabrotica virgifera

<400> SEQUENCE: 2
caaaggtttc gtttcaaact tcacaccgat aaagacttgt ttgttcttgt cagtgtcagt         60
tctggcggta aatatttgc ggtatacaca tttttacgt cgtacgtaat ttgcaggggt          120
tgattactga tctttatttg ataatttgtt tatttatttt gcaacataag caaaatgcgt        180
tcgcctcaaa cctataacat gtcagaagga tcactccaga caatcatgtc tggaggtgaa        240
tttccaaatc ccattatgca agttttgggt agcaaaaaga taaacgccgg attgggtgat        300
aaagaaagaa ttcgtatttt actgtcagat ggaaaataca ctatttcttt tgccatgcta        360
acagcccaaa ttaatgatcg acttggtcca aatggtgtgg aaacttttag cattatacaa        420
atagatagat atgttacgag tatcatcaac aattctggga aggagaagc acgagtactt        480 ttaatcctcg atatgcatgt tgttgtccct ggaactgaag ttacagaaaa agtaggctct        540
cccattcccc taccaactga tgctgacgca gctaaaggct ctactgccgc tccagctaca        600
aacaattcca ttaagaatgt aactgttgct aaaccaaaca tcagtaatgg caatggcaca        660
actgcaatga atgccagtac taatgatgat atagccacac atatgatcca tcctatttca        720
agtctcacac cttaccaaaa cagatggact atcaaagcga gaattactaa taaacctcca        780
ataagaacgt ggtcaaattc tagaggggaa ggaaaattat ttagttttga tctggtggat        840
gaaagtggcg aaatccgttg cacagctttt aaagaaatgg ttgataaatt ctatgattac        900
ctgcaggtgg ataaagtata ttacatcaac aaatgtcaac ttaaacaagc caacaaacag        960
tacagcactc taaaacatga gtatgaaatg actgttacgc atgatactgt cattaaagaa       1020
tgccttgatg cagattctac aatacccacc acacagtata actttgttcc tatagataaa       1080
attgctgata agaagtaaaa ttctgttgta gatgtaatag gtattgccaa aagtgtcagt       1140
gaattacaaa cattccaagc aagatcaaca ggaagagaat tgaaaaagaa agaagttgtc       1200
```

```
ttggttgatc agtcacaaac agctatatcg ttaacacttt ggggccaaga agccgaaaat    1260
tttgatggta ccaataatcc tgtcgtagtt ataaaaagtg ccaaaattgg cgagtttgga    1320
ggtggcaaga atttaactac tcttgttagc agcactgtaa aaataaatcc cgaattaaaa    1380
gaatgttaca ggatcagagg atggtacgac agtgagggtg aaaatctgaa tgcaaagaat    1440
attagtgcca gagttggatc ctcgaatatg tctgccactt ggatgacctt taaggaagtt    1500
aaagatcaaa aattaggatc atctgaaaaa ggtgattatt ataaagctat tgctactgtt    1560
cttcttgtca aagccgataa tattgtgtat agagcttgtc ccaccgctga atgtaataag    1620
aaagttgttg atatggaaaa tagtatgtac agatgtgaaa aatgtaatag agaatttcca    1680
aatttcaaat acagactgtt agccagcatg aatgttggag accacacagg aaaccaatgg    1740
gttagcatgt tcagttcaga agccgaaaaa attctgggga tgactgctga ggaagtagga    1800
cagaccttgg aacacaataa agaagaaata gccaacatcg tagatagagc tcattttaaa    1860
gtatttagtc ttacttgcag ggcaaaaatt gagacttaca atgatgaagc tcgtttaaaa    1920
actgtttgta taagagtcga tccaattaat tatgaggagt atagtgcatt gctcacagaa    1980
aaaattcagc agttaacagg cgaatctcat gattagatat acaccaacac tacagctatg    2040
ctattatttc tagttctttt tttttttaga aaatatcgtt aagaaatctg tgttttgtat    2100
ttatttttta taaacagtga atcagtgaat aagattttat tagaaaggta ctgtataaat    2160
aaaaatctgt atgttcacaa tattttatt tatttaaata tacattggta caaaataaaa    2220
tatatattcg taacaactat attattgttt attattgttt attcttaagc cccatcatct    2280
aaagaggttc taaatgtgct tgtttttcttg catacgcacc taaacaagct aaaattagta    2340
ttacactcat aaataatcct attaataagg ctaaagtatc tccaaaatca aacattttgc    2400
tgtattattg agtgtttaaa taattacatc aaaataaaat attttttatt ttttgcttgt    2460
cttgtatgtt tatttacgtt ttacttgtca atcagctgtc tatttcttct ttttaatta    2519

<210> SEQ ID NO 3
<211> LENGTH: 772
<212> TYPE: DNA
<213> ORGANISM: Diabrotica virgifera
<220> FEATURE:
<221> NAME/KEY: misc_feature
<222> LOCATION: (751)..(751)
<223> OTHER INFORMATION: n is a, c, g, or t

<400> SEQUENCE: 3
aattcaagct gccgcaaaaa agtgttgttt ggtttgtagt taaaaggctc tgtaaaaatc      60
attaaaaatc cgagccatct tttagtttta agtttcttaa atattgtcaa agagtatcac     120
aaggatttct caaatggcag aagcagataa attgaatatc gacagtataa tagcccgttt     180
attagaagtg cgtggagcaa gaccaggcaa aaatgtacaa ctcacagaaa atgaaattag     240
ggggctctgt ttaaaatcta gagagatctt ccttagccag ccgattttgt tggaacttga     300
agctcctctg aagatttgcg gtgatataca tggtcagtac tatgacttgc ttcgtctctt     360
tgaatatgga ggtttccctc ccgaatcaaa ctacttattt ttgggagatt atgtagatcg     420
tggtaaacaa tcattggaaa ccatctgctt acttctcgct tacaaaatta atacccaga     480 aaacttttc ctactcagag gcaaccacga atgcgcatca attaatcgta tatatggatt     540
ctatgatgaa tgcaaaagaa ggtataacat caagttgtgg aaaacttta cggactgttt     600 caattgccta cctgtagcag ccatcgtcga tgaaaaaatt ttctgttgcc atggtggttt     660
aagtccggac ctacaatcaa tggaacaaat tagaagratt aatagagacc gactgatgta     720
```

```
cctgaccaag gstttctttg tgaccttta nggtctgatc cagacaaaga cc            772
```

<210> SEQ ID NO 4
<211> LENGTH: 632
<212> TYPE: DNA
<213> ORGANISM: Diabrotica virgifera

<400> SEQUENCE: 4

```
ataatttgca ggggttgatt actgatcttt atttgattaa tttgtttatt tattttttgca    60
acataagcaa aatgcgttcg cctcaaacct ataacatgtc agaaggatca ctccagacaa   120
tcatgtctgg aggtgaattt ccaaatccca ttatgcaagt tttgggtagc aaaaagataa   180
acgccggatt gggtgataaa gaaagaattc gtattttact gtcagatgga aaatacacta   240
tttcttttgc catgctaaca gcccaaatta atgatcgact tggtccaaat ggtgtggaaa   300
cttttttagca ttatacaaat agatagatat gttacgagta tcatcaacaa ttctgggaaa  360
ggagaagcac gagtactttt aatcctcgat atgcatgttg ttgtccctgg aactgaagtt   420
acagaaaaag taggctctcc cattcccta ccaactgatg ctgackcagc taaaggctct    480
actgccgctc cagctacaaa caattccatt aagaatgtaa ctgttgctaa accaaacatc   540
agtaatggca atggcacaac tgcaatgaat gccagtacta atgatgatat agccacacat   600
atgatccatc ctatttcaag tctcacacct ta                                 632
```

<210> SEQ ID NO 5
<211> LENGTH: 509
<212> TYPE: DNA
<213> ORGANISM: Diabrotica virgifera

<400> SEQUENCE: 5

```
atggtcaaat tctagagggg aaggaaaatt atttagtttt gatctggtgg atgaaagtgg    60
cgaaatccgt tgcacagctt ttaaagaaat ggttgataaw ttctatgatt acctgcaggt   120
ggataaagta tattacatca acaaatgtca acttaaacaa gccaacaaac agtacagcac   180
tctaaaacat gagtatgaaa tgactgttac gcatgatact gtcattaaag aatgccttga   240
tgcagattct acaataccca ccacacagta taactttgtt cctatagata aaattgctga   300
taaagaagta aattctgttg tagatgtaat aggtattgcc aaaagtgtca gtgaattaca   360
aacattccaa gcaagatcaa caggaagaga attgaaaaag aaagaagttg tcttggttga   420
tcagtcacaa acagctatat cgttaacact ttggggccaa gaagccgaaa attttgatgg   480
taccaataat cctgtcgtag ttataaaaa                                     509
```

<210> SEQ ID NO 6
<211> LENGTH: 716
<212> TYPE: DNA
<213> ORGANISM: Diabrotica virgifera

<400> SEQUENCE: 6

```
aactcttgtt agcagcamtr taaaaataaa tcccgaatta aaagaatgtt acaggatcag    60
aggatggtac gacagtgagg gtgaaaatct gaatgcaaag aatattagtg ccagagttgg   120
atcctcgaat atgtctgcca cttggatgac ctttaaggaa gttaaagatc aaaaattagg   180
atcatctgaa aaggtgatt attataaagc tattgctact gttcttcttg tcaaagccga   240
taatattgtg tatagagctt gtcccaccgc tgaatgtaat aagaaagttg ttgatatgga   300
aaatagtatg tacagatgtg aaaaatgtaa tagagaattt ccaaatttca aatacagact   360
```

```
gttagccagc atgaatgttg agaccacac aggaaaccaa tgggttagca tgttcagttc    420
agaagccgaa aaaattctgg ggatgactgc tgaggaagta ggacagacct tggaacacaa    480
taaagaagaa atagccaaca tcgtagatag agctcatttt aaagtattta gtcttacttg    540
cagggcaaaa attgagactt acaatgatga agctcgttta aaaactgttt gtataagagt    600
cgatccaatt aattatgagg agtatagtgc attgctcaca gaaaaaattc agcagttaac    660
aggcgaatct catgattaga tatacaccaa cactacagct atgctattat ttctag        716

<210> SEQ ID NO 7
<211> LENGTH: 933
<212> TYPE: DNA
<213> ORGANISM: Diabrotica virgifera

<400> SEQUENCE: 7
attaattttc tgaaatatcc tttttgaaac atggcagttc catgtgcaca ctaacgagaa     60
gttttccccg tatttagtgt aatttgccaa aaataaagtg tgaaatagta gttttcgagt    120
gcaaaataag tcaatatgaa gttgaacgta tcgtacccgg ccacgggttg ccaaaaactt    180
ttcgaagttg ttgacgaaca caaaattcgt atcttttacg aaaaacgcat gggtcaagaa    240
gttgaggctg atgctcttgg tgacgaatgg aagggctaca tcttgaaaat atctggaggt    300
aacgacaaac aaggattccc catgaaacaa ggtgttctta caaacggtag agtaagactt    360
ttactttcaa aaggtcactc ctgctacaga cccagacgta ccggtgaacg taaaaggaaa    420
tcagttcgtg ggtgcattgt tgatgggaac ctcagcgtgt tggccctagt cattgtaaga    480
aaaggagaac aagaaattcc cggacttact gacaccacca tcccacgtcg cctgggaccc    540
aagagagcat ccagaatccg taagctcttc aaccttagca agaagacga tgtacgtcaa     600 tatgtagtaa agagaccttt ggcccaaaaa gaaggtaaga agttaagaac caaggccccc    660
aaaatccaac gtcttattac acccgttgtt ttgcaaagaa aacgtcatcg tcttgctttg    720
aagaagaaga ggtgccttaa acgtaaagaa caagaagatg catatgctaa actattggct    780
caacgtaaga aggaatccaa ggctcgtcgt gagatgttga agaggcgtag gtctgccagt    840
atgcgtgata gtaaatccag cacgcagagt ggtcagaagt aaattgtaat tttttatatt    900
ttaagacaat gtatgaaata aacgttgttg ctt                                 933

<210> SEQ ID NO 8
<211> LENGTH: 24
<212> TYPE: DNA
<213> ORGANISM: Artificial Sequence
<220> FEATURE:
<223> OTHER INFORMATION: Escherichia coli T7 bacteriophage

<400> SEQUENCE: 8
ttaatacgac tcactatagg gaga                                            24

<210> SEQ ID NO 9
<211> LENGTH: 48
<212> TYPE: DNA
<213> ORGANISM: Artificial Sequence
<220> FEATURE:
<223> OTHER INFORMATION: PCR primer

<400> SEQUENCE: 9
ttaatacgac tcactatagg gagacaaatg gcagaagcag ataaattg                  48

<210> SEQ ID NO 10
<211> LENGTH: 27
```

```
<212> TYPE: DNA
<213> ORGANISM: Artificial Sequence
<220> FEATURE:
<223> OTHER INFORMATION: PCR Primer

<400> SEQUENCE: 10
ctaatttgtt ccattgattg taggtcc                                           27

<210> SEQ ID NO 11
<211> LENGTH: 24
<212> TYPE: DNA
<213> ORGANISM: Artificial Sequence
<220> FEATURE:
<223> OTHER INFORMATION: PDR Primer

<400> SEQUENCE: 11
caaatggcag aagcagataa attg                                              24

<210> SEQ ID NO 12
<211> LENGTH: 51
<212> TYPE: DNA
<213> ORGANISM: Artificial Sequence
<220> FEATURE:
<223> OTHER INFORMATION: PCR Primer

<400> SEQUENCE: 12
ttaatacgac tcactatagg gagactaatt tgttccattg attgtaggtc c                51

<210> SEQ ID NO 13
<211> LENGTH: 46
<212> TYPE: DNA
<213> ORGANISM: Artificial Sequence
<220> FEATURE:
<223> OTHER INFORMATION: PCR Primer

<400> SEQUENCE: 13
ttaatacgac tcactatagg gagaatggtc aaattctaga ggggaa                      46

<210> SEQ ID NO 14
<211> LENGTH: 25
<212> TYPE: DNA
<213> ORGANISM: Artificial Sequence
<220> FEATURE:
<223> OTHER INFORMATION: PCR Primer

<400> SEQUENCE: 14
ctacgacagg attattggta ccatc                                             25

<210> SEQ ID NO 15
<211> LENGTH: 22
<212> TYPE: DNA
<213> ORGANISM: Artificial Sequence
<220> FEATURE:
<223> OTHER INFORMATION: PCR Primer

<400> SEQUENCE: 15
atggtcaaat tctagagggg aa                                                22

<210> SEQ ID NO 16
<211> LENGTH: 49
<212> TYPE: DNA
<213> ORGANISM: Artificial Sequence
<220> FEATURE:
<223> OTHER INFORMATION: PCR Primer

<400> SEQUENCE: 16
```

```
ttaatacgac tcactatagg gagactacga caggattatt ggtaccatc        49
```

<210> SEQ ID NO 17
<211> LENGTH: 50
<212> TYPE: DNA
<213> ORGANISM: Artificial Sequence
<220> FEATURE:
<223> OTHER INFORMATION: PCR Primer

<400> SEQUENCE: 17

```
ttaatacgac tcactatagg gagatcccga attaaaagaa tgttacagga        50
```

<210> SEQ ID NO 18
<211> LENGTH: 26
<212> TYPE: DNA
<213> ORGANISM: Artificial Sequence
<220> FEATURE:
<223> OTHER INFORMATION: PCR Primer

<400> SEQUENCE: 18

```
cgagcttcat cattgtaagt ctcaat                                  26
```

<210> SEQ ID NO 19
<211> LENGTH: 26
<212> TYPE: DNA
<213> ORGANISM: Artificial Sequence
<220> FEATURE:
<223> OTHER INFORMATION: PCR Primer

<400> SEQUENCE: 19

```
tcccgaatta aaagaatgtt acagga                                  26
```

<210> SEQ ID NO 20
<211> LENGTH: 50
<212> TYPE: DNA
<213> ORGANISM: Artificial Sequence
<220> FEATURE:
<223> OTHER INFORMATION: PCR Primer

<400> SEQUENCE: 20

```
ttaatacgac tcactatagg gagacgagct tcatcattgt aagtctcaat        50
```

<210> SEQ ID NO 21
<211> LENGTH: 47
<212> TYPE: DNA
<213> ORGANISM: Artificial Sequence
<220> FEATURE:
<223> OTHER INFORMATION: PCR Primer

<400> SEQUENCE: 21

```
ttaatacgac tcactatagg gagatcaata tgaagttgaa cgtatcg           47
```

<210> SEQ ID NO 22
<211> LENGTH: 20
<212> TYPE: DNA
<213> ORGANISM: Artificial Sequence
<220> FEATURE:
<223> OTHER INFORMATION: PCR Primer

<400> SEQUENCE: 22

```
atgctctctt gggtcccagg                                         20
```

<210> SEQ ID NO 23
<211> LENGTH: 23
<212> TYPE: DNA
<213> ORGANISM: Artificial Sequence

```
<220> FEATURE:
<223> OTHER INFORMATION: PCR Primer

<400> SEQUENCE: 23
tcaatatgaa gttgaacgta tcg                                              23

<210> SEQ ID NO 24
<211> LENGTH: 44
<212> TYPE: DNA
<213> ORGANISM: Artificial Sequence
<220> FEATURE:
<223> OTHER INFORMATION: PCR Primer

<400> SEQUENCE: 24
ttaatacgac tcactatagg gagaatgctc tcttgggtcc cagg                       44

<210> SEQ ID NO 25
<211> LENGTH: 563
<212> TYPE: DNA
<213> ORGANISM: Artificial Sequence
<220> FEATURE:
<223> OTHER INFORMATION: Amplified fragment

<400> SEQUENCE: 25
caaatggcag aagcagataa attgaatatc gacagtataa tagcccgttt attagaagtg      60
cgtggagcaa gaccaggcaa aaatgtacaa ctcacagaaa atgaaattag ggggctctgt     120
ttaaaatcta gagagatctt ccttagccag ccgatttgt  tggaacttga agctcctctg     180
aagatttgcg gtgatataca tggtcagtac tatgacttgc ttcgtctctt tgaatatgga    240
ggtttccctc ccgaatcaaa ctacttattt ttgggagatt atgtagatcg tggtaaacaa    300
tcattggaaa ccatctgctt acttctcgct tacaaaatta ataccccaga aacttttttc    360
ctactcagag gcaaccacga atgcgcatca attaatcgta tatatggatt ctatgatgaa    420
tgcaaaagaa ggtataacat caagttgtgg aaaacttta  cggactgttt caattgccta    480
cctgtagcag ccatcgtcga tgaaaaaatt ttctgttgcc atggtggttt aagtccggac    540
ctacaatcaa tggaacaaat tag                                            563

<210> SEQ ID NO 26
<211> LENGTH: 500
<212> TYPE: DNA
<213> ORGANISM: Artificial Sequence
<220> FEATURE:
<223> OTHER INFORMATION: Amplified fragment

<400> SEQUENCE: 26
atggtcaaat tctagagggg aaggaaaatt atttagtttt gatctggtgg atgaaagtgg      60
cgaaatccgt tgcacagctt ttaaagaaat ggttgataaw ttctatgatt acctgcaggt    120
ggataaagta tattacatca acaaatgtca acttaaacaa gccaacaaac agtacagcac    180
tctaaaacat gagtatgaaa tgactgttac gcatgatact gtcattaaag aatgccttga    240
tgcagattct acaatacccca ccacacagta taactttgtt cctatagata aaattgctga    300
taaagaagta aattctgttg tagatgtaat aggtattgcc aaaagtgtca gtgaattaca    360
aacattccaa gcaagatcaa caggaagaga attgaaaaag aaagaagttg tcttggttga    420
tcagtcacaa acagctatat cgttaacact ttggggccaa gaagccgaaa attttgatgg    480
taccaataat cctgtcgtag                                                500

<210> SEQ ID NO 27
```

<211> LENGTH: 546
<212> TYPE: DNA
<213> ORGANISM: Artificial Sequence
<220> FEATURE:
<223> OTHER INFORMATION: Amplified fragment

<400> SEQUENCE: 27

| | | | | | |
|---|---|---|---|---|---|
| tcccgaatta | aaagaatgtt | acaggatcag | aggatggtac | gacagtgagg | gtgaaaatct | 60 |
| gaatgcaaag | aatattagtg | ccagagttgg | atcctcgaat | atgtctgcca | cttggatgac | 120 |
| ctttaaggaa | gttaaagatc | aaaaattagg | atcatctgaa | aaggtgatt | attataaagc | 180 |
| tattgctact | gttcttcttg | tcaaagccga | taatattgtg | tatagagctt | gtcccaccgc | 240 |
| tgaatgtaat | aagaaagttg | ttgatatgga | aaatagtatg | tacagatgtg | aaaaatgtaa | 300 |
| tagagaattt | ccaaatttca | aatacagact | gttagccagc | atgaatgttg | gagaccacac | 360 |
| aggaaaccaa | tgggttagca | tgttcagttc | agaagccgaa | aaaattctgg | ggatgactgc | 420 |
| tgaggaagta | ggacagacct | tggaacacaa | taaagaagaa | atagccaaca | tcgtagatag | 480 |
| agctcatttt | aaagtattta | gtcttacttg | cagggcaaaa | attgagactt | acaatgatga | 540 |
| agctcg | | | | | 546 |

<210> SEQ ID NO 28
<211> LENGTH: 420
<212> TYPE: DNA
<213> ORGANISM: Artificial Sequence
<220> FEATURE:
<223> OTHER INFORMATION: Amplified fragment

<400> SEQUENCE: 28

| | | | | | |
|---|---|---|---|---|---|
| tcaatatgaa | gttgaacgta | tcgtacccgg | ccacggggttg | ccaaaaactt | ttcgaagttg | 60 |
| ttgacgaaca | caaaattcgt | atcttttacg | aaaaacgcat | gggtcaagaa | gttgaggctg | 120 |
| atgctcttgg | tgacgaatgg | aagggctaca | tcttgaaaat | atctggaggt | aacgacaaac | 180 |
| aaggattccc | catgaaacaa | ggtgttctta | caaacggtag | agtaagactt | ttactttcaa | 240 |
| aaggtcactc | ctgctacaga | cccagacgta | ccggtgaacg | taaaaggaaa | tcagttcgtg | 300 |
| ggtgcattgt | tgatgggaac | ctcagcgtgt | tggccctagt | cattgtaaga | aaaggagaac | 360 |
| aagaaattcc | cggacttact | gacaccacca | tcccacgtcg | cctgggaccc | aagagagcat | 420 |

<210> SEQ ID NO 29
<211> LENGTH: 817
<212> TYPE: DNA
<213> ORGANISM: Artificial Sequence
<220> FEATURE:
<223> OTHER INFORMATION: Hairpin

<400> SEQUENCE: 29

| | | | | | |
|---|---|---|---|---|---|
| cctctgaaga | tttgcggtga | tatacatggt | cagtactatg | acttgcttcg | tctctttgaa | 60 |
| tatggaggtt | tccctcccga | atcaaactac | ttattttttgg | gagattatgt | agatcgtggt | 120 |
| aaacaatcat | tggaaaccat | ctgcttactt | ctcgcttaca | aaattaaata | cccagaaaac | 180 |
| tttttcctac | tcagaggcaa | ccacgaatgc | gcatcaatta | atcgtatata | tggattctat | 240 |
| gatgaatgca | aaagaaggta | taacatcaag | ttgtggaaaa | cttttacgga | ctgtttgact | 300 |
| agtaccggtt | gggaaaggta | tgtttctgct | tctacctttg | atatatatat | aataattatc | 360 |
| actaattagt | agtaatatag | tatttcaagt | attttttttca | aaataaaaga | atgtagtata | 420 |
| tagctattgc | ttttctgtag | tttataagtg | tgtatatttt | aatttataac | ttttctaata | 480 |
| tatgaccaaa | acatggtgat | gtgcaggttg | atccgcggtt | aaaacagtcc | gtaaaagttt | 540 |

```
tccacaactt gatgttatac cttcttttgc attcatcata gaatccatat atacgattaa    600
ttgatgcgca ttcgtggttg cctctgagta ggaaaaagtt ttctgggtat ttaattttgt    660
aagcgagaag taagcagatg gtttccaatg attgtttacc acgatctaca taatctccca    720
aaaataagta gtttgattcg ggagggaaac ctccatattc aaagagacga agcaagtcat    780
agtactgacc atgtatatca ccgcaaatct tcagagg                            817

<210> SEQ ID NO 30
<211> LENGTH: 807
<212> TYPE: DNA
<213> ORGANISM: Artificial Sequence
<220> FEATURE:
<223> OTHER INFORMATION: Hairpin

<400> SEQUENCE: 30
tacctgcagg tggataaagt atattacatc aacaaatgtc aacttaaaca agccaacaaa     60
cagtacagca ctctaaaaca tgagtatgaa atgactgtta cgcatgatac tgtcattaaa    120
gaatgccttg atgcagattc tacaataccc accacacagt ataactttgt tcctatagat    180
aaaattgctg ataagaagt aaattctgtt gtagatgtaa taggtattgc caaaagtgtc     240
agtgaattac aaacattcca agcaagatca acaggaagag aattgaaaaa ggactagtac    300
cggttgggaa aggtatgttt ctgcttctac ctttgatata tataataaa ttatcactaa     360 ttagtagtaa tatagtattt caagtatttt tttcaaaata aaagaatgta gtatatagct    420
attgcttttc tgtagtttat aagtgtgtat atttaatttt ataacttttc taatatatga    480
ccaaaacatg gtgatgtgca ggttgatccg cggttacttt tcaattctc ttcctgttga     540 tcttgcttgg aatgtttgta attcactgac acttttggca atacctatta catctacaac    600
agaatttact tctttatcag caatttatc tataggaaca aagttatact gtgtggtggg     660
tattgtagaa tctgcatcaa ggcattcttt aatgacagta tcatgcgtaa cagtcatttc    720
atactcatgt tttagagtgc tgtactgttt gttggcttgt ttaagttgac atttgttgat    780
gtaatatact ttatccacct gcaggta                                       807

<210> SEQ ID NO 31
<211> LENGTH: 825
<212> TYPE: DNA
<213> ORGANISM: Artificial Sequence
<220> FEATURE:
<223> OTHER INFORMATION: Hairpin

<400> SEQUENCE: 31
aacgacaaac aaggattccc catgaaacaa ggtgttctta caaacggtag agtaagactt     60
ttactttcaa aaggtcactc ctgctacaga cccagacgta ccggtgaacg taaaaggaaa    120
tcagttcgtg ggtgcattgt tgatgggaac ctcagcgtgt tggccctagt cattgtaaga    180
aaaggagaac aagaaattcc cggacttact gacaccacca tcccacgtcg cctgggaccc    240
aagagagcat ccagaatccg taagctcttc aaccttagca aagaagacga tgtacgtcaa    300
gactagtacc ggttgggaaa ggtatgtttc tgcttctacc tttgatatat atataataat    360
tatcactaat tagtagtaat atagtatttc aagtattttt tcaaaataa aagaatgtag     420 tatatagcta ttgcttttct gtagtttata agtgtgtata ttttaattta aacttttct    480 aatatatgac caaaacatgg tgatgtgcag gttgatccgc ggttattgac gtacatcgtc    540
ttctttgcta aggttgaaga gcttacggat tctggatgct ctcttgggtc ccaggcgacg    600
```

| | |
|---|---|
| tgggatggtg gtgtcagtaa gtccgggaat ttcttgttct ccttttctta caatgactag | 660 |
| ggccaacacg ctgaggttcc catcaacaat gcacccacga actgatttcc ttttacgttc | 720 |
| accggtacgt ctgggtctgt agcaggagtg acctttttgaa agtaaaagtc ttactctacc | 780 |
| gtttgtaaga acaccttgtt tcatggggaa tccttgtttg tcgtt | 825 |

<210> SEQ ID NO 32
<211> LENGTH: 218
<212> TYPE: DNA
<213> ORGANISM: Artificial Sequence
<220> FEATURE:
<223> OTHER INFORMATION: Amplified fragment

<400> SEQUENCE: 32

| | |
|---|---|
| tagctctgat gacagagccc atcgagtttc aagccaaaca gttgcataaa gctatcagcg | 60 |
| gattgggaac tgatgaaagt acaatmgtmg aaattttaag tgtmcacaac aacgatgaga | 120 |
| ttataagaat ttcccaggcc tatgaaggat tgtaccaacg mtcattggaa tctgatatca | 180 |
| aaggagatac ctcaggaaca ttaaaaaaga attattag | 218 |

<210> SEQ ID NO 33
<211> LENGTH: 424
<212> TYPE: DNA
<213> ORGANISM: Artificial Sequence
<220> FEATURE:
<223> OTHER INFORMATION: Amplified fragment
<220> FEATURE:
<221> NAME/KEY: misc_feature
<222> LOCATION: (393)..(395)
<223> OTHER INFORMATION: n is a, c, g, or t

<400> SEQUENCE: 33

| | |
|---|---|
| ttgttacaag ctggagaact tctctttgct ggaaccgaag agtcagtatt taatgctgta | 60 |
| ttctgtcaaa gaaataaacc acaattgaat ttgatattcg acaaatatga agaaattgtt | 120 |
| gggcatccca ttgaaaaagc cattgaaaac gagtttcag gaaatgctaa acaagccatg | 180 |
| ttacacctta tccagagcgt aagagatcaa gttgcatatt tggtaaccag gctgcatgat | 240 |
| tcaatggcag gcgtcggtac tgacgataga acttttaatca gaattgttgt ttcgagatct | 300 |
| gaaatcgatc tagaggaaat caaacaatgc tatgaagaaa tctacagtaa aaccttggct | 360 |
| gataggatag cggatgacac atctggcgac tannnaaaag ccttattagc cgttgttggt | 420 |
| taag | 424 |

<210> SEQ ID NO 34
<211> LENGTH: 397
<212> TYPE: DNA
<213> ORGANISM: Artificial Sequence
<220> FEATURE:
<223> OTHER INFORMATION: Amplified fragment

<400> SEQUENCE: 34

| | |
|---|---|
| agatgttggc tgcatctaga gaattacaca agttcttcca tgattgcaag gatgtactga | 60 |
| gcagaatagt ggaaaaacag gtatccatgt ctgatgaatt gggaagggac gcaggagctg | 120 |
| tcaatgccct tcaacgcaaa caccagaact tcctccaaga cctacaaaca ctccaatcga | 180 |
| acgtccaaca atccaagaa gaatcagcta aacttcaagc tagctatgcc ggtgatagag | 240 |
| ctaaagaaat caccaacagg gagcaggaag tggtagcagc ctgggcagcc ttgcagatcg | 300 |
| cttgcgatca gagacacgga aaattgagcg atactggtga tctattcaaa ttcttttaact | 360 |
| tggtacgaac gttgatgcag tggatggacg aatggac | 397 |

<210> SEQ ID NO 35
<211> LENGTH: 490
<212> TYPE: DNA
<213> ORGANISM: Artificial Sequence
<220> FEATURE:
<223> OTHER INFORMATION: Amplified fragment

<400> SEQUENCE: 35

| | | | | | |
|---|---|---|---|---|---|
| gcagatgaac | accagcgaga | aaccaagaga | tgttagtggt | gttgaattgt | tgatgaacaa | 60 |
| ccatcagaca | ctcaaggctg | agatcgaagc | cagagaagac | aactttacgg | cttgtatttc | 120 |
| tttaggaaag | gaattgttga | gccgtaatca | ctatgctagt | gctgatatta | aggataaatt | 180 |
| ggtcgcgttg | acgaatcaaa | ggaatgctgt | actacagagg | tgggaagaaa | gatgggagaa | 240 |
| cttgcaactc | atcctcgagg | tataccaatt | cgccagagat | gcggccgtcg | ccgaagcatg | 300 |
| gttgatcgca | caagaacctt | acttgatgag | ccaagaacta | ggacacacca | ttgacgacgt | 360 |
| tgaaaacttg | ataaagaaac | acgaagcgtt | cgaaaaatcg | gcagcggcgc | aagaagagag | 420 |
| attcagtgct | ttggagagac | tgacgacgtt | cgaattgaga | gaaataaaga | ggaaacaaga | 480 |
| agctgcccag | | | | | | 490 |

<210> SEQ ID NO 36
<211> LENGTH: 330
<212> TYPE: DNA
<213> ORGANISM: Artificial Sequence
<220> FEATURE:
<223> OTHER INFORMATION: Amplified fragment

<400> SEQUENCE: 36

| | | | | | |
|---|---|---|---|---|---|
| agtgaaatgt | tagcaaatat | aacatccaag | tttcgtaatt | gtacttgctc | agttagaaaa | 60 |
| tattctgtag | tttcactatc | ttcaaccgaa | aatagaataa | atgtagaacc | tcgcgaactt | 120 |
| gcctttcctc | caaaatatca | agaacctcga | caagtttggt | tggagagttt | agatacgata | 180 |
| gacgacaaaa | aattgggtat | tcttgagctg | catcctgatg | ttttttgctac | taatccaaga | 240 |
| atagatatta | tacatcaaaa | tgttagatgg | caaagtttat | atagatatgt | aagctatgct | 300 |
| catacaaagt | caagatttga | agtgagaggt | | | | 330 |

<210> SEQ ID NO 37
<211> LENGTH: 320
<212> TYPE: DNA
<213> ORGANISM: Artificial Sequence
<220> FEATURE:
<223> OTHER INFORMATION: Amplified fragment

<400> SEQUENCE: 37

| | | | | | |
|---|---|---|---|---|---|
| caaagtcaag | atttgaagtg | agaggtggag | gtcgaaaacc | gtggccgcaa | aagggattgg | 60 |
| gacgtgctcg | acatggttca | attagaagtc | cactttggag | aggtggagga | gttgttcatg | 120 |
| gaccaaaatc | tccaaccccct | cattttaca | tgattccatt | ctacacccgt | ttgctggggtt | 180 |
| tgactagcgc | acttttcagta | aaatttgccc | aagatgactt | gcacgttgtg | gatagtctag | 240 |
| atctgccaac | tgacgaacaa | agttatatag | aagagctggt | caaaagccgc | ttttgggggt | 300 |
| ccttcttgtt | ttatttgtag | | | | | 320 |

<210> SEQ ID NO 38
<211> LENGTH: 503
<212> TYPE: DNA
<213> ORGANISM: Artificial Sequence
<220> FEATURE:

```
<223> OTHER INFORMATION: Amplified fragment

<400> SEQUENCE: 38
caccatgggc tccagcggcg ccctgctgtt ccacggcaag atcccctacg tggtggagat    60
ggagggcaat gtggatggcc acaccttcag catccgcggc aagggctacg gcgatgccag   120
cgtgggcaag gtggatgccc agttcatctg caccaccggc gatgtgcccg tgccctggag   180
caccctggtg accaccctga cctacggcgc ccagtgcttc gccaagtacg gccccgagct   240
gaaggatttc tacaagagct gcatgcccga tggctacgtg caggagcgca ccatcacctt   300
cgagggcgat ggcaatttca gacccgcgc cgaggtgacc ttcgagaatg cagcgtgta   360 caatcgcgtg aagctgaatg ccagggctt caagaaggat ggccacgtgc tgggcaagaa   420
tctggagttc aatttcaccc cccactgcct gtacatctgg ggcgatcagg ccaatcacgg   480
cctgaagagc gccttcaaga tct                                          503

<210> SEQ ID NO 39
<211> LENGTH: 46
<212> TYPE: DNA
<213> ORGANISM: Artificial Sequence
<220> FEATURE:
<223> OTHER INFORMATION: PCR Primer

<400> SEQUENCE: 39
ttaatacgac tcactatagg gagagctcca acagtggttc cttatc                   46

<210> SEQ ID NO 40
<211> LENGTH: 29
<212> TYPE: DNA
<213> ORGANISM: Artificial Sequence
<220> FEATURE:
<223> OTHER INFORMATION: PCR Primer

<400> SEQUENCE: 40
ctaataattc tttttaatg ttcctgagg                                       29

<210> SEQ ID NO 41
<211> LENGTH: 22
<212> TYPE: DNA
<213> ORGANISM: Artificial Sequence
<220> FEATURE:
<223> OTHER INFORMATION: PCR Primer

<400> SEQUENCE: 41
gctccaacag tggttcctta tc                                             22

<210> SEQ ID NO 42
<211> LENGTH: 53
<212> TYPE: DNA
<213> ORGANISM: Artificial Sequence
<220> FEATURE:
<223> OTHER INFORMATION: PCR Primer

<400> SEQUENCE: 42
ttaatacgac tcactatagg gagactaata attcttttt aatgttcctg agg            53

<210> SEQ ID NO 43
<211> LENGTH: 48
<212> TYPE: DNA
<213> ORGANISM: Artificial Sequence
<220> FEATURE:
<223> OTHER INFORMATION: PCR Primer

<400> SEQUENCE: 43
```

```
ttaatacgac tcactatagg gagattgtta caagctggag aacttctc                        48
```

<210> SEQ ID NO 44
<211> LENGTH: 24
<212> TYPE: DNA
<213> ORGANISM: Artificial Sequence
<220> FEATURE:
<223> OTHER INFORMATION: PCR Primer

<400> SEQUENCE: 44

```
cttaaccaac aacggctaat aagg                                                  24
```

<210> SEQ ID NO 45
<211> LENGTH: 24
<212> TYPE: DNA
<213> ORGANISM: Artificial Sequence
<220> FEATURE:
<223> OTHER INFORMATION: PCR Primer

<400> SEQUENCE: 45

```
ttgttacaag ctggagaact tctc                                                  24
```

<210> SEQ ID NO 46
<211> LENGTH: 48
<212> TYPE: DNA
<213> ORGANISM: Artificial Sequence
<220> FEATURE:
<223> OTHER INFORMATION: PCR Primer

<400> SEQUENCE: 46

```
ttaatacgac tcactatagg gagacttaac caacaacggc taataagg                        48
```

<210> SEQ ID NO 47
<211> LENGTH: 47
<212> TYPE: DNA
<213> ORGANISM: Artificial Sequence
<220> FEATURE:
<223> OTHER INFORMATION: PCR Primer

<400> SEQUENCE: 47

```
ttaatacgac tcactatagg gagaagatgt tggctgcatc tagagaa                         47
```

<210> SEQ ID NO 48
<211> LENGTH: 22
<212> TYPE: DNA
<213> ORGANISM: Artificial Sequence
<220> FEATURE:
<223> OTHER INFORMATION: PCR Primer

<400> SEQUENCE: 48

```
gtccattcgt ccatccactg ca                                                    22
```

<210> SEQ ID NO 49
<211> LENGTH: 23
<212> TYPE: DNA
<213> ORGANISM: Artificial Sequence
<220> FEATURE:
<223> OTHER INFORMATION: PCR Primer

<400> SEQUENCE: 49

```
agatgttggc tgcatctaga gaa                                                   23
```

<210> SEQ ID NO 50
<211> LENGTH: 46
<212> TYPE: DNA

```
<213> ORGANISM: Artificial Sequence
<220> FEATURE:
<223> OTHER INFORMATION: PCR Primer

<400> SEQUENCE: 50
ttaatacgac tcactatagg gagagtccat tcgtccatcc actgca        46

<210> SEQ ID NO 51
<211> LENGTH: 46
<212> TYPE: DNA
<213> ORGANISM: Artificial Sequence
<220> FEATURE:
<223> OTHER INFORMATION: PCR Primer

<400> SEQUENCE: 51
ttaatacgac tcactatagg gagagcagat gaacaccagc gagaaa        46

<210> SEQ ID NO 52
<211> LENGTH: 22
<212> TYPE: DNA
<213> ORGANISM: Artificial Sequence
<220> FEATURE:
<223> OTHER INFORMATION: PCR Primer

<400> SEQUENCE: 52
ctgggcagct tcttgtttcc tc                                  22

<210> SEQ ID NO 53
<211> LENGTH: 22
<212> TYPE: DNA
<213> ORGANISM: Artificial Sequence
<220> FEATURE:
<223> OTHER INFORMATION: PCR Primer

<400> SEQUENCE: 53
gcagatgaac accagcgaga aa                                  22

<210> SEQ ID NO 54
<211> LENGTH: 46
<212> TYPE: DNA
<213> ORGANISM: Artificial Sequence
<220> FEATURE:
<223> OTHER INFORMATION: PCR Primer

<400> SEQUENCE: 54
ttaatacgac tcactatagg gagactgggc agcttcttgt ttcctc        46

<210> SEQ ID NO 55
<211> LENGTH: 51
<212> TYPE: DNA
<213> ORGANISM: Artificial Sequence
<220> FEATURE:
<223> OTHER INFORMATION: PCR Primer

<400> SEQUENCE: 55
ttaatacgac tcactatagg gagaagtgaa atgttagcaa atataacatc c   51

<210> SEQ ID NO 56
<211> LENGTH: 26
<212> TYPE: DNA
<213> ORGANISM: Artificial Sequence
<220> FEATURE:
<223> OTHER INFORMATION: PCR Primer

<400> SEQUENCE: 56
acctctcact tcaaatcttg actttg                              26
```

<210> SEQ ID NO 57
<211> LENGTH: 27
<212> TYPE: DNA
<213> ORGANISM: Artificial Sequence
<220> FEATURE:
<223> OTHER INFORMATION: PCR Primer

<400> SEQUENCE: 57
agtgaaatgt tagcaaatat aacatcc                                          27

<210> SEQ ID NO 58
<211> LENGTH: 50
<212> TYPE: DNA
<213> ORGANISM: Artificial Sequence
<220> FEATURE:
<223> OTHER INFORMATION: PCR Primer

<400> SEQUENCE: 58
ttaatacgac tcactatagg gagaacctct cacttcaaat cttgactttg                  50

<210> SEQ ID NO 59
<211> LENGTH: 50
<212> TYPE: DNA
<213> ORGANISM: Artificial Sequence
<220> FEATURE:
<223> OTHER INFORMATION: PCR Primer

<400> SEQUENCE: 59
ttaatacgac tcactatagg gagacaaagt caagatttga agtgagaggt                  50

<210> SEQ ID NO 60
<211> LENGTH: 25
<212> TYPE: DNA
<213> ORGANISM: Artificial Sequence
<220> FEATURE:
<223> OTHER INFORMATION: PCR Primer

<400> SEQUENCE: 60
ctacaaataa aacaagaagg acccc                                            25

<210> SEQ ID NO 61
<211> LENGTH: 26
<212> TYPE: DNA
<213> ORGANISM: Artificial Sequence
<220> FEATURE:
<223> OTHER INFORMATION: PCR Primer

<400> SEQUENCE: 61
caaagtcaag atttgaagtg agaggt                                           26

<210> SEQ ID NO 62
<211> LENGTH: 49
<212> TYPE: DNA
<213> ORGANISM: Artificial Sequence
<220> FEATURE:
<223> OTHER INFORMATION: PCR Primer

<400> SEQUENCE: 62
ttaatacgac tcactatagg gagactacaa ataaaacaag aaggacccc                   49

<210> SEQ ID NO 63
<211> LENGTH: 47
<212> TYPE: DNA
<213> ORGANISM: Artificial Sequence
<220> FEATURE:

<223> OTHER INFORMATION: PCR Primer

<400> SEQUENCE: 63
ttaatacgac tcactatagg gagacaccat gggctccagc ggcgccc                47

<210> SEQ ID NO 64
<211> LENGTH: 23
<212> TYPE: DNA
<213> ORGANISM: Artificial Sequence
<220> FEATURE:
<223> OTHER INFORMATION: PCR Primer

<400> SEQUENCE: 64
agatcttgaa ggcgctcttc agg                                          23

<210> SEQ ID NO 65
<211> LENGTH: 23
<212> TYPE: DNA
<213> ORGANISM: Artificial Sequence
<220> FEATURE:
<223> OTHER INFORMATION: PCR Primer

<400> SEQUENCE: 65
caccatgggc tccagcggcg ccc                                          23

<210> SEQ ID NO 66
<211> LENGTH: 47
<212> TYPE: DNA
<213> ORGANISM: Artificial Sequence
<220> FEATURE:
<223> OTHER INFORMATION: PCR Primer

<400> SEQUENCE: 66
ttaatacgac tcactatagg gagaagatct tgaaggcgct cttcagg                47

<210> SEQ ID NO 67
<211> LENGTH: 327
<212> TYPE: PRT
<213> ORGANISM: Diabrotica virgifera

<400> SEQUENCE: 67

Met Ala Glu Ala Asp Lys Leu Asn Ile Asp Ser Ile Ile Ala Arg Leu
1               5                   10                  15

Leu Glu Val Arg Gly Ala Arg Pro Gly Lys Asn Val Gln Leu Thr Glu
            20                  25                  30

Asn Glu Ile Arg Gly Leu Cys Leu Lys Ser Arg Glu Ile Phe Leu Ser
        35                  40                  45

Gln Pro Ile Leu Leu Glu Leu Glu Ala Pro Leu Lys Ile Cys Gly Asp
    50                  55                  60

Ile His Gly Gln Tyr Tyr Asp Leu Leu Arg Leu Phe Glu Tyr Gly Gly
65                  70                  75                  80

Phe Pro Pro Glu Ser Asn Tyr Leu Phe Leu Gly Asp Tyr Val Asp Arg
                85                  90                  95

Gly Lys Gln Ser Leu Glu Thr Ile Cys Leu Leu Leu Ala Tyr Lys Ile
            100                 105                 110

Lys Tyr Pro Glu Asn Phe Phe Leu Leu Arg Gly Asn His Glu Cys Ala
        115                 120                 125

Ser Ile Asn Arg Ile Tyr Gly Phe Tyr Asp Glu Cys Lys Arg Arg Tyr
    130                 135                 140

Asn Ile Lys Leu Trp Lys Thr Phe Thr Asp Cys Phe Asn Cys Leu Pro
145                 150                 155                 160

Val Ala Ala Ile Val Asp Glu Lys Ile Phe Cys Cys His Gly Gly Leu
                165                 170                 175

Ser Pro Asp Leu Gln Ser Met Glu Gln Ile Arg Arg Ile Met Arg Pro
            180                 185                 190

Thr Asp Val Pro Asp Gln Gly Leu Leu Cys Asp Leu Leu Trp Ser Asp
        195                 200                 205

Pro Asp Lys Asp Gln Met Gly Trp Gly Glu Asn Asp Arg Gly Val Ser
    210                 215                 220

Phe Thr Phe Gly Ala Glu Val Val Gly Lys Phe Leu His Lys His Asp
225                 230                 235                 240

Phe Asp Leu Ile Cys Arg Ala His Gln Val Val Glu Asp Gly Tyr Glu
                245                 250                 255

Phe Phe Ala Lys Arg Gln Leu Val Thr Leu Phe Ser Ala Pro Asn Tyr
            260                 265                 270

Cys Gly Glu Phe Asp Asn Ala Gly Ala Met Met Ser Val Asp Glu Thr
        275                 280                 285

Leu Met Cys Ser Phe Gln Ile Leu Lys Pro Ala Asp Lys Arg Lys Phe
    290                 295                 300

Gln Tyr Asn Met Asn Ala Gly Arg Pro Val Thr Pro Arg Gly Ala
305                 310                 315                 320

Thr Asn Lys Asn Lys Lys Lys
                325

<210> SEQ ID NO 68
<211> LENGTH: 613
<212> TYPE: PRT
<213> ORGANISM: Diabrotica virgifera

<400> SEQUENCE: 68

Met Arg Ser Pro Gln Thr Tyr Asn Met Ser Glu Gly Ser Leu Gln Thr
1               5                   10                  15

Ile Met Ser Gly Gly Glu Phe Pro Asn Pro Ile Met Gln Val Leu Gly
            20                  25                  30

Ser Lys Lys Ile Asn Ala Gly Leu Gly Asp Lys Glu Arg Ile Arg Ile
        35                  40                  45

Leu Leu Ser Asp Gly Lys Tyr Thr Ile Ser Phe Ala Met Leu Thr Ala
    50                  55                  60

Gln Ile Asn Asp Arg Leu Gly Pro Asn Gly Val Glu Thr Phe Ser Ile
65                  70                  75                  80

Ile Gln Ile Asp Arg Tyr Val Thr Ser Ile Ile Asn Asn Ser Gly Lys
                85                  90                  95

Gly Glu Ala Arg Val Leu Leu Ile Leu Asp Met His Val Val Val Pro
            100                 105                 110

Gly Thr Glu Val Thr Glu Lys Val Gly Ser Pro Ile Pro Leu Pro Thr
        115                 120                 125

Asp Ala Asp Ala Ala Lys Gly Ser Thr Ala Ala Pro Thr Ala Asn Asn
    130                 135                 140

Ser Ile Lys Asn Val Thr Val Ala Lys Pro Asn Ile Ser Asn Gly Asn
145                 150                 155                 160

Gly Thr Thr Ala Met Asn Ala Ser Thr Asn Asp Asp Ile Ala Thr His
                165                 170                 175

Met Ile His Pro Ile Ser Ser Leu Thr Pro Tyr Gln Asn Arg Trp Thr
            180                 185                 190

Ile Lys Ala Arg Ile Thr Asn Lys Pro Pro Ile Arg Thr Trp Ser Asn

-continued

```
            195                 200                 205
Ser Arg Gly Glu Gly Lys Leu Phe Ser Phe Asp Leu Val Asp Glu Ser
210                 215                 220

Gly Glu Ile Arg Cys Thr Ala Phe Lys Glu Met Val Asp Lys Phe Tyr
225                 230                 235                 240

Asp Tyr Leu Gln Val Asp Lys Val Tyr Ile Asn Lys Cys Gln Leu
                    245                 250                 255

Lys Gln Ala Asn Lys Gln Tyr Ser Thr Leu Lys His Glu Tyr Glu Met
                260                 265                 270

Thr Val Thr His Asp Thr Val Ile Lys Glu Cys Leu Asp Ala Asp Ser
                275                 280                 285

Thr Ile Pro Thr Thr Gln Tyr Asn Phe Val Pro Ile Asp Lys Ile Ala
290                 295                 300

Asp Lys Glu Val Asn Ser Val Val Asp Val Ile Gly Ile Ala Lys Ser
305                 310                 315                 320

Val Ser Glu Leu Gln Thr Phe Gln Ala Arg Ser Thr Gly Arg Glu Leu
                    325                 330                 335

Lys Lys Lys Glu Val Val Leu Val Asp Gln Ser Gln Thr Ala Ile Ser
                340                 345                 350

Leu Thr Leu Trp Gly Gln Glu Ala Glu Asn Phe Asp Gly Thr Asn Asn
                355                 360                 365

Pro Val Val Ile Lys Ser Ala Lys Ile Gly Glu Phe Gly Gly Gly
370                 375                 380

Lys Asn Leu Thr Thr Leu Val Ser Ser Thr Val Lys Ile Asn Pro Glu
385                 390                 395                 400

Leu Lys Glu Cys Tyr Arg Ile Arg Gly Trp Tyr Asp Ser Glu Gly Glu
                    405                 410                 415

Asn Leu Asn Ala Lys Asn Ile Ser Ala Arg Val Gly Ser Ser Asn Met
                420                 425                 430

Ser Ala Thr Trp Met Thr Phe Lys Glu Val Lys Asp Gln Lys Leu Gly
                435                 440                 445

Ser Ser Glu Lys Gly Asp Tyr Tyr Lys Ala Ile Ala Thr Val Leu Leu
                450                 455                 460

Val Lys Ala Asp Asn Ile Val Tyr Arg Ala Cys Pro Thr Ala Glu Cys
465                 470                 475                 480

Asn Lys Lys Val Val Asp Met Glu Asn Ser Met Tyr Arg Cys Glu Lys
                    485                 490                 495

Cys Asn Arg Glu Phe Pro Asn Phe Lys Tyr Arg Leu Leu Ala Ser Met
                500                 505                 510

Asn Val Gly Asp His Thr Gly Asn Gln Trp Val Ser Met Phe Ser Ser
                515                 520                 525

Glu Ala Glu Lys Ile Leu Gly Met Thr Ala Glu Val Gly Gln Thr
                530                 535                 540

Leu Glu His Asn Lys Glu Ile Ala Asn Ile Val Asp Arg Ala His
545                 550                 555                 560

Phe Lys Val Phe Ser Leu Thr Cys Arg Ala Lys Ile Glu Thr Tyr Asn
                    565                 570                 575

Asp Glu Ala Arg Leu Lys Thr Val Cys Ile Arg Val Asp Pro Ile Asn
                580                 585                 590

Tyr Glu Glu Tyr Ser Ala Leu Leu Thr Glu Lys Ile Gln Gln Leu Thr
                595                 600                 605

Gly Glu Ser His Asp
        610
```

<210> SEQ ID NO 69
<211> LENGTH: 248
<212> TYPE: PRT
<213> ORGANISM: Diabrotica virgifera

<400> SEQUENCE: 69

```
Met Lys Leu Asn Val Ser Tyr Pro Ala Thr Gly Cys Gln Lys Leu Phe
1               5                   10                  15
Glu Val Val Asp Glu His Lys Ile Arg Ile Phe Tyr Glu Lys Arg Met
            20                  25                  30
Gly Gln Glu Val Glu Ala Asp Ala Leu Gly Asp Glu Trp Lys Gly Tyr
        35                  40                  45
Ile Leu Lys Ile Ser Gly Gly Asn Asp Lys Gln Gly Phe Pro Met Lys
    50                  55                  60
Gln Gly Val Leu Thr Asn Gly Arg Val Arg Leu Leu Leu Ser Lys Gly
65                  70                  75                  80
His Ser Cys Tyr Arg Pro Arg Arg Thr Gly Glu Arg Lys Arg Lys Ser
                85                  90                  95
Val Arg Gly Cys Ile Val Asp Gly Asn Leu Ser Val Leu Ala Leu Val
            100                 105                 110
Ile Val Arg Lys Gly Glu Gln Glu Ile Pro Gly Leu Thr Asp Thr Thr
        115                 120                 125
Ile Pro Arg Arg Leu Gly Pro Lys Arg Ala Ser Arg Ile Arg Lys Leu
    130                 135                 140
Phe Asn Leu Ser Lys Glu Asp Asp Val Arg Gln Tyr Val Val Lys Arg
145                 150                 155                 160
Pro Leu Ala Gln Lys Glu Gly Lys Lys Leu Arg Thr Lys Ala Pro Lys
                165                 170                 175
Ile Gln Arg Leu Ile Thr Pro Val Val Leu Gln Arg Lys Arg His Arg
            180                 185                 190
Leu Ala Leu Lys Lys Lys Arg Cys Leu Lys Arg Lys Glu Gln Glu Asp
        195                 200                 205
Ala Tyr Ala Lys Leu Leu Ala Gln Arg Lys Lys Glu Ser Lys Ala Arg
    210                 215                 220
Arg Glu Met Leu Lys Arg Arg Ser Ala Ser Met Arg Asp Ser Lys
225                 230                 235                 240
Ser Ser Thr Gln Ser Gly Gln Lys
                245
```

<210> SEQ ID NO 70
<211> LENGTH: 1150
<212> TYPE: DNA
<213> ORGANISM: Zea mays

<400> SEQUENCE: 70

| | | |
|---|---|---|
| caacggggca gcactgcact gcactgcaac tgcgaatttc cgtcagcttg agcggtcca | | 60 |
| agcgccctgc gaagcaaact acgccgatgg cttcggcggc ggcgtgggag ggtccgacgg | | 120 |
| ccgcggagct gaagacagcg ggggcggagg tgattcccgg cggcgtgcga gtgaaggggt | | 180 |
| gggtcatcca gtcccacaaa ggccctatcc tcaacgccgc ctctctgcaa cgctttgaag | | 240 |
| atgaacttca acaacacat ttacctgaga tggttttttgg agagagtttc ttgtcacttc | | 300 |
| aacatacaca aactggcatc aaatttcatt ttaatgcgct tgatgcactc aaggcatgga | | 360 |
| agaaagaggc actgccacct gttgaggttc ctgctgcagc aaaatggaag ttcagaagta | | 420 |

```
agccttctga ccaggttata cttgactacg actatacatt tacgacacca tattgtggga    480
gtgatgctgt ggttgtgaac tctggcactc cacaaacaag tttagatgga tgcggcactt    540
tgtgttggga ggatactaat gatcggattg acattgttgc cctttcagca aaagaaccca    600
ttcttttcta cgacgaggtt atcttgtatg aagatgagtt agctgacaat ggtatctcat    660
ttcttactgt gcgagtgagg gtaatgccaa ctggttggtt tctgcttttg cgttttggc    720 ttagagttga tggtgtactg atgaggttga gagacactcg gttacattgc ctgtttggaa    780
acggcgacgg agccaagcca gtggtacttc gtgagtgctg ctggagggaa gcaacatttg    840
ctactttgtc tgcgaaagga tatccttcgg actctgcagc gtacgcggac ccgaacctta    900
ttgcccataa gcttcctatt gtgacgcaga agacccaaaa gctgaaaaat cctacctgac    960
tgacacaaag gcgccctacc gcgtgtacat catgactgtc ctgtcctatc gttgccttt    1020 gtgtttgcca catgttgtgg atgtacgttt ctatgacgaa acaccatagt ccatttcgcc    1080
tgggccgaac agagatagct gattgtcatg tcacgtttga attagaccat tccttagccc    1140
tttttccccc                                                            1150
```

<210> SEQ ID NO 71
<211> LENGTH: 20
<212> TYPE: DNA
<213> ORGANISM: Artificial Sequence
<220> FEATURE:
<223> OTHER INFORMATION: PCR Primer

<400> SEQUENCE: 71
agccaagcca gtggtacttc                                                   20

<210> SEQ ID NO 72
<211> LENGTH: 22
<212> TYPE: DNA
<213> ORGANISM: Artificial Sequence
<220> FEATURE:
<223> OTHER INFORMATION: PCR Primer

<400> SEQUENCE: 72
tcgcagacaa agtagcaaat gt                                                22

<210> SEQ ID NO 73
<211> LENGTH: 20
<212> TYPE: DNA
<213> ORGANISM: Artificial Sequence
<220> FEATURE:
<223> OTHER INFORMATION: PCR Primer

<400> SEQUENCE: 73
ttgtgatgtt ggtggcgtat                                                   20

<210> SEQ ID NO 74
<211> LENGTH: 24
<212> TYPE: DNA
<213> ORGANISM: Artificial Sequence
<220> FEATURE:
<223> OTHER INFORMATION: PCR Primer

<400> SEQUENCE: 74
tgttaaataa aaccccaaag atcg                                              24

<210> SEQ ID NO 75
<211> LENGTH: 2013
<212> TYPE: DNA
<213> ORGANISM: Zea mays

<400> SEQUENCE: 75

```
atgatccctg ccgttgctga tccgacgacg ctggacggcg ggggcgcgcg caggccgttg      60
ctcccggaga cggaccctcg ggggcgtgct gccgccggcg ccgagcagaa gcggccgccg     120
gctacgccga ccgttctcac cgccgtcgtc tccgccgtgc tcctgctcgt cctcgtggcg     180
gtcacagtcc tcgcgtcgca gcacgtcgac gggcaggctg ggggcgttcc cgcgggcgaa     240
gatgccgtcg tcgtcgaggt ggccgcctcc cgtggcgtgg ctgagggcgt gtcggagaag     300
tccacggccc cgctcctcgg ctccggcgcg ctccaggact tctcctggac caacgcgatg     360
ctggcgtggc agcgcacggc gttccacttc cagcccccca gaactggat gaacgatccg      420
aacggtccgc tgtatcacaa gggctggtac cacctcttct accagtggaa cccggactcc     480
gcggtatggg gcaacatcac ctggggccac gccgtctcgc gcgacctcct ccactggctg     540
cacctaccgc tggccatggt gcccgatcac ccgtacgacg ccaacggcgt ctggtccggg     600
tcggcgacgc gcctgccgga cggccggatc gtcatgctct acacgggctc cacggcggag     660
tcgtcggcgc aggtgcagaa cctcgcggag ccggccgacg cgtccgaccc gctgctgcgg     720
gagtgggtca gtcggacgc caacccggtg ctggtgccgc cgccgggcat cgggccgacg      780
gacttccgcg acccgacgac ggcgtgtcgg acgccggccg gcaacgacac ggcgtggcgg     840
gtcgccatcg gtccaagga ccgggaccac gcggggctgg cgctggtgta ccggacggag      900
gacttcgtgc ggtacgaccc ggcgccggcg ctgatgcacg ccgtgccggg caccggcatg     960
tgggagtgcg tggacttcta cccggtggcc gcgggatcag gcgccgcggc gggcagcggg    1020
gacgggctgg agacgtccgc ggcgccggga cccggggtga agcacgtgct caaggctagc    1080
ctcgacgacg acaagcacga ctactacgcg atcggcacct acgacccggc gacggacacc    1140
tggaccccg acagcgcgga ggacgacgtc gggatcggcc tccggtacga ctatggcaag     1200
tactacgcgt cgaagacctt ctacgacccc gtccttcgcc ggcgggtgct ctggggtgtg    1260
gtcggcgaga ccgacagcga gcgcgcggac atcctcaagg gctgggcatc cgtgcagtca    1320
atccccagga cggtcctcct ggacacgaag acgggcagca acctgctcca gtggccggtg    1380
gtggaggtgg agaacctccg gatgagcggc aagagcttcg acggcgtcgc gctggaccgc    1440
ggatccgtcg tgccctcga cgtcggcaag gcgacgcagt ggacatcga ggctgtgttc     1500
gaggtggacg cgtcggacgc ggcgggcgtc acggaggccg acgtgacgtt caactgcagc    1560
accagcgcag gcgcggcggg ccgggggcctg ctcggcccgt tcggccttct cgtgctggcg   1620
gacgacgact tgtccgagca gaccgccgtg tacttctacc tgctcaaggg cacggacggc    1680
agcctccaaa ctttcttctg ccaagacgag ctcagggcat ccaaggcgaa cgatctggtt    1740
aagagagtat acgggagctt ggtccctgtg ctagatgggg agaatctctc ggtcagaata    1800
ctggttgacc actccatcgt ggagagcttt gctcaaggcg ggaggacgtg catcacgtcg    1860
cgagtgtacc ccacacgagc catctacgac tccgcccgcg tcttcctctt caacaacgcc    1920
acacatgctc acgtcaaagc aaaatccgtc aagatctggc agctcaactc cgcctacatc    1980
cggccatatc cggcaacgac gacttctcta tga                                 2013
```

<210> SEQ ID NO 76
<211> LENGTH: 786
<212> TYPE: DNA
<213> ORGANISM: Escherichia coli

<400> SEQUENCE: 76

```
atgagggaag cggtgatcgc cgaagtatcg actcaactat cagaggtagt tggcgtcatc    60
gagcgccatc tcgaaccgac gttgctggcc gtacatttgt acggctccgc agtggatggc   120
ggcctgaagc cacacagtga tattgatttg ctggttacgg tgaccgtaag gcttgatgaa   180
acaacgcggc gagctttgat caacgacctt ttggaaactt cggcttcccc tggagagagc   240
gagattctcc gcgctgtaga agtcaccatt gttgtgcacg acgacatcat tccgtggcgt   300
tatccagcta agcgcgaact gcaatttgga gaatggcagc gcaatgacat tcttgcaggt   360
atcttcgagc cagccacgat cgacattgat ctggctatct tgctgacaaa agcaagagaa   420
catagcgttg ccttggtagg tccagcggcg gaggaactct ttgatccggt tcctgaacag   480
gatctatttg aggcgctaaa tgaaacctta acgctatgga actcgccgcc cgactgggct   540
ggcgatgagc gaaatgtagt gcttacgttg tcccgcattt ggtacagcgc agtaaccggc   600
aaaatcgcgc gaaggatgt cgctgccgac tgggcaatga agcgcctgcc ggcccagtat   660
cagcccgtca tacttgaagc taggcaggct tatcttggac aagaagatcg cttggcctcg   720
cgcgcagatc agttggaaga atttgttcac tacgtgaaag gcgagatcac caaggtagtc   780
ggcaaa                                                              786

<210> SEQ ID NO 77
<211> LENGTH: 189
<212> TYPE: DNA
<213> ORGANISM: Artificial Sequence
<220> FEATURE:
<223> OTHER INFORMATION: Amplified fragment

<400> SEQUENCE: 77
gtatgtttct gcttctacct ttgatatata tataataatt atcactaatt agtagtaata    60
tagtatttca agtatttttt tcaaaataaa agaatgtagt atatagctat tgcttttctg   120
tagtttataa gtgtgtatat tttaatttat aacttttcta atatatgacc aaaacatggt   180
gatgtgcag                                                           189

<210> SEQ ID NO 78
<211> LENGTH: 20
<212> TYPE: DNA
<213> ORGANISM: Artificial Sequence
<220> FEATURE:
<223> OTHER INFORMATION: PCR Primer

<400> SEQUENCE: 78
tgttcggttc cctctaccaa                                                20

<210> SEQ ID NO 79
<211> LENGTH: 22
<212> TYPE: DNA
<213> ORGANISM: Artificial Sequence
<220> FEATURE:
<223> OTHER INFORMATION: PCR Primer

<400> SEQUENCE: 79
caacatccat caccttgact ga                                             22

<210> SEQ ID NO 80
<211> LENGTH: 24
<212> TYPE: DNA
<213> ORGANISM: Artificial Sequence
<220> FEATURE:
<223> OTHER INFORMATION: Probe Oligonucleotide

<400> SEQUENCE: 80
```

```
cacagaaccg tcgcttcagc aaca                                          24

<210> SEQ ID NO 81
<211> LENGTH: 18
<212> TYPE: DNA
<213> ORGANISM: Artificial Sequence
<220> FEATURE:
<223> OTHER INFORMATION: PCR Primer

<400> SEQUENCE: 81
tggcggacga cgacttgt                                                 18

<210> SEQ ID NO 82
<211> LENGTH: 19
<212> TYPE: DNA
<213> ORGANISM: Artificial Sequence
<220> FEATURE:
<223> OTHER INFORMATION: PCR Primer

<400> SEQUENCE: 82
aaagtttgga ggctgccgt                                                19

<210> SEQ ID NO 83
<211> LENGTH: 26
<212> TYPE: DNA
<213> ORGANISM: Artificial Sequence
<220> FEATURE:
<223> OTHER INFORMATION: Probe Oligonucleotide

<400> SEQUENCE: 83
cgagcagacc gccgtgtact tctacc                                        26

<210> SEQ ID NO 84
<211> LENGTH: 25
<212> TYPE: DNA
<213> ORGANISM: Artificial Sequence
<220> FEATURE:
<223> OTHER INFORMATION: PCR Primer

<400> SEQUENCE: 84
gtatgtttct gcttctacct ttgat                                         25

<210> SEQ ID NO 85
<211> LENGTH: 29
<212> TYPE: DNA
<213> ORGANISM: Artificial Sequence
<220> FEATURE:
<223> OTHER INFORMATION: PCR Primer

<400> SEQUENCE: 85
ccatgttttg gtcatatatt agaaaagtt                                     29

<210> SEQ ID NO 86
<211> LENGTH: 34
<212> TYPE: DNA
<213> ORGANISM: Artificial Sequence
<220> FEATURE:
<223> OTHER INFORMATION: Probe Oligonucleotide

<400> SEQUENCE: 86
agtaatatag tatttcaagt attttttca aaat                                34

<210> SEQ ID NO 87
<211> LENGTH: 19
<212> TYPE: DNA
```

```
<213> ORGANISM: Artificial Sequence
<220> FEATURE:
<223> OTHER INFORMATION: PCR Primer

<400> SEQUENCE: 87
cttagctgga taacgccac                                           19

<210> SEQ ID NO 88
<211> LENGTH: 19
<212> TYPE: DNA
<213> ORGANISM: Artificial Sequence
<220> FEATURE:
<223> OTHER INFORMATION: PCR Primer

<400> SEQUENCE: 88
gaccgtaagg cttgatgaa                                           19

<210> SEQ ID NO 89
<211> LENGTH: 21
<212> TYPE: DNA
<213> ORGANISM: Artificial Sequence
<220> FEATURE:
<223> OTHER INFORMATION: Probe Oligonucleotide

<400> SEQUENCE: 89
cgagattctc cgcgctgtag a                                        21

<210> SEQ ID NO 90
<211> LENGTH: 20
<212> TYPE: DNA
<213> ORGANISM: Artificial Sequence
<220> FEATURE:
<223> OTHER INFORMATION: PCR Primer

<400> SEQUENCE: 90
gaatccttgc gtcatttggt                                          20

<210> SEQ ID NO 91
<211> LENGTH: 20
<212> TYPE: DNA
<213> ORGANISM: Artificial Sequence
<220> FEATURE:
<223> OTHER INFORMATION: PCR Primer

<400> SEQUENCE: 91
caatggactc acgcacaact                                          20

<210> SEQ ID NO 92
<211> LENGTH: 38
<212> TYPE: DNA
<213> ORGANISM: Artificial Sequence
<220> FEATURE:
<223> OTHER INFORMATION: PCR Primer

<400> SEQUENCE: 92
gaatccttgc gtcatttggt gactagtacc ggttggga                      38

<210> SEQ ID NO 93
<211> LENGTH: 34
<212> TYPE: DNA
<213> ORGANISM: Artificial Sequence
<220> FEATURE:
<223> OTHER INFORMATION: PCR Primer

<400> SEQUENCE: 93
caatggactc acgcacaact taaccgcgga tcaa                          34
```

-continued

```
<210> SEQ ID NO 94
<211> LENGTH: 12
<212> TYPE: DNA
<213> ORGANISM: Artificial Sequence
<220> FEATURE:
<223> OTHER INFORMATION: Probe Oligonucleotide

<400> SEQUENCE: 94
tgggaaaggt tg                                                         12

<210> SEQ ID NO 95
<211> LENGTH: 213
<212> TYPE: PRT
<213> ORGANISM: Diabrotica virgifera
<220> FEATURE:
<221> NAME/KEY: misc_feature
<222> LOCATION: (200)..(200)
<223> OTHER INFORMATION: Xaa can be any naturally occurring amino acid
<220> FEATURE:
<221> NAME/KEY: misc_feature
<222> LOCATION: (206)..(206)
<223> OTHER INFORMATION: Xaa can be any naturally occurring amino acid

<400> SEQUENCE: 95
```

Met Ala Glu Ala Asp Lys Leu Asn Ile Asp Ser Ile Ile Ala Arg Leu
1               5                   10                  15

Leu Glu Val Arg Gly Ala Arg Pro Gly Lys Asn Val Gln Leu Thr Glu
            20                  25                  30

Asn Glu Ile Arg Gly Leu Cys Leu Lys Ser Arg Glu Ile Phe Leu Ser
        35                  40                  45

Gln Pro Ile Leu Leu Glu Leu Glu Ala Pro Leu Lys Ile Cys Gly Asp
    50                  55                  60

Ile His Gly Gln Tyr Tyr Asp Leu Leu Arg Leu Phe Glu Tyr Gly Gly
65                  70                  75                  80

Phe Pro Pro Glu Ser Asn Tyr Leu Phe Leu Gly Asp Tyr Val Asp Arg
                85                  90                  95

Gly Lys Gln Ser Leu Glu Thr Ile Cys Leu Leu Leu Ala Tyr Lys Ile
            100                 105                 110

Lys Tyr Pro Glu Asn Phe Phe Leu Leu Arg Gly Asn His Glu Cys Ala
        115                 120                 125

Ser Ile Asn Arg Ile Tyr Gly Phe Tyr Asp Glu Cys Lys Arg Arg Tyr
    130                 135                 140

Asn Ile Lys Leu Trp Lys Thr Phe Thr Asp Cys Phe Asn Cys Leu Pro
145                 150                 155                 160

Val Ala Ala Ile Val Asp Glu Lys Ile Phe Cys Cys His Gly Gly Leu
                165                 170                 175

Ser Pro Asp Leu Gln Ser Met Glu Gln Ile Arg Arg Ile Asn Arg Asp
            180                 185                 190

Arg Leu Met Tyr Leu Thr Lys Xaa Phe Phe Val Thr Phe Xaa Gly Leu
        195                 200                 205

Ile Gln Thr Lys Thr
    210

```
<210> SEQ ID NO 96
<211> LENGTH: 120
<212> TYPE: PRT
<213> ORGANISM: Diabrotica virgifera
<220> FEATURE:
<221> NAME/KEY: misc_feature
<222> LOCATION: (66)..(66)
```

<223> OTHER INFORMATION: Xaa can be any naturally occurring amino acid

<400> SEQUENCE: 96

```
Met Ile Asp Leu Val Gln Met Val Trp Lys Leu Phe Ser Ile Ile Gln
1               5                   10                  15

Ile Asp Arg Tyr Val Thr Ser Ile Ile Asn Asn Ser Gly Lys Gly Glu
            20                  25                  30

Ala Arg Val Leu Leu Ile Leu Asp Met His Val Val Val Pro Gly Thr
        35                  40                  45

Glu Val Thr Glu Lys Val Gly Ser Pro Ile Pro Leu Pro Thr Asp Ala
50                  55                  60

Asp Xaa Ala Lys Gly Ser Thr Ala Ala Pro Ala Thr Asn Asn Ser Ile
65                  70                  75                  80

Lys Asn Val Thr Val Ala Lys Pro Asn Ile Ser Asn Gly Asn Gly Thr
                85                  90                  95

Thr Ala Met Asn Ala Ser Thr Asn Asp Asp Ile Ala Thr His Met Ile
            100                 105                 110

His Pro Ile Ser Ser Leu Thr Pro
            115                 120
```

<210> SEQ ID NO 97
<211> LENGTH: 169
<212> TYPE: PRT
<213> ORGANISM: Diabrotica virgifera
<220> FEATURE:
<221> NAME/KEY: misc_feature
<222> LOCATION: (33)..(33)
<223> OTHER INFORMATION: Xaa can be any naturally occurring amino acid

<400> SEQUENCE: 97

```
Trp Ser Asn Ser Arg Gly Glu Gly Lys Leu Phe Ser Phe Asp Leu Val
1               5                   10                  15

Asp Glu Ser Gly Glu Ile Arg Cys Thr Ala Phe Lys Glu Met Val Asp
            20                  25                  30

Xaa Phe Tyr Asp Tyr Leu Gln Val Asp Lys Val Tyr Tyr Ile Asn Lys
        35                  40                  45

Cys Gln Leu Lys Gln Ala Asn Lys Gln Tyr Ser Thr Leu Lys His Glu
50                  55                  60

Tyr Glu Met Thr Val Thr His Asp Thr Val Ile Lys Glu Cys Leu Asp
65                  70                  75                  80

Ala Asp Ser Thr Ile Pro Thr Thr Gln Tyr Asn Phe Val Pro Ile Asp
                85                  90                  95

Lys Ile Ala Asp Lys Glu Val Asn Ser Val Val Asp Val Ile Gly Ile
            100                 105                 110

Ala Lys Ser Val Ser Glu Leu Gln Thr Phe Gln Ala Arg Ser Thr Gly
        115                 120                 125

Arg Glu Leu Lys Lys Lys Glu Val Val Leu Val Asp Gln Ser Gln Thr
130                 135                 140

Ala Ile Ser Leu Thr Leu Trp Gly Gln Glu Ala Glu Asn Phe Asp Gly
145                 150                 155                 160

Thr Asn Asn Pro Val Val Val Ile Lys
                165
```

<210> SEQ ID NO 98
<211> LENGTH: 225
<212> TYPE: PRT
<213> ORGANISM: Diabrotica virgifera
<220> FEATURE:

```
<221> NAME/KEY: misc_feature
<222> LOCATION: (6)..(7)
<223> OTHER INFORMATION: Xaa can be any naturally occurring amino acid

<400> SEQUENCE: 98

Thr Leu Val Ser Ser Xaa Xaa Lys Ile Asn Pro Glu Leu Lys Glu Cys
1               5                   10                  15

Tyr Arg Ile Arg Gly Trp Tyr Asp Ser Glu Gly Glu Asn Leu Asn Ala
            20                  25                  30

Lys Asn Ile Ser Ala Arg Val Gly Ser Ser Asn Met Ser Ala Thr Trp
        35                  40                  45

Met Thr Phe Lys Glu Val Lys Asp Gln Lys Leu Gly Ser Ser Glu Lys
    50                  55                  60

Gly Asp Tyr Tyr Lys Ala Ile Ala Thr Val Leu Leu Val Lys Ala Asp
65              70                  75                  80

Asn Ile Val Tyr Arg Ala Cys Pro Thr Ala Glu Cys Asn Lys Lys Val
                85                  90                  95

Val Asp Met Glu Asn Ser Met Tyr Arg Cys Lys Cys Asn Arg Glu
            100                 105                 110

Phe Pro Asn Phe Lys Tyr Arg Leu Leu Ala Ser Met Asn Val Gly Asp
        115                 120                 125

His Thr Gly Asn Gln Trp Val Ser Met Phe Ser Ser Glu Ala Glu Lys
    130                 135                 140

Ile Leu Gly Met Thr Ala Glu Glu Val Gly Gln Thr Leu Glu His Asn
145                 150                 155                 160

Lys Glu Glu Ile Ala Asn Ile Val Asp Arg Ala His Phe Lys Val Phe
                165                 170                 175

Ser Leu Thr Cys Arg Ala Lys Ile Glu Thr Tyr Asn Asp Glu Ala Arg
            180                 185                 190

Leu Lys Thr Val Cys Ile Arg Val Asp Pro Ile Asn Tyr Glu Glu Tyr
        195                 200                 205

Ser Ala Leu Leu Thr Glu Lys Ile Gln Gln Leu Thr Gly Glu Ser His
    210                 215                 220

Asp
225

<210> SEQ ID NO 99
<211> LENGTH: 17
<212> TYPE: DNA
<213> ORGANISM: Diabrotica virgifera

<400> SEQUENCE: 99
aattcaagct gccgcaa                                                    17

<210> SEQ ID NO 100
<211> LENGTH: 134
<212> TYPE: DNA
<213> ORGANISM: Diabrotica virgifera
<220> FEATURE:
<221> NAME/KEY: misc_feature
<222> LOCATION: (113)..(113)
<223> OTHER INFORMATION: n is a, c, g, or t

<400> SEQUENCE: 100
ttttctgttg ccatggtggt ttaagtccgg acctacaatc aatggaacaa attagaagra    60
ttaatagaga ccgactgatg tacctgacca aggstttctt tgtgacccttt tanggtctga   120 tccagacaaa gacc                                                      134
```

<210> SEQ ID NO 101
<211> LENGTH: 225
<212> TYPE: DNA
<213> ORGANISM: Diabrotica virgifera

<400> SEQUENCE: 101

| | | | | | |
|---|---|---|---|---|---|
| tggaactgaa | gttacagaaa | aagtaggctc | tcccattccc | ctaccaactg | atgctgackc | 60 |
| agctaaaggc | tctactgccg | ctccagctac | aaacaattcc | attaagaatg | taactgttgc | 120 |
| taaaccaaac | atcagtaatg | gcaatggcac | aactgcaatg | aatgccagta | ctaatgatga | 180 |
| tatagccaca | catatgatcc | atcctatttc | aagtctcaca | cctta | | 225 |

<210> SEQ ID NO 102
<211> LENGTH: 244
<212> TYPE: DNA
<213> ORGANISM: Diabrotica virgifera

<400> SEQUENCE: 102

| | | | | | |
|---|---|---|---|---|---|
| aactcttgtt | agcagcamtr | taaaaataaa | tcccgaatta | aaagaatgtt | acaggatcag | 60 |
| aggatggtac | gacagtgagg | gtgaaaatct | gaatgcaaag | aatattagtg | ccagagttgg | 120 |
| atcctcgaat | atgtctgcca | cttggatgac | ctttaaggaa | gttaaagatc | aaaaattagg | 180 |
| atcatctgaa | aaggtgatt | attataaagc | tattgctact | gttcttcttg | tcaaagccga | 240 |
| taat | | | | | | 244 |

<210> SEQ ID NO 103
<211> LENGTH: 5134
<212> TYPE: DNA
<213> ORGANISM: Diabrotica virgifera

<400> SEQUENCE: 103

| | | | | | |
|---|---|---|---|---|---|
| acagttaaat | attgaaaatg | gcctggtgtt | ttgataaaac | ggaagaggcg | aatttctagt | 60 |
| agcattttaa | ggtttcattt | gcatttaaaa | caaattcatg | tattataaaa | tgtaggatac | 120 |
| gtttcctcgt | atccatctac | ttaatttagg | ataacaataa | agggtgtgag | acagttaaat | 180 |
| attgaaaatg | gccagtgctt | cattattacc | caaaactttc | acttctattg | gtggcaaagc | 240 |
| cctacctacc | aactcacaac | aaaacattca | gtcaaaattt | aaagagatta | cagttccacc | 300 |
| aggaaatact | cctcaagatg | ttaaagaagg | ccccagtcac | caatcaaatc | caaaccattt | 360 |
| ggcttctctt | caaaaggcca | ttgaaactat | ggaagagaag | ggcttacaag | ctgatcctag | 420 |
| atattcacag | ttacttgcat | tgcgagctag | cattcctggg | gcagaagaaa | atggttctcc | 480 |
| cttctcaaac | aaccaaatca | agcaattaag | aaaccaaata | atggcttaca | ggtgtttggc | 540 |
| aagaaatcaa | cctgttccaa | caatttagt | attaggtttg | catggaaaaa | ctcctgaaaa | 600 |
| agttccacat | attgtacctc | caccgcaacc | tcaagaagta | cctaatgggg | gcgatccagg | 660 |
| accttcaaca | agttctgctg | ctgctgtagc | tcctagaaca | ccacaaaagc | tgccagcaaa | 720 |
| accaattgag | gctcagcttg | tcaacagaga | accaagagtc | actactttat | ctaaaccatc | 780 |
| ttccatagac | cctgttgttc | tattacaaga | acgagaaaac | agggtagcag | ctcgtatagc | 840 |
| agcgaggatt | gaacaagtca | gtaatctgcc | gactgatatg | tctgaggcat | acgtattcg | 900 |
| ggcacaaata | gaactcagag | ctttgagatg | tctaaacctc | cagagacaac | ttcgtagtga | 960 |
| ggttttgagc | tgtattcgac | gggacacaac | attagaaaca | gcagtaaatg | taaaagcgtt | 1020 |
| taaacgacc | aaacgtcaag | gtcttcgaga | agctagagca | acagaaaaac | ttgagaaaca | 1080 |
| acaaaagctg | gaagcagaga | gaaagaaacg | ccagaagaac | caagagttct | taaacaatgt | 1140 |

```
gatggcacac gctaaagatt tcaaagaatt ccacaggcag aaccaagcaa aactttctaa      1200
acttaataaa gctattctta cttatcacgc taatgcggag agagaacaaa agaaggaaca      1260
agagagaaga gaaaaggaac gtatgaagaa attgatggca gaagatgaag aaggttatag      1320
acagttgatc gatcaaaaga aagacaaacg tctagcgttc ttgctttcgc aaacagatga      1380
gtatataact aacctcacgg agatggtaaa gcaacacaag ttggaacaaa ccaataaaaa      1440
gaaagaggag gaaaaacgca agaagaagca gcagaaaatg caacaaccag ataggaaagt      1500
tacagttctg gaaactgcaa caggtaaaaa agtaacagga gaggctgctc ctacactgcg      1560
acaagttcag gaatggttaa tccaacatcc tggatgggag atggtcgata cagatgatga      1620
ggatgatgaa aacggggaga gagggatga tgactatgat gaaaatcaag aagtggatga       1680
tgcaaaagaa gttattaaaa aagctaaagt tgaagatgac gaatatcaca aaaacacaaa      1740
agaagaacag acttactaca gtattgctca cactgttcat gaagtggtaa cagaacaagc      1800
atccattctg gttaatggaa agcttaagga atatcaaatt agagggttag aatggatggt      1860
gtctttgtac aataacaatc tgaatggtat tctagcagat gagatgggtc taggtaaaac      1920
cattcaaacg attggcttgt tgacctattt gatggaaaaa aagaagataa atggaccgtt      1980
tttgatcata gtgccacttt caaccatttc taattggatg ttggaatttc aaaagtgggc      2040
ccctactgta gttgtcattt catacaaagg ctctcctgtg gttagaaaag tgatccagag      2100
ccagttaaaa gctgctaaat tcaatgtgct tctcactacc tacgagtaca ttattaagga      2160
caagggtgta ttagcaaaaa tcccatttaa atatatgatc atagatgagg gtcatcgtat      2220
gaaaaaccac cactgcaaat tgactcaagt cctgaatacg cactatttgg cgccctacag      2280
actcctgctt actggtactc ccctacaaaa taaattacca gaattatggg ccttgttgaa      2340
tttcttgttg ccttcgattt tcaagagttg ctccactttt gaacaatggt tcaatgcgcc      2400
attcgcaaca acaggagaaa aggttgagtt aaacgaagaa gaaactatcc ttatcatccg      2460
tcgtcttcac aaagtactca ggccgtttct cctgagacgt ctcaagaaag aagtcgaatc      2520
tcagcttcca gacaaagtgg aatatatcat aaagtgtgac atgtcgggcc tacaaaaggt      2580
tctctatgca cacatgcaga gcaagggtgt gttacttacc gatggttccg agaagggcag      2640
taaaggaagg ggatctaagg cactgatgaa caccattatg cagctgagga aactgtgcaa      2700
tcatccgttt atgttccaaa atatcgaaga gaaatattgt gatcatgttg gtattgctgg      2760
tggagtggtt tctggacccg acacttatag ggtatctggt aagtttgagc tcttggacag      2820
aatattgccc aaaatgaaag caactaacca taggattctt cttttctgtc aaatgactca      2880
attaatgacc atcatggaag attatctaaa ttggagagga ttcaaatatc ttcgtcttga      2940
tggtacaatc aaatcagaag atcgcgggga cctattatcg aaatttaatg ataaaaatag      3000
tgaatatttt ttgttttgc tatctacacg ggctggaggt ctgggactta atttgcagac       3060
agctgatact gtgattatct tcgattccga ttggaatcct catcaggatt acaagctcaa      3120
ggatcgagct catcgtattg acagcaaaaa tgaggtccga gttttgcgtt tgatgactgt      3180
taactctgtt gaggaacgaa ttttagctgc agctaaatac aagcttacta tggacgaaaa      3240
ggtcattcaa gctggtatgt tcgatcagaa gtctacaggc tcagagagac atcagttttt      3300
gcagagtatt ttacaccatg acggaagcga cgaagaagag gaaaacgaag ttcctgatga      3360
cgaaacagtg aaccagatgt tggcccgaag ggaaaacgaa tttcagcttt tccagaagat      3420
ggatcaggaa agaaaggaag aagatgaaaa gaccggaaag tcgcgactta ttcaagaaag      3480
```

| | |
|---|---|
| cgaattgccc gaatggctgt tgaagcaaga cgatgaaatc tactcgtggg gccttgatga | 3540 |
| tccagatgct gttttaggaa ggggtagtag gcaaagaaaa gaagttgatt atgttgacag | 3600 |
| cctgacggag aaagagtggc ttaaggctat tgacgaagag ggagaatttg aggaagaaca | 3660 |
| agaaggtgat aaagaaggtc tcagaaagaa aagagggagg aagaggaaga agcgcgatga | 3720 |
| tgacgaagag gcaagccaaa ttaagagaag aaaggtgcat ctagccgaga tcaagatgaa | 3780 |
| gaaaaagatg aagaggctta tggaagttgt tgtgaactac agggacaggg atggtagagt | 3840 |
| attgagcgaa ccgtttatga aacttccatc aaagaaggag ttacctgagt attacgatac | 3900 |
| gattaagaaa cctattgata ttgaaaaagt cgttgccaac gtagaagaag gaaaatattt | 3960 |
| cacgatgcac gatttggaaa gagatttcga cttgctgtgc caaaacgccc aacaatacaa | 4020 |
| cgaagaagac tccatgatct acgaggacag cctcgttctt cgacaggtgt ttagaagcgc | 4080 |
| gagggaaaag atcgacggta cctcagacca cgacgacaac gccgatggac cggcggtggc | 4140 |
| tcagatcaaa cgacctcgtg gtagacctcg aaaacacaag agacccgaag agatcgaggc | 4200 |
| cgaagcggcg gctcagaaag ctatggagga ggcatcgaag ctgagagctc aagctgaggc | 4260 |
| ggaagagctt agatctaagg tggaggaggc atctcagaga gccaaagagg aagcgaaagc | 4320 |
| aagggaggaa gccaaagcta gggaagaagc cgaaatcgag aacatggagg agattcccac | 4380 |
| aagcacatga tctatagagc aaccggaaac aaaaaggcaa aaaagaaata ttatatagaa | 4440 |
| aagatgtaca tgttcaatgg agatacattt tcgccgagtt acaacgggta atgcttttac | 4500 |
| aacggatatt ttgacgtatg aatgttgacg ttcagatgaa gtatatttat aaaataatcc | 4560 |
| agaccttttac gttttggttg atttgttttc tgtattgttc agtttattga caaccatta | 4620 |
| atagcagctt acctaaatga tttagaaaag catctgagtt atttagataa gttttgagat | 4680 |
| tatatttatt aactttaata ttactatctt tattatagca tattgtaatt atttttttcct | 4740 |
| gtccttcttt cgttgtgtgg tagataatcc gagagtcaac agttataagc aaatgaaatt | 4800 |
| cagttaaacc tcaaatgtac aaaatgatca aattaatgtt tacaatttat tttttttacca | 4860 |
| cgcacattca ctattactat tgtcagtcat tgagatatca ttttatatag ctccatgtct | 4920 |
| gtcttcctca atttacagag aagcaattag acaagtaatg acataatatg gtgctgaaat | 4980 |
| aatgtgcttg atagtgatgt tcacaaagta actattcgtt acaaagtact cgttacttac | 5040 |
| aaataccgaa actaacgatt actatacaga gaggcaaatc gttactttga ttacactgat | 5100 |
| tacttcgtat caatcgtatc agagcgagta acga | 5134 |

<210> SEQ ID NO 104
<211> LENGTH: 451
<212> TYPE: DNA
<213> ORGANISM: Diabrotica virgifera
<220> FEATURE:
<221> NAME/KEY: misc_feature
<222> LOCATION: (119)..(119)
<223> OTHER INFORMATION: n is a, c, g, or t
<220> FEATURE:
<221> NAME/KEY: misc_feature
<222> LOCATION: (128)..(128)
<223> OTHER INFORMATION: n is a, c, g, or t
<220> FEATURE:
<221> NAME/KEY: misc_feature
<222> LOCATION: (289)..(289)
<223> OTHER INFORMATION: n is a, c, g, or t
<220> FEATURE:
<221> NAME/KEY: misc_feature
<222> LOCATION: (403)..(403)
<223> OTHER INFORMATION: n is a, c, g, or t
<220> FEATURE:
<221> NAME/KEY: misc_feature

```
<222> LOCATION: (414)..(414)
<223> OTHER INFORMATION: n is a, c, g, or t

<400> SEQUENCE: 104
attctggtta ataggaaagc ttaaggaata ttcaaattag agggttagaa tggatggtgt      60
cttttgtacaa taacaatctg aatggtattc tagcagatga gatgggtcta ggtaaaccnt    120
tcaaacgntt ggcttgttga cctatttgat ggaaaaaaag aagataaatg gaccgttttt    180
gatcatagtg ccactttcaa ccattctaat tggatagttg gaatttcaaa gtagggccct    240
actagtagtt gtcatttcat acaaaggctc tcctgtggtt agaaaagtna tccagagcca    300
gttaaaagct gctaaattca atgtgcttct cactacctac gagtacatta ttaaggcaag    360
gtgattagca aaaaatccca gtttaaatat atgatcatag atnaggtcat catnaaacac    420
actgcaattg aactcaaggc ctgaatacgc a                                    451

<210> SEQ ID NO 105
<211> LENGTH: 538
<212> TYPE: DNA
<213> ORGANISM: Diabrotica virgifera

<400> SEQUENCE: 105
agtgtattag caaaaatccc atttaaatat atgatcatag atgagggtca tcgtatgaaa      60
aaccaccact gcaaattgac tcaagtcctg aatacgcact atttggcgcc ctacagactc    120
ctgcttactg gtactcccct acaaaataaa ttaccagaat tatgggcctt gttgaatttc    180
ttgttgcctt cgattttcaa gagttgctcc acttttgaac aatggttcaa tgcgccattc    240
gcaacaacag gagaaaaggt tgagttaaac gaagaagaaa ctatccttat catccgtcgt    300
cttcacaaag tactcaggcc gtttctcctg agacgtctca agaaagaagt cgaatctcag    360
cttccagaca aagtggaata tatcataaag tgtgacatgt cgggcctaca aaaggttctc    420
tatgcacaca tgcagagcaa gggtgtgtta cttaccgatg gttccgagaa gggcagtaaa    480
ggaaggggat ctaaggacaa ctagatgaac accattatgc agctgaggaa actgtgct      538

<210> SEQ ID NO 106
<211> LENGTH: 303
<212> TYPE: DNA
<213> ORGANISM: Diabrotica virgifera

<400> SEQUENCE: 106
agggctggag gtctgggact taatttgcag acagctgata ctgtgattat cttcgattcc      60
gattggaatc ctcatcagga tttacaagct caggatcgag ctcatcgtat tggacagcaa    120
aatgaggtcc gagttttgcg tttgatgact gttaactctg ttgaggaacg aattttagct    180
gcagctaaat acaagcttac tatggacgaa aaggtcattc aagctggtat gttcgatcag    240
aagtctacgg gatctgaaag gcagcagttt cttcagagta ttttacacaa tgatggtagt    300
gat                                                                  303

<210> SEQ ID NO 107
<211> LENGTH: 14
<212> TYPE: DNA
<213> ORGANISM: Diabrotica virgifera

<400> SEQUENCE: 107
agggctggag gtct                                                       14

<210> SEQ ID NO 108
```

<211> LENGTH: 459
<212> TYPE: DNA
<213> ORGANISM: Artificial Sequence
<220> FEATURE:
<223> OTHER INFORMATION: Amplified fragment

<400> SEQUENCE: 108

```
atgagggtca tcgtatgaaa accaccact gcaaattgac tcaagtcctg aatacgcact      60
atttggcgcc ctacagactc ctgcttactg gtactcccct acaaaataaa ttaccagaat    120
tatgggcctt gttgaatttc ttgttgcctt cgattttcaa gagttgctcc acttttgaac    180
aatggttcaa tgcgccattc gcaacaacag gagaaaaggt tgagttaaac gaagaagaaa    240
ctatccttat catccgtcgt cttcacaaag tactcaggcc gtttctcctg agacgtctca    300
agaaagaagt cgaatctcag cttccagaca aagtggaata tatcataaag tgtgacatgt    360
cgggcctaca aaaggttctc tatgcacaca tgcagagcaa gggtgtgtta cttaccgatg    420
gttccgagaa gggcagtaaa ggaaggggat ctaaggaca                            459
```

<210> SEQ ID NO 109
<211> LENGTH: 812
<212> TYPE: DNA
<213> ORGANISM: Artificial Sequence
<220> FEATURE:
<223> OTHER INFORMATION: Hairpin

<400> SEQUENCE: 109

```
gcgccctaca gactcctgct tactggtact cccctacaaa ataaattacc agaattatgg     60
gccttgttga atttcttgtt gccttcgatt ttcaagagtt gctccacttt tgaacaatgg    120
ttcaatgcgc cattcgcaac aacaggagaa aaggttgagt taaacgaaga gaaactatc     180
cttatcatcc gtcgtcttca caaagtactc aggccgtttc tcctgagacg tctcaagaaa    240
gaagtcgaat ctcagcttcc agacaaagtg gaatatatca taagtgtga catgtgacta    300
gtaccggttg ggaaaggtat gtttctgctt ctacctttga tatatatata ataattatca    360
ctaattagta gtaatatagt atttcaagta ttttttttcaa aataaaagaa tgtagtatat    420
agctattgct tttctgtagt ttataagtgt gtatatttta atttataact tttctaatat    480
atgaccaaaa catggtgatg tgcaggttga tccgcggaca tgtcacactt tatgatatat    540
tccactttgt ctggaagctg agattcgact tctttcttga gacgtctcag agaaacggc     600
ctgagtactt tgtgaagacg acggatgata aggatagttt cttcttcgtt taactcaacc    660
ttttctcctg ttgttgcgaa tggcgcattg aaccattgtt caaaagtgga gcaactcttg    720
aaaatcgaag gcaacaagaa attcaacaag gcccataatt ctggtaatt attttgtagg    780
ggagtaccag taagcaggag tctgtagggc gc                                  812
```

<210> SEQ ID NO 110
<211> LENGTH: 167
<212> TYPE: PRT
<213> ORGANISM: Diabrotica virgifera

<400> SEQUENCE: 110

```
Ser Val Leu Ala Lys Ile Pro Phe Lys Tyr Met Ile Ile Asp Glu Gly
 1               5                  10                  15

His Arg Met Lys Asn His His Cys Lys Leu Thr Gln Val Leu Asn Thr
            20                  25                  30

His Tyr Leu Ala Pro Tyr Arg Leu Leu Leu Thr Gly Thr Pro Leu Gln
        35                  40                  45
```

```
Asn Lys Leu Pro Glu Leu Trp Ala Leu Leu Asn Phe Leu Leu Pro Ser
    50                  55                  60

Ile Phe Lys Ser Cys Ser Thr Phe Glu Gln Trp Phe Asn Ala Pro Phe
65              70                  75                      80

Ala Thr Thr Gly Glu Lys Val Glu Leu Asn Glu Glu Glu Thr Ile Leu
                85                  90                  95

Ile Ile Arg Arg Leu His Lys Val Leu Arg Pro Phe Leu Leu Arg Arg
            100                 105                 110

Leu Lys Lys Glu Val Glu Ser Gln Leu Pro Asp Lys Val Glu Tyr Ile
        115                 120                 125

Ile Lys Cys Asp Met Ser Gly Leu Gln Lys Val Leu Tyr Ala His Met
    130                 135                 140

Gln Ser Lys Gly Val Leu Leu Thr Asp Gly Ser Glu Lys Gly Ser Lys
145                 150                 155                 160

Gly Arg Gly Ser Lys Asp Asn
                165
```